(12) United States Patent
Fang et al.

(10) Patent No.: US 7,569,601 B2
(45) Date of Patent: *Aug. 4, 2009

(54) CYCLOALKYLIDENE COMPOUNDS AS MODULATORS OF ESTROGEN RECEPTOR

(75) Inventors: Jing Fang, Durham, NC (US); Dennis Heyer, Durham, NC (US); Aaron Bayne Miller, Durham, NC (US); Frank Navas, III, Durham, NC (US); Terrence Lee Smalley, Jr., Durham, NC (US); William J. Zuercher, Durham, NC (US); Subba Reddy Katamreddy, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/748,096

(22) Filed: May 14, 2007

(65) Prior Publication Data

US 2007/0213348 A1 Sep. 13, 2007

Related U.S. Application Data

(63) Continuation of application No. 10/565,296, filed as application No. PCT/US2004/024308 on Jul. 27, 2004.

(60) Provisional application No. 60/490,588, filed on Jul. 28, 2003.

(51) Int. Cl.
*A61K 31/351* (2006.01)
*C07D 315/00* (2006.01)

(52) U.S. Cl. ............................ 514/459; 549/426
(58) Field of Classification Search ................. 514/459; 549/426
See application file for complete search history.

(56) References Cited

U.S. PATENT DOCUMENTS

| | | | |
|---|---|---|---|
| 3,287,397 | A | 11/1966 | Ollson et al. |
| 3,760,007 | A | 9/1973 | Steinman |
| 3,936,493 | A | 2/1976 | Karmas |
| 4,857,516 | A | 8/1989 | Terao et al. |
| 5,432,175 | A | 7/1995 | Piwinski et al. |
| 5,686,460 | A | 11/1997 | Nicolai et al. |
| 6,043,279 | A | 3/2000 | Boehm et al. |
| 6,455,545 | B2 | 9/2002 | Delorme et al. |
| 2001/0021715 | A1 | 9/2001 | Delorme et al. |
| 2002/0115662 | A1 | 8/2002 | Boyd et al. |

FOREIGN PATENT DOCUMENTS

| | | |
|---|---|---|
| AU | 9348934 | 4/1994 |
| EP | 308839 A2 | 3/1981 |
| EP | 392805 A2 | 4/1990 |
| JO | 2264263 | 10/1990 |
| JO | 2285356 | 11/1990 |
| JO | 3015853 | 1/1991 |
| JO | 3158852 | 7/1991 |
| JP | 06051546 | 2/1994 |
| JP | 06332206 | 12/1994 |
| JP | 2002008865 | 1/2002 |
| WO | 9219585 A1 | 11/1992 |
| WO | 9415901 A1 | 7/1994 |
| WO | 9703046 A1 | 1/1997 |
| WO | 9857922 A1 | 12/1998 |
| WO | 01/36360 A1 | 5/2001 |
| WO | 0244141 A1 | 6/2002 |
| WO | 03016270 A1 | 2/2003 |

OTHER PUBLICATIONS

Gilbert, Jacques et al.; Cytotoxicity and Antiestrogenicity of a Novel Series of Basic Diphenylethylenes; Journal of Medicinal Chemistry; 1997; 40; 1104-1111.
Garg S. et al.; Structure-Activity Relationship of Estrogens: A Study Involving Cyclofenyl As The Model Compound; J. Steroid Biochem.; 1983; 18; 89-95.
Laios I. et al.; Mechanisms Governing the Accumulation of Estrogen Receptor Alpha in MCF-7 Breast Cancer Cells Treated with Hydroxytamoxifen and Related Antiestrogens; Journal of Steroid Biochemistry & Molecular Biology; 2003; 87; 207-221.
Watts C.K.W. et al.; Studies on the Ligand Specificity and Potential Identity of Microsomal Antiestrogen-Binding Sites; Molecular Pharmacology; 1987; 31; 541-551.
Database Search Conducted By GlaxoSmithKline, Mar. 27, 2003.
Durani S. et al.; A Possible Basis for Structure-Function Relationship of Estrogens; International Journal of Quantum Chemistry; 1981; XX; 71-83.
Muthyala et al.; Bridged Bicycle Cores Containing a 1,1-Diarylene Motif Are High-Affinity Subtype-Selective Ligands for the Estrogen Receptor; J Med Chem; Apr. 2, 2003; vol. 46; 1589-1602.
Rubin et al.; Identification of New Triarylethylene Oxyalkanioc Acid Analogues as Bone Selectivo Estrogen Mimics; Bioorganic & Medicinal Chemistry; 2001; 9; 1579-1587; Elsevier Science Ltd.
Gilbert, Jacques et al.; Inhibition of Prostaglandin synthetase by di- and triphenylethylene derivative: a structure-activity study; Journal of Medicinal Chemistry; 1983; 26(5); 693-9.
Jendralla, H. et al.; Synthesis and biological activity of new HMG-CoA reductase inhibitors, 3, Lactones of 6-phenoxy-3,5-dihydroxyhexanoic acids; Journal of Medicinal Chemistry; 1991; 34(10); 2962-83.
Lubczyk et al.; Investigations on Estrogen Receptor Binding. The Estrogenic, Antiestrogenic, and Cytotoxic Properties of C2-Alkyl-Substituted 1,1-Bis(4-hydroxyphenyl)-2-phenylthenes; Journal of Medicinal Chemistry; 2002; 45; 5358-5364.
Wallace et al.; A Selective Estrogen Receptor Modulator for the Treatment of Hot Flushes; Journal of Medicinal Chemistry; 2006; 49; 843-846; American Chemical Society.

*Primary Examiner*—Taofiq A Solola
(74) *Attorney, Agent, or Firm*—J. Scott Young

(57) ABSTRACT

The present invention relates to novel compounds with a variety of therapeutic uses, more particularly novel substituted cyclic alkylidene compounds that are particularly useful for selective estrogen receptor modulation.

15 Claims, No Drawings

CYCLOALKYLIDENE COMPOUNDS AS MODULATORS OF ESTROGEN RECEPTOR

CROSS-REFERENCE TO RELATED APPLICATIONS

This application is filed as a continuation application of U.S. Ser. No. 10/565,296 filed on Feb. 15, 2007 which was filed pursuant to 35 U.S.C. § 371 as a United States National Phase Application of International Application No. PCT/US2004/024308 filed Jul. 27, 2004, which claims priority from U.S. 60/490,588 filed Jul. 28, 2003.

FIELD OF THE INVENTION

The present invention relates to novel compounds with a variety of therapeutic uses, more particularly novel substituted cycloalkylidene compounds that are particularly useful for selective estrogen receptor modulation.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. The most widely accepted hypothesis of how estrogens exert their effects is by binding to an intracellular steroid hormone receptor. After the receptor and bound ligand are transferred to the nucleus of the cell, the complex binds to recognition sites in DNA, which allows for the modulation of certain genes. Additionally, it is now becoming apparent that estrogens may mediate their effects via membrane-initiated signaling cascade, though much of this work is still experimental. Kousteni et al., *Journal of Clinical Investigation*, (2003), 111, 1651-1664, herein incorporated by reference with regard to such teaching.

Certain substances have demonstrated the ability to exhibit their biological activity in a "tissue-selective" manner. In other words, tissue selectivity allows functionality as estrogen agonists in certain tissues, while acting as estrogen antagonists in other tissues. The term "selective estrogen receptor modulators" (SERMs) has been given to these molecules. Examples of SERMs include tamoxifen, raloxifene, lasofoxifene, clomiphene, and nafoxidine. The molecular basis for this tissue-selective activity is not completely understood. Without being limited to any particular theory, the ability of the ligand to place the estrogen receptor into different conformational states and allowing for differential capabilities in recruiting coactivator and corepressor proteins, as well as other important proteins involved in transcriptional regulation, is believed to play a role. See, McDonnell, D. P., *The Molecular Pharmacology of SERMs*, Trends Endocrinol. Metab. 1999, 301-311, herein incorporated by reference with regard to such description.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930, herein incorporated by reference with regard to such subtype. ERβ is expressed in humans. See, Mosselman et al., *ERβ: Identification and Characterization of a Novel Human Estrogen Receptor*, FEBR S Lett., 1996, pp. 49-53, herein incorporated by reference with regard to such expression. The discovery of this second subtype of estrogen receptor significantly increased the biological complexity of estrogen signaling and may be responsible for some of the tissue-selective actions of the currently available SERMs.

As noted above, estrogens have important effects in many non-reproductive tissues. Thus, estrogen modulation is believed useful in the treatment or prophylaxis of diseases and conditions associated with such tissues, including bone, liver, and the central nervous system. For example, osteoporosis is characterized by the net loss of bone mass per unit volume. Such bone loss results in a failure of the skeleton to provide adequate structural support for the body, thereby creating an increased risk of fracture. One of the most common types of osteoporosis is postmenopausal osteoporosis, which is associated with accelerated bone loss subsequent to cessation of menses and declining levels of endogenous estrogen in women. There is an inverse relationship between densitometric measures of bone mass and fracture risk, for peri- and postmenopausal women in the process of rapid bone loss due to declining levels of estrogen. See, Slemenda, et al., *Predictors of Bone Mass in Perimenopausal Women, A Prospective Study of Clinical Data Using Photon Abr sorptiometry*, Ann. Intern. Med., 1990, pp. 96-101 and Marshall, et al., *Meta-Analysis of How Well Measures of Bone Mineral Density Predict Occurrence of Osteoporotic Fractures, Br Med. J.*, 1996, pp. 1254-1259, each of which is herein incorporated by reference with regard to such relationship. Elderly women currently have a lifetime risk of fractures of about 75%. In addition there is an approximate 40% risk of hip fracture for Caucasian women over age 50 in the United States. The economic burden from osteoporotic fractures is considerable because of the necessity of hospitalization. In addition, although osteoporosis is generally not thought of as life-threatening, the mortality within 4 months of hip fracture is currently approximately 20 to 30%. Current therapies for postmenopausal osteoporosis include hormone replacement therapy or treatment with other antiresorptive agents such as bisphosphonates or calcitonin. Similarly, SERMS have been shown to be effective in the treatment of postmenopausal osteoporosis (see, Lindsay, R.: *Sex steroids in the pathogenesis and prevention of osteoporosis*. In: Osteoporosis 1988. Etiology, Diagnosis and Management. Riggs B L (ed)l, Raven Press, New York, USA (1988):333-358; Barzel US:*Estrogens in the prevention and treatment of postmenopausal osteoporosis*:a review. *Am J. Med* (1988) 85:847-850; and Ettinger, B., Black, D. M., et al., *Reduction of Vertebral Fracture Risk in Postmenopausal Women with Osteoporosis Treated with Raloxifene, JAMA,* 1999, 282, 637-645, each of which is incorporated by reference with regard to such teaching).

As another example, the effects of estrogens on breast tissue, particularly breast cancer, have been well documented. For example, a previously identified SERM, tamoxifen, decreases the risk of recurrent breast cancer, contralateral breast cancer, and mortality as well as increases the disease-free survival rate of patients with breast cancer at multiple stages of the disease. See, Cosman, F., Lindsay, R. *Selective Estrogen Receptor Modulators: Clinical Spectrum*, Endocrine Rev., 1999, pp. 418-434, herein incorporated by reference with regard to such teaching. The profile of tamoxifen, however, is not ideal due to potential interactive properties on reproductive tissues, such as uterine tissues. There is room for an improved therapy for the treatment of such cancers, namely a SERM with no agonist properties on any reproductive tissues.

Cardiovascular disease is the leading cause of death among postmenopausal women. Until recently, the preponderance of data suggested that estrogen replacement therapy in postmenopausal women reduced the risk of cardiovascular disease, although some studies reported no beneficial effect on overall mortality. See, Barrett-Connor, E. et al., *The Potential of SERMs for Reducing the Risk of Coronary Heart Disease*, Trends Endocrinol. Metab., 1999, pp. 320-325, herein incorporated by reference. The mechanism(s) by which estrogens were believed to exert their beneficial effects on the cardiovascular system are not entirely clear. Potentially estrogen's effects on serum cholesterol and lipoproteins, antioxidant properties, vascular smooth muscle proliferation, and inhibition of arterial cholesterol accumulation were believed to play a role. Id. See also, Cosman, F., Lindsay, R. *Selective Estrogen Receptor Modulators: Clinical Spectrum*, Endocrine Rev., 1999, pp. 418-434, herein incorporated by reference. In light of the recent reports of the HERS II and WHI studies, however, continuous combined Hormone Therapy, namely, CEE+MPA [Conjugated Equine Estrogen+Medroxy Progesterone Acetate], confers no cardiovascular benefit in menopausal women. See, Hulley S., Grady, D., Bush, T., et al., *Randomized trial of estrogen plus progestin for secondary prevention of coronary heart disease in postmenopausal women*. Heart and Estrogen/progestin Replacement Study (HERS) Research Group. *J. Am. Med. Assoc.* (1998) 280:605-613 and Wassertheil-Smoller S., Hendrix, S. L., Limacher, M., et al., for the WHI Investigators. *Effect of estrogen plus progestin on stroke in postmenopausal women: the Women's Health Initiative: a randomized trial.* JAMA (2003) 289, 2673-2684, each herein incorporated by reference with regard to such teaching). To what extent these findings may be extrapolated to SERMs is an issue that remains to be determined.

Other therapeutic alternatives include estrogen replacement therapy and/or hormone replacement therapy, which may be useful in the treatment of vasomotor symptoms, genitourinary atrophy, depression, and diabetes. Over 75% of women experience vasomotor symptoms during the climacteric years. Clinical signs, such as vasomotor symptoms and genitourinary atrophy, abate upon treatment with estrogen replacement therapy. Sagraves, R., *J. Clin. Pharmacol.* (1995), 35(9 *Suppl*):2S-10S, herein incorporated by reference with regard to such teaching. Preliminary data suggest that estradiol may alleviate depression during perimenopause and that the combination of estrogens and selective serotonin reuptake inhibitors may alleviate depression during the postmenopausal period. Soares, C. N., Poitras, J. R., and Prouty, J., *Drugs Aging*, (2003), 20(2), 85-100, herein incorporated by reference with regard to such teaching. Furthermore, hormone replacement therapy may improve glycemic control among women with diabetes. Palin, S. L. et al., *Diabetes Research and Clinical Practice*, (2001), 54, 67-77; Ferrara, A. et al., *Diabetes Care*, (2001), 24(7), 1144-1150, each incorporated herein by reference with regard to such teaching. There is a need, however, for improved therapies that present better side effect profiles.

The present inventors discovered a novel group of cycloalkylidene compounds, which bind to and modulate estrogen receptor alpha and estrogen receptor beta. As SERMS, these compounds are believed to be useful for the treatment and/or prophylaxis of menopausal or postmenopausal disorders, —vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

SUMMARY OF THE INVENTION

The present invention includes novel compounds. The present invention includes compounds of formula (I):

(I)

including salts, solvates, and pharmacologically functional derivatives thereof wherein $R^1$ is OH;

each of $R^2$ and $R^4$ independently are selected from OH, alkyl, or halogen;

each of p and q independently are selected from 0, 1, or 2;

$R^3$ is —$(Y)_z$—$R^8$;

z is 0 or 1;

Y is —C≡C— or —$CR^e$=$CR^f$—;

X is —$(CH_2)_n$— where n is 0, 1, 2, or 3, —$C(R^g)_2$—, —O—, or —S—;

each $R^5$ is H; or both $R^5$s together combine to form a bridging alkylene chain —$(CH_2)_m$—, where m is 2, 3, or 4, when each $R^6$ and each $R^7$ is H and X is —$(CH_2)_{m-2}$—;

each of $R^6$ and $R^7$ are selected from H or alkyl; or

X is —$(CH_2)_m$—, both $R^6$s are H, and both $R^7$s together combine to form a bridging alkylene chain —$(CH_2)_m$—, where each m is the same and is as defined; or X is —$(CH_2)_m$—, both $R^7$s are H, and both $R^6$s together combine to form a bridging alkylene chain —$(CH_2)_m$—, where each m is the same and is as defined;

when z is 0, then $R^8$ is alkyl, halogen, alkoxy, aryl, heteroaryl, heterocyclyl, cyano, —$O(R^h)_t$CN, —$CO_2H$, —$(R^h)_t$$CO_2H$, —$O(R^h)_t$$CO_2H$, —$(R^h)_t$OH, —$O(R^h)_t$OH, —$O(R^h)_t$$O(R^h)_t$OH, —$CONR^aR^b$, —$SO_2R^d$, —$NR^aSO_2R^d$, —$COR^c$, or —$NR^aCOR^c$;

when z is 1, then $R^8$ is —$CO_2H$, —$(R^h)_t$$CO_2H$, —$(R^h)_t$OH, —$CONR^aR^b$, or —$PO_3HR^a$; or when z is 1, and Y is —C≡C—, then $R^8$ may also be H;

t is 1 to 8;

$R^a$ is H, alkyl, cycloalkyl, aryl, heteroaryl, or heterocyclyl;

$R^b$ is H, alkyl, cycloalkyl, aryl, heteroaryl, or heterocyclyl;

$R^c$ is alkyl, cycloalkyl, aryl, heteroaryl, or heterocyclyl;

$R^d$ is alkyl, cycloalkyl, aryl, heteroaryl, or heterocyclyl; or $R^a$ and $R^b$, $R^a$ and $R^c$, or $R^a$ and $R^d$ may combine with the atoms to which they are bound to form a heteroaryl or heterocyclyl ring; and $R^e$ and $R^f$ each are independently selected from H, alkyl, halogen, and haloalkyl;

$R^g$ is alkyl;

each $R^h$ independently is —$CR^jR^k$—, where each of $R^j$ and $R^k$ independently are selected from H and alkyl;

wherein each occurrence of alkyl, cycloalkyl, aryl, heteroaryl, and heterocyclyl may be optionally substituted.

Preferably The compound of claim 1 wherein alkyl is $C_{1-8}$alkyl, alkoxy is $C_{1-8}$alkoxy, alkenyl is $C_{2-8}$alkenyl, and alkynyl is $C_{2-8}$alkynyl.

In one embodiment, $R^1$ is substituted para on the depicted ring.

In one embodiment, p and q each are 0.

In one embodiment, z is 1, Y is —$CR^e$=$CR^f$—, and $R^8$ is —$CO_2H$. Preferably $R^e$ and $R^f$ are H or $C_{1-8}$alkyl.

In one embodiment, z is 1, Y is —$CR^e$=$CR^f$—, and $R^8$ is —$C(O)NR^aR^b$. Preferably $R^a$ and $R^b$ each are H.

In one embodiment, z is 1, Y is —C≡C—, and $R^8$ is —$CO_2H$, —$(R^h)_tCO_2H$, or —$(CH_2)_tOH$.

In one embodiment each of $R^6$ and $R^7$ are H or $C_{1-8}$alkyl.

In one embodiment, X is —$(CH_2)_n$—. Preferably n is 1. Preferably $R^6$ and $R^7$ are alkyl. In another embodiment preferably n is 2 or 3 and preferably $R^6$ and $R^7$ are hydrogen.

In one embodiment X is —O—. Preferably $R^6$ and $R^7$ are alkyl.

In one embodiment, z is 0 and $R^8$ is —$CO_2H$, —$NR^aSO_2R^d$, aryl, or heteroaryl. In one embodiment $R^8$ is aryl. Preferably aryl is phenyl, optionally substituted with one or more of cyano, halogen, heterocyclyl, —$CO_2H$, —$(R^h)_t$OH, —$SO_2R^d$, —$C(O)NR^aR^b$, —$NR^aCOR^c$, —$NR^aSO_2R^d$, and —CH=CH—$CO_2H$. Preferably $R^a$ is H, $R^b$ is H, $R^c$ is alkyl, and $R^d$ is alkyl. In another embodiment $R^8$ is —$CO_2H$. In another embodiment $R^8$ is —$NR^aSO_2R^d$, $R^a$ is H, and $R^d$ is alkyl or aryl. In another embodiment $R^8$ is isooxazolyl, oxazolyl, pyrimidyl, pyridyl, or furyl. In one embodiment $R^8$ is —$CONR^aR^b$, and $R^a$ and $R^b$ combine to form a 5 or 6 membered heterocyclyl ring optionally substituted with —$CO_2H$.

Particularly preferred compounds of the present invention include:

(2E)-3-{4-[Cyclopentylidene(4-hydroxyphenyl)methyl]phenyl}-2-propenoic acid;
(2E)-3-{4-[Cyclohexylidene(4-hydroxyphenyl)methyl]phenyl}-2-propenoic acid;
(2E)-3-{4-[Cycloheptylidene(4-hydroxyphenyl)methyl]phenyl}-2-propenoic acid;
(2E)-3-{4-[Cyclohexylidene(4-hydroxyphenyl)methyl]phenyl}-2-propenamide;
(2E)-3-{4-[Cycloheptylidene(4-hydroxyphenyl)methyl]phenyl}-2-propenamide;
(2E)-3-{4-[(4-Hydroxyphenyl)(3,3,5,5-tetramethylcyclohexylidene)methyl]phenyl}-2-propenoic acid;
(2E)-3-{4-[(4-Hydroxyphenyl)(3,3,5,5-tetramethylcyclohexylidene)methyl]phenyl}-2-propenamide;
4-[[4-(1H-Pyrrol-2-yl)phenyl](3,3,5,5-tetramethylcyclohexylidene)methyl]phenol;
(2E)-3-{4-[(4,4-Dimethylcyclohexylidene)(4-hydroxyphenyl)methyl]phenyl}-2-propenoic acid;
4-[(4-Hydroxyphenyl)(3,3,5,5-tetramethylcyclohexylidene)methyl]benzoic acid;
(2E)-3-{4-[Cyclohexylidene(4-hydroxy-2-methylphenyl)methyl]phenyl}-2-propenoic acid;
(2E)-3-{4-[cyclohexylidene(4-hydroxy-3-methylphenyl)methyl]phenyl}-2-propenoic acid;
(2E)-3-{-4-[(4-Hydroxyphenyl)(tetrahydro-4H-thiopyran-4-ylidene)methyl]phenyl}-2-propenoic acid;
1-((2E)-3-{4-[Cycloheptylidene(4-hydroxyphenyl)methyl]phenyl}-2-propenoyl)-3-piperidinecarboxylic acid;
1-((2E)-3-{4-[Cycloheptylidene(4-hydroxyphenyl)methyl]phenyl}-2-propenoyl)-4-piperidinecarboxylic acid;
1-((2E)-3-{4-[Cycloheptylidene(4-hydroxyphenyl)methyl]phenyl}-2-propenoyl)proline;
(2E)-3-{4-[bicyclo[3.3.1]non-9-ylidene(4-hydroxyphenyl)methyl]phenyl}-2-propenoic acid;
(2E)-3-{4-[(4-hydroxyphenyl)(tetrahydro-4H-pyran-4-ylidene)methyl]phenyl}prop-2-enoic acid;
(2E)-3-{4-[Cyclooctylidene(4-hydroxyphenyl)methyl]phenyl}prop-2-enoic acid;
(2E)-3-{4-[(4-Hydroxyphenyl)(2,2,6,6-tetramethyltetrahydro-4H-pyran-4-ylidene)methyl]phenyl}prop-2-enoic acid;
N-{4-[(4-hydroxyphenyl)(3,3,5,5-tetramethylcyclohexylidene)methyl]phenyl}acetamide;
(2E)-3-{4-[(4-hydroxyphenyl)(tetrahydro-4H-pyran-4-ylidene)methyl]phenyl}-2-methylprop-2-enoic acid;
4-[[4-({2-[(2-Hydroxyethyl)oxy]ethyl}oxy)phenyl](3,3,5,5-tetramethylcyclohexylidene)methyl]phenol;
Ethyl hydrogen (E)-2-{4-[cycloheptylidene(4-hydroxyphenyl)methyl]phenyl}ethenylphosphonate;
(2E)-3-{4-[Cyclohexylidene(4-hydroxyphenyl)methyl]-2-methylphenyl}-2-propenoic acid;
(2E)-3-{3-Chloro-4-[cyclohexylidene(4-hydroxyphenyl)methyl]phenyl}-2-propenoic acid;
(2E)-3-{4-[Cyclohexylidene(4-hydroxyphenyl)methyl]-3-fluorophenyl}-2-propenoic acid;
(2E)-3-{4-[Cyclohexylidene(3-fluoro-4-hydroxyphenyl)methyl]phenyl}-2-propenoic acid;
(2E)-3-{4-[Cyclohexylidene(4-hydroxyphenyl)methyl]-2-fluorophenyl}-2-propenoic acid;
4-[[4-(Methylsulfonyl)phenyl](3,3,5,5 tetramethylcyclohexylidene)methyl]phenol;
4-[(4-hydroxyphenyl)(3,3,5,5-tetramethylcyclohexylidene)methyl]benzamide;
4-[{4-[(2-Hydroxyethyl)oxy]phenyl}(3,3,5,5-tetramethylcyclohexylidene)methyl]phenol;
4'-[(4-Hydroxyphenyl)(3,3,5,5-tetramethylcyclohexylidene)methyl]-3-biphenylcarboxylic acid;
4'-[(4-Hydroxyphenyl)(3,3,5,5-tetramethylcyclohexylidene)methyl]-4-biphenylcarboxylic acid;
(2E)-3-{4-[(3-Chloro-4-hydroxyphenyl)(cyclohexylidene)methyl]phenyl}-2-propenoic acid;
(2E)-3-{4-[Cyclohexylidene(2-fluoro-4-hydroxyphenyl)methyl]phenyl}-2-propenoic acid;
(2E)-3-{4-[Cyclohexylidene(4-hydroxy-2,3-dimethylphenyl)methyl]phenyl}-2-propenoic acid;
(2E)-3-{4-[Cyclohexylidene(2,3-difluoro-4-hydroxyphenyl)methyl]phenyl}-2-propenoic acid;
(2E)-3-{4-[(3-Chloro-4-hydroxyphenyl)(cycloheptylidene)methyl]phenyl}-2-propenoic acid;
(2E)-3-{4-[(3-Chloro-4-hydroxyphenyl)(3,3,5,5-tetramethylcyclohexylidene)methyl]phenyl}-2-propenoic acid;
(2E)-3-{4-[(3-Chloro-4-hydroxyphenyl)(2,2,6,6-tetramethyltetrahydro-4H-pyran-4-ylidene)methyl]phenyl}-2-propenoic acid;
(2E)-3-{4-[(3-fluoro-4-hydroxyphenyl)(cycloheptylidene)methyl]phenyl}-2-propenoic acid;
(2E)-3-{4-[(3-fluoro-4-hydroxyphenyl)(2,2,6,6-tetramethyltetrahydro-4H-pyran-4-ylidene)methyl]phenyl}-2-propenoic acid;
(2E)-3-{4-[(3-fluoro-4-hydroxyphenyl)(3,3,5,5-tetramethylcyclohexylidene)methyl]phenyl}-2-propenoic acid;
4-[[4-(3-hydroxy-1-propyn-1-yl)phenyl](3,3,5,5-tetramethylcyclohexylidene)methyl]phenol;
4-[(4-Ethynylphenyl)(3,3,5,5-tetramethylcyclohexylidene)methyl]phenol;
3-{4-[(4-Hydroxyphenyl)(3,3,5,5-tetramethylcyclohexylidene)methyl]phenyl}-2-propynoic acid;
{4-[(4-Hydroxyphenyl)(3,3,5,5-tetramethylcyclohexylidene)methyl]phenyl}acetic acid;
4-[Cycloheptylidene(4-hydroxyphenyl)methyl]benzoic acid;

4-[Cyclohexylidene(4-hydroxyphenyl)methyl]benzoic acid;
4-[Cyclooctylidene(4-hydroxyphenyl)methyl]benzoic acid;
4-[[4-(1,3-Oxazol-2-yl)phenyl](3,3,5,5-tetramethylcyclohexylidene)methyl]phenol;
4'-[(4-Hydroxyphenyl)(3,3,5,5-tetramethylcyclohexylidene)methyl]-3-biphenylcarboxamide;
4-[[4-(5-Pyrimidinyl)phenyl](3,3,5,5-tetramethylcyclohexylidene)methyl]phenol;
4-[[4'-(Methylsulfonyl)-4-biphenylyl](3,3,5,5-tetramethylcyclohexylidene)methyl]phenol;
(2E)-3-{4'-[(4-Hydroxyphenyl)(3,3,5,5-tetramethylcyclohexylidene)methyl]-3-biphenylyl}-2-propenoic acid;
4-[[4-(3-Pyridinyl)phenyl](3,3,5,5-tetramethylcyclohexylidene)methyl]phenol trifluoroacetate;
3-{4-[(4-Hydroxyphenyl)(3,3,5,5-tetramethylcyclohexylidene)methyl]phenyl}propanoic acid;
4-[(4,4-Dimethyl-cyclohexylidene)-(4-hydroxy-phenyl)-methyl]-benzoic acid;
4-[Cycloheptylidene-(3-fluoro-4-hydroxy-phenyl)-methyl]-benzoic acid;
3-{4-[Cycloheptylidene-(4-hydroxy-phenyl)-methyl]-3-fluoro-phenyl}-acrylic acid;
N-{4-[(4-Hydroxy-phenyl)-(3,3,5,5-tetramethyl-cyclohexylidene)-methyl]-phenyl}-methanesulfonamide;
N-{4-[(4-Hydroxy-phenyl)-(3,3,5,5-tetramethyl-cyclohexylidene)-methyl]-phenyl}-benzenesulfonamide;
(2E)-3-{4-[Cycloheptylidene(4-hydroxyphenyl)methyl]-2-fluorophenyl}-2-propenoic acid;
({4-[Cycloheptylidene(4-hydroxyphenyl)methyl]phenyl}oxy)acetic acid;
(2E)-3-{4-[cycloheptylidene(3-hydroxyphenyl)methyl]phenyl}-2-propenoic acid;
(2E)-3-{4-[Cycloheptylidene (3-hydroxyphenyl)methyl]-2-fluorophenyl}-2-propenoic acid;
4-{cycloheptylidene[4-(3-furanyl)phenyl]methyl}phenol;
4-{Cycloheptylidene[4-(2-furanyl)phenyl]methyl}phenol;
4-{cyclooctylidene[4-(2-furanyl)phenyl]methyl}phenol;
4-{Cyclooctylidene[4-(3-furanyl)phenyl]methyl}phenol;
4-{cyclooctylidene[4-(3,5-dimethyl-4-isoxazolyl)phenyl]methyl}phenol;
4-{cycloheptylidene[4-(3,5-dimethyl-4-isoxazolyl)phenyl]methyl}phenol;
4-[cycloheptylidene(4-hydroxyphenyl)methyl]benzonitrile;
4-[(4-Hydroxyphenyl)(3,3,5,5-tetramethylcyclohexylidene)methyl]benzonitrile;
(2E)-3-{4-[(4-Hydroxyphenyl)(2,2,6,6-tetramethyltetrahydro-4H-pyran-4-ylidene)methyl]phenyl}-2-methyl-2-propenoic acid;
(2E)-3-{4-[cyclooctylidene(4-hydroxyphenyl)methyl]phenyl}-2-methyl-2-propenoic acid;
({4-[Cycloheptylidene(4-hydroxyphenyl)methyl]phenyl}oxy)acetonitrile;
4-({4-[cycloheptylidene(4-hydroxyphenyl)methyl]phenyl}oxy)butanoic acid;
({4-[(4-Hydroxyphenyl)(3,3,5,5-tetramethylcyclohexylidene)methyl]phenyl}oxy)acetic acid;
4-({4-[(4-hydroxyphenyl)(3,3,5,5-tetramethylcyclohexylidene)methyl]phenyl}oxy)butanoic acid;
4-(Cycloheptylidene{4-[(2-hydroxyethyl)oxy]phenyl}methyl)phenol;
2-({4-[Cycloheptylidene(4-hydroxyphenyl)methyl]phenyl}oxy)-2-methylpropanoic acid;
2-({4-[(4-Hydroxyphenyl)(3,3,5,5-tetramethylcyclohexylidene)methyl phenyl}oxy)-2-methylpropanoic acid;
({4-[(4-Hydroxyphenyl)(3,3,5,5-tetramethylcyclohexylidene)methyl]phenyl}oxy)acetonitrile;
4-(Cycloheptylidene{4-[(2-hydroxy-1,1-dimethylethyl)oxy]phenyl}methyl)phenol;
4-[(4-Fluorophenyl)(3,3,5,5-tetramethylcyclohexylidene)methyl]phenol;
({4-[(4-fluorophenyl)(3,3,5,5-tetramethylcyclohexylidene)methyl]phenyl}oxy)acetic acid;
4-({4-[(4-Fluorophenyl)(3,3,5,5-tetramethylcyclohexylidene)methyl]phenyl}oxy)butanoic acid;
({4-[(4-Fluorophenyl)(3,3,5,5-tetramethylcyclohexylidene)methyl]phenyl}oxy)acetonitrile;
4-[[4-(3-Hydroxypropyl)phenyl](3,3,5,5-tetramethylcyclohexylidene)methyl]phenol;
N-{4'-[(4-Hydroxy-phenyl)-(3,3,5,5-tetramethyl-cyclohexylidene)-methyl]-biphenyl-4-yl}-acetamide;
N-{4'-[(4-Hydroxy-phenyl)-(3,3,5,5-tetramethyl-cyclohexylidene)-methyl]-biphenyl-4-yl}-methanesulfonamide;
4-[[4-(3-furanyl)phenyl](3,3,5,5-tetramethylcyclohexylidene)methyl]phenol;
4-[[4-(3,5-dimethyl-4-isoxazolyl)phenyl](3,3,5,5-tetramethylcyclohexylidene)methyl]phenol;
4-[[4'-(4-morpholinyl)-4-biphenylyl](3,3,5,5-tetramethylcyclohexylidene)methyl]phenol;
3-fluoro-4'-[(4-hydroxyphenyl)(3,3,5,5-tetramethylcyclohexylidene)methyl]-4-biphenylcarbonitrile;
4'-[(4-hydroxyphenyl)(3,3,5,5-tetramethylcyclohexylidene)methyl]-4-biphenyl carbonitrile;
4'-[cyclooctylidene(4-hydroxyphenyl)methyl]-4-biphenylcarbonitrile;
4-{Cycloheptylidene[4-(5-hydroxy-1-pentyn-1-yl)phenyl]methyl}phenol;
4-[[4-(3-hydroxy-3-methyl-1-butyn-1-yl)phenyl](3,3,5,5-tetramethyl cyclohexylidene)methyl]phenol;
4-[[4-(4-hydroxy-1-butyn-1-yl)phenyl](3,3,5,5-tetramethylcyclohexylidene)methyl]phenol;
5-{4-[(4-Hydroxyphenyl)(3,3,5,5-tetramethylcyclohexylidene)methyl]phenyl}-4-pentynoic acid;
1-{4-[(4-Hydroxyphenyl)(3,3,5,5-tetramethylcyclohexylidene)methyl]phenyl}ethanone;
4-[[4'-(Hydroxymethyl)-4-biphenylyl](3,3,5,5-tetramethylcyclohexylidene)methyl]phenol;
4-[[3'-(Hydroxymethyl)-4-biphenylyl](3,3,5,5-tetramethylcyclohexylidene)methyl]phenol;
4'-[(4-Hydroxyphenyl)(3,3,5,5-tetramethylcyclohexylidene)methyl]-2-biphenylcarboxylic acid; and
4-[[2'-(Hydroxymethyl)-4-biphenylyl](3,3,5,5-tetramethylcyclohexylidene)methyl]phenol;

including salts, solvates, and pharmacologically functional derivatives thereof.

The present invention includes:

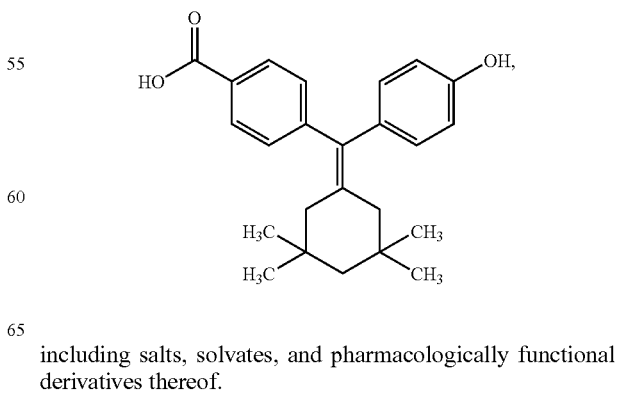

including salts, solvates, and pharmacologically functional derivatives thereof.

Another aspect of the present invention includes compounds substantially as hereinbefore defined with reference to any one of the Examples.

Another aspect of the present invention includes pharmaceutical compositions comprising the compounds and a pharmaceutically acceptable carrier.

Another aspect of the present invention includes the compounds for use as an active therapeutic substance.

Another aspect of the present invention includes the compounds for use in the treatment or prophylaxis of conditions or disorders affected by selective estrogen receptor modulation. Preferably the treatment or prophylaxis relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. More preferably the treatment or prophylaxis relates to menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

Another aspect of the present invention includes the use of the compounds in the manufacture of a medicament for use in the treatment or prophylaxis of conditions or disorders associated with selective estrogen receptor modulation. Preferably the medicament is for use in the treatment or prophylaxis of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. More preferably the condition or disorder is menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

Another aspect of the present invention includes a method for the treatment or prophylaxis of conditions or disorders associated with selective estrogen receptor modulation comprising the administration of the compounds. Preferably the treatment or prophylaxis relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. More preferably the condition or disorder is menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

DETAILED DESCRIPTION OF THE PREFERRED EMBODIMENT

The present invention is described in terms known and appreciated by those skilled in the art. For ease of reference certain terms hereafter are defined. The fact that certain terms are defined, however, should not be considered as indicative that any term that is undefined is indefinite. Rather, all terms used herein are believed to describe the invention in terms such that one of ordinary skill can appreciate the scope of the present invention.

As used herein the term "alkyl" refers to a straight or branched chain hydrocarbon, preferably having from one to twelve carbon atoms. Examples of "alkyl" as used herein include, but are not limited to, methyl, ethyl, propyl, isopropyl, isobutyl, n-butyl, tert-butyl, isopentyl, n-pentyl, and the like.

As used herein, the term "alkylene" refers to a straight or branched chain divalent hydrocarbon radical, preferably having from one to ten carbon atoms. Examples of "alkylene" as used herein include, but are not limited to, methylene, ethylene, n-propylene, n-butylene, and the like.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups and the like.

As used herein the term "alkoxy" refers to the group —OR, where R is alkyl as defined above.

As used herein the term "acyl" refers to the group —C(O)R, where R is alkyl, aryl, heteroaryl, or heterocyclyl, as each is defined herein.

As used herein the term "hydroxy" refers to the group —OH.

As used herein the term "carboxy" refers to the group —C(O)OH.

As used herein the term "nitro" refers to the group —$NO_2$.

As used herein the term "amino" refers to the group —$NH_2$, or when referred to as substituted amino defines such groups substituted with alkyl.

As used herein, the term "cycloalkyl" refers to a non-aromatic cyclic hydrocarbon ring, preferably having from three to ten carbon atoms. Exemplary "cycloalkyl" groups include, but are not limited to, cyclopropyl, cyclobutyl, cyclopentyl, cyclohexyl, and cycloheptyl.

As used herein, the term "aryl" refers to a benzene ring or to a benzene ring system fused to one or more additional benzene rings to form, for example, anthracene, phenanthrene, or naphthalene ring systems. Examples of "aryl" groups include, but are not limited to, phenyl, 2-naphthyl, 1-naphthyl, biphenyl, and the like.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen atoms, where N-oxides, sulfur oxides, and dioxides are permissible heteroatom substitutions. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and the like.

As used herein, the term "heterocycle" or "heterocyclyl" refers to a mono- or poly-cyclic ring system containing optionally one or more degrees of unsaturation and also containing one or more heteroatoms. Preferred heteroatoms include N, O, and/or S, including N-oxides, sulfur oxides, and dioxides. Preferably the ring is three to ten-membered and is either saturated or has one or more degrees of unsaturation. Such rings may be optionally fused to one or more of another "heterocyclic" ring(s), heteroaryl ring(s), aryl ring(s), or cycloalkyl ring(s). Examples of "heterocyclic" groups include, but are not limited to, tetrahydrofuran, pyran, 1,4- dioxane, 1,3-dioxane, piperidine, pyrrolidine, morpholine, tetrahydrothiopyran, and tetrahydrothiophene.

As used herein throughout the present specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims.

Exemplary optional substituent groups include acyl; alkyl; alkenyl; alkynyl; alkylsulfonyl; alkoxy; cyano; halogen; haloalkyl; hydroxy; nitro; cycloalkyl, which may be further substituted with acyl, alkoxy, alkyl, alkenyl, alkynyl, alkylsulfonyl, cyano, halogen, haloalkyl, hydroxy, or nitro; heterocyclyl, which may be further substituted with acyl, alkoxy, alkyl, alkenyl, alkynyl, alkylsulfonyl, cyano, halogen, haloalkyl, hydroxy, or nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; —$CO_2H$; —$(R^h)_xOH$; —$CONR^aR^b$; —$NR^aSO_2R^d$; —$NR^aCOR^c$; —$SO_2NR^aR^b$; —$SO_2NR^aCOR^c$; and —$CONR^aSO_2R^d$, where each of $R^a$, $R^b$, $R^c$, and $R^d$ independently are as herein defined.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5th Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition. Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. For example, an effective amount of a compound of formula (I) for the treatment of humans suffering from osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein that are mediated by estrogen.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders, such as carboxymethylcellulose, aliginates, gelatins, or polyvinyl pyrrolidone, solution retardants, such as paraffin, resorption accelerators such as a quaternary salt and/or abr sorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone (PVP), pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring agents.

The compounds of the present invention and their salts, solvates, and physiologically functional derivatives thereof, may be employed alone or in combination with other therapeutic agents for the treatment of the conditions herein described. For example, in osteoporosis therapy, combination with other osteoporosis therapeutic agents is envisaged. Osteoporosis combination therapies according to the present invention thus comprise the administration of at least one compound of formula (I) or a salt, solvate, or physiologically functional derivative thereof, and the use of at least one other osteoporosis treatment method. Preferably, combination therapies according to the present invention comprise the administration of at least one compound of formula (I) or a salt, solvate, or physiologically functional derivative thereof, and at least one other osteoporosis treatment agent, for example, a bone building agent. The compound(s) of formula (I) and the other pharmaceutically active agent(s) may be administered together or separately and, when administered separately, administration may occur simultaneously or sequentially in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other osteoporosis treatment agents may be in combination by administration concomitantly in: (1) a unitary pharmaceutical composition including each compound; or (2) separate pharmaceutical compositions each including one of the compounds. Alternatively, the combination may be administered separately in a sequential manner wherein one treatment agent is administered first and the other(s) subsequently or vice versa. Such sequential administration may be close in time or remote in time.

The compounds of the present invention and their salts, solvates, and physiologically functional derivatives thereof, may be employed alone or in combination with other therapeutic agents for the treatment of the conditions herein described. For example, regarding the use of the compounds of the present invention in the prevention of reduced bone mass, density, or growth, combination may be had with other anabolic or osteoporosis therapeutic agents. As one example, osteoporosis combination therapies according to the present invention would thus comprise the administration of at least one compound of the present invention or a salt, solvate, or physiologically functional derivative thereof, and the use of at least one other osteoporosis therapy. As a further example, combination therapies according to the present invention include the administration of at least one compound of the present invention or a salt, solvate, or physiologically functional derivative thereof, and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) and the agent(s) and the relative timings of administration will be selected in order to achieve the desired combined therapeutic effect. The administration in combination of a compound of the present invention including salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

As noted, one potential additional osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-ardenergic agonists, serotonin 5-$HT_D$ agonists, selective serotonin reuptake inhibitors, agents that inhibit somatostatin or its release, 5-α-reductase inhibitors, aromatase inhibitors, GnRH inhibitors, parathyroid hormone, bisphosphonates, estrogen, testosterone, SERMs, progesterone receptor agonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis, bone demineralization and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, reperfusion damage of ischemic myocardium, In particular, the compounds of the present invention are believed useful, either alone or in combination with other agents, in the treatment of menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

Experimental Section

Abbreviations:

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
Hz (Hertz); MHz (megahertz);
mol (moles); mmol (millimoles);
RT (room temperature); h (hours);
d (days); EI (electron impact);
min (minutes); TLC (thin layer chromatography);
mp (melting point); RP (reverse phase);
$T_r$ (retention time); TFA (trifluoroacetic acid);
TEA (triethylamine); THF (tetrahydrofuran);
TFAA (trifluoroacetic anhydride); $CD_3OD$ (deuterated methanol);
$CDCl_3$ (deuterated chloroform); DMSO (dimethylsulfoxide);
$SiO_2$ (silica); atm (atmosphere);
EtOAc (EtOAc); $CHCl_3$ (chloroform);
HCl (hydrochloric acid); Ac (acetyl);
DMF (N,N-dimethylformamide); Me (methyl);
$Cs_2CO_3$ (cesium carbonate); EtOH (ethanol);
Et (ethyl); tBu (tert-butyl);
MeOH (methanol); $CH_2Cl_2$ (dichloromethane);
$MgSO_4$ (magnesium sulfate); $CH_3CN$ (acetonitrile);
$K_2CO_3$ (potassium carbonate); $TiCl_4$ (titanium tetrachloride);
EtOAc (EtOAc); $CO_2$ (carbon dioxide);
$Pd(OAc)_2$ (palladium acetate); $Et_2O$ (diethyl ether);
$P(o-tolyl)_3$ (tri-o-tolylphosphine); $Na_2SO_4$ (sodium sulfate);
NaH (sodium hydride); DME (1,2-dimethoxyethane);
NaI (sodium iodide); NaOH (sodium hydroxide);
$NH_4Cl$ (ammonium chloride); $NaHCO_3$ (sodium bicarbonate);
$AlCl_3$ (aluminum chloride); $(C_2H_5O)_2P(O)H$ (diethyl phosphite);
$NaN_3$ (sodium azide); $CBr_4$ (carbon tetrabromide);
PPh (triphenylphosphine); CuI (copper (I) iodide);
$Pd(Ph_3P)_4$ (tetrakis(triphenylphosphine)palladium (0));
$(iPrO)_3B$ (triisopropyl borate); nBuLi (butyllithium);
$Na_2CO_3$ (sodium carbonate); DMAP (4-(dimethylamino)pyridine);
eq (equivalents);

-continued

HRMS (high resolution mass spectrometry);
LCMS (liquid chromatography mass spectrometry);
LRMS (low resolution mass spectrometry);
APCI (Atmospheric Pressure Chemical Ionization);
LiHMDS (lithium bis(trimethylsilyl)amide);
$Pd(Ph_3P)_2Cl_2$ (dichlorobis(triphenylphosphine)palladium(II));
EDC (N-(3-dimethylaminopropyl)-N'-ethyl-carbodimide;
dpppe (1,5-bis(diphenylphosphanyl)pentane;
DMAc (N,N-dimethylacetamide);
HPLC (high performance liquid chromatography);
tmeda (N,N,N',N',-tetramethylethylenediamine);
$Pd_2(dba)_3$ (dipalladiumtris(dibenzylidene acetone)).

Unless otherwise noted, reagents and solvents were obtained from commercial suppliers and were used without further purification. Unless otherwise indicated, all reactions were conducted at room temperature and all temperatures are expressed in ° C. (degrees Centigrade).

Thin-layer chromatography (TLC) was performed on silica gel 60 $F_{254}$ precoated plates. Detection was effected by exposure to UV light (254 nm). Flash and flush column chromatography was performed using Silica Gel 60. Reverse phase preparative and analytical HPLC were performed using C18 columns and acetonitrile:water gradients with 0.05% TFA as a modifier.

Compound purity and characterization were determined by $^1$H-NMR, liquid chromatography-mass spectrometry (LCMS), high resolution mass spectrometry (HRMS), combustion (elemental) analysis, HPLC, and melting point. Compounds of general formula I were typically found to have purities of >90%.

$^1$H NMR spectra were recorded on Varian INOVA-300 and Varian INOVA-400 instruments. Chemical shifts are expressed in parts per million (ppm, δ units). Coupling constants are in units of hertz (Hz). Splitting patterns describe apparent multiplicities and are designated as s (singlet), d (doublet), dd (doublet of doublet), t (triplet), q (quartet), m (multiplet), or br (broad).

Low resolution mass spectra were obtained on Micromass ZQ, Micromass ZMD, Micromass QuattroMicro, and Micromass GCT instruments from Micromass Ltd., Altricham, UK, using either Atmospheric Pressure Chemical Ionization (APCI) or ESI Ionization (ESI).

High resolution mass spectral data (HRMS) were recorded with Micromass LCT and Micromass GCT instruments.

Combustion analyses were performed by Atlantic Microlab, Inc. (Norcross, Ga.).

Melting points were recorded in open capillary tubes and are uncorrected.

The bolded numerals reference the compounds as depicted in the following schemes. For the following schemes, depending on subsequent chemistry and functional group compatibility, the phenol groups of specific intermediates may need to be protected using synthetic methods appreciated by those skilled in the art.

Scheme 1

General Route to Substituted Cycloalkylidene Diphenylethylenes

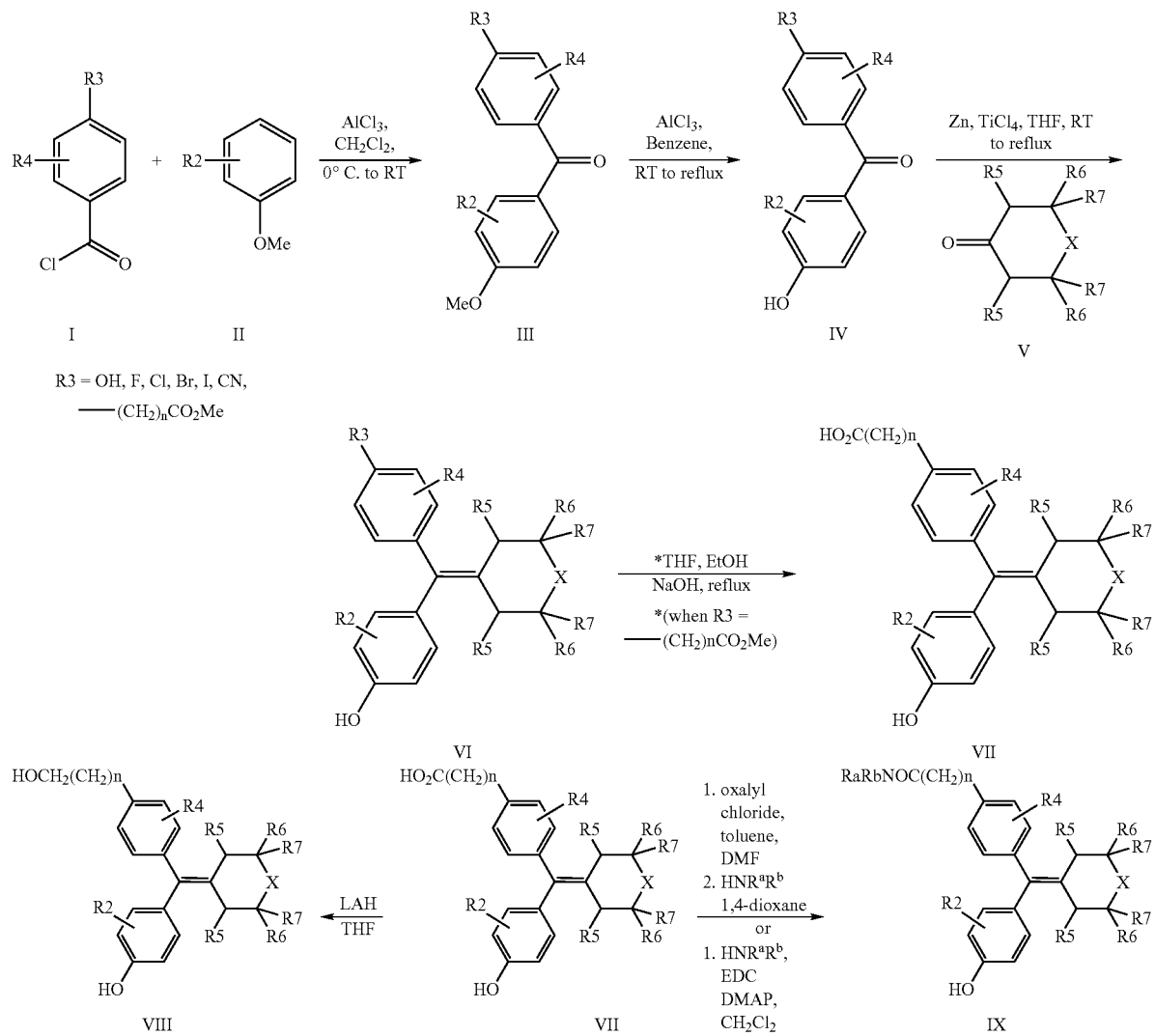

R3 = OH, F, Cl, Br, I, CN,
—(CH$_2$)$_n$CO$_2$Me

The substituted symmetric alkylidene compound VI can be prepared in three steps as described in Scheme 1. Friedel-Crafts acylation between acid chloride I and anisole II provides benzophenone III. For Friedel-Crafts reaction conditions, see *Friedel-Crafts and Related Reactions*, G. A. Olah, ed., Vol 3, Pt 1, pp 1-382, J. Wiley and Sons, New York (1964); G. A. Olah, *Friedel-Crafts Chemistry*, Wiley Interscience, New York, (1973); and Larock, R. C., *Comprehensive Organic Transformations*, VCH Publishers, New York, 1989, each herein incorporated by reference with regard to such teaching. Deprotection of III with aluminum chloride in refluxing benzene gives benzophenone (IV). McMurry coupling between benzophenone IV and ketone V provides the cycloalkylidene diphenylethylene VI. For McMurry reaction conditions, see Mukaiyama et al., *Chem. Lett.* (1973), 1041; Lenoir, *Synthesis*, (1977), 553; Lenoir and Burghard, *J. Chem. Res.* (S) (1980), 396; McMurry, *Chem. Rev.* (1989), 89, 1513-1524; McMurry, *Acc. Chem. Res.* (1983) 16, 405-511; and S. Gauthier et al., *J. Org. Chem.*, (1996), 61, 3890-3893, each herein incorporated by reference with regard to such teaching. Ketone V is either commercially available or may be prepared by synthetic methods appreciated by those skilled in the art.

Further elaboration of the R3 substituent of VI can be carried out. For example, when R3 is an ester, saponification will yield the carboxylic acid VII and treatment with a reducing agent such as LAH yields the corresponding alcohol VIII. Acid VII can also be converted to a carboxamide IX. Treatment of acid (VII) with an amine in the presence of a coupling agent such as EDC and DMAP in dichloromethane provides amide IX. Alternatively, acid VII can be converted to the acid chloride using oxalyl chloride and DMF in toluene followed by treatment of the crude acid chloride with an amine to give amide IX. For conversion of carboxylic acids to amides, see Larock, R. C., Comprehensive Organic Transformations, VCH Publishers, New York, 1989.

Similarly, preparation of analogues of compounds VI-IX from a benzophenone related to compound III in which the methoxy group is meta to the carbonyl group can be accomplished using identical procedures (See Example 68).

Scheme 2

General Route to Cycloalkylidene Diphenylethylene Acrylic Acids and Acrylamides

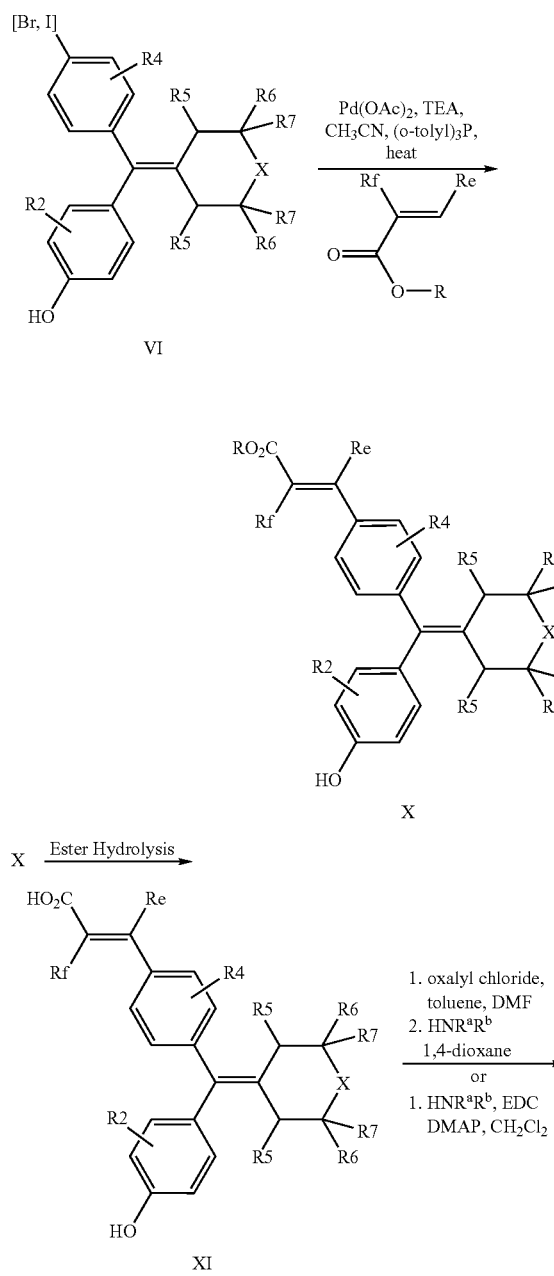

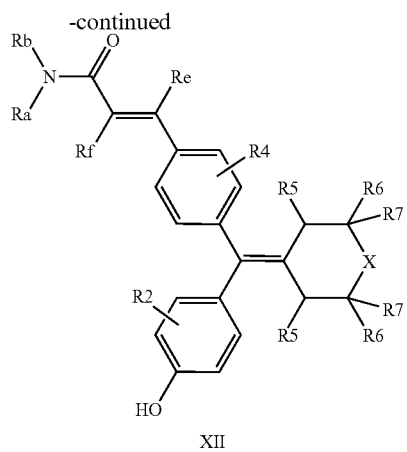

Acrylic acid XI can be prepared in two steps from compound VI as illustrated in Scheme 2. Heck coupling of VI with an acrylate ester (wherein R is a suitable alkyl group (e.g. methyl, ethyl, tert-butyl) provides X. For reviews of the Heck reaction, see Heck, *Acc. Chem. Res.* (1979), 12, 146-151; Heck, *Pure Appl. Chem.* (1978), 50, 691-701; R. F. Heck, *Palladium Reagents in Organic Syntheses*, Academic Press, New York (1985), 179-321, Bender, Stakem, and Heck, *J. Org. Chem.* (1982), 47,1278; Spencer, *J. Organomet. Chem.* (1983), 258, 101; and Brase, Stefan; De Meijere, Armin. Palladium-catalyzed Coupling of Organyl Halides to Alkenes—the Heck Reaction, *Metal-Catalyzed Cross-Coupling Reactions* (1998), 99-166, Publisher: Wiley-VCH Verlag GmbH, Weinheim, Germany, each herein incorporated by reference with regard to such teaching. Ester hydrolysis of X provides acrylic acid XI.

An analogue of XI wherein the phenolic hydroxyl group is replaced by hydrogen (i.e. $R^1$ is H as herein described) may be prepared according to the methods described in Schemes 1 and 2 by employing commercially available (4-bromophenyl) (phenyl)methanone.

An analogue of XI wherein the phenolic hydroxyl group is replaced by fluorine (i.e. $R^1$ is F as herein described) can be prepared by the methods described in Schemes 1 and 2 by employing (4-bromophenyl)(4-fluorophenyl)methanone which can be prepared by methods described in the literature (for example, Z. Vejdelek et al., *Collect. Czech. Chem. Commun.*, (1984), 49(11), 2649-2660, herein incorporated by reference with regard to such teaching).

Alternative routes to preparing acrylic acid compounds illustrated by XI in Scheme 2 are described in Examples 28 and 29 below.

Acrylic acid XI can be converted to an amide as illustrated in Scheme 2. Treatment of acrylic acid (XI) with an amine in the presence of a coupling agent such as EDC and DMAP in dichloromethane provides amide XII. Alternatively, acrylic acid XI can be converted to the acid chloride using oxalyl chloride and DMF in toluene followed by treatment of the crude acid chloride with an amine to give amide XII. For conversion of carboxylic acids to amides, see Larock, R. C., Comprehensive Organic Transformations, VCH Publishers, New York, 1989.

Scheme 3

General Route to Cycloalkylidene
Diphenylethylenes from Aryl Halide VI

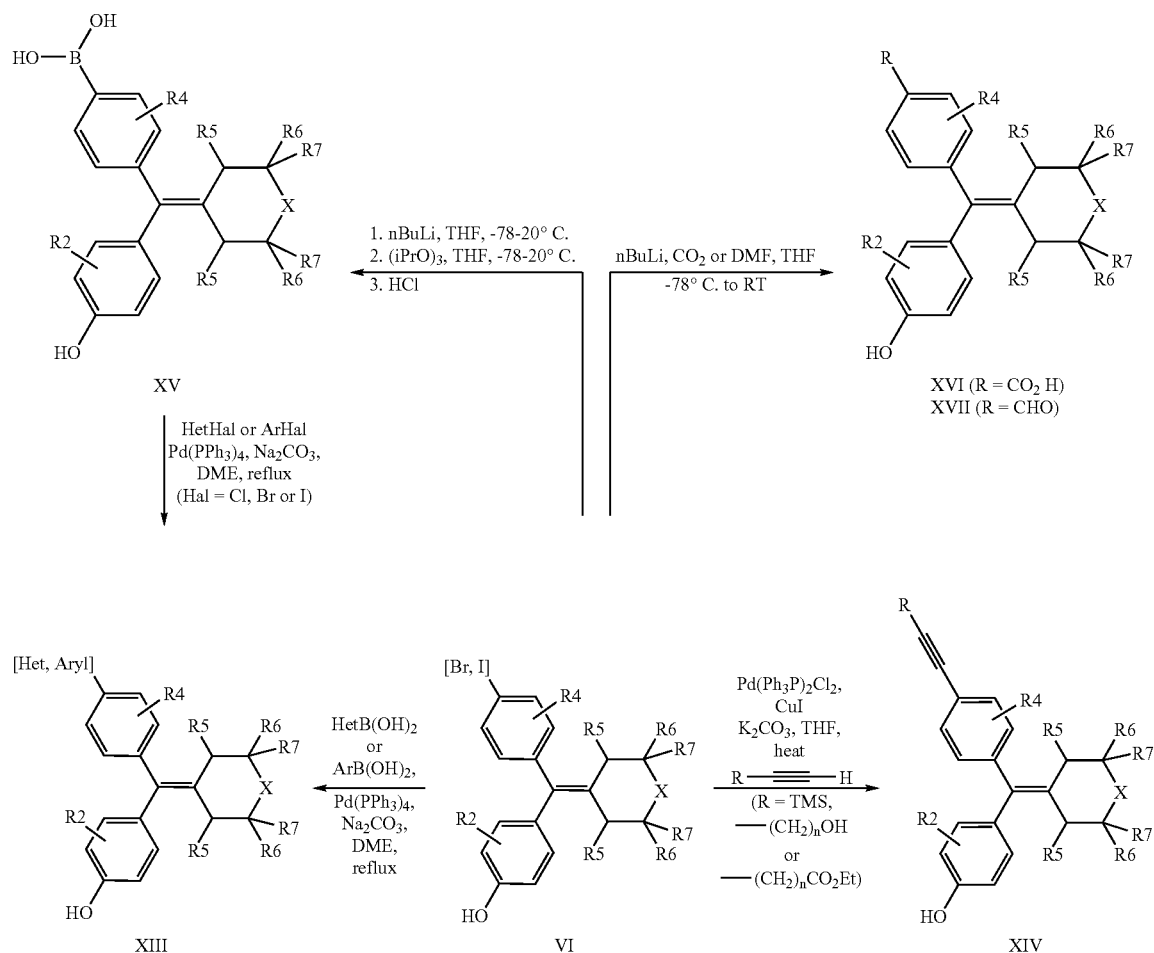

Cycloalkylidene VI is a versatile intermediate that can be used to prepare a variety of compounds as described in Scheme 3.

Coupling of VI with an aryl or heteroaryl-substituted boronic acid using Suzuki reaction conditions provides XIII. For reaction conditions of the Suzuki coupling reaction, see, Miyaura, N., Suzuki, A. Chem. Rev. 1995, 95, 2457-2483; Suzuki, A., J. Organometallic Chem. (1999), 576, 147-168; and Suzuki, A. in Metal-catalyzed Cross-coupling Reactions, Diederich, F., and Stang, P. J., Eds.; Wiley-VCH: New York, (1998), pp. 49-97, each herein incorporated by reference with regard to such teaching. Alternatively, XIII can be prepared by Suzuki-coupling of boronic acid XV with an aryl or heteroaryl halide. Boronic acid XV can be prepared by metal-halogen exchange of VI using butyllithium followed by treatment of the resulting organolithium with triisopropyl borate and subsequent hydrolysis. For reaction conditions, see. X. Deng et al., J. Org. Chem., (2002), 67(15), 5279-5283 and P. J. Hajduk et al., J. Amer. Chem. Soc., (1997), 119(25), 5818-5827, each herein incorporated by reference.

Metal-halogen exchange of VI using butyl lithium followed by treatment with carbon dioxide or DMF provides benzoic acid XVI and benzaldehyde XVII respectively. For reaction conditions, see T. Mizuno et al., Tetrahedron, (1999), 55(31), 9455-9468; J. W. Lampe et al., J. Med. Chem., (2002), 45(12), 2624-2643; R. G. Leenders et al., Bioorg. Med. Chem. (1999), 7(8), 1597-1610; and A. Endo et al., J. Amer. Chem. Soc., (2002), 124(23), 6552-6554, each herein incorporated by reference.

Amides can be prepared from XVI by methods illustrated and described in Scheme 2. Benzaldehyde XVII can be converted to acrylate ester X via Wadsworth-Emmons chemistry (For Wadsworth-Emmons chemistry, see J. Boutagy and R. Thomas Chem. Rev. (1974), 74, 87-99; Wadsworth, Org. React (1977), 25, 73-253; Y. Momose, et al., J. Med. Chem., (2002), 45(7), 1518-1534; and S. D. Bull et al., J. Chem. Soc.

*Perkin Trans I*, (2001), 23, 3112-3121, each herein incorporated by reference with regard to such teaching.

Sonagashira coupling of VI with a propiolate ester, propiolate alcohol or (trimethylsilyl)acetylene provides aromatic alkyne XIV. See Campbell, I. B. *"The Sonagashira Cu—Pd-catalyzed alkyne coupling reaction" in Organocopper Reagents*, Taylor, Richard J. K. ed., (1994), 217-35. Publisher: IRL Press, Oxford, UK; G. C. Nwokogu et al., *J. Org. Chem.*, (1994), 59(9), 2506-2510; and A. P. Kozikowski *J. Med. Chem.* (2000), 43 (6), 1215-1222 and T. Eckert and J. Ipaktschi *Synth. Commun.* (1998), 28, 327-336, each herein incorporated by reference with regard to such teaching. Compound XIV can be further treated to prepare additional new analogues. For example, when R=TMS, the TMS group can be removed to yield the corresponding terminal acetylene (R=H). When R=ester, hyrolysis or reduction affords the corresponding acid and alcohol respectively (see conditions described in Scheme 1).

Scheme 4

General Synthesis of Cycloalkylidene Diphenylethylene Oxazole

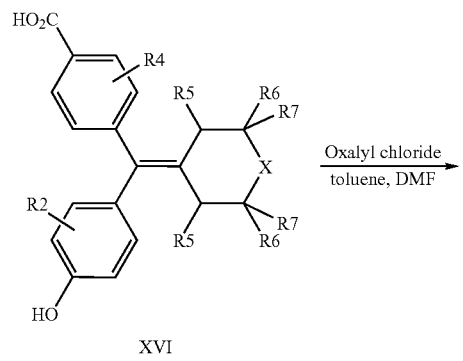

XVI

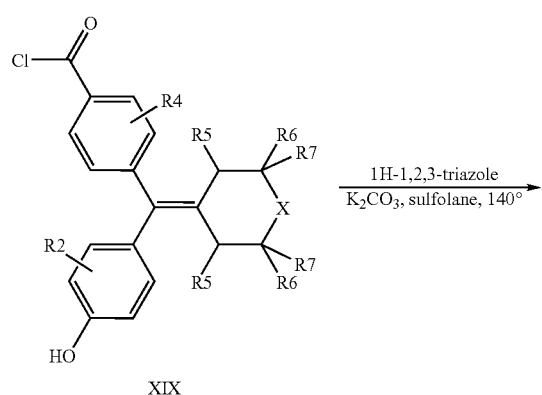

XIX

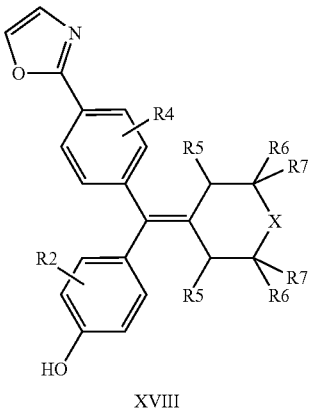

XVIII

The 2-substituted oxazole XVIII is prepared in two steps from benzoic acid XVI as described in Scheme 4. Treatment of XVI with oxalyl chloride gives acid chloride XIX which is then treated with 1H-1,2,3-triazole in the presence of base to provide oxazole XVIII. For reaction conditions leading to the formation of an oxazole from either an aromatic acid chloride or benzamide, see Murugesan, N. et al., *J. Med. Chem.* (2000), 43, 3111-3117, herein incorporated by reference with regard to such teaching.

Scheme 5

General Synthesis of Cycloalkylidene Diphenylethylene Sulfonamides and Amides

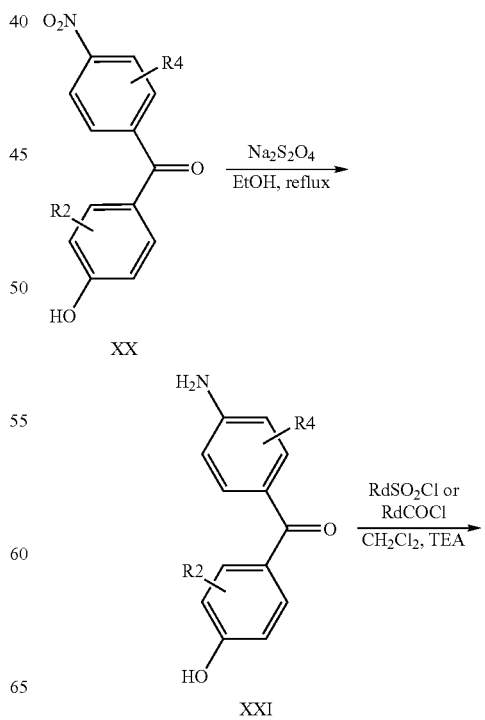

XX

XXI

-continued

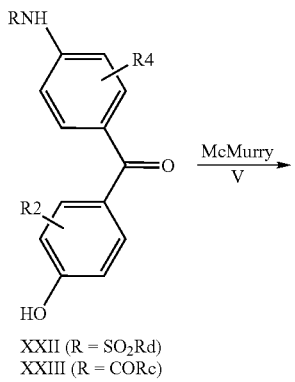

XXII (R = SO₂Rd)
XXIII (R = CORc)

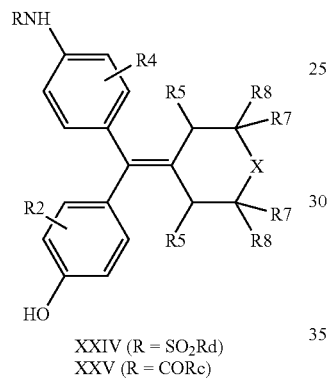

XXIV (R = SO₂Rd)
XXV (R = CORc)

XXI →(Reductive Alkylation, O=C(Ra)Rb)

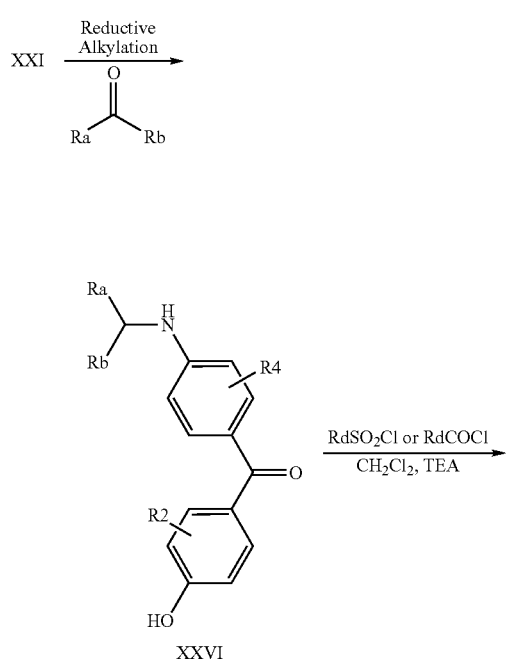

XXVI

-continued

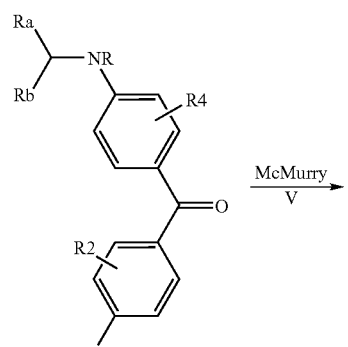

XXVII (R = SO₂Rd)
XXVIII (R = CORc)

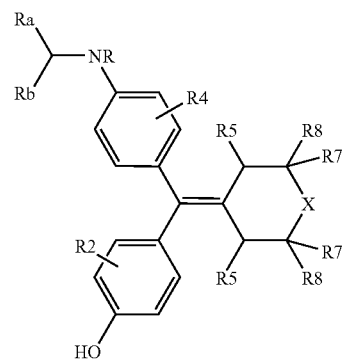

XXIX (R = SO₂Rd)
XXX (R = CORc)

Nitroaniline XX can be converted to a sulfonamide (XXIV) or amide (XXV) as described in Scheme 5. Treatment of XX with a reducing agent such as sodium dithionite provides aniline XXI. Acylation of XXI with a sulfonyl chloride or an acid chloride provides sulfonamide XXII or carboxamide XXIII respectively. McMurry coupling of XXII or XXIII with ketone V as described in Scheme 1 provides XXIV or XXV. Reductive alkylation of XXI by methods known to one skilled in the art gives aniline XXVI which can then be treated as described above to give sulfonamide XXVII or amide XXVIII. Treatment of XXVII or XXVIII with ketone V yields sulfonamide XXIX or amide XXX.

Scheme 6

Synthesis of Oxyalkyl Substituted Cycloalkylidene Diphenylethylenes

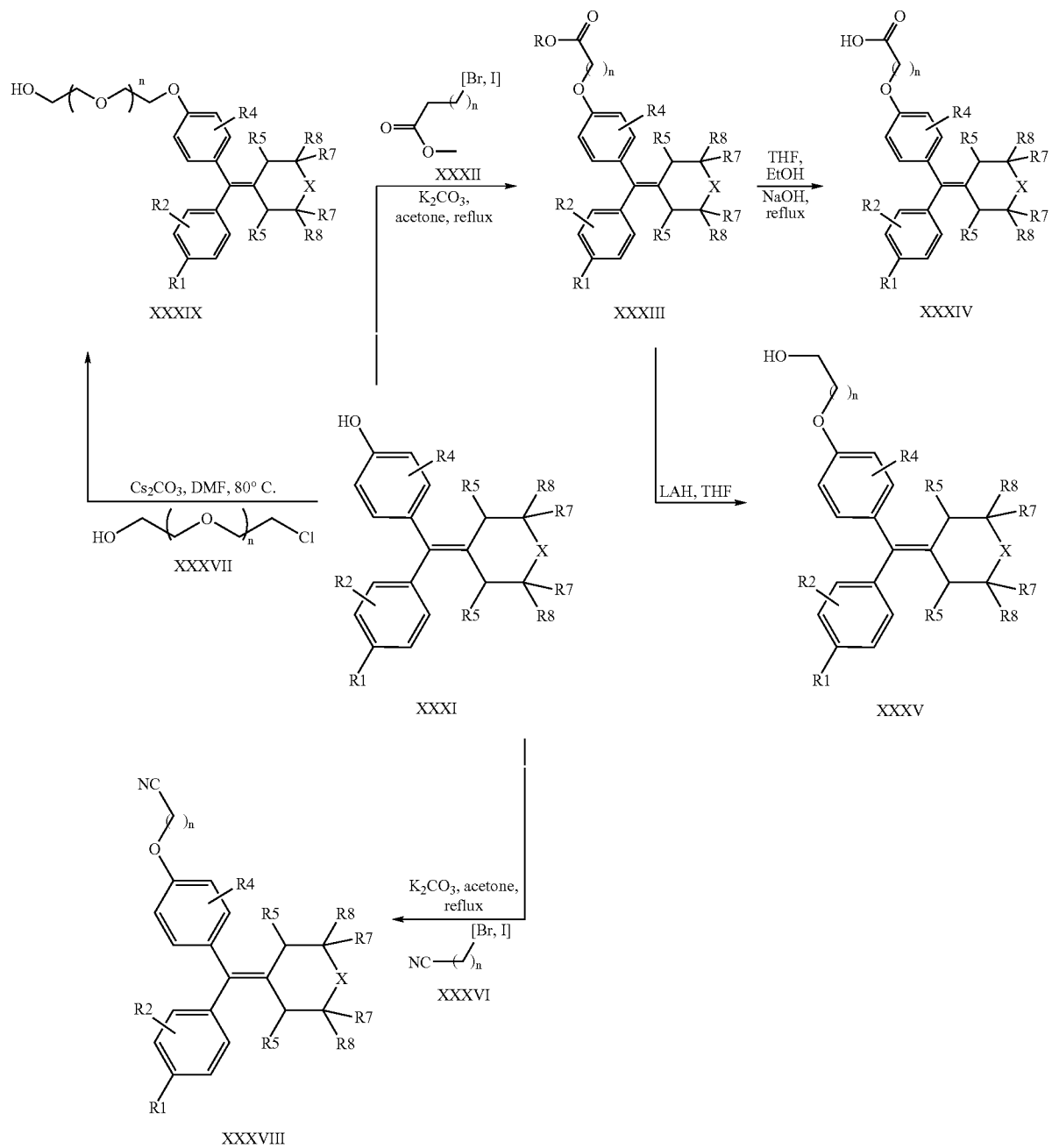

A variety of alkyl derivatives can be prepared in two or three steps via o-alkylation of phenol XXXI as illustrated in Scheme 6. As described above, compounds similar to XXXI can be prepared by McMurry coupling between an appropriately substituted benzophenone and ketone V. For McMurry reaction conditions, see references cited for Scheme 1 above. o-Alkylation of XXXI can be accomplished in the presence of a suitable base and a haloester such as XXXII (wherein R is a suitable alkyl group, e.g. methyl, ethyl, tert-butyl). Saponification of the resulting ester XXXIII provides acid XXXIV. Conversion of ester XXXIII to the alcohol XXXV can be effected by treatment with a reducing agent such as lithium aluminum hydride (LAH). Similarly, phenol XXXI can be alkylated with a haloacetonitrile XXXVI or haloalcohol XXXVII to yield compounds XXXVIII and XXXIX respectively. For examples of related phenol alkylation reactions see Rubin, V. et al., *Bioorganic & Med. Chem.* (2001), 9, 1579-1586, herein incorporated by reference with regard to such teaching.

EXAMPLES

The following specific examples are included as illustrations and are not to be construed as limiting the scope of the present invention.

Example 1 (5)

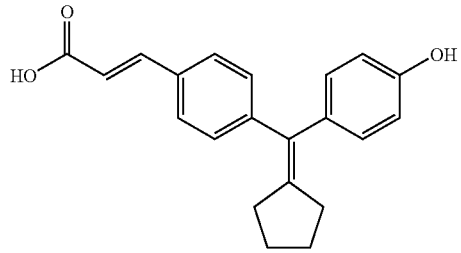

Step 1:
(4-Bromophenyl)[4-(methyloxy)phenyl]methanone
(1)

To a cooled (ice bath, 5° C.) mixture of 4-bromobenzoyl chloride (25.0 g, 0.114 mol) and anisole (15.5 g, 0.143 mol, 1.25 eq) in $CH_2Cl_2$ (500 mL) was added $AlCl_3$ (19.0 g, 0.143 mol, 1.25 eq) portion-wise over a period of 20 minutes with stirring under a nitrogen atmosphere. The resulting reaction mixture was allowed to stir between 5° C. and 20° C. for 3 h. The reaction mixture was poured slowly into 20% aqueous HCl (500 mL), stirred for 15 min, and layers were separated. The aqueous layer was further extracted with $CH_2Cl_2$ (3×250 mL). The combined organic layer washed with water (200 mL), brine (200 mL) dried ($Na_2SO_4$), filtered, and concentrated under reduced pressure to afford 33.48 g (100%) of compound 1 as a white solid. $^1H$ NMR (300 MHz, $CDCl_3$): δ 3.91 (s, 3 H), 6.99 (d, J=8.7 Hz, 2 H), 7.65 (s, 4 H), 7.82 (d, J=8.7 Hz, 2 H).

Step 2:
(4-Bromophenyl)(4-hydroxyphenyl)methanone (2)

To a stirred solution of (4-bromophenyl)[4-(methyloxy)phenyl]methanone (1) (27.0 g, 0.93 mol) in toluene (400 mL) was slowly added $AlCl_3$ (32.0 g, 0.23 mol, 2.5 eq) via a powder addition funnel under a nitrogen atmosphere at RT. The stirred reaction mixture was heated at reflux for 5 h under a blanket of $N_2$. The reaction mixture was allowed to cool to RT and then poured into 10% aqueous HCl (1 L). The reaction mixture was transferred to a separatory funnel and the layers were separated. The aqueous phase was extracted with EtOAc (4×250 mL). The combined organic layer washed with brine (2×100 mL), dried ($Na_2SO_4$), and filtered. The filtrate was concentrated under reduced pressure to afford 25.75 g (100%) of compound 2 as a tan solid that was used in subsequent reactions without any further purification. $^1H$ NMR (300 MHz, DMSO-$d_6$): δ 6.89 (d, J=8.7 Hz, 2 H), 7.60 (d, J=8.4 Hz, 2 H), 7.66 (d, J=8.7 Hz, 2 H), 7.74 (d, J=8.4 Hz, 2 H), 10.48 (s, 1 H).

Step 3:
4-[(4-Bromophenyl)(cyclopentylidene)methyl]phenol
(3)

To a stirred suspension of zinc powder (0.71 g, 10.9 mmoL) in anhydrous THF (15 mL) was slowly added, via syringe, $TiCl_4$ (0.58 mL, 1.0 g, 5.3 mmoL) at RT under a nitrogen atmosphere. The stirred reaction mixture was heated at reflux under a nitrogen atmosphere for 2.5 h. To the refluxing reaction mixture was added a solution of (4-bromophenyl)(4-hydroxyphenyl)methanone (2) (0.408 g, 1.47 mmol) and cyclopentanone (0.38 mL, 0.36 g, 4.3 mmol) in THF (15 mL) and heating continued an additional 2 h. The reaction mixture was allowed to cool to room temperature and water (10 mL) slowly added. The reaction mixture was then filtered through a pad of Celite and the Celite pad washed with EtOAc. The filtrate was transferred to a separatory funnel and the organic layer was separated. The organic phase washed with brine, dried ($MgSO_4$), filtered, and the filtrate concentrated in vacuo to give the crude product. The crude product was purified by flash chromatography on silica gel with hexanes:EtOAc (100:0 to 60:40) to give 0.391 g (81%) of compound 3 as a pale yellow solid. $^1H$ NMR (400 MHz, DMSO-$d_6$): δ 1.59 (m, 4 H), 2.27 (m, 4 H), 6.66 (d, J=8.5 Hz, 2 H), 6.89 (d, J=8.4 Hz, 2 H), 7.04 (d, J=8.4 Hz, 2 H), 7.45 (d, J=8.4 Hz, 2 H), 9.32 (s, 1 H). HRMS (EI) Calcd for $C_{18}H_{17}BrO$: 328.0463 ($M^+$). Found: 328.0469.

Step 4: 1,1-Dimethylethyl(2E)-3-{4-[cyclopentylidene(4-hydroxyphenyl)methyl]phenyl}-2-propenoate (4)

4-[(4-Bromophenyl)(cyclopentylidene)methyl]phenol (3) (0.351 g, 1.07 mmol), tert-butyl acrylate (0.94 mL, 0.82 g, 6.4 mmol, 6 eq), $Pd(OAc)_2$ (0.051 g, 0.23 mmol, 0.21 eq), $Et_3N$ (0.89 mL, 0.65 g, 6.4 mmol, 6 eq), $P(o-tolyl)_3$ (0.139 g, 0.46 mmol, 0.43 eq), and anhydrous $CH_3CN$ (16 mL) were combined in a round-bottomed flask and the reaction mixture was heated overnight at 85° C., with stirring, under a nitrogen atmosphere. The reaction mixture was allowed to cool to room temperature and transferred to a separatory funnel with the aid of EtOAc and water. The layers were separated and the organic phase washed with brine, dried over $MgSO_4$, filtered, and the filtrate was concentrated to give the crude product. The crude product was purified by flash chromatography on silica gel with hexanes:EtOAc (100:0 to 50:50) to give 0.30 g (74%) of compound 4 as a pale yellow solid. $^1H$ NMR (400 MHz, DMSO-$d_6$) δ 1.45 (s, 9 H), 1.60 (m, 4 H), 2.30 (m, 4 H), 6.43 (d, J=15.9 Hz, 1 H), 6.67 (d, J=8.6 Hz, 2 H), 6.90 (d, J=8.4 Hz, 2 H), 7.12 (d, J=8.2 Hz, 2 H), 7.49 (d, J=15.9 Hz, 1 H), 7.58 (d, J=8.3 Hz, 2 H), 9.32 (s, 1 H). HRMS (EI) Calcd for $C_{25}H_{28}O_3$: 376.2038 ($M^+$). Found: 376.2046.

Step 5: (2E)-3-{4-[Cyclopentylidene(4-hydroxyphenyl)methyl]phenyl}-2-propenoic acid (5)

To an ice-water cooled solution of 1,1-dimethylethyl(2E)-3-{4-[cyclopentylidiene(4-hydroxyphenyl)methyl]phenyl}-2-propenoate (4) (0.28 g, 0.74 mmol) in dichloromethane (5 mL) was slowly added trifluoroacetic acid (5 mL) with stirring under a nitrogen atmosphere. After 1 h, the reaction mixture was concentrated in vacuo to give a solid. The solid was dissolved in dichloromethane and the solution was concentrated in vacuo to give a pale tan solid. The solid was triturated with diethyl ether and filtered to give the acrylic acid as an off-white solid. The solid was dried overnight under vacuum at 70° C., however, $^1$H NMR indicated that solvent remained in the sample. The solid was dissolved in methanol and the solution was concentrated in vacuo to give an oil. The oil was dissolved in methanol and the solution was concentrated in vacuo under high vacuum at 60° C. to give an oil. Dichloromethane was added to the oil and crystallization was induced with the aid of a spatula. The suspension was filtered and the solid was dried in a vacuum oven overnight at 70° C. to give 0.072 g (30%) of compound 5 as a yellow solid. $^1$H NMR (400 MHz, DMSO-$d_6$): δ 1.60 (m, 4 H), 2.30 (m, 4 H), 6.44 (d, J=15.9 Hz, 1 H), 6.67 (d, J=8.4 Hz, 2 H), 6.90 (d, J=8.4 Hz, 2 H), 7.13 (d, J=8.2 Hz, 2 H), 7.53 (d, J=15.9 Hz, 1 H), 7.57 (d, J=8.3 Hz, 2 H), 9.32 (s, 1 H). The compound was silated prior to EI analysis. HRMS (EI) Calcd for $C_{27}H_{36}Si_2O_3$: 464.2203 (M$^+$). Found: 464.2210.

Example 2 (8)

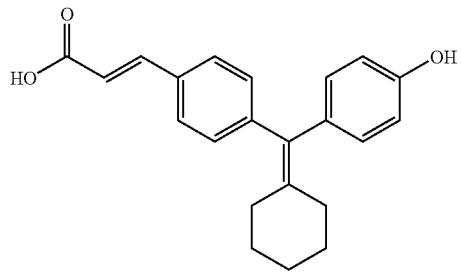

Step 1:
4-[(4-Bromophenyl)(cyclohexylidene)methyl]phenol (6)

To a 3-neck round-bottomed flask were added zinc powder (1.96 g, 30 mmol) followed by anhydrous THF (40 mL). To the stirred suspension was slowly added, via syringe, TiCl$_4$ (1.6 mL, 2.77 g, 14.6 mmol) at room temperature. The reaction mixture was heated at reflux with stirring under a nitrogen atmosphere for 2 h. To the refluxing reaction mixture was added a solution of (4-bromophenyl)(4-hydroxyphenyl)methanone (2) (1.1 g, 3.61 mmol) and cyclohexanone (1.1 mL, 1.04 g, 10.6 mmol) in anhydrous tetrahydrofuran (40 mL). The stirred reaction mixture was heated at reflux under a nitrogen atmosphere for 2 h. The oil bath was removed and the reaction mixture was allowed to cool to room temperature. To the reaction mixture was slowly added water (24 mL) followed by 10% aqueous K$_2$CO$_3$ (24 mL). The reaction mixture was filtered through a pad of Celite and the pad washed with EtOAc. The filtrate was transferred to a separatory funnel with the aid of water and EtOAc and the layers were separated. The organic phase washed with brine, dried over MgSO$_4$, filtered, and the filtrate was concentrated in vacuo to give the crude product. The crude product was purified by flash chromatography on silica gel with hexanes:EtOAc (100:0 to 60:40) to give 1.17 g (95%) of compound 6 as an off-white solid. $^1$H NMR (400 MHz, DMSO-$d_6$): δ 1.52 (m, 6 H), 2.12 (m, 4 H), 6.65 (d, J=8.4 Hz, 2 H), 6.82 (d, J=8.4 Hz, 2 H), 6.97 (d, J=8.3 Hz, 2 H), 7.44 (d, J=8.3 Hz, 2 H), 9.32 (s, 1 H). HRMS (EI) Calcd for $C_{19}H_{19}BrO$: 342.0619 (M$^+$). Found: 342.0627.

Step 2: 1,1-Dimethylethyl(2E)-3-{4-[cyclohexylidene(4-hydroxyphenyl)methyl]phenyl}-2-propenoate (7)

To a round-bottomed flask were added 4-[(4-bromophenyl)(cyclohexylidene)methyl]phenol (6) (0.465 g, 1.35 mmol), tert-butyl acrylate (0.58 mL, 0.508 g, 3.96 mmol, 2.9 eq), Pd(OAc)$_2$ (0.03 g, 0.134 mmol, 0.1 eq), triethylamine (0.54 mL, 0.39 g, 3.87 mmol, 2.9 eq), P(o-tolyl)$_3$ (0.08 g, 0.26 mmol, 0.19 eq), and CH$_3$CN (6 mL). The reaction mixture was heated overnight at 75° C. with stirring under a nitrogen atmosphere. Thin layer chromatography indicated the reaction was not complete. To the reaction mixture were added P(o-tolyl)$_3$ (0.087 g, 0.29 mmol, 0.21 eq), tert-butyl acrylate (0.58 mL, 0.51 g, 3.96 mmol, 2.9 eq), paladium II acetate (0.033 g, 0.147 mmol), triethylamine (0.54 mL, 0.39 g, 3.87 mmol), and CH$_3$CN (2 mL). The reaction mixture was heated at 75° C. with stirring under a nitrogen atmosphere for three days. The reaction mixture was allowed to cool to room temperature and transferred to a separatory funnel with the aid of EtOAc and H$_2$O. The layers were separated and the organic phase was washed with brine. The organic solution was dried over MgSO$_4$, filtered, and the filtrate was concentrated to give the crude product as an oil. The crude product was purified by flash chromatography on silica gel with hexanes:EtOAc (100:0 to 50:50) to give 0.40 g (76%) of compound 7 as a pale yellow solid. $^1$H NMR (400 MHz, DMSO-$d_6$): δ 1.45 (s, 9 H), 1.52 (m, 6 H), 2.14 (m, 4 H), 6.43 (d, J=15.9 Hz, 1 H), 6.66 (d, J=8.5 Hz, 2 H), 6.84 (d, J=8.4 Hz, 2 H), 7.05 (d, J=8.1 Hz, 2 H), 7.48 (d, J=15.9 Hz, 1 H), 7.57 (d, J=8.1 Hz, 2 H), 9.31 (s, 1 H). The sample was silated prior to EI analysis. HRMS (EI) Calcd for $C_{29}H_{38}O_3Si$: 462.2590 (M$^+$). Found: 462.2592.

Step 3: (2E)-3-{4-[Cyclohexylidene(4-hydroxyphenyl)methyl]phenyl}-2-propenoic acid (8)

A solution of 1,1-dimethylethyl(2E)-3-{4-[cyclohexylidene(4-hydroxyphenyl)methyl]phenyl}-2-propenoate (7) (0.24 g, 0.61 mmol) in CH$_2$Cl$_2$ (6 mL) was cooled in an ice-water bath and stirred under a nitrogen atmosphere. To the cold solution was slowly added trifluoroacetic acid (6 mL). The reaction mixture was stirred in the ice-water bath under a nitrogen atmosphere for 1 h. The reaction mixture was concentrated to give the crude product as a solid. The crude product was dissolved in CH$_2$Cl$_2$ and the solution was concentrated to give a solid. The crude product was transferred to a separatory funnel with the aid of CH$_2$Cl$_2$ and H$_2$O. The organic phase was removed and the aqueous phase that contained suspended solids was extracted twice with CH$_2$Cl$_2$. The organic phase was removed and the aqueous suspension was filtered with the aid of H$_2$O. The filtered white solid was dissolved in CH$_2$Cl$_2$ and MeOH and the solution was filtered. The filtrate was concentrated and the resulting solid was dried in a vacuum oven to give 135 mg (67%) of compound 8 as an off-white solid. $^1$H NMR (400 MHz, DMSO-$d_6$): δ 1.52 (m, 6 H), 2.15 (m, 4 H), 6.44 (d, J=15.9 Hz, 1 H), 6.66 (d, J=8.4 Hz, 2 H), 6.84 (d, J=8.4 Hz, 2 H), 7.05 (d, J=8.0 Hz, 2 H), 7.52 (d, J=15.9 Hz, 1 H), 7.57 (d, J=8.0 Hz, 2 H), 9.31 (s, 1 H), 12.31 (br s, 1 H). The sample was silated prior to EI analysis. HRMS (EI) Calcd for $C_{28}H_{38}O_3Si_2$: 478.2360 (M$^+$). Found: 478.2376.

Example 3 (11)

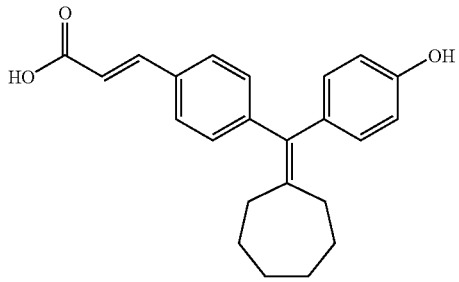

Step 1:
4-[(4-Bromophenyl)(cycloheptylidene)methyl]phenol (9)

To a three-neck round-bottomed flask equipped with a magnetic stir bar, reflux condenser, rubber septum, and two nitrogen inlets, was added zinc powder (13.0 g, 199 mmol) followed by anhydrous THF (200 mL). To the stirred suspension was slowly added $TiCl_4$ (11.0 mL, 19.0 g, 100.0 mmol) via syringe (caution: vigorous fuming). The reaction mixture was heated at reflux for 2 h. To the refluxing reaction mixture was added a solution of cycloheptanone (9.0 mL, 8.56 g, 76.3 mmol) and (4-bromophenyl)(4-hydroxyphenyl)methanone (2) (6.91 g, 24.9 mmol) in THF (200 mL) slowly via syringe. The reaction mixture was heated at reflux under a nitrogen atmosphere with stirring for 2 h. The oil bath was removed and the reaction mixture was allowed to cool to room temperature. The three neck round-bottomed flask was equipped with an addition funnel and water (150 mL) was slowly added to the reaction mixture followed by 10% aqueous $K_2CO_3$ (150 mL). The reaction mixture was filtered through a pad of Celite. The pad washed with EtOAc. The filtrate was transferred to a separatory funnel and the layers were separated. The organic phase washed with brine, dried over $MgSO_4$, filtered, and the filtrate was concentrated to give the crude product as an orange oil. The crude product was partially purified by flush chromatography on silica gel with hexanes:EtOAc (100:0 to 95:5) to give a solid. The solid was triturated with hexanes and filtered to give 6.3 g (71%) of compound (9) as an off-white solid. $^1$H NMR (400 MHz, DMSO-$d_6$): δ 1.50 (m, 8 H), 2.20 (m, 4 H), 6.66 (d, J=8.5 Hz, 2 H), 6.89 (d, J=8.4 Hz, 2 H), 7.04 (d, J=8.4 Hz, 2 H), 7.45 (d, J=8.4 Hz, 2 H), 9.30 (s, 1 H).

Step 2: 1,1-Dimethylethyl(2E)-3-{4-[cycloheptylidene(4-hydroxyphenyl)methyl]phenyl}-2-propenoate (10)

To a round-bottomed flask were added 4-[(4-bromophenyl)(cycloheptylidene)methyl]phenol (9) (4.0 g, 11.2 mmol), t-butyl acrylate (7.2 mL, 6.3 g, 49.2 mmol, 4.4 eq), Pd(OAc)$_2$ (0.52 g, 2.3 mmol, 0.21 eq), Et$_3$N (9.5 mL, 6.90 g, 68.2 mmol, 6.1 eq), P(o-tolyl)$_3$ (1.3 g, 4.2 mmol, 0.38 eq), and $CH_3CN$ (100 mL). The reaction mixture was heated overnight at 75° C. with stirring under a nitrogen atmosphere. The reaction mixture was allowed to cool to room temperature and then transferred to a separatory funnel with the aid of EtOAc and $H_2O$. The layers were separated, and the organic phase washed with brine, dried (MgSO$_4$), filtered, and the filtrate was concentrated to give the crude product as a red-orange oil. The crude product was purified by flush chromatography on silica gel with hexanes:EtOAc (9:1 to 4:1) to give 4.46 g (98%) of compound 10 as a yellow solid. $^1$H NMR (400 MHz, DMSO-$d_6$): δ 1.45 (s, 9 H), 1.50 (m, 8 H), 2.21 (m, 4 H), 6.42 (d, J=16.1 Hz, 1 H), 6.65 (d, J=8.4 Hz, 2 H), 6.90 (d, J=8.4 Hz, 2 H), 7.10 (d, J=8.2 Hz, 2 H), 7.48 (d, J=15.9 Hz, 1 H), 7.57 (d, J=8.1 Hz, 2 H), 9.28 (s, 1 H).

Step 3: (2E)-3-{4-[Cycloheptylidene(4-hydroxyphenyl)methyl]phenyl}-2-propenoic acid (11)

To an ice-water cooled mixture of 1,1-dimethylethyl(2E)-3-{4-[cycloheptylidene(4-hydroxyphenyl)methyl]phenyl}-2-propenoate (10) (4.42 g, 10.9 mmol) and $CH_2Cl_2$ (20 mL) was slowly added trifluoroacetic acid (10 mL) with stirring under a nitrogen atmosphere. After 3 h, the reaction mixture was filtered. The filtered solid was washed with $CH_2Cl_2$ and dried to give 2.2 g of compound 11 as a white solid. The filtrate was concentrated and the impure product was partially purified by flash chromatography on silica gel with $CH_2Cl_2$:MeOH (100:0 to 9:1) to give a yellow solid. The solid was triturated with Et$_2$O and the suspension was filtered. The filtered solid was dried to give a second crop of compound 11 (354 mg) as a pale tan solid. The Et$_2$O filtrate noted above was concentrated in vacuo and the impure product was crystallized from hexanes and EtOAc. The solid was dried to give a third crop of compound 11 (185 mg) as a pale tan solid. The total yield of 11 was 2.74 g (72%). Analytical data for all three batches were comparable. The analytical data is herein presented for the first batch. $^1$H NMR (400 MHz, DMSO-$d_6$): δ 1.50 (m, 8 H), 2.21 (m, 4 H), 6.43 (d, J=15.9 Hz, 1 H), 6.65 (d, J=8.4 Hz, 2 H), 6.90 (d, J=8.5 Hz, 2 H), 7.11 (d, J=8.0 Hz, 2 H), 7.52 (d, J=16.1 Hz, 1 H), 7.57 (d, J=8.0 Hz, 2 H), 9.28 (s, 1 H), 12.21 (br s, 1 H). LRMS (ESI): m/z 347 (M–H)$^-$. Anal. Calcd for $C_{23}H_{24}O_3$: C, 79.28; H, 6.94. Found: C, 79.16; H, 6.97.

Example 4 (12)

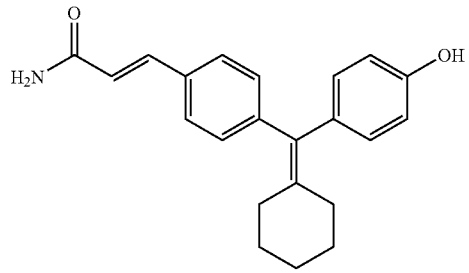

Step 1: (2E)-3-{4-[Cyclohexylidene(4-hydroxyphenyl)methyl]phenyl}-2-propenamide (12)

To a stirred solution of 1-[3-(dimethylamino)propyl]-3-ethylcarbodiimide hydrochloride (0.121 g, 0.63 mmol), 1-hydroxybenzotriazole hydrate (0.087 g, 0.644 mmol), 4-dimethylaminopyridine (0.012 g, 0.098 mmol), pyridine (5 mL), and ammonia (0.5 M in 1,4-dioxane) (1.4 mL, 0.7 mmol) was added a solution of (2E)-3-{4-[cyclohexylidene(4-hydroxyphenyl)methyl]phenyl}-2-propenoic acid (8) (174 mg, 0.52 mmol) in pyridine (5 mL). The reaction mixture was stirred at room temperature under a nitrogen atmosphere for 4 d. The reaction mixture was concentrated and the crude product was partitioned between $H_2O$ and $CH_2Cl_2$. The organic phase was separated and washed with 1 N HCl (aq.) followed by brine. The organic phase was dried over $MgSO_4$, filtered, and the filtrate was concentrated to give the crude product. The crude product was purified by flash chromatography on silica gel with $CH_2Cl_2$:MeOH (100:0 to 90:10) to give the desired product. The solid was dried under vacuum at 70° C. to give 29 mg (17%) of compound 12 as a white solid. $^1$H NMR (400 MHz, DMSO-$d_6$): δ 1.54 (m, 6 H), 2.15 (m, 4 H), 6.53 (d, J=15.8 Hz, 1 H), 6.67 (d, J=8.5 Hz, 2 H), 6.85 (d, J=8.4 Hz, 2 H), 7.06 (m, 3 H), 7.36 (d, J=15.9 Hz, 1 H), 7.45 (d, J=8.2 Hz, 2 H), 7.50 (br s, 1 H), 9.33 (s, 1). The compound was silated prior to EI analysis. HRMS (EI) Calcd for $C_{25}H_{31}\ _NO_2Si$: 405.2124 (M$^+$). Found: 405.2126.

Example 5 (13)

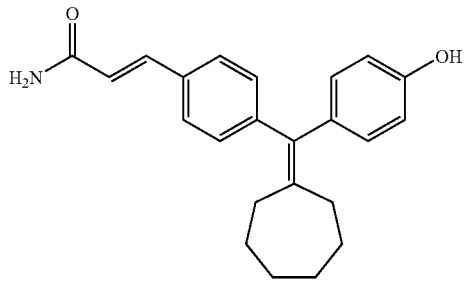

Step 1: (2E)-3-{4-[Cycloheptylidene(4-hydroxyphenyl)methyl]phenyl}-2-propenamide (13)

To a stirred suspension of (2E)-3-{4-[cycloheptylidene(4-hydroxyphenyl)methyl]phenyl}-2-propenoic acid (11) (0.23 g, 0.66 mmol) in toluene (6 mL) was slowly added oxalyl chloride (0.12 mL, 0.175 g, 1.38 mmol, 2.1 eq) followed by DMF (2-3 drops) at room temperature under a nitrogen atmosphere. The reaction mixture was stirred for 0.25 h. Dichloromethane (6 mL) was added to the reaction mixture (to aid the dissolution of solids) and the reaction mixture was stirred at room temperature for 2 h. Oxalyl chloride (0.12 mL, 0.175 g, 1.38 mmol, 2.1 eq) and DMF (2 drops) were added to the reaction mixture and stirring was continued for 3 h. The reaction mixture was concentrated in vacuo. Toluene was added to the crude acid chloride and the solvent was removed in vacuo. To the crude acid chloride were added ammonia (0.5 M in 1,4-dioxane) (6 mL, 3 mmol, 4.5 eq) followed by $CH_2Cl_2$ (5 mL). The reaction mixture was stirred overnight at room temperature under a nitrogen atmosphere. The reaction mixture was transferred to a separatory funnel with the aid of $CH_2Cl_2$ and the solution washed with water. The layers were separated and the organic phase was dried over $MgSO_4$, filtered, and the filtrate was concentrated to give the crude amide as a gold-yellow oil. The crude product was purified by flash chromatography on silica gel with $CH_2Cl_2$:MeOH (100:0 to 95:5) to give a solid which was dried at 70° C. under vacuum to give 0.058 g (25%) of compound 13 as a tan solid. $^1$H NMR (400 MHz, DMSO-$d_6$): δ 1.51 (m, 8 H), 2.22 (m, 4 H), 6.53 (d, J=15.9 Hz, 1 H), 6.66 (d, J=8.5 Hz, 2 H), 6.91 (d, J=8.3 Hz, 2 H), 7.06 (br s, 1 H), 7.12 (d, J=8.1 Hz, 2 H), 7.35 (d, J=15.9 Hz, 1 H), 7.45 (d, J=8.1 Hz, 2 H), 7.50 (br s, 1 H), 9.29 (s, 1 H). HRMS (ESI) Calcd for $C_{23}H_{26}NO_2$: 348.1964 (M+H)$^+$. Found: 348.1951.

Example 6 (16)

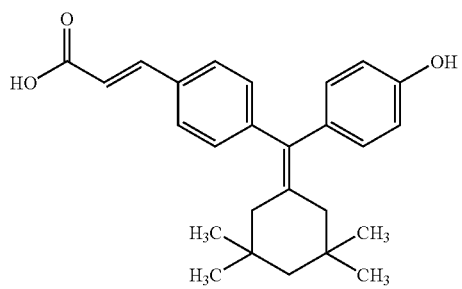

Step 1: 4-[(4-Bromophenyl)(3,3,5,5-tetramethylcyclohexylidene)methyl]phenol (14)

To a stirred suspension of zinc powder (23.4 g, 0.36 mol) in THF (300 mL) was slowly added $TiCl_4$ (20 mL, 0.18 mol) via a syringe at room temperature under a nitrogen atmosphere. The reaction mixture was heated at reflux for 1 h. A solution of (4-bromophenyl)(4-hydroxyphenyl)methanone (2) (10.0 g, 0.036 mol) and 3,3,5,5-tetramethylcyclohexanone (16.7 g, 0.108 mol) in THF (100 mL) was added to the reaction mixture. The reaction mixture was heated at reflux with stirring under a nitrogen atmosphere for an additional 2 h. The reaction mixture was allowed to cool to room temperature. To the reaction mixture was poured into a 10% aqueous $K_2CO_3$ (1 L). The reaction mixture was filtered through a pad of Celite and the pad washed with EtOAc. The filtrate was transferred to a separatory funnel and the layers were separated. The aqueous phase was further extracted with EtOAc (4×250 mL). The combined organic phase washed with brine (2×10 mL), dried ($Na_2SO_4$), filtered, and then filtrate was concentrated under reduced pressure to give the crude product as a gold-yellow oil. The crude product was purified by flash chromatography on silica gel with hexanes:EtOAc (100:0 to 1:1) as an eluent to afford 10.45 g (73%) of compound 14 as a white solid. $^1$H NMR (300 MHz, CDCl$_3$): δ 0.91 (s, 6 H), 0.95 (s, 6H), 1.31 (s, 2 H), 1.96 (s, 2 H), 1.99 (s, 2 H), 4.67 (s, 1H), 6.76 (d, J=8.7 Hz, 2 H), 7.03 (d, J=6.0 Hz, 2 H), 7.05 (d, J=6.0 Hz, 2 H), 7.41 (d, J=8.4 Hz, 2 H). HRMS (EI) Calcd for $C_{23}H_{27}BrO$: 398.1245 (M$^+$). Found: 398.1248.

Step 2: Ethyl(2E)-3-{4-[(4-hydroxyphenyl)(3,3,5,5-tetramethylcyclohexylidene)methyl]phenyl}-2-propenoate (15)

To a round-bottomed flask were added 4-[(4-bromophenyl)(3,3,5,5-tetramethylcyclohexylidene)methyl]phenol (14) (10.2 g, 0.0255 mol), ethyl acrylate (28 mL, 0.255 mol.), dichlorobis(triphenylphosphine) palladium (II) (0.895 g, 1.28 mmol, 5 mol %), Et$_3$N (17.6 mL, 0.128 mol), and DMF (50 mL). The stirred reaction mixture was heated to 110° C. for 18 h under a nitrogen atmosphere. The reaction mixture was allowed to cool to room temperature and then diluted with Et$_2$O (200 mL). The reaction mixture was filtered and the filtrate was concentrated under reduced pressure to give crude product. The crude reaction mixture in DMF was diluted with EtOAc (400 mL), washed with water (2×100 mL), brine (1×100 mL), dried (Na$_2$SO$_4$), filtered, and then concentrated under reduced pressure to afford the crude product as an oil. The crude product was purified by flash chromatography on silica gel with hexanes:EtOAc (19:1 to 1:1) as an eluent to give 8.02 g (75%) of compound 15 as a pale yellow solid. $^1$H NMR (300 MHz, CDCl$_3$): δ 0.88 (s, 6 H), 0.91 (s, 6 H), 1.31 (s, 2 H), 1.35 (t, J=7.2 Hz, 3 H), 1.99 (s, 2 H), 2.00 (s, 2 H), 4.28 (q, J=7.2 Hz, 2 H), 5.35 (broad s, 1H), 6.41 (d, J=16.2 Hz, 1 H), 6.77 (d, J=8.4 Hz, 2 H), 7.04 (d, J=8.4 Hz, 2 H), 7.20 (d, J=8.10 Hz, 1 H), 7.44 (d, J=8.40 Hz, 2 H), 7.68 (d, J=16.2 Hz, 1H). HRMS (EI) Calcd for C$_{28}$H$_{34}$O$_3$: 418.57 (M$^+$). Found: 419.17. Note: Excess ethyl acrylate can be distilled from the reaction mixture before work-up.

Step 3: (2E)-3-{4-[(4-Hydroxyphenyl)(3,3,5,5-tetramethylcyclohexylidene)methyl]phenyl}-2-propenoic acid (16)

To a stirred solution of ethyl(2E)-3-{4-[(4-hydroxyphenyl)(3,3,5,5-tetramethylcyclohexylidene)methyl]phenyl}-2-propenoate (15) (7.75 g, 0.0185 mmol) in THF (100 mL) and EtOH (100 mL) was slowly added 1 N NaOH (93 mL) solution at RT. The reaction mixture was heated to 70° C. and stirred at that temperature for 4.5 h. Reaction mixture was cooled to room temperature and then poured into 20% aqueous HCl (350 mL). The product was separated out as an off-white solid. The suspension was filtered and the filtered solid was dried to afford 6.01 g (83%) of compound 16 as an off-white solid. mp 219-220° C. $^1$H NMR (300 MHz, DMSO-d$_6$): δ 0.89 (s, 6 H), 0.90 (s, 6 H), 1.27 (s, 2 H), 1.91 (s, 2 H), 1.94 (s, 2 H), 6.47 (d, J=15.9 Hz, 1 H), 6.68 (d, J=8.1 Hz, 2 H), 6.95 (d, J=8.4 Hz, 2 H), 7.16 (d, J=8.1 Hz, 2 H), 7.52 (d, J=15.9 Hz, 1 H), 7.60 (d, J=8.1 Hz, 2 H), 9.31 (s, 1 H), 12.35 (s, 1H). LRMS (ESI): m/z 389 (M−H)$^-$.

Example 7 (17)

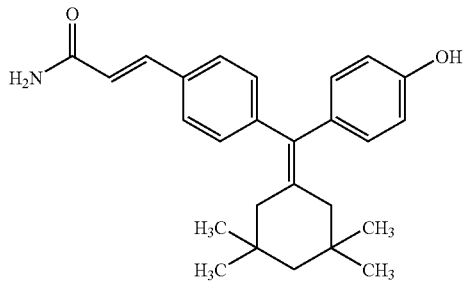

Step 1: (2E)-3-{4-[(4-Hydroxyphenyl)(3,3,5,5-tetramethylcyclohexylidene)methyl]phenyl}-2-propenamide (17)

To a stirred suspension of (2E)-3-{4-[(4-hydroxyphenyl)(3,3,5,5-tetramethylcyclohexylidene)methyl]phenyl}-2-propenoic acid (16) (0.18 g, 0.46 mmol) in CH$_2$Cl$_2$ (6 mL) at room temperature was added oxalyl chloride (0.15 mL, 0.218 g, 1.72 mmol, 3.7 eq) followed by several drops of DMF (Note: vigorous bubbling occurred upon addition of DMF). The reaction mixture was stirred under a nitrogen atmosphere for 1 h and concentrated in vacuo. Toluene was added to the crude acid chloride and the solvent was removed in vacuo. To the crude acid chloride was added ammonia (0.5 M in 1,4-dioxane) (6 mL) and the turbid reaction mixture stirred at room temperature under a nitrogen atmosphere for 3 h. Ammonia (0.5 M in 1,4-dioxane) (2 mL) was added to the reaction mixture and stirring was continued overnight at room temperature under a nitrogen atmosphere. The reaction mixture was concentrated in vacuo. Ammonia (0.5 M in 1,4-dioxane) (8 mL) and CH$_2$Cl$_2$ (8 mL) were added to the residue. The flask was equipped with a rubber septum and the reaction mixture was stirred at room temperature for 2 d. The reaction mixture was transferred to a separatory funnel and partitioned between CH$_2$Cl$_2$ and H$_2$O. The layers were separated and the aqueous phase was extracted with CH$_2$Cl$_2$. The organic extracts were combined, washed with brine, dried (MgSO$_4$) filtered, and the filtrate was concentrated to give the crude product as an amorphous solid. The crude product was purified by flash chromatography on silica gel with CH$_2$Cl$_2$: MeOH (100:0 to 19:1) as eluant to provide the product which was dried to give 0.026 g (15%) of compound 17 as a pale yellow solid. $^1$H NMR (400 MHz, DMSO-d$_6$): δ 0.87 (s, 6 H), 0.88 (s, 6 H), 1.25 (s, 2 H), 1.89 (s, 2 H), 1.92 (s, 2 H), 6.53 (d, J=15.8 Hz, 1 H), 6.66 (d, J=8.5 Hz, 2 H), 6.93 (d, J=8.5 Hz, 2 H), 7.06 (br s, 1), 7.14 (d, J=8.1 Hz, 2 H), 7.35 (d, J=15.9 Hz, 1 H), 7.45 (d, J=8.1 Hz, 2 H), 7.50 (br s, 1 H), 9.30 (s, 1). HRMS (ESI) Calcd for C$_{26}$H$_{32}$ $_N$O$_2$: 390.2433 (M+H)$^+$. Found: 390.2427.

Example 8 (19)

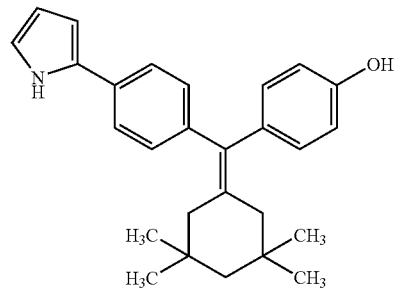

Step 1: 1,1-Dimethylethyl 2-{4-[(4-hydroxyphenyl)(3,3,5,5-tetramethylcyclohexylidene)methyl]phenyl}-1H-pyrrole-1-carboxylate (18)

To a round-bottomed flask were added 4-[(4-bromophenyl)(3,3,5,5-tetramethylcyclohexylidene)methyl]phenol (14) (0.127 g, 0.32 mmol), 1-N-BOC-pyrrole-2-boronic acid (0.21 g, 1.0 mmoL), tetrakis(triphenylphosphine)palladium (0) (0.033 g, 0.029 mmoL), 2 M Na$_2$CO$_3$ (3 mL), and ethylene glycol dimethyl ether (8 mL). The stirred reaction mixture was heated at reflux overnight under a nitrogen atmosphere. The oil bath was removed and the reaction mixture was allowed to cool at RT. The reaction mixture was transferred to a separatory funnel and partitioned between H$_2$O and EtOAc. The organic phase was separated, dried over MgSO$_4$, filtered, and the filtrate was concentrated in vacuo to give an orange-brown oil. The crude product was purified by flash chromatography on silica gel with a hexanes:EtOAc gradient (100:0 to 80:20) to give 111 mg (72%) of compound 18 as an off-white solid. $^1$H NMR (400 MHz, DMSO-d$_6$): δ 0.88 (s, 12 H), 1.24 (m, 11 H), 1.92 (s, 2 H), 1.94 (s, 2 H), 6.19 (m, 1 H), 6.23 (m, 1 H), 6.65 (d, J=8.5 Hz, 2 H), 6.92 (d, J=8.4 Hz, 2 H), 7.09 (d, J=8.1 Hz, 2 H), 7.21 (d, J=8.0 Hz, 2 H), 7.31 (m, 1 H), 9.27 (s, 1 H). LCMS (ESI): m/z 508 (M+Na)$^+$.

Step 2: 4-[[4-(1H-Pyrrol-2-yl)phenyl](3,3,5,5-tetramethylcyclohexylidene)methyl]phenol (19)

To a stirred solution of 1,1-dimethylethyl 2-{4-[(4-hydroxyphenyl)(3,3,5,5-tetramethylcyclohexylidene)methyl]phenyl}-1H-pyrrole-1-carboxylate (18) (0.087 g, 0.18 mmoL) in anhydrous THF (1.8 mL) was added slowly sodium methoxide (0.5 M in MeOH) (1.4 mL, 0.7 mmoL) at RT under a nitrogen atmosphere. The reaction mixture was allowed to stir at RT overnight. The reaction mixture was concentrated in vacuo and the crude product was purified by reverse phase preparative HPLC on a C-18 column with a $CH_3CN:H_2O$ gradient (75:25 to 100:0) and 0.05% TFA as a modifier to give 34 mg (49%) of compound 19 as an off-white solid. $^1H$ NMR (400 MHz, DMSO-$d_6$): δ 0.87 (s, 6 H), 0.88 (s, 6 H), 1.25 (s, 2 H), 1.91 (s, 4 H), 6.06 (m, 1 H), 6.42 (m, 1 H), 6.65 (d, J=8.5 Hz, 2 H), 6.78 (m, 1 H), 6.93 (d, J=8.5 Hz, 2 H), 7.05 (d, J=8.0 Hz, 2 H), 7.49 (d, J=8.0 Hz, 2 H), 9.25 (s, 1 H), 11.18 (s, 1 H). LCMS (ESI): m/z 386 (M+H)$^+$.

Example 9 (22)

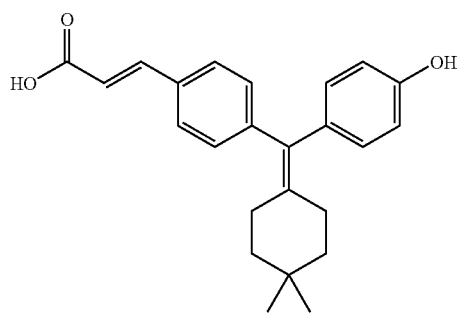

Step 1: 4,4-Dimethylcyclohexanone (20)

This compound was prepared according to the method described by H-J Liu, et al., (*Can. J. Chem.* (1988), 66, 2345) with modification. To a three-neck round-bottomed flask was added palladium on carbon (Degussa Type, 10% wt. (dry basis)) (0.167 g). The flask was evacuated and then filled with nitrogen and the evacuation/fill cycle was repeated twice more. To the flask was added a solution of 4,4-dimethyl-2-cyclohexene-1-one (2.1 mL, 2.0 g, 16 mmol) in EtOAc (100 mL). The flask was evacuated and then filled with nitrogen and the evacuation/fill cycle was repeated once more. The flask was evacuated and then filled with hydrogen using a balloon. The reaction mixture was stirred under a hydrogen atmosphere at room temperature overnight. The flask was evacuated and filled with nitrogen. The reaction mixture was filtered through a pad of Celite and the pad washed with EtOAc. The filtrate was concentrated to give 1.63 g (82%) of compound 20 as a colorless liquid that solidified to a white solid. $^1$HNMR is consistent with that reported in the cited reference. $^1H$ NMR (400 MHz, CDCl$_3$): δ 1.08 (s, 6 H), 1.65 (t, J=6.9 Hz, 4 H), 2.33 (t, J=6.9 Hz, 4 H).

Step 2: 1,1-Dimethylethyl(2E)-3-{4-[(4,4-dimethylcyclohexylidene)(4-hydroxyphenyl)methyl]phenyl}-2-propenoate (21)

To a three-neck round-bottomed flask equipped with two nitrogen inlets, reflux condenser, rubber septum, and magnetic stir bar were added zinc powder (0.53 g, 8.1 mmol) and THF (15 mL). To the stirred suspension was slowly added TiCl$_4$ via syringe at room temperature under a nitrogen atmosphere (Note: significant fuming occurred upon addition of TiCl$_4$). The reaction mixture was heated at reflux for 2 h. To the refluxing reaction mixture was added a solution of 4,4-dimethylcyclohexanone (20) (0.447 g, 3.54 mmol) and (4-bromophenyl)(4-hydroxyphenyl)methanone (2) (0.314 g, 1.13 mmol) in THF (15 mL). The reaction mixture was heated at reflux with stirring under a nitrogen atmosphere for 2 h. The reaction mixture was allowed to cool to room temperature. To the stirred reaction mixture was added water (8 mL) followed by 10% aqueous K$_2$CO$_3$ (8 mL). The mixture was filtered through a pad of Celite. The pad washed with EtOAc. The filtrate was transferred to a separatory funnel and washed with water. The organic phase was separated, washed with brine, dried over MgSO$_4$, filtered, and the filtrate was concentrated to give a pale tan solid. The intermediate aryl bromide was partially purified by flash chromatography on silica gel with hexanes:EtOAc (100:0 to 3:1) to give 0.381 g of impure 4-[(4-bromophenyl)(4,4-dimethylcyclohexylidene)methyl]phenol as an oil. To the impure intermediate aryl bromide (0.37 g) were added tert-butyl acrylate (0.60 mL, 0.525 g, 4.1 mmol), Pd(OAc)$_2$ (0.067 g, 0.30 mmol), Et$_3$N (0.84 mL, 0.61 g, 6.03 mmol), P(o-tolyl)$_3$ (0.134 g, 0.44 mmol) and CH$_3$CN (15 mL). The stirred reaction mixture was heated overnight at 85° C. under a nitrogen atmosphere. The reaction mixture was allowed to cool to room temperature and transferred to a separatory funnel. The reaction mixture was partitioned between EtOAc and H$_2$O. The layers were separated and the organic phase was dried (MgSO$_4$) and filtered. Silica gel was added to the filtrate and the solvent was removed in vacuo. The crude product was purified by flash chromatography on silica gel with hexanes:EtOAc (100:0 to 1:1) as eluant to give 0.24 g (51% from (4-bromophenyl)(4-hydroxyphenyl) methanone) of compound 21 as an oil. $^1H$ NMR (400 MHz, DMSO-$d_6$): δ 0.93 (s, 6 H), 1.31 (m, 4 H), 1.45 (s, 9 H), 2.16 (m, 4 H), 6.43 (d, J=15.9 Hz, 1 H), 6.65 (d, J=8.4 Hz, 2 H), 6.84 (d, J=8.4 Hz, 2 H), 7.05 (d, J=8.2 Hz, 2 H), 7.48 (d, J=15.9 Hz, 1 H), 7.57 (d, J=8.1 Hz, 2 H), 9.32 (s, 1H). LRMS (ESI) m/z 417 (M−H)$^-$.

Step 3: (2E)-3-{4-[(4,4-Dimethylcyclohexylidene)(4-hydroxyphenyl)methyl]phenyl}-2-propenoic acid (22)

To a stirred solution of 1,1-dimethylethyl(2E)-3-{4-[(4,4-dimethylcyclohexylidene)(4-hydroxyphenyl)methyl]phenyl}-2-propenoate (21) (0.24 g, 0.57 mmol) in CH$_2$Cl$_2$ (5 mL) was added trifluoroacetic acid (4 mL) at room temperature under a nitrogen atmosphere. The reaction mixture was stirred for 1 h and concentrated in vacuo to give an oil. The oil was dissolved in CH$_2$Cl$_2$ and the solvent was removed in vacuo to give a solid which was dried under vacuum at 90° C. to give 0.170 g (82%) of compound 22 as a pale tan solid. $^1H$ NMR (400 MHz, DMSO-$d_6$): δ 0.93 (s, 6 H), 1.31 (m, 4 H), 2.16 (m, 4 H), 6.44 (d, J=15.9 Hz, 1 H), 6.65 (d, J=8.4 Hz, 2 H), 6.84 (d, J=8.3 Hz, 2 H), 7.05 (d, J=7.9 Hz, 2 H), 7.52 (d, J=15.9 Hz, 1 H), 7.57 (d, J=8.1 Hz, 2 H), 9.32 (s, 1 H), 12.33 (br s, 1 H). The compound was silated prior to EI analysis. HRMS (EI) Calcd for C$_{30}$H$_{42}$O$_3$Si$_2$: 506.2673 (M$^+$). Found: 506.2669.

Example 10 (26)

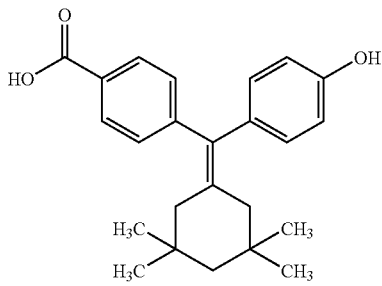

Step 1: Methyl 4-{[4-(methyloxy)phenyl]carbonyl}benzoate (23)

To a 3-necked round-bottomed flask equipped with a magnetic stir bar were added anisole (31 mL, 30.8 g, 0.285 mol.) and terephthalic acid monomethyl ester chloride (19.6 g, 0.099 mol.). The flask was equipped with a powder addition funnel and nitrogen inlet. The powder addition funnel was charged with $AlCl_3$ (40.2 g, 0.301 mol.). The reaction mixture was cooled in an ice-water bath and the $AlCl_3$ was added slowly, portionwise with stirring, under a nitrogen atmosphere. The ice-water bath was removed and the stirred reaction mixture was allowed to warm to room temperature for 3.5 h. The viscous reaction mixture was cooled in an ice-water bath and ice was added very slowly portionwise (Note: significant HCl was released upon addition of ice) followed by the slow addition of ice-water. The reaction mixture solidified upon quenching. The solid was filtered, washed with water, and allowed to stand overnight at RT. The solid washed with water and triturated with hexanes (2×) to give a pink solid. The crude product was recrystallized from EtOAc to give a white solid. The solid was dried to give 16.0 g (60%) of compound 23 as a white solid. $^1$H NMR (400 MHz, DMSO-$d_6$): δ 3.84 (s, 3 H), 3.88 (s, 3 H), 7.08 (d, J=8.8 Hz, 2 H), 7.74 (d, J=8.8 Hz, 2 H), 7.77 (d, J=8.3 Hz, 2 H), 8.08 (d, J=8.3 Hz, 2 H).

Step 2: Methyl 4-[(4-hydroxyphenyl)carbonyl]benzoate (24)

To a 3-necked round-bottomed flask was added $AlCl_3$ (32 g, 0.24 mol.) followed by anhydrous toluene (250 mL). The flask was equipped with a reflux condenser and nitrogen inlet and the suspension was stirred at RT under a nitrogen atmosphere. To the stirred suspension was added methyl 4-{[4-(methyloxy)phenyl]carbonyl}benzoate (23) (16.0 g, 0.059 mol.) portionwise at RT under a nitrogen atmosphere. The reaction mixture was heated at 85° C. with stirring under a nitrogen atmosphere. After 2 h, the oil bath was removed and the reaction mixture was allowed to cool at RT. The reaction mixture was cooled in an ice-water bath and ice was added very slowly portionwise (Note: significant HCl evolved upon addition of ice to the reaction mixture.) followed by the slow addition of ice-water. The reaction mixture was partitioned between EtOAc and water. The organic phase washed with brine, dried over $MgSO_4$, filtered, and the filtrate was concentrated to give the crude product as a red-brown solid. The crude product was triturated with hot hexanes and the brown solid was filtered to give 14.0 g (93%) of compound 24. $^1$H NMR (400 MHz, DMSO-$d_6$): δ 3.88 (s, 3 H), 6.88 (d, J=8.6 Hz, 2 H), 7.65 (d, J=8.7 Hz, 2 H), 7.74 (d, J=8.2 Hz, 2 H), 8.07 (d, J=8.2 Hz, 2 H), 10.51 (s, 1 H).

Step 3: Methyl 4-[(4-hydroxyphenyl)(3,3,5,5-tetramethylcyclohexylidene)methyl]benzoate (25)

To a 1 L 3-necked round-bottomed flask equipped with a reflux condenser, magnetic stir bar, and two nitrogen inlets, was added zinc powder (14.3 g, 219 mmoL) followed by anhydrous THF (200 mL). The suspension was stirred at RT under a nitrogen atmosphere and $TiCl_4$ (12 mL, 20.8 g, 109 mmoL) was added slowly via syringe. (Note: the reaction mixture fumed and warmed during addition of $TiCl_4$) The stirred reaction mixture was heated at reflux under a nitrogen atmosphere. After 2 h, the oil bath was removed and the reaction was allowed to stand at RT for 10 min. The flask was equipped with an addition funnel which was charged with a solution of 3,3,5,5-tetramethylcyclohexanone (15 mL, 13.2 g, 85.7 mmoL) and methyl 4-[(4-hydroxyphenyl)carbonyl]benzoate (24) (7.0 g, 27.3 mmoL) in anhydrous THF (150 mL). The flask was placed in the oil bath and the solution of 3,3,5,5-tetramethylcyclohexanone and methyl 4-[(4-hydroxyphenyl)carbonyl]benzoate was added to the reaction mixture. The reaction mixture was heated at reflux for 1.75 h. The oil bath was removed and the reaction mixture was allowed to stand at RT for 90 min. The reaction mixture was cooled in an ice-water bath and water (75 mL) was slowly added via an addition funnel followed by 10% aqueous $K_2CO_3$ (75 mL). The quenched reaction mixture was filtered through a pad of Celite and the pad was washed with EtOAc. The filtrate was partitioned between EtOAc and water. The organic phase washed with water followed by brine, dried over $MgSO_4$, filtered, and the filtrate was concentrated to give the crude product as an orange liquid. The crude product was purified by flash chromatography on silica gel with hexanes:EtOAc (100:0 to 95:5 to 90:10) to give 8.09 g (78%) of compound 25 as an off-white solid. $^1$H NMR (400 MHz, DMSO-$d_6$): δ 0.85 (s, 6 H), 0.88 (s, 6 H), 1.24 (s, 2 H), 1.84 (s, 2 H), 1.92 (s, 2 H), 3.80 (s, 3 H), 6.66 (d, J=8.4 Hz, 2 H), 6.93 (d, J=8.5 Hz, 2 H), 7.25 (d, J=8.2 Hz, 2 H), 7.86 (d, J=8.3 Hz, 2 H), 9.31 (s, 1H). LRMS (ESI) m/z 377 (M−H)$^-$.

Step 4: 4-[(4-Hydroxyphenyl)(3,3,5,5-tetramethylcyclohexylidene)methyl]benzoic acid (26)

To a round-bottomed flask was added methyl 4-[(4-hydroxyphenyl)(3,3,5,5-tetramethylcyclohexylidene)methyl]benzoate (25) (8.06 g, 21 mmoL), EtOH (100 mL), and THF (100 mL). To the solution was added 1 N aqueous NaOH (200 mL). The reaction mixture was stirred at 65° C. under a nitrogen atmosphere for 3 h. The reaction mixture was partially concentrated in vacuo to remove the EtOH and THF. The aqueous mixture was cooled in an ice-water bath and 1 N aqueous HCl was slowly added to pH ~1. The acidic aqueous suspension was extracted with $CH_2Cl_2$ (1×) followed by EtOAc (3×). Those EtOAc extracts that contained the majority of product, as indicated by TLC, were independently washed with brine, combined, dried over $MgSO_4$, filtered, and the filtrate was concentrated to give 6.0 g of the crude product as a pale tan solid. The $CH_2Cl_2$ extract noted above was concentrated to give 1.9 g of the crude product as an off-white solid. The two crops of crude product were combined and purified by flash chromatography on silica gel with $CH_2Cl_2$:MeOH (95:5) to give 6.07 g (79%) of compound 26 as a white solid. A portion of the product was dried under vacuum at 90° C. to give the following $^1$H NMR data. $^1$H NMR (400 MHz, DMSO-$d_6$): δ 0.86 (s, 6 H), 0.88 (s, 6 H), 1.24 (s, 2 H), 1.85 (s, 2 H), 1.92 (s, 2 H), 6.66 (d, J=8.5 Hz, 2 H), 6.93 (d, J=8.4 Hz, 2 H), 7.22 (d, J=8.3 Hz, 2 H), 7.84 (d, J=8.3 Hz, 2 H), 9.30 (s, 2 H), 12.78 (br s, 1 H). The compound was silylated prior to EI analysis. HRMS (EI) Calcd for $C_{30}H_{44}O_3Si_2$: 508.2829 (M+). Found: 508.2833.

Example 11 (31)

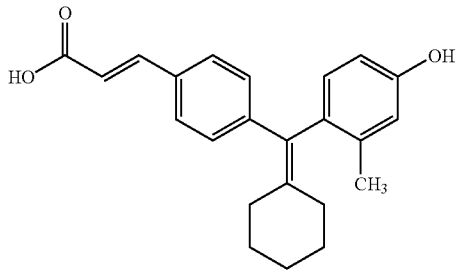

Step 1: (4-Bromophenyl)[2-methyl-4-(methyloxy) phenyl]methanone (27)

To a mixture of 4-bromobenzoyl chloride (1.12 g, 5.12 mmol) and 3-methyl anisole (1.95 mL, 15.47 mmol) at 0° C. was added $AlCl_3$ (0.83 g, 6.20 mmol). The mixture was allowed to warm to RT over 12 h with stirring. Water was added slowly, and the mixture was extracted with $CH_2Cl_2$. The organics were dried with $MgSO_4$ and concentrated. The crude material was purified by chromatography on silica gel (EtOAc:hexanes) to yield 1.14 g (73%) of compound 27. $^1$H NMR (400 MHz, $CDCl_3$): δ 2.41 (s, 3H), 3.86 (s, 3H), 6.74 (dd, J=2.5 Hz, 8.6 Hz, 1H), 6.82 (d, J=2.6 Hz, 1H), 7.31 (d, J=8.6 Hz, 1H), 7.58 (d, J=8.5 Hz, 2H), 7.62 (d, J=8.5 Hz, 2H).

Step 2: (4-Bromophenyl)(4-hydroxy-2-methylphenyl)methanone (28)

To a solution of (4-bromophenyl)[2-methyl-4-(methyloxy) phenyl]methanone (27) (1.12 g, 3.67 mmoL) in benzene (25 mL) was added $AlCl_3$ (1.98 g, 14.85 mmol). The mixture was heated at 90° C. for 3 h. Upon cooling, water (25 mL) was added, and the mixture was extracted with $Et_2O$. The organics were dried with $MgSO_4$ and concentrated. The crude material was purified by chromatography on silica gel (EtOAc:hexanes) to yield 1.32 g (86%) of compound 28. $^1$H NMR (400 MHz, DMSO-$d_6$): δ 2.26 (s, 3H), 6.63 (dd, J=2.4 Hz, 8.4 Hz, 1H), 6.72 (d, J=2.2 Hz, 1H), 7.18 (d, J=8.4 Hz, 1H), 7.55 (d, J=8.4 Hz, 2H), 7.70 (d, J=8.4 Hz, 2H), 10.10 (s, 1H).

Step 3: 4-[(4-Bromophenyl)(cyclohexylidene)methyl]-3-methylphenol (29)

To a slurry of zinc powder (1.15 g, 17.59 mmol) in THF (10 mL) was added $TiCl_4$ (0.90 mL, 8.21 mmol) dropwise. The mixture was heated at reflux for 1 h. A mixture of cyclohexanone (0.64 mL, 6.17 mmol) and (4-bromophenyl)(4-hydroxy-2-methylphenyl)methanone (28) (0.60 g, 2.06 mmol) in THF (10 mL) was added dropwise and continued to stir at reflux for 20 min. Upon cooling, the reaction mixture was poured into a 10% aqueous $K_2CO_3$ solution. The quenched reaction mixture was filtered through a pad of Celite and the pad washed with EtOAc. The filtrate was dried over $MgSO_4$, filtered, and concentrated to yield 0.60 g (81%) of the compound 29. $^1$H NMR (400 MHz, $CDCl_3$): δ 1.50-1.63 (m, 6H), 1.96-2.01 (m, 2H), 2.05 (s, 3H), 2.27-2.28 (m, 2H), 4.54 (s, 1H), 6.60-6.62 (m, 2H), 6.93-6.95 (m, 1H), 6.98 (d, J=8.4 Hz, 2H), 7.35 (d, J=8.4 Hz, 2H).

Step 4: Ethyl(2E)-3-{4-[cyclohexylidene(4-hydroxy-2-methylphenyl)methyl]phenyl}-2-propenoate (30)

To a solution of 4-[(4-bromophenyl)(cyclohexylidene)methyl]-3-methylphenol (29) (0.60 g, 1.68 mmol) in DMF (6 mL) was added ethyl acrylate (0.54 mL, 4.98 mmol), P(o-tolyl)$_3$ (0.056 g, 0.184 mmol), $Et_3N$ (0.70 mL, 5.02 mmol), and $Pd(OAc)_2$ (0.023 g, 0.10 mmol). The mixture was heated at 140° C. for 30 min in a microwave. Upon cooling, water (25 mL) was added, and the mixture was extracted with $Et_2O$ (3×20 mL). The organics were combined, dried ($MgSO_4$), and concentrated. The crude material was purified by chromatography on silica gel (EtOAc:hexanes) to yield 0.13 g, (60%) of compound 30. $^1$H NMR (400 MHz, $CDCl_3$): δ 1.32 (t, J=7.1 Hz, 3H), 1.52-1.61 (m, 6H), 1.98-2.01 (m, 2H), 2.06 (s, 3H), 2.32 (m, 2H), 4.24 (q, J=7.1 Hz, 2H), 4.78 (s, 1H), 6.36 (d, J=16.1 Hz, 1H), 6.62-6.63 (m, 2H), 6.96 (m, 1H), 7.13 (d, J=8.2 Hz, 2H), 7.39 (d, J=8.2 Hz, 2H), 7.63 (d, J=15.9 Hz, 1H).

Step 5: (2E)-3-{4-[Cyclohexylidene(4-hydroxy-2-methylphenyl)methyl]phenyl}-2-propenoic acid (31)

To a solution of ethyl(2E)-3-{4-[cyclohexylidene(4-hydroxy-2-methylphenyl)methyl]phenyl}-2-propenoate (30) (0.42 g, 1.11 mmol) in a mixture of EtOH/THF (1 mL, 4 mL) was added an aqueous solution of 5M NaOH (1.4 mL, 7.00 mmol). The mixture was stirred at 85° C. for 4 h. Upon cooling, the mixture was acidified to pH=2 with an aqueous solution of 5 M HCl. The mixture was extracted with EtOAc (1×20 mL). The organics were washed with water and brine (1×10 mL each) and dried with $MgSO_4$. Concentration yielded 0.39 g (100%) of compound 31. $^1$H NMR (400 MHz, DMSO-$d_6$): δ 1.46-1.58 (m, 6H), 1.91-1.96 (m, 2H), 1.97 (s, 3H), 2.22-2.26 (m, 2H), 6.43 (d, J=16.1 Hz, 1H), 6.53 (m, 2H), 6.83-6.85 (m, 1H), 7.08 (d, J=8.1 Hz, 2H), 7.50 (d, J=16.2 Hz, 1H), 7.55 (d, J=8.1 Hz, 2H), 9.16 (s, 1H), 12.32 (s, 1H). LCMS (ESI): m/z 349 (M+H)+.

Example 12 (35)

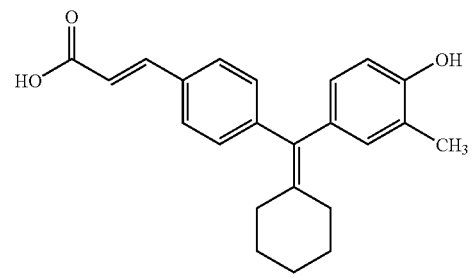

Step 1: (4-Bromophenyl)(4-hydroxy-3-methylphenyl)methanone (32)

To a solution of 4-bromobenzoyl chloride (1.04 g, 4.74 mmol) and o-cresol (0.58 g, 5.33 mmol) in $CH_2Cl_2$ (20 mL)

was added AlCl$_3$ (0.76 g, 5.72 mmol) portion-wise. The mixture was allowed to warm to RT over 12 h. Water was added, and the mixture was extracted with CH$_2$Cl$_2$. The organics were dried with MgSO$_4$ and concentrated. The crude material was purified by chromatography on silica gel (EtOAc:hexanes) to yield 0.21 g (15%) of compound 32. $^1$H NMR (400 MHz, DMSO-d$_6$): δ 2.15 (s, 3H), 6.89 (d, J=8.3 Hz, 1H), 7.46 (dd, J=2.2 Hz, 8.4 Hz, 1H), 7.54 (d, J=1.9 Hz, 1H), 7.58 (d, 2H), 7.72 (d, 2H), 10.42 (s, 1H).

Step 2: 4-[(4-Bromophenyl)(cyclohexylidene)methyl]-2-methylphenol (33)

The title compound (33) (0.21 g, 82%) was obtained from 32 in a similar manner previously reported for compound 29. $^1$H NMR (400 MHz, CDCl$_3$): δ 1.56-1.62 (m, 6H), 2.18 (s, 3H), 2.21-2.24 (m, 4H), 4.71 (s, 1H), 6.67 (d, J=7.7, 1H), 6.80 (d, J=7.9 Hz, 2H), 6.97 (d, J=8.2 Hz, 2H), 7.37 (d, J=8.4 Hz, 2H).

Step 3: Ethyl(2E)-3-{4-[cyclohexylidene(4-hydroxy-3-methylphenyl)methyl]phenyl}-2-propenoate (34)

The title compound (34) (0.13 g, 60%) was obtained from 33 in a similar manner previously reported for compound 30. $^1$H NMR (400 MHz, CDCl$_3$): δ 1.32 (t, J=7.1 Hz, 3H), 1.57 (m, 6H), 2.19 (s, 3H), 2.22-2.25 (m, 4H), 4.25 (q, J=7.1 Hz, 2H), 4.60 (s, 1H), 6.38 (d, J=16.1 Hz, 1H), 6.68 (d, J=7.9 Hz, 1H), 6.81 (m, 1H), 6.83 (s, 1H), 7.12 (d, J=8.1 Hz, 2H), 7.42 (d, J=8.1 Hz, 2H), 7.65 (d, J=15.9 Hz, 1H).

Step 4: (2E)-3-{4-[cyclohexylidene(4-hydroxy-3-methylphenyl)methyl]phenyl}-2-propenoic acid (35)

The title compound (35) (0.11 g, 96%) was obtained from 34 in a similar manner previously reported for compound 31. $^1$H NMR (400 MHz, DMSO-d$_6$): δ 1.52 (m, 6H), 2.02 (s, 3H), 2.12-2.15 (m, 4H), 6.44 (d, J=16.1 Hz, 1H), 6.67-6.71 (m, 3H), 7.05 (d, J=8.2 Hz, 2H), 7.52 (d, J=16.1 Hz, 1H), 7.56 (d, J=8.2 Hz, 2H), 9.20 (s, 1H), 12.32 (s, 1H). LRMS (APCI): m/z 349 (M+H)$^+$.

Example 13 (38)

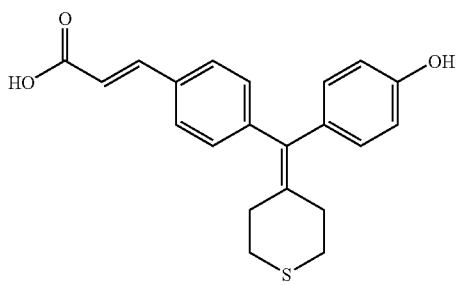

Step 1: 4-[(4-Bromophenyl)(tetrahydro-4H-thiopyran-4-ylidene)methyl]phenol (36)

In a 3-neck round-bottomed flask equipped with a condenser and a nitrogen inlet, TiCl$_4$ (0.51 mL, 4.67 mmol) was slowly added to a suspension of zinc powder (0.63 g, 9.60 mmol) in anhydrous THF (13 mL) at room temperature. The reaction was heated at reflux for 2.5 h. The reaction was taken out of the oil bath then a solution of (4-bromophenyl)(4-hydroxyphenyl)methanone (2)(0.35 g, 1.26 mmol) and tetrahydrothiopyran-4-one (0.44 g, 3.79 mmol) in anhydrous THF (13 mL) was added and the reaction mixture was heated at reflux for 2 h. The reaction mixture was cooled to room temperature and water (10 mL) added, via syringe, followed by addition of 10% aqueous K$_2$CO$_3$ (10 mL). The reaction mixture was filtered through a pad of Celite and the pad washed with EtOAc. The filtrate was transferred to a separatory funnel and the layers were separated. The organic layer washed with brine, dried (MgSO$_4$), filtered, and the filtrate was concentrated to give an oil. The crude product was purified by flash column chromatography on silica gel using a hexanes:EtOAc gradient (100:0 to 75:25) to give compound 36 as a white powder (0.323 g, 71%). $^1$H NMR (400 MHz, DMSO-d$_6$): δ 2.38-2.41 (m, 2H), 2.45-2.47 (m, 2H), 2.62-2.66 (m, 4H), 6.67 (d, J=8.5 Hz, 2H), 6.86 (d, J=8.5 Hz, 2H), 7.01 (d, J=8.2 Hz, 2H), 7.47 (d, J=8.3 Hz, 2H), 9.39 (s, 1H).

Step 2: 1,1-Dimethylethyl(2E)-3-{4-[(4-hydroxyphenyl)(tetrahydro-4H-thiopyran-4-ylidene)methyl]phenyl}-2-propenoate (37)

Reagents 36 (0.32 g, 0.886 mmol), t-butyl acrylate (0.78 mL, 5.31 mmol), Pd(OAc)$_2$ (0.042 g, 0.186 mmol), P(o-tolyl)$_3$ (0.12 g, 0.381 mmol) and Et$_3$N (0.74 mL, 5.31 mmol) were added to a flask containing CH$_3$CN (13 mL) and the reaction mixture was heated at 85° C. for 24 h. The reaction mixture was allowed to cool at RT and partitioned between water and EtOAc. The organic layer was separated, washed with brine, dried (MgSO$_4$), filtered, and the filtrate was concentrated to give the crude product. The crude product was purified by flash column chromatography on silica gel using a hexanes:EtOAc gradient (100:0 to 50:50) to give compound 37 as a yellow foam. $^1$H NMR (400 MHz, DMSO-d$_6$): δ 1.46 (s, 9H), 2.65-2.66 (m, 5H), 6.45 (d, J=16 Hz, 1H), 6.68 (d, J=8.4 Hz, 2H), 6.87 (d, J=8.5 Hz, 2H), 7.09 (d, J=8.1 Hz, 2H), 7.49 (d, J=16.1 Hz, 1H), 7.60 (d, J=8.1 Hz, 2H), 9.37 (s, 1H).

Step 3: (2E)-3-{4-[(4-Hydroxyphenyl)(tetrahydro-4H-thiopyran-4-ylidene)methyl]phenyl}-2-propenoic acid (38)

To an ice-cooled solution of 37 (0.16 g, 0.392 mmol) in dry CH$_2$Cl$_2$ (2 mL) was added TFA (2 mL) slowly. After stirring at 0° C. for 3 h, the reaction mixture was concentrated to give a yellow solid. The crude product was purified by flash column chromatography on silica gel using a CH$_2$Cl$_2$:MeOH gradient (100:0 to 0:100) to give compound 38 a yellow foam (0.074 g, 54%). $^1$H NMR (400 MHz, DMSO-d$_6$): δ 2.42-2.46 (m, 4H), 2.63-2.66 (m, 4H), 6.46 (d, J=16 Hz, 1H), 6.68 (d, J=8.4 Hz, 2H), 6.87 (d, J=8.5 Hz, 2H), 7.09 (d, J=8.2 Hz, 2H), 7.53 (d, J=15.9 Hz, 1H), 7.59 (d, J=8.2 Hz, 2H), 9.39 (s, 1H), 12.38 (s, 1H). LRMS (ESI) m/z 353 (M+H)$^+$. HRMS (ESI) Calcd for C$_{21}$H$_{21}$O$_3$S: 353.1211 (M+H)$^+$. Found: 353.1208.

Example 14 (40)

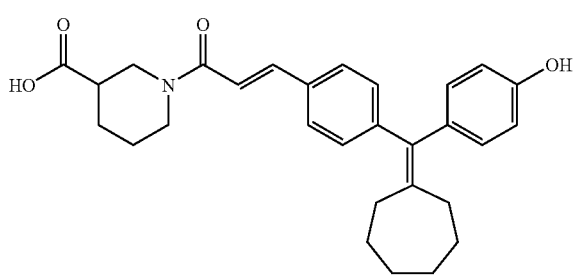

Step 1: (2E)-3-{4-[Cycloheptylidene(4-hydroxyphenyl)methyl]phenyl}-2-propenoyl chloride (39)

To a mixture of (2E)-3-{4-[cycloheptylidene(4-hydroxyphenyl)methyl]phenyl}-2-propenoic acid (11) (0.3 g, 0.861 mmol) and dry CH$_2$Cl$_2$ (5 mL) was added oxalyl chloride (0.15 mL, 1.72 mmol) slowly, followed by DMF (2 drops). The reaction mixture became a clear solution immediately after the addition of DMF. The reaction mixture was stirred at room temperature for 2 h under nitrogen. The reaction mixture was concentrated to give 39 as an oily residue that was used without further purification. $^1$H NMR (400 MHz, DMSO-d$_6$): δ 1.53 (s, 8H), 2.21-2.25 (m, 4H), 6.48 (d, J=16 Hz, 1H), 7.19 (d, J=8.1 Hz, 2H), 7.33 (d, J=8.8 Hz, 2H), 7.45 (d, J=8.6 Hz, 2H), 7.54 (d, J=16 Hz, 1H), 7.62 (d, J=8.1 Hz, 2H), 9.35 (s, 1H).

Step 2: 1-((2E)-3-{4-[Cycloheptylidene(4-hydroxyphenyl)methyl]phenyl}-2-propenoyl)-3-piperidinecarboxylic acid (40)

To a solution of nipecotic acid (0.058 g, 0.450 mmol) in water (0.5 mL) was added triethylamine (0.125 mL, 0.899 mmol) followed by the slow addition of a solution of 39 (0.15 g, 0.409 mmol) in THF (3 mL). The reaction mixture was allowed to stir at RT for 24 h. To the reaction mixture was added 1 N HCl to pH of ~1. The acidic reaction mixture was extracted with EtOAc. The organic extract washed with brine, dried (Na$_2$SO$_4$), filtered, and the filtrate was concentrated to yield an oily residue. The crude material was purified by reverse phase preparative HPLC using a C18 column and a CH$_3$CN:H$_2$O gradient (10:90 to 100:0) with 0.05% TFA as a modifier to give compound 40 as a white powder (87 mg, 47%). $^1$H NMR (400 MHz, DMSO-d$_6$): δ 1.40-1.47 (m, 1H), 1.57 (s, 8H), 1.66-1.73 (m, 2H), 1.96-1.98 (m, 1H), 2.24-2.30 (m, 4H), 2.39-2.44 (m, 1H), 3.14-3.21 (m, 2H), 3.92-3.95 (m, 1H), 4.18-4.22 (m, 1H), 6.69 (d, J=8.3 Hz, 2H), 6.93 (d, J=8.3 Hz, 2H), 7.04 (d, J=15.3 Hz, 1H), 7.13 (d, J=8 Hz, 2H), 7.39 (d, J=15.5 Hz, 1H), 7.52 (d, J=8.1 Hz, 2H), 8.79 (s, 1H). HRMS (ESI) Calcd for C$_{29}$H$_{34}$NO$_4$: 460.2488 (M+H)$^+$. Found: 460.2490.

Example 15 (41)

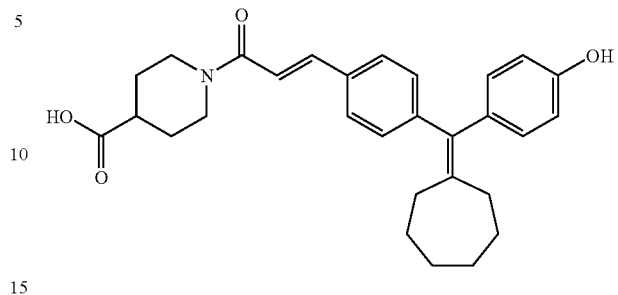

Step 1: 1-((2E)-3-{4-[Cycloheptylidene(4-hydroxyphenyl)methyl]phenyl}-2-propenoyl)-4-piperidinecarboxylic acid (41)

To a solution of isonipecotic acid (0.057 g, 0.44 mmol) in water (0.5 mL) was added Et$_3$N (0.12 mL, 2.2 eq) followed by a solution of 39 (0.147 g, 0.399 mmol) in dry THF (3 mL). The reaction mixture was stirred at RT under nitrogen for 24 h. Isonipecotic acid (1.1 eq, 0.44 mmol) was added and the reaction mixture was stirred at RT for 24 h. The reaction mixture was heated at 45° C. for 1.3 h and then heated at 55° C. for 24 h. The reaction mixture was allowed to cool at RT. To the reaction mixture was added 1 N HCl to pH of ~1. The acidic reaction mixture was extracted with EtOAc. The organic layer washed with brine, dried (Na$_2$SO$_4$), filtered, and the filtrate was concentrated. The crude product was purified by preparative reverse phase HPLC using a C18 column and a CH$_3$CN:H$_2$O gradient (10:90 to 100:0) with 0.05% TFA as a modifier to give compound 41 as a powder (0.018 g, 10%). $^1$H NMR (400 MHz, DMSO-d$_6$): δ 1.51 (s, 9H), 1.82-1.85 (m, 2H), 2.19-2.23 (m, 4H), 2.78-2.81 (m, 1H), 3.13-3.16 (m, 1H), 4.12-4.15 (m, 1H), 4.25-4.28 (m, 1H), 6.65 (d, J=8.4 Hz, 2H), 6.90 (d, J=8.4 Hz, 2H), 7.09 (d, J=8.1 Hz, 2H), 7.17 (d, J=15.4 Hz, 1H), 7.40 (d, J=15.4 Hz, 1H), 7.59 (d, J=8.2 Hz, 2H), 9.28 (s, 1H), 12.24 (d, 1H). HRMS (ESI) Calcd for C$_{29}$H$_{34}$NO$_4$: 460.2488 (M+H)$^+$. Found: 460.2497.

Example 16 (42)

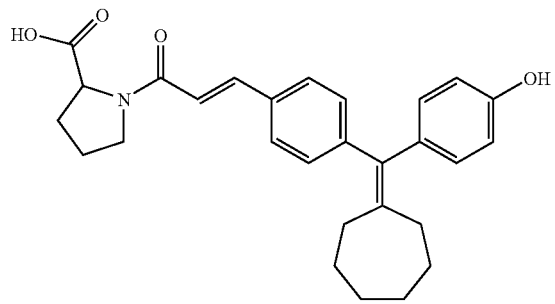

Step 1: 1-((2E)-3-{4-[Cycloheptylidene(4-hydroxyphenyl)methyl]phenyl}-2-propenoyl)proline (42)

To a solution of L-proline (0.051 g, 0.44 mmol) in water (0.5 mL) was added Et$_3$N (0.12 mL, 2.2 eq) followed by a solution of 39 (0.147 g, 0.399 mmol) in dry THF (3 mL). The reaction mixture was stirred at RT under nitrogen for 24 h. L-proline (0.44 mmol, 1.1 eq,) was added and the reaction mixture was allowed to stir for another 24 h. The reaction mixture was heated at 45° C. for 1.3 h and then heated at 55° C. for 24 h. The reaction mixture was allowed to cool to room temperature. To the reaction mixture was added 1 N HCl to a pH of ~1. The acidic reaction mixture was extracted with EtOAc. The organic layer was separated, washed with brine, dried ($Na_2SO_4$), filtered, and the filtrate was concentrated. The crude product was purified preparative reverse phase HPLC using a C18 column and a $CH_3CN:H_2O$ gradient (10:90 to 100:0) and 0.05% TFA as a modifier to give a powder (0.052 g, 30%). $^1$H NMR (400 MHz, DMSO-$d_6$): δ 1.56 (s, 8H), 1.92 (s, 3H), 2.21-2.29 (m, 5H), 3.64 (s, 3H), 4.48 (s, 1H), 6.69 (d, J=8.6 Hz, 2H), 6.81 (br, 1H), 6.93 (d, J=8.5 Hz, 2H), 7.14 (d, J=8.2 Hz, 2H), 7.42 (d, J=15.4 Hz, 1H), 7.50 (d, J=7.9 Hz, 2H). HRMS (ESI) Calcd for $C_{28}H_{32}NO_4$: 446.2331 (M+H)$^+$. Found: 446.2321

Example 17 (45)

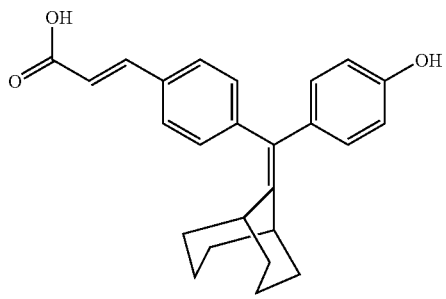

Step 1: 4-[Bicyclo[3.3.1]non-9-ylidene(4-bromophenyl)methyl]phenol (43)

In a 3-neck round-bottomed flask equipped with a reflux condenser and a nitrogen inlet, $TiCl_4$ (0.51 mL, 4.67 mmol) was slowly added to a suspension of zinc powder (0.63 g, 9.60 mmol) in dry THF (13 mL) at room temperature. The reaction mixture was heated at reflux for 2.5 h. The reaction mixture was taken out of the oil bath and a solution of (4-bromophenyl)(4-hydroxyphenyl)methanone (2) (0.35 g, 1.26 mmol) and bicyclo[3.3.1]nonan-9-one (0.52 g, 3.79 mmol) in dry THF (13 mL) was added. The reaction mixture was heated at reflux for 2 h. The reaction mixture was allowed to cool at RT. Water (10 mL) was added to the reaction mixture via a syringe followed by 10% $K_2CO_3$ (10 mL). The reaction mixture was filtered through a pad of Celite. The pad of Celite washed with EtOAc. The filtrate was transferred to a separatory funnel and the layers were separated. The organic layer washed with brine, dried (MgSO$_4$), filtered, and the filtrate was concentrated to give an oily residue. The crude product was adsorbed onto silica and purified by flash column chromatography using $SiO_2$ and a hexanes:EtOAc gradient (100:0 to 75:25) to afford compound 43 as a white powder (0.32 g, 67%). $^1$H NMR (400 MHz, DMSO-$d_6$): δ 1.50-1.54 (m, 2H), 1.71-1.73 (m, 8H), 1.93-1.99 (m, 2H), 2.60 (s, 1H), 6.67 (d, J=8.4 Hz, 2H), 6.87 (d, J=8.5 Hz, 2H), 7.02 (d, J=8.5 Hz, 2H), 7.46 (d, J=8.3 Hz, 2H), 9.32 (s, 1H).

Step 2: 1,1-Dimethylethyl(2E)-3-{4-[bicyclo[3.3.1]non-9-ylidene(4-hydroxyphenyl)methyl]phenyl}-2-propenoate (44)

Compound 43 (0.32 g, 0.834 mmol), t-butyl acrylate (0.734 mL, 5.01 mmol), P(o-tolyl)$_3$ (0.11 g, 0.359 mmol), Pd(OAc)$_2$ (0.0394 g, 0.175 mmol) and Et$_3$N (0.7 mL, 5.01 mmol) were added to a flask containing $CH_3CN$ (13 mL) and the stirred reaction mixture was heated at 85° C. for 24 h under a nitrogen atmosphere. The reaction mixture was allowed to cool at RT and then partitioned between water and EtOAc. The layers were separated, and the organic phase washed with brine, dried (MgSO$_4$), filtered, and the filtrate was concentrated to give an oily residue. The crude oil was adsorbed onto silica and purified by flash column chromatography on silica gel with a hexanes:EtOAc gradient (100:0 to 50:50) to give compound 44 as a yellow foam (0.33 g, 92%). $^1$H NMR (400 MHz, DMSO-$d_6$): δ 1.45-1.53 (m, 10H), 1.72-1.73(m, 7H), 1.96-2.01(m, 2H), 2.53-2.64 (m, 4H), 6.42 (d, J=16.1 Hz, 1H), 6.66 (d, J=8.5 Hz, 2H), 6.87 (d, J=8.3 Hz, 2H), 7.08 (d, J=8.1 Hz, 2H), 7.48 (d, J=16.1 Hz, 1H), 7.57 (d, J=8.1 Hz, 2H), 9.30 (s, 1H).

Step 3: (2E)-3-{4-[bicyclo[3.3.1]non-9-ylidene(4-hydroxyphenyl)methyl]phenyl}-2-propenoic acid (45)

To an ice-cooled solution of 44 (0.32 g, 0.755 mmol) in $CH_2Cl_2$ (4 mL) was added TFA (4 mL) slowly. The stirred reaction mixture was allowed to warm to RT over a period of 3 h. The reaction mixture was concentrated to give a yellow solid. The solid was dissolved in toluene, and the solution was concentrated to give a powder. The powder was triturated with $CH_2Cl_2$ and dried to give compound 45 as a tan powder (0.21 g, 74%). $^1$H NMR (400 MHz, DMSO-$d_6$): δ 1.50-1.53 (m, 2H), 1.72 (s, 8H), 1.93-2.01 (m, 2H), 2.53-2.60 (m, 2), 6.43 (d, J=16.1 Hz, 1H), 6.66 (d, J=8.4 Hz, 2H), 6.88 (d, J=8.3 Hz, 2H), 7.09 (d, J=7.8 Hz, 2H), 7.52 (d, J=16.0 Hz, 1H), 7.57 (d, J=8.1 Hz, 2H), 9.30 (s, 1H), 12.33 (s, 1H). The compound was silated prior to EI analysis. HRMS (EI) Calcd for $C_{31}H_{42}O_3Si_2$: 518.2673 (M$^+$). Found: 518.2685.

Example 18 (48)

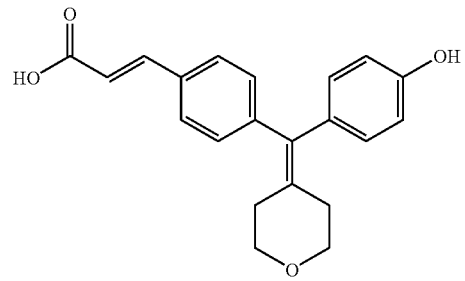

Step 1: 4-[(4-Bromophenyl)(tetrahydro-4H-pyran-4-ylidene)methyl]phenol (46)

Zinc powder (0.759 g, 11.6 mmole) was suspended in THF (13 mL). TiCl$_4$ (0.640 mL, 5.84 mmole) was added dropwise and the resulting mixture was heated to reflux for 60 min. A solution of (4-bromophenyl)(4-hydroxyphenyl)methanone (2) (0.404 g, 1.46 mmole) and tetrahydropyran-4-one (0.405 mL, 4.38 mmole) in THF (2 mL) was added. The resulting mixture was heated to reflux for 2 h, then was allowed to cool to RT. A 10% aqueous solution of $K_2CO_3$ (25 mL) was added and the mixture was filtered through a pad of Celite. The filtrate was separated and the aqueous layer was extracted with EtOAc (2×20 mL). The organics were washed with water (25 mL) and brine (25 mL), then dried ($MgSO_4$) and concentrated. The residue was purified by silica gel chromatography (Isco Sg100c, RediSep 12 g cartridge and a gradient consisting of 10% EtOAc:hexanes for 5 min, 10% to 30% EtOAc:hexanes over 15 min, then 30% EtOAc:hexanes for 5 min) to provide 0.31 g (62%) of compound 46 as a white solid. $^1$H NMR ($CDCl_3$): δ 7.41 (d, J=8.3 Hz, 2H), 6.97 (d, J=8.6 Hz, 2H), 6.95 (d, J=8.6 Hz, 2H), 6.75 (d, J=8.3 Hz, 2H), 4.97 (s, 1H), 3.72 (dd, J=10.0, 5.0 Hz, 4H), 2.40 (t, J=5.0 Hz, 2H), 2.36 (t, J=5.0 Hz, 2H).

Step 2: tert-Butyl (2E)-3-{4-[(4-hydroxyphenyl)(tetrahydro-4H-pyran-4-ylidene)methyl]phenyl}prop-2-enoate (47)

4-[(4-Bromophenyl)(tetrahydro-4H-pyran-4-ylidene)methyl]phenol (L) (0.106 g, 0.307 mmole) was dissolved in DMF (1 mL). tert-Butyl acrylate (0.090 mL, 0.614 mmole), P(o-tolyl)$_3$ (0.0099 g, 0.0325 mmole) and Et$_3$N (0.130 mL, 0.933 mmole) were added followed by Pd(OAc)$_2$ (0.0037 g, 0.0165 mmole). The mixture was heated to 160° C. in a microwave synthesizer for 30 min then was cooled to RT. Water (20 mL) was added and the mixture was extracted with Et$_2$O (3×10 mL). The organics were dried (MgSO$_4$) and concentrated. The residue was purified by silica gel chromatography (Isco Sg100c, RediSep 12 g cartridge, 15% EtOAc:hexanes for 5 min, 15% to 40% EtOAc:hexanes over 15 min, 40% EtOAc:hexanes for 5 min to yield 0.071 g (59%) of 47 as a white solid. $^1$H NMR (CDCl$_3$): δ 7.55 (d, J=16.0 Hz, 1H), 7.41 (d, J=8.1 Hz, 2H), 7.10 (d, J=8.1 Hz, 2H), 6.97 (d, J=8.5 Hz, 2H), 6.76 (d, J=8.5 Hz, 2H), 6.32 (d, J=16.0 Hz, 1H), 5.01 (s, 1H), 3.74 (m, 4H), 2.40 (dd, J=11.1, 5.6 Hz, 4H), 1.53 (s, 9H).

Step 3: (2E)-3-{4-[(4-hydroxyphenyl)(tetrahydro-4H-pyran-4-ylidene)methyl]phenyl}prop-2-enoic acid (48)

tert-Butyl (2E)-3-{4-[(4-hydroxyphenyl)(tetrahydro-4H-pyran-4-ylidene)methyl]phenyl}prop-2-enoate (47) (0.071 g, 0.182 mmol) was dissolved in CH$_2$Cl$_2$ (1 mL) and TFA (1 mL). The solution was stirred at RT for 4 h, then was concentrated. The residue was recrystallized from EtOAc to provide 0.020 g (33%) of compound 48 as a tan solid. $^1$H NMR (DMSO-d$_6$): δ 12.34 (s, 1H), 9.37 (s, 1H), 7.58 (d, J=8.2 Hz, 2H), 7.53 (d, J=16.0 Hz, 1H), 7.07 (d, J=8.2 Hz, 2H), 6.85 (d, J=8.4 Hz, 2H), 6.67 (d, J=8.4 Hz, 2H), 6.45 (d, J=16.0 Hz, 1H), 3.59 (m, 4H), 2.25 (m, 4H). LRMS (ESI): m/z 335 (M−H)$^-$.

Example 19 (51)

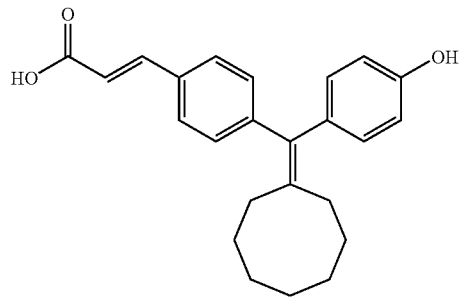

Step 1:
4-[(4-Bromophenyl)cyclooctylidene)methyl]phenol (49)

Following the procedure described for compound 46, zinc powder (0.764 g, 11.7 mmole), TiCl$_4$ (0.640 mL, 5.84 mmole), (4-bromophenyl)(4-hydroxyphenyl)methanone (2) (0.404 g, 1.46 mmole) and cyclooctanone (0.580 mL, 4.40 mmole), yielded 332 mg (61%) of compound 49 as a white solid. $^1$H NMR (CDCl$_3$): δ 7.39 (d, J=8.3 Hz, 2H), 7.04 (d, J=8.4 Hz, 2H), 7.02 (d, J=8.4 Hz, 2H), 6.74 (d, J=8.4 Hz, 2H), 4.61 (s, 1H), 2.25 (m, 4H), 1.63 (m, 2H), 1.52 (m, 8).

Step 2: tert-Butyl (2E)-3-{4-[cyclooctylidene(4-hydroxyphenyl)methyl]phenyl}prop-2-enoate (50)

Following the procedure described for compound 47, 4-[(4-bromophenyl)cyclooctylidene)methyl]phenol (49) (0.105 g, 0.283 mmole), tert-butyl acrylate (0.084 mL, 0.573 mmole), P(o-tolyl)$_3$ (0.0097 g, 0.0319 mmole), Et$_3$N (0.125 mL, 0.897 mmole), Pd(OAc)$_2$ (0.0042 g, 0.0187 mmole) and DMF (1.5 mL) yielded 0.059 g (49%) of compound 50 as a white solid. $^1$H NMR (CDCl$_3$): δ 7.54 (d, J=15.9 Hz, 1H), 7.41 (d, J=8.2 Hz, 2H), 7.17 (d, J=8.2 Hz, 2H), 7.04 (d, J=8.4 Hz, 2H), 6.75 (d, J=8.4 Hz, 2H), 6.30 (d, J=15.9 Hz, 1H), 4.73 (s, 1H), 2.27 (m, 4H), 1.64 (m, 2H), 1.57 (m, 8H), 1.52 (s, 9H).

Step 3: (2E)-3-{4-[Cyclooctylidene(4-hydroxyphenyl)methyl]phenyl}prop-2-enoic acid (51)

tert-Butyl (2E)-3-{4-[cyclooctylidene(4-hydroxyphenyl)methyl]phenyl}prop-2-enoate (50) (0.0586 g, 0.140 mmole) was dissolved in methylene chloride (1 mL) and trifluoroacetic acid (1 mL). The solution was stirred at RT for 4 h, then was concentrated. The residue was recrystallized from EtOAc to provide compound 51 (0.013 g, 25%) as a white solid. $^1$H NMR (DMSO-d$_6$): δ 12.32 (s, 1H), 9.27 (s, 1H), 7.58 (d, J=8.1 Hz, 2H), 7.51 (d, J=16.1 Hz, 1H), 7.14 (d, J=8.1 Hz, 2H), 6.92 (d, J=8.4 Hz, 2H), 6.66 (d, J=8.4 Hz, 2H), 6.43 (d, J=16.1 Hz, 1H), 2.18 (m, 4H), 1.59 (m, 2H), 1.45 (m, 8H). LRMS (ESI): m/z 361 (M−H)$^-$.

Example 20 (55)

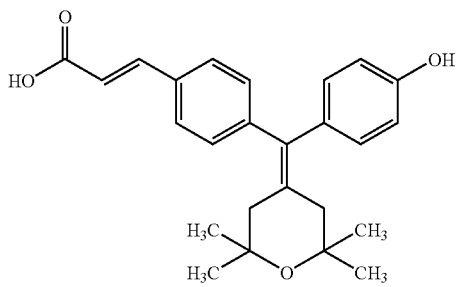

Step 1: 2,2,6,6-Tetramethyltetrahydro-4H-pyran-4-one (52)

Phorone (9.967 g, 72.1 mmole) was suspended in 1 N aqueous hydrochloric acid (100 mL). The mixture was heated to 40° C. for 7 days, then was cooled to RT. The mixture was extracted with ether (3×25 mL). The organics were dried (MgSO$_4$) and concentrated. The residue was purified by silica gel chromatography (Isco Sg100c, RediSep 120 g cartridge, 5% EtOAc:hexanes for 5 min, 5% to 15% EtOAc:hexanes over 10 min, 15% EtOAc for 5 min, 15% to 25% EtOAc:hexanes over 10 min, 25% EtOAc:hexanes for 5 min) to provide 52 (2.80 g, 25%) as a pale yellow liquid. $^1$H NMR (CDCl$_3$): δ 2.43 (s, 4H), 1.32 (s, 12H).

Step 2: 4-[(4-Bromophenyl)(2,2,6,6-tetramethyltetrahydro-4H-pyran-4-ylidene)methyl]phenol (53)

Following the procedure described for compound 46, zinc powder (0.957 g, 14.6 mmole), TiCl$_4$ (0.800 mL, 7.30 mmole), (4-bromophenyl)(4-hydroxyphenyl)methanone (2) (0.512 g, 1.85 mmole) and 2,2,6,6-tetramethyltetrahydro-4H-pyran-4-one (52) (0.851 mL, 5.45 mmole), afforded 0.564 g (76%) of 53 as a white foamy solid. $^1$H NMR (CDCl$_3$): δ 7.41 (d, J=8.3 Hz, 2H), 7.02 (d, J=8.4 Hz, 2H), 7.01 (d, J=8.4 Hz, 2H), 6.76 (d, J=8.3 Hz, 2H), 4.99 (s, 1H), 2.24 (s, 2H), 2.20 (s, 2H), 1.22 (s, 6H), 1.21 (s, 6H).

Step 3: Ethyl(2E)-3-{4-[(4-hydroxyphenyl)(2,2,6,6-tetramethyltetrahydro-4H-pyran-4-ylidene)methyl]phenyl}prop-2-enoate (54)

Following the procedure described for compound 47, 4-[(4-bromophenyl)(2,2,6,6-tetramethyltetrahydro-4H-pyran-4-ylidene)methyl]phenol (53) (0.152 g, 0.379 mmole), ethyl acrylate (0.125 mL, 1.15 mmole), P(o-tolyl)$_3$ (0.0126 g, 0.041 mmole), Et$_3$N (0.160 mL, 1.15 mmole), Pd(OAc)$_2$ (0.0044 g, 0.020 mmole) and DMF (1.5 mL) afforded 0.110 g (69%) of compound 54 as a white solid. $^1$H NMR (CDCl$_3$): δ 7.65 (d, J=16.0 Hz, 1H), 7.45 (d, J=8.1 Hz, 2H), 7.18 (d, J=8.1 Hz, 2H), 7.03 (d, J=8.4 Hz, 2H), 6.77 (d, J=8.4 Hz, 2H), 6.40 (d, J=16.0 Hz, 1H), 4.84 (s, 1H), 4.25 (q, J=7.1 Hz, 2H), 2.25 (s, 2H), 2.24 (s, 2H), 1.34 (t, J=7.1 Hz, 3H), 1.23 (s, 6H), 1.22 (s, 6H).

Step 4: (2E)-3-{4-[(4-Hydroxyphenyl)(2,2,6,6-tetramethyltetrahydro-4H-pyran-4-ylidene)methyl]phenyl}prop-2-enoic acid (55)

Ethyl(2E)-3-{4-[(4-hydroxyphenyl)(2,2,6,6-tetramethyltetrahydro-4H-pyran-4-ylidene)methyl]phenyl}prop-2-enoate (54) (0.1095 g, 0.260 mmole) was dissolved in ethanol (5 mL). Potassium hydroxide (0.260 mL of a 3 M aqueous solution, 0.780 mmole) was added and the mixture was heated to 75° C. for 2.5 h. The solution was cooled to RT and concentrated. Water (25 mL) was added and the mixture was extracted with ether (10 mL). The organics were thrown out and the aqueous layer was treated with 1 N aqueous HCl to pH=3. The resulting mixture was extracted with methylene chloride (3×10 mL). The organics were dried (Na$_2$SO$_4$) and concentrated to provide 0.097 g (95%) of compound 55 as a pale yellow solid. $^1$H NMR (DMSO-d$_6$): δ 12.33 (s, 1H), 9.34 (s, 1H), 7.59 (d, J=8.2 Hz, 2H), 7.52 (d, J=15.9 Hz, 1H), 7.15 (d, J=8.2 Hz, 2H), 6.93 (d, J=8.4 Hz, 2H), 6.67 (d, J=8.4 Hz, 2H), 6.44 (d, J=15.9 Hz, 1H), 2.14 (s, 2H), 2.11 (s, 2H), 1.11 (s, 6H), 1.10 (s, 6H). LRMS (ESI): m/z 391 (M−H)$^-$.

Example 21 (58)

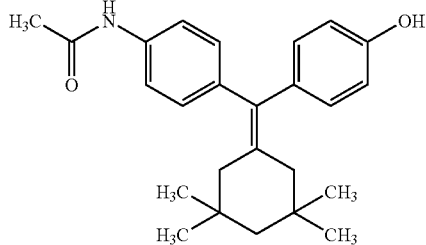

Step 1: N-(4-{[4-(methyloxy)phenyl]carbonyl}phenyl)acetamide (56)

A round-bottomed flask was charged with 4-acetamidobenzoyl chloride (0.95 g, 4.57 mmol), anisole (0.60 mL, 5.48 mmoL) and CH$_2$Cl$_2$ (15 mL). Cooled in an ice bath, AlCl$_3$ (0.93 g, 6.85 mmol) was added in portions. The mixture was stirred at 0° C. for 4 h. The resulting dark brown solution was poured into 1 N HCl (25 mL) with ice and the mixture was extracted with EtOAc (2×60 mL). The combined EtOAc extract was washed with water, brine, dried over Na$_2$SO$_4$, filtered, and the filtrate was concentrated to give brown solid. The crude product was purified by chromatography on a silica gel column eluted with hexanes:EtOAc (1:1) to give 0.55 g (45%) of compound 56 as light brown solid. mp 160-162° C. $^1$H NMR (400 MHz, CDCl$_3$): δ 2.22 (s, 3H), 3.88 (s, 3H), 6.96 (d, J=8.8 Hz, 2H), 7.34 (br s, 1H), 7.55-7.65 (m, 2H), 7.77 (d, J=8.6 Hz, 2H), 7.79 (d, J=8.8 Hz, 2H). LCMS (ESI): m/z 270 (M+H)$^+$, 268 (M−H)$^-$.

Step 2: N-{4-[[4-(methyloxy)phenyl](3,3,5,5-tetramethylcyclohexylidene)methyl]phenyl}acetamide (57)

To a stirred suspension of zinc powder (0.39 g, 5.94 mmol) in THF (15 mL) was slowly added TiCl$_4$ (0.33 mL, 2.97 mmol) via syringe at RT under a nitrogen atmosphere. The mixture was heated at reflux for 2 h. A solution of N-(4-{[4-(methyloxy)phenyl]carbonyl}phenyl)acetamide (56) (0.20 g, 0.74 mmol) and 3,3,5,5-tetramethylcyclohexanone (0.35 g, 2.23 mmol) in THF (4 mL) was added to the mixture. The reaction mixture was heated at reflux with stirring under a nitrogen atmosphere for 1 h. The reaction mixture was allowed to cool to room temperature. To the reaction mixture was slowly added 10% aqueous K$_2$CO$_3$ (15 mL). The reaction mixture was filtered through a pad of Celite and the pad washed with EtOAc (100 mL). The filtrate was transferred to a separatory funnel and the layers were separated. The aqueous layer was further extracted with EtOAc (25 mL). The combined organic phase washed with water, brine, dried (Na$_2$SO$_4$) filtered, and the filtrate was concentrated to give the crude product as yellow oil. The crude product was purified by chromatography on a silica gel column eluted with a gradient from hexanes to 40% EtOAc:hexanes to give 0.27 g (93%) of compound 57 as colorless viscous oil. $^1$H NMR (400 MHz, CDCl$_3$): δ 0.91 (s, 6H), 0.92 (s, 6H), 1.27 (s, 2H), 1.96 (s, 2H), 1.97 (s, 2H), 2.16 (s, 3H), 3.78 (s, 3H), 6.80 (d, J=8.6 Hz, 2H), 7.06 (d, J=8.8 Hz, 2H), 7.10 (d, J=8.5 Hz, 2H), 7.39 (d, J=8.5 Hz, 2H). LCMS (ESI): m/z 392 (M+H)$^+$, 390 (M−H)$^−$.

Step 3: N-{4-[(4-hydroxyphenyl)(3,3,5,5-tetramethylcyclohexylidene)methyl]phenyl}acetamide (58)

N-{4-[[4-(methyloxy)phenyl](3,3,5,5-tetramethylcyclohexylidene)methyl]phenyl}acetamide (57) (0.27 g, 0.69 mmol) was dissolved in CH$_2$Cl$_2$ (25 mL). The mixture was cooled to −10° C. in an ice-acetone bath. To this solution was added 1 M BBr$_3$ in CH$_2$Cl$_2$ (2.1 mL, 2.07 mmol). The reaction mixture was stirred at −10° C. to 0° C. for 3 h, then poured onto ice, extracted with EtOAc (2×60 mL). The combined organic extract washed with water, brine and dried over Na$_2$SO$_4$. Upon concentration and trituration with 1:1 hexanes:CH$_2$Cl$_2$, compound 58 was obtained as a light brown solid (0.10 g, 39%). mp 118-121° C. $^1$H NMR (400 MHz, DMSO-d$_6$): δ 0.85 (s, 6H), 0.86 (s, 6H), 1.23 (s, 2H), 1.87 (s, 2H), 1.89 (s, 2H), 1.98 (s, 3H), 6.64 (d, J=8.3 Hz, 2H), 6.89 (d, J=8.5 Hz, 2H), 7.00 (d, J=8.5 Hz, 2H), 7.44 (d, J=8.4 Hz, 2H), 9.24 (s, 1H), 9.84 (s, 1H); LCMS (ES): m/z 378 (M+H)$^+$, 376 (M−H)$^−$. Anal. Calcd for C$_{25}$H$_{31}$$_N$O$_2$·⅓H$_2$O: C, 78.29; H, 8.32; N, 3.65; Found: C, 78.33; H, 8.26; N, 3.62.

Example 22 (60)

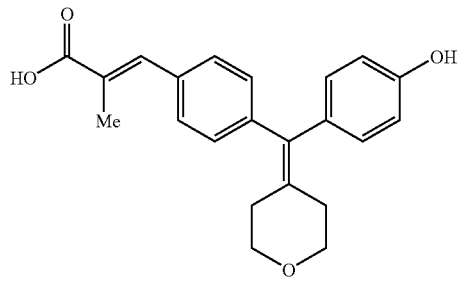

Step 1: tert-Butyl (2E)-3-{4-[(4-hydroxyphenyl)(tetrahydro-4H-pyran-4-ylidene)methyl]phenyl}-2-methylprop-2-enoate (59)

Following the procedure described for compound 47, from 4-[(4-bromophenyl)(tetrahydro-4H-pyran-4-ylidene)methyl]phenol (46) (0.101 g, 0.293 mmole), tert-butyl methacrylate (0.095 mL, 0.585 mmole), P(o-tolyl)$_3$ (0.0092 g, 0.0302 mmole), Et$_3$N (0.125 mL, 0.897 mmole), Pd(OAc)$_2$ (0.0038 g, 0.0169 mmole) and DMF (1.5 mL) yielded compound 59 (0.070 g, 59%) as a white solid. $^1$H NMR (CDCl$_3$): δ 7.55 (s, 1H), 7.31 (d, J=8.1 Hz, 2H), 7.11 (d, J=8.1 Hz, 2H), 6.98 (d, J=8.5 Hz, 2H), 6.76 (d, J=8.5 Hz, 2H), 4.91 (s, 1H), 3.73 (m, 4H), 2.41 (m, 4H), 1.58 (s, 3H), 1.54 (s, 9H).

Step 2: (2E)-3-{4-[(4-hydroxyphenyl)(tetrahydro-4H-pyran-4-ylidene)methyl]phenyl}-2-methylprop-2-enoic acid (60)

tert-Butyl (2E)-3-{4-[(4-hydroxyphenyl)(tetrahydro-4H-pyran-4-ylidene)methyl]phenyl}-2-methylprop-2-enoate (59) (0.0702 g, 0.173 mmole) was dissolved in CH$_2$Cl$_2$ (1 mL) and TFA (1 mL). The solution was stirred at RT for 4 h, then was concentrated. The residue was triturated with CH$_2$Cl$_2$ to provide compound 60 (0.029 g, 47%) as a tan solid. $^1$H NMR (DMSO-d$_6$): δ 12.49 (br s, 1H), 9.38 (s, 1H), 7.54 (s, 1H), 7.40 (d, J=8.1 Hz, 2H), 7.11 (d, J=8.1 Hz, 2H), 6.87 (d, J=8.4 Hz, 2H), 6.68 (d, J=8.4 Hz, 2H), 3.60 (m, 4H), 2.25 (m, 4H), 2.01 (s, 3H). LRMS (ESI): m/z 349 (M−H)$^−$.

Example 23 (62)

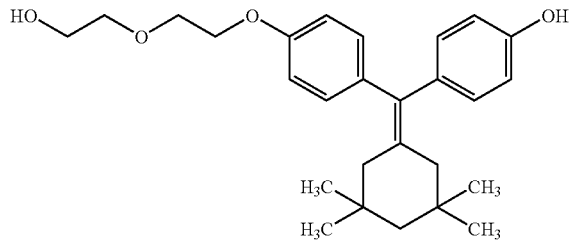

Step 1: [4-({2-[(2-Hydroxyethyl)oxy]ethyl}oxy)phenyl](4-hydroxyphenyl)methanone (61)

To a solution of 4,4'-dihydroxybenzophenone (3.0 g, 13.9 mmol) in DMF (30 mL) was added Cs$_2$CO$_3$ (13.55 g, 41.6 mmol). The mixture was heated at 80° C. under nitrogen for 1 h. The stirred reaction was cooled to room temperature and NaI (2.08 g, 13.9 mmol) was added, followed by dropwise addition of a solution of 2-(2-chloroethoxy)ethanol (1.63 mL, 15.3 mmol) in DMF (7 mL). The reaction mixture was heated at 80° C. under nitrogen overnight. The mixture was cooled to room temperature and quenched with saturated aqueous NH$_4$Cl (100 mL), then extracted with EtOAc (3×60 mL). The organic layers were combined and washed with water, brine, and dried over Na$_2$SO$_4$, then concentrated to a light brown oil which was further purified by chromatography on a silica gel column eluted with a gradient from hexanes to 95% EtOAc:hexanes to give a light brown oil which contained some DMF. The residue was dissolved in EtOAc (100 mL) and further washed with water (2×50 mL), saturated aqueous CuSO$_4$ (50 mL), water (50 mL) and brine (50 mL). The EtOAc solution was dried (Na$_2$SO$_4$) and concentrated to 15 mL and 30 mL of hexanes added. A white solid precipitated and washed with 1:1 hexanes:EtOAc to afford compound 61 (1.90 g, 45%). mp 126-127° C. $^1$H NMR (400 MHz, CD$_3$OD): δ 3.60-3.65 (m, 2H), 3.65-3.70 (m, 2H), 3.85-3.90 (m, 2H), 4.20-4.25 (m, 2H), 6.87 (d, J=8.6 Hz, 2H), 7.05 (d, J=8.8 Hz, 2H), 7.67 (d, J=8.6 Hz, 2H), 7.73 (d, J=8.8 Hz, 2H). LRMS (APCI): m/z, 303 (M+H)$^+$, 301 (M−H)$^−$.

Step 2: 4-[[4-({2-[(2-Hydroxyethyl)oxy]ethyl}oxy)phenyl](3,3,5,5-tetramethylcyclohexylidene)methyl]phenol (62)

To a stirred suspension of Zn (0.59 g, 9.00 mmol) in THF (10 mL) was added TiCl$_4$ (0.50 mL, 4.50 mmol) dropwise. The mixture was refluxed under nitrogen for 2.5 h. After cooling to room temperature, a solution of 61 (0.34 g, 1.12 mmol) and 3,3,5,5-tetramethylcyclohexanone (0.53 g, 3.37 mmol) in THF (15 mL) was added and the reaction mixture refluxed for an additional 2.5 h. Cooled to room temperature, the reaction was quenched with 10% K$_2$CO$_3$ (20 mL). The quenched reaction mixture was filtered through a pad of Celite and the pad washed with EtOAc (100 mL). The filtrate was transferred to a separatory funnel, the layers were separated, and the aqueous phase was extracted with EtOAc (50 mL). The combined organic extracts were washed with brine, dried (Na$_2$SO$_4$) and concentrated to give a pale yellow oil. The residue was further purified by chromatography on a silica gel column eluted with a gradient from hexanes to 55% EtOAc:hexanes to give 62 as a white solid (0.36 g, 75%). mp 122-124° C. $^1$H NMR (400 MHz, CD$_3$OD): δ 0.91 (s, 6H), 0.92 (s, 6H), 1.28 (s, 2H), 1.96 (s, 2H), 1.98 (s, 2H), 3.60-3.65 (m, 2H), 3.65-3.70 (m, 2H), 3.80-3.85 (m, 2H), 4.05-4.15 (m, 2H), 6.67 (d, J=8.4 Hz, 2H), 6.83 (d, J=8.6 Hz, 2H), 6.94 (d, J=8.6 Hz, 2H), 7.03 (d, J=8.6 Hz, 2H). LRMS (APCI): m/z 425 (M+H)$^+$, 423 (M–H)$^-$. Anal. Calcd for C$_{27}$H$_{36}$O$_4$: C, 76.38; H, 8.55; Found: C, 76.17; H, 8.65.

Example 24 (64)

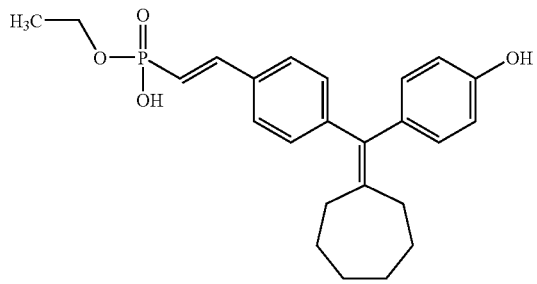

Step 1: Diethyl(E)-2-{4-[cycloheptylidene(4-hydroxyphenyl)methyl]phenyl}ethenylphosphonate (63)

Following the procedure described for compound 47, from 4-[(4-bromophenyl)cycloheptylidene)methyl]phenol (9)(0.146 g, 0.409 mmole), diethyl vinylphosphonate (0.190 mL, 1.24 mmole), P(o-tolyl)$_3$ (0.0123 g, 0.0404 mmole), Et$_3$N (0.170 mL, 1.22 mmole), Pd(OAc)$_2$ (0.0046 g, 0.0205 mmole) and DMF (1.5 mL) yielded 63 (0.0502 g, 28%) as a white solid. $^1$H NMR (DMSO-d$_6$): δ 9.28 (s, 1H), 7.57 (d, J=8.3 Hz, 2H), 7.30 (dd, J=22.7, 17.6 Hz, 1H), 7.11 (d, J=8.3 Hz, 2H), 6.89 (d, J=8.4 Hz, 2H), 6.65 (d, J=8.4 Hz, 2H), 6.48 (dd, J=22.7, 17.6 Hz, 1H), 4.01-3.91 (m, 4H), 2.20 (m, 4H), 1.50 (m, 8H), 1.21 (m, 6H).

Step 2: Ethyl hydrogen (E)-2-{4-[cycloheptylidene(4-hydroxyphenyl)methyl]phenyl}ethenylphosphonate (64)

To a solution of diethyl(E)-2-{4-[cycloheptylidene(4-hydroxyphenyl)methyl]phenyl}ethenylphosphonate (63) (0.051 g, 0.115 mmol) in EtOH (4 mL) was added aqueous NaOH (1 mL of a 5M solution, 5 mmol). The solution was heated to reflux for 4 h, then cooled to RT and concentrated. The residue was dissolved in water (1 mL) and the pH adjusted to ~2 with 1 N aqueous HCl. The mixture was extracted with EtOAc (2×10 mL). The organics were dried (Na$_2$SO$_4$) and concentrated to provide compound 64 (0.041 g, 86%) as a waxy yellow solid. $^1$H NMR (DMSO-d$_6$): δ 9.28 (s, 1H), 7.53 (d, J=8.1 Hz, 2H), 7.20 (dd, J=22.0 Hz, 17.6 Hz, 1H), 7.10 (d, J=8.1 Hz, 2H), 6.89 (d, J=8.4 Hz, 2H), 6.65 (d, J=8.4 Hz, 2H), 6.41 (t, J=17.6 Hz, 1H), 3.90-3.84 (m, 2H), 2.20 (m, 4H), 1.50 (m, 8H), 1.18 (t, J=6.9 Hz, 3H). LRMS (ESI): m/z 411 (M–H)$^-$.

Example 25 (69)

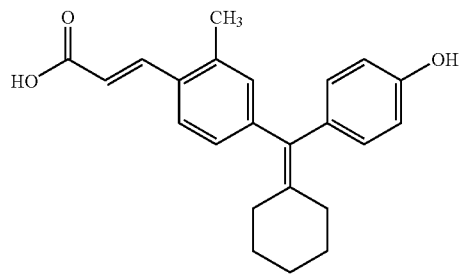

Step 1: (4-Bromo-3-methylphenyl)(4-methoxyphenyl)methanone (65)

AlCl$_3$ (3.63 g, 27.2 mmol) was added portionwise to 4-bromo-3-methylbenzoyl chloride (5.30 g, 22.7 mmol) dissolved in anisole (7 mL) at 0° C. The reaction mixture was warmed to RT, stirred for 1 h, and then cooled to 0° C. Water (200 mL) was cautiously added dropwise, and the mixture was extracted with ether (3×100 mL). The combined ethereal extracts were washed with water (250 mL), brine (250 mL), and dried over MgSO$_4$. Concentration followed by flash chromatography (20:1 to 5:1 hexanes:EtOAc) afforded 6.42 g (93%) of 65 as a white solid. $^1$H NMR (400 MHz, CDCl$_3$): δ 2.45 (s, 3H), 3.88 (s, 3H), 6.96 (d, J=8.8 Hz, 2H), 7.40 (d, J=8.1 Hz, 1H), 7.62 (m, 2H), 7.79 (d, J=8.8 Hz, 2H).

Step 2: (4-Bromo-3-methylphenyl)(4-hydroxyphenyl)methanone (66)

A mixture of 65 (2.00 g, 6.55 mmol) and AlCl$_3$ (3.50 g, 26.2 mmol) were refluxed in benzene (50 mL) for 3 h and then cooled to RT. Water (100 mL) was cautiously added dropwise, and the mixture was extracted with Et$_2$O (3×100 mL). The combined ethereal extracts were washed with water (200 mL), brine (200 mL), and dried over MgSO$_4$. Concentration afforded 1.78 g (93%) of 66 that was used without further purification. $^1$H NMR (400 MHz, CDCl$_3$): δ 2.45 (s, 3H), 5.68 (br s, 1H), 6.90 (d, J=8.6 Hz, 2H), 7.40 (dd, J=8.2 Hz, 1.8 Hz, 1H), 7.63 (m, 2H), 7.75 (d, J=8.6 Hz, 2H).

Step 3: 4-[(4-Bromo-3-methylphenyl)(cyclohexylidene)methyl]phenol (67)

Titanium tetrachloride (2.70 mL, 24.5 mmol) was added dropwise to a suspension of zinc powder (3.24 g, 49.5 mmol)

in anhydrous THF (60 mL) at RT. After refluxing for 1 h, a mixture of 66 (1.78 g, 6.11 mmol) and cyclohexanone (1.80 g, 18.3 mmol) dissolved in THF (20 mL) was added dropwise. Refluxing was continued for 30 min. The reaction mixture was cooled to RT and filtered through Celite. Water (250 mL) was added and the mixture was extracted with Et$_2$O (3×100 mL). The combined ethereal extracts were washed with water (200 mL), brine (200 mL), and dried over MgSO$_4$. Concentration followed by flash chromatography (20:1 to 5:1 hexanes:EtOAc) afforded 1.85 g (85%) of 67 as an orange solid. $^1$H NMR (400 MHz, CDCl$_3$): δ 1.58 (m, 6H), 2.20 (m, 4H), 2.32 (s, 3H), 5.95 (br s, 1H), 6.73 (d, J=8.4 Hz, 2H), 6.79 (dd, J=8.1 Hz, 2.0 Hz, 1H), 6.95 (m, 3H), 7.40 (d, J=8.1 Hz, 1H).

Step 4: 1,1-Dimethylethyl(2E)-3-{4-[cyclohexylidene(4-hydroxyphenyl)methyl]-2-methylphenyl}-2-propenoate (68)

A mixture of 67 (380 mg, 1.06 mmol), tert-butyl acrylate (0.369 mL, 2.55 mmol), Pd(OAc)$_2$ (15.0 mg, 0.067 mmol), P(o-tolyl)$_3$ (40.0 mg, 0.131 mmol), and Et$_3$N (0.520 mL, 3.73 mmol) were heated under microwave irradiation at 140° C. for 30 min. Water (30 mL) was added and the mixture was extracted with Et$_2$O (3×20 mL). The combined ethereal extracts were washed with water (30 mL), brine (30 mL), and dried over MgSO$_4$. Concentration followed by flash chromatography (20:1 to 5:1 hexanes:EtOAc) afforded 220 mg (51%) of 68. $^1$H NMR (400 MHz, CDCl$_3$): δ 1.52 (s, 9H), 1.58 (m, 6H), 2.22 (m, 4H), 2.34 (s, 3H), 4.85 (s, 1H), 6.25 (d, J=16.0 Hz, 1H), 6.74 (d, J=8.4 Hz, 2H), 6.90-6.97 (m, 4H), 7.44 (d, J=8.1 Hz, 1H), 7.84 (d, J=16.0 Hz, 1H).

Step 5: (2E)-3-{4-[Cyclohexylidene(4-hydroxyphenyl)methyl]-2-methylphenyl}-2-propenoic acid (69)

Trifluoroacetic acid (2.0 mL) was added dropwise to 68 (210 mg, 0.519 mmol) dissolved in CH$_2$Cl$_2$ (2 mL) at 0° C. The reaction mixture was stirred at RT for 3 h and the volatiles were removed under reduced pressure. The residue was chromatographed on silica gel (20:1 CH$_2$Cl$_2$:MeOH) and recrystallized (EtOAc:hexanes) to afford 138 mg (76%) of 69 as a pale yellow solid. $^1$H NMR (400 MHz, DMSO-d$_6$): δ 1.51 (br s, 6H), 2.13 (m, 4H), 2.30 (s, 3H), 6.35 (d, J=16.0 Hz, 1H), 6.66 (d, J=8.2 Hz, 2H), 6.82-6.91 (m, 4H), 7.59 (d, J=7.9 Hz, 1H), 7.75 (d, J=16.0 Hz, 1H), 9.31 (s, 1H), 12.36 (br s, 1H). LRMS (ESI): m/z 349 (M+H)$^+$.

Example 26 (74)

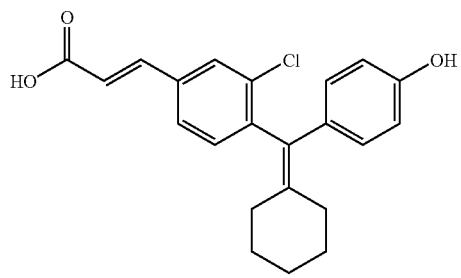

Step 1: (4-Bromo-2-chlorophenyl)(4-methoxyphenyl)methanone (70)

Oxalyl chloride (4.10 mL, 47.3 mmol) was added dropwise to 4-bromo-2-chlorobenzoic acid (5.57 g, 23.7 mmol) dissolved in CH$_2$Cl$_2$ (100 mL). After stirring overnight at RT, additional oxalyl chloride (2.05 mL, 23.7 mmol) was added and the reaction mixture was refluxed for 26 h. The volatiles were removed and the residue was dissolved in anisole (10 mL) and cooled to 0° C. AlCl$_3$ (4.50 g, 33.7 mmol) was added portionwise and the reaction mixture was stirred for 2 h. Water (200 mL) was cautiously added dropwise, and the mixture was extracted with Et$_2$O (3×100 mL). The combined ethereal extracts were washed with water (250 mL), brine (250 mL), and dried over MgSO$_4$. Concentration followed by flash chromatography (20:1 to 5:1 hexanes:EtOAc) afforded 6.60 g (90%) of 70 as a pale yellow solid. $^1$H NMR (400 MHz, CDCl$_3$): δ 3.87 (s, 3H), 6.93 (d, J=8.8 Hz, 2H), 7.23 (d, J=8.1 Hz, 1H), 7.50 (dd, J=8.1 Hz, 1.8 Hz, 1H), 7.63 (d, J=1.8 Hz, 1H), 7.76 (d, J=8.8 Hz, 2H).

Step 2: (4-Bromo-2-chlorophenyl)(4-hydroxyphenyl)methanone (71)

A mixture of 70 (2.00 g, 6.14 mmol) and AlCl$_3$ (3.50 g, 26.2 mmol) were refluxed in benzene (50 mL) for 3 h and then cooled to RT. Water (100 mL) was cautiously added dropwise, and the mixture was extracted with Et$_2$O (3×100 mL). The combined ethereal extracts were washed with water (200 mL), brine (200 mL), and dried over MgSO$_4$. Concentration followed by flash chromatography (20:1 to 5:1 hexanes:EtOAc) afforded 1.42 g (74%) of 71. $^1$H NMR (400 MHz, CDCl$_3$): δ 5.97 (br s, 1H), 6.89 (d, J=8.8 Hz, 2H), 7.23 (d, J=8.1 Hz, 1H), 7.50 (dd, J=8.1 Hz, 1.7 Hz, 1H), 7.64 (d, J=1.7 Hz, 1H), 7.73 (d, J=8.8 Hz, 2H).

Step 3: 4-[(4-Bromo-2-chlorophenyl)(cyclohexylidene)methyl]phenol (72)

TiCl$_4$ (2.01 mL, 18.2 mmol) was added dropwise to a suspension of zinc powder (2.41 g, 36.9 mmol) in anhydrous THF (60 mL) at RT. After refluxing for 1 h, a mixture of 71 (1.42 g, 4.56 mmol) and cyclohexanone (1.34 g, 13.7 mmol) dissolved in THF (20 mL) was added dropwise. Refluxing was continued for 30 min. The reaction mixture was cooled to RT and filtered through Celite. Water (250 mL) was added and the mixture was extracted with Et$_2$O (3×100 mL). The combined ethereal extracts were washed with water (200 mL), brine (200 mL), and dried over MgSO$_4$. Concentration followed by flash chromatography (20:1 to 5:1 hexanes:EtOAc) afforded 1.61 g (93%) of compound 72 as a light green oil. $^1$H NMR (400 MHz, CDCl$_3$): δ 1.59 (m, 6H), 1.97 (m, 2H), 2.28 (m, 2H), 4.93 (br s, 1H), 6.72 (d, J=8.6 Hz, 2H), 7.04 (m, 3H), 7.32 (dd, J=8.2 Hz, 2.0 Hz, 1H), 7.51 (d, J=2.0 Hz, 1H).

Step 4: 1,1-Dimethylethyl(2E)-3-{3-chloro-4-[cyclohexylidene(4-hydroxyphenyl)-methyl]phenyl}-2-propenoate (73)

A mixture of 72 (459 mg, 1.22 mmol), tert-butyl acrylate (0.369 mL, 2.55 mmol), Pd(OAc)$_2$ (15.0 mg, 0.067 mmol), P(o-tolyl)$_3$ (40.0 mg, 0.131 mmol), and Et$_3$N (0.520 mL, 3.73 mmol) were heated under microwave irradiation at 140° C. for 30 min. Water (30 mL) was added and the mixture was extracted with Et₂O (3×20 mL). The combined ethereal extracts were washed with water (30 mL), brine (30 mL), and dried over MgSO₄. Concentration followed by flash chromatography (20:1 to 5:1 hexanes:EtOAc) afforded 310 mg (60%) of 73. ¹H NMR (400 MHz, CDCl₃): δ 1.52 (s, 9H), 1.58 (m, 6H), 1.99 (m, 2H), 2.28 (m, 2H), 4.71 (s, 1H), 6.31 (d, J=16.0 Hz, 1H), 6.73 (d, J=8.6 Hz, 2H), 7.05 (d, J=8.6 Hz, 2H), 7.17 (d, J=7.9 Hz, 1H), 7.31 (dd, J=7.9 Hz, 1.5 Hz, 1H), 7.47 (m, 2H).

Step 5: (2E)-3-{3-Chloro-4-[cyclohexylidene(4-hydroxyphenyl)methyl]phenyl}-2-propenoic acid (74)

Trifluoroacetic acid (2.0 mL) was added dropwise to 73 (300 mg, 0.706 mmol) dissolved in CH₂Cl₂ (2 mL) at 0° C. The reaction mixture was stirred at RT for 3 h and the volatiles were removed under reduced pressure. The residue was chromatographed on silica gel (20:1 CH₂Cl₂:MeOH) to afford 225 mg (86%) of 74 as a yellow solid. ¹H NMR (400 MHz, DMSO-d₆): δ 1.53 (br s, 6H), 1.88 (br s, 2H), 2.20 (m, 2H), 6.54 (d, J=16.0 Hz, 1H), 6.65 (d, J=8.8 Hz, 2H), 6.92 (d, J=8.4 Hz, 2H), 7.23 (d, J=7.9 Hz, 1H), 7.52 (d, J=16.0 Hz, 1H), 7.59 (d, J=7.9 Hz, 1H). LRMS (ESI): m/z 370 (M+H)⁺.

Example 27 (79)

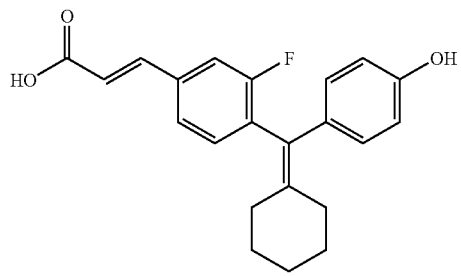

Step 1: (4-Bromo-2-fluorophenyl)(4-methoxyphenyl)methanone (75)

Oxalyl chloride (4.00 mL, 45.8 mmol) was added dropwise to 4-bromo-2-fluorobenzoic acid (5.1 g, 23.3 mmol) dissolved in CHCl₃ (50 mL). After refluxing for 18 h, additional oxalyl chloride (4.00 mL) was added and refluxing was continued for 4 h. The volatiles were removed under reduced pressure to afford 5.0 g of the crude acid chloride that was used without purification. AlCl₃ (10.0 g, 75.0 mmol) was added portionwise to the crude acid chloride (5.0 g) dissolved in anisole (10 mL) at 0° C. The reaction mixture was stirred at RT for 3 days and then cooled to 0° C. Water (200 mL) was cautiously added dropwise, and the mixture was extracted with Et₂O (3×100 mL). The combined ethereal extracts were washed with water (250 mL), brine (250 mL), and dried over MgSO₄. Concentration followed by flash chromatography (20:1 to 5:1 hexanes:EtOAc) and recrystallization from hexanes afforded 4.1 g (57% based on 4-bromo-2-fluorobenzoic acid) of 75 as a white solid. ¹H NMR (400 MHz, CDCl₃): δ 3.87 (s, 3H), 6.94 (d, J=8.8 Hz, 2H), 7.33-7.40 (m, 3H), 7.79 (d, J=8.2 Hz, 2H).

Step 2: (4-Bromo-2-fluorophenyl)(4-hydroxyphenyl)methanone (76)

A mixture of 75 (1.50 g, 5.08 mmol) and AlCl₃ (3.50 g, 26.2 mmol) were refluxed in benzene (50 mL) for 3 h and then cooled to RT. Water (100 mL) was cautiously added dropwise, and the mixture was extracted with Et₂O (3×100 mL). The combined ethereal extracts were washed with water (200 mL), brine (200 mL), and dried over MgSO₄. Concentration afforded 1.39 g (97%) of 76 that was used without further purification. ¹H NMR (400 MHz, CDCl₃): δ 5.73 (br s, 1H), 6.90 (d, J=8.8 Hz, 2H), 7.35-7.41 (m, 3H), 7.77 (d, J=8.4 Hz, 2H).

Step 3: 4-[(4-bromo-2-fluorophenyl)(cyclohexylidene)methyl]phenol (77)

TiCl₄ (2.10 mL, 19.0 mmol) was added dropwise to a suspension of zinc powder (2.51 g, 38.4 mmol) in anhydrous THF (60 mL) at RT. After refluxing for 1 h, a mixture of 76 (1.40 g, 4.74 mmol) and cyclohexanone (1.40 g, 14.3 mmol) dissolved in THF (20 mL) was added dropwise. Refluxing was continued for 30 min. The reaction mixture was cooled to RT and filtered through Celite. Water (250 mL) was added and the mixture was extracted with Et₂O (3×100 mL). The combined ethereal extracts were washed with water (200 mL), brine (200 mL), and dried over MgSO₄. Concentration followed by flash chromatography (20:1 to 5:1 hexanes:EtOAc) afforded 1.23 g (72%) of 77 as a white solid. ¹H NMR (400 MHz, CDCl₃): δ 1.58 (br s, 6H), 2.05 (m, 2H), 2.25 (m, 2H), 4.68 (br s, 1H), 6.73 (d, J=8.6 Hz, 2H), 6.94-7.00 (m, 3H), 7.19 (d, J=7.9 Hz, 2H).

Step 4: 1,1-Dimethylethyl(2E)-3-{4-[cyclohexylidene(4-hydroxyphenyl)methyl]-3-fluorophenyl}-2-propenoate (78)

A mixture of 77 (312 mg, 0.864 mmol), tert-butyl acrylate (0.369 mL, 2.55 mmol), P(OAc)₂ (15.0 mg, 0.067 mmol), P(o-tolyl)₃ (40.0 mg, 0.131 mmol), and Et₃N (0.520 mL, 3.73 mmol) were heated under microwave irradiation at 140° C. for 30 min. Water (30 mL) was added and the mixture was extracted with Et₂O (3×20 mL). The combined ethereal extracts were washed with water (30 mL), brine (30 mL), and dried over MgSO₄. Concentration followed by flash chromatography (20:1 to 5:1 hexanes:EtOAc) afforded 220 mg (62%) of compound 78. ¹H NMR (400 MHz, CDCl₃): δ 1.52 (s, 9H), 1.58 (m, 6H), 2.07 (br s, 2H), 2.25 (br s, 2H), 4.78 (s, 1H), 6.30 (d, J=16.0 Hz, 1H), 6.74 (d, J=8.6 Hz, 2H), 7.01 (d, J=8.4 Hz, 2H), 7.08 (t, J=7.6 Hz, 1H), 7.13-7.18 (m, 2H), 7.49 (d, J=16.0 Hz, 1H).

Step 5: (2E)-3-{4-[Cyclohexylidene(4-hydroxyphenyl)methyl]-3-fluorophenyl}-2-propenoic acid (79)

Trifluoroacetic acid (2.0 mL) was added dropwise to 78 (210 mg, 0.514 mmol) dissolved in CH₂Cl₂ (2 mL) at 0° C. The reaction mixture was stirred at RT for 3 h and the volatiles were removed under reduced pressure. The residue was recrystallized (EtOAc:hexanes) to afford 98.0 mg (54%) of 79 as a yellow solid. ¹H NMR (400 MHz, DMSO-d₆): δ 1.52 (br s, 6H), 1.98 (br s, 2H), 2.19 (br s, 2H), 6.52 (d, J=16.0 Hz, 1H), 6.66 (d, J=8.4 Hz, 2H), 6.87 (d, J=8.4 Hz, 2H), 7.11 (t, J=7.9 Hz, 1H), 7.42 (d, J=7.9 Hz, 1H), 7.52 (m, 2H), 9.33 (s, 1H), 12.40 (br s, 1H). LRMS (ESI): m/z 353 (M+H)⁺.

Example 28 (85)

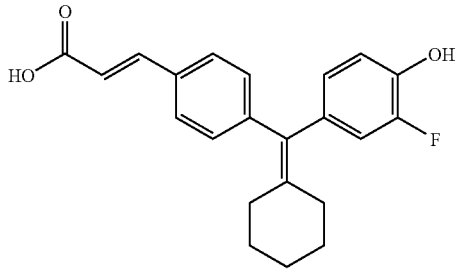

Step 1:
4-Bromo-N-methyl-N-(methyloxy)benzamide (80)

Pyridine (4.40 mL, 54.2 mmol) was added dropwise to N,O-dimethylhydroxylamine hydrochloride (3.44 g, 35.2 mmol) dissolved in $CH_2Cl_2$ (100 mL) at RT. The reaction mixture was stirred for 30 min, and 4-bromobenzoyl chloride (5.95 g, 27.1 mmol) dissolved in $CH_2Cl_2$ (50 mL) was added dropwise. The mixture was stirred for 24 h and the volatiles were removed under reduced pressure. Water (200 mL) was added and the mixture was extracted with EtOAc (3×200 mL). The combined extracts were washed successively with 5% aqueous HCl (200 mL), 5% aqueous $NaHCO_3$ (200 mL), water (200 mL), and brine (200 mL). The mixture was dried over $MgSO_4$ and concentrated to afford 6.35 g (74%) of 80 as a colorless oil which was used without further purification. $^1H$ NMR (400 MHz, $CDCl_3$): δ 3.35 (s, 3H), 3.53 (s, 3H), 7.54 (d, J=8.6 Hz, 2H), 7.58 (d, J=8.6 Hz, 2H).

Step 2:
(4-Bromophenyl)(3-fluoro-4-methoxyphenyl)methanone (81)

To a stirred solution of 2-fluoro-4-bromoanisole (3.03 g, 14.8 mmol) in anhydrous THF (100 mL) was added n-butyl-lithium (1.6 M in hexanes, 10.2 mL, 16.3 mol) dropwise at −78° C. The reaction mixture was stirred for 1 h and 80 (4.02 g, 16.3 mmol) dissolved in THF (20 mL) was added dropwise. The reaction mixture was warmed to −20° C. over 1 h, water (100 mL) was added, and the volatiles were removed under reduced pressure. The mixture was extracted with ether (3×100 mL) and the combined extracts were washed with water (100 mL) and brine (100 mL). The mixture was dried over $MgSO_4$ and concentrated. The residue was chromatographed on silica gel (20:1 to 5:1 hexanes:EtOAc) to afford 2.35 g (51%) of 81 as a white crystalline solid. $^1H$ NMR (400 MHz, $CDCl_3$): δ 3.97 (s, 3H), 7.01 (t, J=8.4 Hz, 1H), 7.55-7.62 (m, 6H).

Step 3:
(4-Bromophenyl)(3-fluoro-4-hydroxyphenyl)methanone (82)

A mixture of 81 (1.28 g, 4.34 mmol) and $AlCl_3$ (3.50 g, 26.2 mmol) were refluxed in benzene (50 mL) for 3 h and cooled to RT. Water (100 mL) was cautiously added dropwise, and the mixture was extracted with ether (3×100 mL). The combined ethereal extracts were washed with water (200 mL), brine (200 mL), and dried over $MgSO_4$. Concentration afforded 1.19 g (98%) of 82 that was used without further purification. $^1H$ NMR (400 MHz, $CDCl_3$): δ 5.80 (br s, 1H), 7.09 (t, J=8.4 Hz, 1H), 7.53 (d, J=8.4 Hz, 1H), 7.61-7.64 (m, 5H).

Step 4: 4-[(4-Bromophenyl)(cyclohexylidene)methyl]-2-fluorophenol (83)

Titanium tetrachloride (1.70 mL, 15.5 mmol) was added dropwise to a suspension of zinc powder (2.12 g, 32.4 mmol) in anhydrous THF (60 mL) at RT. After refluxing for 1 h, a mixture of 82 (1.18 g, 4.00 mmol) and cyclohexanone (1.18 g, 12.0 mmol) dissolved in THF (20 mL) was added dropwise. Refluxing was continued for 30 min. The reaction mixture was cooled to RT and filtered through Celite. Water (250 mL) was added and the mixture was extracted with ether (3×100 mL). The combined ethereal extracts were washed with water (200 mL), brine (200 mL), and dried over $MgSO_4$. Concentration followed by flash chromatography (20:1 to 5:1 hexanes:EtOAc) afforded 1.15 g (80%) of compound 83 as a light yellow solid. $^1H$ NMR (400 MHz, $CDCl_3$): δ 1.58 (br s, 6H), 2.20 (m, 4H), 5.10 (br s, 1H), 6.77 (m, 2H), 6.89 (t, J=8.6 Hz, 1H), 6.96 (d, J=8.4 Hz, 2H), 7.39 (d, J=8.4 Hz, 2H).

Step 5: 1,1-Dimethylethyl(2E)-3-{4-[cyclohexylidene(3-fluoro-4-hydroxyphenyl)-methyl]phenyl}-2-propenoate (84)

A mixture of 83 (317 mg, 0.877 mmol), tert-butyl acrylate (0.369 mL, 2.55 mmol), palladium acetate (15.0 mg, 0.067 mmol), P(o-tolyl)$_3$ (40.0 mg, 0.131 mmol), and $Et_3N$ (0.520 mL, 3.73 mmol) were heated under microwave irradiation at 140° C. for 30 min. Water (30 mL) was added and the mixture was extracted with ether (3×20 mL). The combined ethereal extracts were washed with water (30 mL), brine (30 mL), and dried over $MgSO_4$. Concentration followed by flash chromatography (20:1 to 5:1 hexanes:EtOAc) afforded 190 mg (54%) of 84. $^1H$ NMR (400 MHz, $CDCl_3$): δ 1.52 (s, 9H), 1.57-1.60 (m, 6H), 2.23 (m, 4H), 5.07 (d, 1H), 6.31 (d, J=16 Hz, 1H), 6.78 (m, 2H), 6.90 (t, J=8.6 Hz, 1H), 7.09 (d, J=8.1 Hz, 2H), 7.40 (d, J=8.1 Hz, 2H), 7.54 (d, J=16.0 Hz, 1H).

Step 6: (2E)-3-{4-[Cyclohexylidene(3-fluoro-4-hydroxyphenyl)methyl]phenyl}-2-propenoic acid (85)

Trifluoroacetic acid (2.0 mL) was added dropwise to 84 (179 mg, 0.438 mmol) dissolved in $CH_2Cl_2$ (2 mL) at 0° C. The reaction mixture was stirred at RT for 3 h and the volatiles were removed under reduced pressure. The residue was recrystallized (EtOAc:hexanes) to afford 120 mg (78%) of 85 as a yellow solid. $^1H$ NMR (400 MHz, DMSO-$d_6$): δ 1.52 (br s, 6H), 2.13 (m, 4H), 6.45 (d, J=16.0 Hz, 1H), 6.67 (d, J=8.2 Hz, 1H), 6.76 (dd, J=12.3 Hz, 1.7 Hz, 1H), 6.85 (t, J=8.8 Hz, 1H), 7.08 (d, J=8.1 Hz, 2H), 7.53 (d, J=16.0 Hz, 1H), 7.58 (d, J=8.1 Hz, 2H) 9.76 (s, 1H), 12.31 (br s, 1H). LRMS (ESI): m/z 353 (M+H)$^+$.

Example 29 (91)

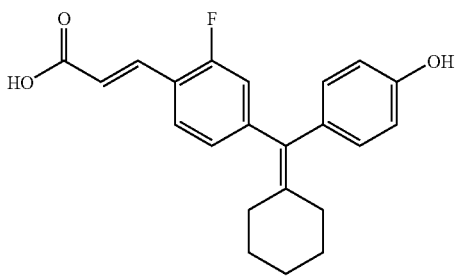

Step 1: 1-Bromo-4-(methoxymethoxy)benzene (86)

To a suspension of 60% NaH in mineral oil (12.7 g, 31.8 mmol) in anhydrous THF (300 mL) at 0° C. was added 4-bromophenol (50.0 g, 28.9 mmol) dissolved in THF (100 mL) dropwise over 1 h. The reaction mixture was stirred at 0° C. for 30 min, and chloromethylmethyl ether (24.8 mL, 32.6 mmol) dissolved in THF (30 mL) was added dropwise over 20 min. The reaction mixture was stirred overnight at RT. Water (250 mL) was added, and the mixture was extracted with ether (3×250 mL). The combined ethereal extracts were washed with brine, dried (MgSO$_4$), and concentrated. The residue was distilled under vacuum to afford 57.6 g (92%) of 86 as a colorless oil. $^1$H NMR (400 MHz, DMSO-d$_6$): δ 3.33 (s, 3H), 5.15 (s, 2H), 6.96 (d, J=9.0 Hz, 2H), 7.43 (d, J=9.0 Hz, 2H).

Step 2: Cyclohexyl[4-(methoxymethoxy)phenyl]methanone (87)

n-Butyllithium (1.6 M in hexanes, 50.5 mL, 80.8 mmol) was added dropwise to 86 (17.5 g, 80.8 mmol) dissolved in DME (150 mL) at −78° C. The reaction mixture was stirred at −40° C. for 1 h, and then cannulated into a suspension of lithium cyclohexanes carboxylate [prepared in situ by the addition of n-butyllithium (50.5 mL, 80.8 mmol) to cyclohexanes carboxylic acid (10.4 g, 80.8 mmol)] in DME (150 mL) at RT. The mixture was stirred for 1 h, poured into ice water (300 mL), and extracted with ether (3×150 mL). The combined ethereal extracts were washed with brine (300 mL) and dried over MgSO$_4$. Concentration followed by flash chromatography (20:1 to 5:1 hexanes:EtOAc) afforded 10.2 g (51%) of 87 as a colorless oil. $^1$H NMR (400 MHz, CDCl$_3$): δ 1.18-1.57 (m, 5H), 1.72 (m, 1H), 1.84 (m, 4H), 3.21 (m, 1H), 3.47 (s, 3H). 5.22 (s, 2H), 7.06 (d, J=8.8 Hz, 2H), 7.92 (d, J=8.8 Hz, 2H).

Step 3: 2-(4-Bromo-2-fluorophenyl)-1,3-dioxolane (88)

A mixture of 4-bromo-2-fluorobenzaldehyde (5.00 g, 24.6 mmol), p-toluenesulfonic acid monohydrate (190 mg, 1.00 mmol) and ethylene glycol (10 mL) were refluxed in benzene (50 mL) and EtOH (10 mL) under a Dean-Stark trap for 3 h. The reaction mixture was cooled and poured into a mixture of 5% aqueous NaHCO$_3$ (100 mL) and ice (100 mL). The mixture was extracted with ether (3×150 mL), and the combined ethereal extracts were washed with brine (200 mL) and dried (MgSO$_4$). Concentration under reduced pressure afforded 6.02 g (99%) of 88 that was used without further purification. $^1$H NMR (400 MHz, CDCl$_3$): δ 4.01-4.14 (m, 4H), 6.02 (s, 1H), 7.24-7.31 (m, 2H), 7.41 (t, J=7.9 Hz, 1H).

Step 4: 4-[Cyclohexylidene(4-hydroxyphenyl)methyl]-2-fluorobenzaldehyde (89)

n-Butyllithium (1.6 M in hexanes, 1.33 mL, 2.13 mmol) was added dropwise to 88 (503 mg, 2.04 mmol) dissolved in anhydrous THF (25 mL) at −78° C. The reaction mixture was stirred for 20 min and 87 (460 mg, 1.85 mmol), dissolved in THF (25 mL), was added dropwise. The mixture was warmed slowly to RT and stirred overnight. Water (150 mL) was added and the mixture was extracted with ether (3×100 mL). The combined ethereal extracts were washed with water (200 mL), brine (200 mL), dried (MgSO$_4$), and concentrated under reduced pressure. The resulting crude oil was taken up in a mixture of EtOH (10 mL) and 12 M HCl (2 mL) and refluxed for 2 h. Removal of solvent and flash chromatography (20:1 to 5:1 hexanes:EtOAc) afforded 200 mg (35%) of 89 as a white solid. $^1$H NMR (400 MHz, CDCl$_3$): δ 1.60 (br s, 6H), 2.23 (m, 4H), 6.00 (s, 1H), 6.79 (d, J=8.2 Hz, 2H), 6.89-6.95 (m, 3H), 7.02 (d, J=7.9 Hz, 1H), 7.76 (t, J=7.6 Hz, 1H), 10.28 (s, 1H).

Step 5: tert-Butyl (2E)-3-{4-[cyclohexylidene(4-hydroxyphenyl)methyl]-2-fluorophenyl}prop-2-enoate (90)

A solution of (tert-butoxycarbonylmethylene)triphenylphosphorane (610 mg, 1.62 mmol) in CH$_2$Cl$_2$ (10 mL) was added dropwise to 89 (200 mg, 0.644 mmol) dissolved in CH$_2$Cl$_2$ (10 mL) at RT. After stirring for 2 h at RT, water (50 mL) was added and the mixture was extracted with CH$_2$Cl$_2$ (3×25 mL). The combined organic layers were washed with brine (50 mL) and dried over MgSO$_4$. Concentration followed by flash chromatography (20:1 to 5:1 hexanes:EtOAc) and recrystallization (hexanes:EtOAc) afforded 180 mg (68%) of 90 as a white crystalline solid. $^1$H NMR (400 MHz, CDCl$_3$): δ 1.52 (s, 9H), 1.59 (br s, 6H), 2.22 (br s, 4H), 5.24 (s, 1H), 6.40 (d, J=16.3 Hz, 1H), 6.76 (d, J=8.4 Hz, 2H), 6.80-6.89 (m, 2H), 6.94 (d, J=8.4 Hz, 2H), 7.37 (t, J=7.9 Hz, 1H), 7.67 (d, J=16.3 Hz, 1H).

Step 6: (2E)-3-{4-[Cyclohexylidene(4-hydroxyphenyl)methyl]-2-fluorophenyl}-2-propenoic acid (91)

Trifluoroacetic acid (1.5 mL) was added dropwise to 90 (180 mg, 0.551 mmol) dissolved in CH$_2$Cl$_2$ (3 mL) at 0° C. The reaction mixture was stirred at RT for 2 h and the volatiles were removed under reduced pressure. Water (30 mL) was added and the mixture was extracted with EtOAc (3×20 mL). The combined organic layers were washed with water (30 mL), brine (30), and dried over MgSO$_4$. Concentration followed by recrystallization (EtOAc) afforded 99 mg (64%) of 91 as a pale yellow solid. $^1$H NMR (400 MHz, DMSO-d$_6$): δ 1.52 (br s, 6H), 2.13 (br s, 4H), 6.51 (d, J=16.0 Hz, 1H), 6.67 (d, J=8.4 Hz, 2H), 6.85-6.91 (m, 4H), 7.59 (d, J=16.0 Hz, 1H), 7.72 (t, J=8.1 Hz, 1H), 9.36 (s, 1H), 12.51 (br s, 1H). LRMS (APCI): m/z 353 (M+H)$^+$.

Example 30 (94)

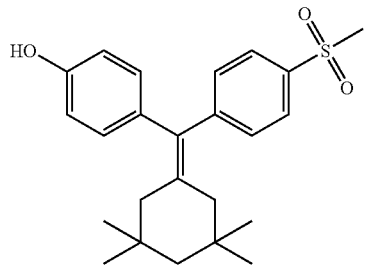

Step 1: [4-(Methyloxy)phenyl][4-(methylsulfonyl)phenyl]methanone (92)

4-(Methylsulfonyl)benzoic acid (0.5 g, 2.42 mmol) was suspended in $CH_2Cl_2$ (15 mL). Oxalyl chloride (0.44 mL, 4.85 mmol) was added dropwise, followed by addition of two drops of DMF. The reaction mixture was stirred at room temperature for 3 h. $CH_2Cl_2$ and the excess of oxalyl chloride were removed under vacuum. The residue was dissolved in $CH_2Cl_2$ (10 mL) with anisole (0.54 mL, 4.84 mmol). Cooled in an ice bath, aluminum chloride (0.49 g, 3.63 mmol) was added in portions. The mixture was stirred at 0° C. for 2 h, then heated at reflux overnight. Cooled to room temperature, the mixture was poured into 1 N HCl (15 mL) with ice, the pinkish solid was collected and washed with water, hexanes and dried to give 0.50 g (71%) of the title compound (92) as light pink solid. $^1$H NMR (400 MHz, DMSO-$d_6$): δ 3.28 (s, 3H), 3.85 (s, 3H), 7.09 (d, J=8.8 Hz, 2H), 7.76 (d, J=8.8 Hz, 2H), 7.88 (d, J=8.3 Hz, 2H), 8.07 (d, J=8.2 Hz, 2H). LCMS (ESI): m/z 291 (M+H)$^+$.

Step 2: (4-Hydroxyphenyl)[4-(methylsulfonyl)phenyl]methanone (93)

A mixture of [4-(Methyloxy)phenyl][4-(methylsulfonyl)phenyl]methanone (92) (0.20 g, 0.69 mmol) and aluminum chloride (0.38 g, 2.76 mmol) were refluxed in benzene (10 mL) for 2 h and then cooled to 0° C. in an ice bath. Water (10 mL) was added slowly, and the mixture was extracted with EtOAc (2×75 mL). The combined organic extract washed with water, brine, and dried over $Na_2SO_4$. Concentration of the extract gave the title compound (93) as light brown solid (0.19 g, 100%), which was used without further purification. $^1$H NMR (400 MHz, DMSO-$d_6$): δ 3.28 (s, 3H), 6.89 (d, J=8.6 Hz, 2H), 7.66 (d, J=8.8 Hz, 2H), 7.85 (d, J=8.2 Hz, 2H), 8.05 (d, J=8.2 Hz, 2H), 10.56 (s, 1H). LCMS (ES): m/z 277 (M+H)$^+$, m/z 275 (M−H)$^-$.

Step 3: 4-[[4-(Methylsulfonyl)phenyl](3,3,5,5 tetramethylcyclohexylidene)methyl]phenol (94)

To a stirred suspension of zinc powder (0.36 g, 5.50 mmol) in THF (15 mL) was slowly added $TiCl_4$ (0.30 mL, 2.75 mmol) via syringe at room temperature under a nitrogen atmosphere. The mixture was heated at reflux for 2 h. A solution of (4-hydroxyphenyl) [4-(methylsulfonyl)phenyl] methanone (93) (0.19 g, 0.69 mmol) and 3,3,5,5-tetramethyl cyclohexanone (0.33 g, 2.06 mmol) in THF (4 mL) was added to the mixture. The reaction mixture was heated at reflux with stirring under a nitrogen atmosphere for 1.5 h. The reaction mixture was allowed to cool at room temperature. To the reaction mixture was slowly added 10% aqueous $K_2CO_3$ (15 mL). The reaction mixture was filtered through a pad of celite and the pad washed with ethyl acetate (70 mL). The filtrate was transferred to a separatory funnel and the layers were separated. The aqueous layer was further extracted with ethyl acetate (25 mL). The combined organic phase washed with water, brine, dried over $Na_2SO_4$, filtered, and the filtrate was concentrated to give the crude product as yellow oil. The crude product was purified by chromatography on a silica gel column eluted with a gradient from hexanes to 25% EtOAc:hexanes to give white foam residue, which was triturated with hot hexanes (containing 1% MeOH) to afford 0.21 g (76%) of the title compound (94) as white solid, m.p. 149-150° C. $^1$H NMR (300 MHz, DMSO-$d_6$): δ 0.90 (s, 6H), 0.91 (s, 6H), 1.28 (s, 2H), 1.88 (s, 2H), 1.95 (s, 2H), 3.20 (s, 3H), 6.70 (d, J=8.4 Hz, 2H), 6.97 (d, J=8.4 Hz, 2H), 7.40 (d, J=8.2 Hz, 2H), 7.84 (d, J=8.2 Hz, 2H), 9.34 (s, 1H). LCMS (ES): m/z 397 (M−H)$^-$.

Example 31 (95)

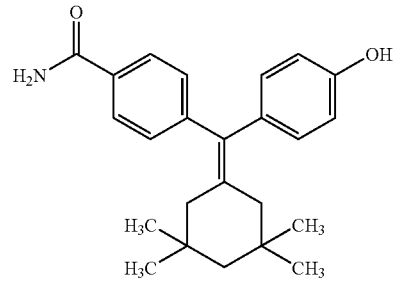

Step 1: 4-[(4-hydroxyphenyl)(3,3,5,5-tetramethylcyclohexylidene)methyl]benzamide (95)

To a cold (−15° C.) solution of 4-[(4-hydroxyphenyl)(3,3,5,5-tetramethylcyclohexylidene)methyl]benzoic acid (0.100 g, 0.274 mmol) (26) in THF were added $Et_3N$ (0.042 mL, 0.302 mmol) and ethyl chloroformate (0.029 mL, 0.302 mmol) sequentially. The resultant solution was stirred at that temperature for 0.5 h. An aqueous 28% $NH_4OH$ solution was added slowly to the above mixture at −15° C. and stirred the resultant mixture at room temperature for 15 h. Reaction mixture was poured into sat. $NH_4Cl$ solution (30 mL) and then extracted with EtOAc (2×40 mL). The combined organic layer washed with brine (1×25 mL), dried ($Na_2SO_4$), and concentrated under reduced pressure to afford the crude product. The product was purified by $SiO_2$ column chromatography using $CHCl_3$ and MeOH (100:00 to 9:1) as an eluent to afford 0.035 g (35%) of the title compound (95) as white crystalline solid. Around 25 mg of starting material was also recovered from this reaction. mp 209° C.-210° C. $^1$H NMR (400 MHz, DMSO-$d_6$): δ 9.29 (s, 1H), 7.87 (s, 1H), 7.75 (d, J=8.0 Hz, 2H), 7.27 (s, 1H), 7.15 (d, J=8.0 Hz, 2H), 6.92 (d, J=8.4 Hz, 2H), 6.65 (d, J=8.4 Hz, 2H), 1.91 (s, 2H), 1.85 (s, 2H), 1.24 (s, 2H), 0.87 (s, 6H), 0.85 (s, 6H). LCMS (ESI): m/z 362.31 (M−H)$^-$.

Example 32 (97)

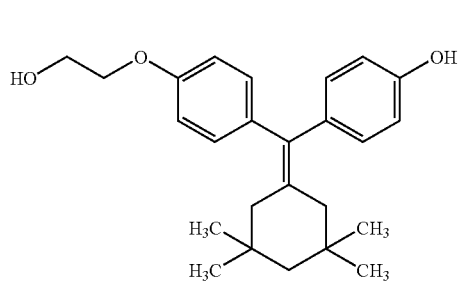

Step 1: {4-[(2-Hydroxyethyl)oxy]phenyl}(4-hydroxyphenyl)methanone (96)

To a solution of 4,4'-dihydroxybenzophenone (3.0 g, 13.9 mmol) in DMF (30 mL) was added $Cs_2CO_3$ (13.55 g, 41.6 mmol). The mixture was heated at 80° C. under nitrogen for 1 h. Cooled to room temperature, NaI (2.08 g, 13.9 mmol) was added, followed by dropwise addition of a solution of 2-chloroethanol (1.03 mL, 15.3 mmol) in DMF (7 mL) with stirring. The reaction mixture was heated at 80° C. under nitrogen overnight. The mixture was cooled to room temperature and quenched with saturated aqueous $NH_4Cl$ (100 mL), then extracted with EtOAc (3×60 mL). The organic layers were combined and washed with water, brine and dried over $Na_2SO_4$. Concentration gave a reddish brown oil which was further purified by chromatography on a silica gel column eluted with a gradient from hexanes to 80% EtOAc:hexanes yielded a pale white solid. Trituration with 10% EtOAc:hexanes afforded 1.30 g (36%) of 96 as a white solid. mp 146-147° C. $^1$H NMR (400 MHz, $CD_3OD$): δ 3.85-3.95 (m, 2H), 4.10-4.20 (m, 2H), 6.87 (d, J=8.8 Hz, 2H), 7.06 (d, J=8.7 Hz, 2H), 7.67 (d, J=8.6 Hz, 2H), 7.73 (d, J=8.8 Hz, 2H). LRMS (ESI): m/z 259 $(M+H)^+$, 257 $(M-H)^-$.

Step 2: 4-[{4-[(2-Hydroxyethyl)oxy]phenyl}(3,3,5,5-tetramethylcyclohexylidene)methyl]phenol (97)

To a stirred suspension of Zn (0.50 g, 7.59 mmol) in THF (10 mL) was added $TiCl_4$ (0.42 mL, 3.79 mmol) dropwise. The mixture was refluxed under nitrogen for 2.5 h. Cooled to room temperature, a solution of 96 (0.245 g, 0.95 mmol) and 3,3,5,5-tetramethylcyclohexanone (0.45 g, 2.85 mmol) in THF (15 mL) was added at once. The reaction mixture was refluxed for another 2.5 h. Cooled to room temperature, the reaction was quenched with 10% $K_2CO_3$ (20 mL). The quenched reaction mixture was filtered through a pad of Celite and the pad washed with EtOAc (100 mL). The filtrate was transferred to a separatory funnel, the layers were separated and the aqueous phase was extracted with EtOAc (50 mL). The organic extracts were combined, washed with brine and dried ($Na_2SO_4$). Concentration yielded a pale brown oil which was further purified by chromatography on a silica gel column eluted with a gradient from hexanes to 45% EtOAc:hexanes to give a light yellow solid, Crystallization from 7:1 hexanes:EtOAc yielded 97 as colorless needles (0.15 g, 42%). mp 154-155° C. $^1$H NMR (400 MHz, $CD_3OD$): δ 0.91 (s, 6H), 0.92 (s, 6H), 1.28 (s, 2H), 1.96 (s, 2H), 1.98 (s, 2H), 3.80-3.90 (m, 2H), 4.00-4.10 (m, 2H), 6.67 (d, J=8.5 Hz, 2H), 6.84 (d, J=8.6 Hz, 2H), 6.94 (d, J=8.6 Hz, 2H), 7.03 (d, J=8.6 Hz, 2H). LRMS (ESI): m/z 381 $(M+H)^+$, 379 $(M-H)^-$. The sample was silated prior to EI analysis. HRMS (EI) Calcd for $C_{31}H_{48}O_3Si_2$: 524.3142 $(M^+)$. Found: 524.3128.

Example 33 (98)

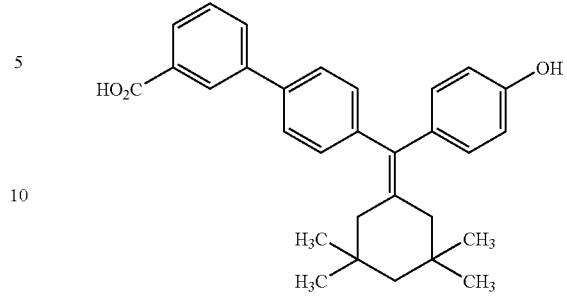

Step 1: 4'-[(4-Hydroxyphenyl)(3,3,5,5-tetramethylcyclohexylidene)methyl]-3-biphenylcarboxylic acid (98)

To a round-bottomed flask were added 4-[(4-bromophenyl)(3,3,5,5-tetramethyl cyclohexylidene)methyl]phenol (14) (0.102 g, 0.255 mmol), 3-carboxyphenylboronic acid (0.085 g, 0.51 mmol, 2 eq), tetrakis(triphenylphosphine)palladium (0) (0.020 g, 0.017 mmol, 0.07 eq), aqueous $Na_2CO_3$ (2 M, 8 mL), and ethylene glycol dimethyl ether (5 mL). The stirred reaction mixture was heated at reflux overnight under a nitrogen atmosphere. The reaction mixture was allowed to cool to room temperature and transferred to a separatory funnel. The reaction mixture was partitioned between 1 N HCl (aqueous) and $CH_2Cl_2$. The layers were separated and the organic phase washed with brine, dried over $MgSO_4$, filtered, and the filtrate was concentrated to give an oil. The crude product was purified by reverse phase preparative HPLC using a C18 column and a $CH_3CN:H_2O$ (50:50 to 100:0) gradient with 0.05% TFA as a modifier to give 0.052 g (46%) of compound 98 as a white solid. $^1$H NMR (400 MHz, DMSO-$d_6$): δ 0.89 (s, 12 H), 1.26 (s, 2 H), 1.93 (s, 4 H), 6.67 (d, J=8.4 Hz, 2 H), 6.95 (d, J=8.5 Hz, 2 H), 7.22 (d, J=8.0 Hz, 2 H), 7.55 (t, J=7.7 Hz, 1 H), 7.61 (d, J=8.3 Hz, 2 H), 7.89 (dd, J=7.8, 1.6 Hz, 2 H), 8.14 (s, 1 H), 9.28 (s, 1 H), 13.04 (s, 1 H). HRMS (ESI) Calcd for $C_{30}H_{33}O_3$: 441.2430 $(M+H)^+$. Found: 441.2419.

Example 34 (99)

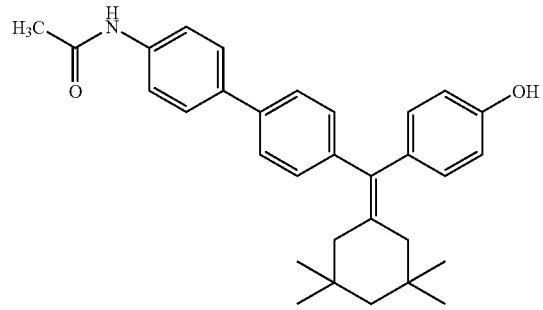

Step 1: N-{4'-[(4-Hydroxy-phenyl)-(3,3,5,5-tetramethyl-cyclohexylidene)-methyl]-biphenyl-4-yl}-acetamide (99)

To a solution of 4-[(4-bromophenyl)(3,3,5,5-tetramethylcyclohexylidene)methyl]phenol (14) (0.1 g, 0.250 mmol) and (4-acetylaminophenyl)boronic acid (0.148, 0.826 mmol) in ethylene glycol dimethyl ether (8 mL) was added tetrakis (triphenylphosphine)palladium (0) (0.026 g, 0.023 mmol) followed by 2 M $Na_2CO_3$ (3 mL). The reaction mixture was refluxed for 4 h, cooled to room temperature then diluted with water followed by EtOAc. The layers were separated and the aqueous layer was extracted with EtOAc. The combined organic layers were washed with water followed by brine, dried (MgSO$_4$) filtered and concentrated to an oil. The crude oil was dissolved in DCM, loaded onto silica gel and purified with a gradient of 100% hexanes to 40% hexanes:EtOAc over 60 mins. Pure fractions were combined and concentrated to give 0.05 g (41%) of the title compound 99 as an off white powder. $^1$H NMR (400 MHz, DMSO-d$_6$): δ 0.89 (s, 12 H), 1.25 (s, 2 H), 1.93 (s, 4 H), 2.03 (s, 3 H), 6.66 (d, J=8.5 Hz, 2 H), 6.94 (d, J=8.4 Hz, 2 H), 7.16 (d, J=8.3 Hz, 2 H) 7.52-7.64 (m, 6 H), 9.27 (s, 1 H), 9.99 (s, 1 H). HRMS (ESI) Calcd for C$_{31}$H$_{36}$NO$_2$: 454.2746 (M+H)$^+$. Found 454.2757.

Example 35 (100)

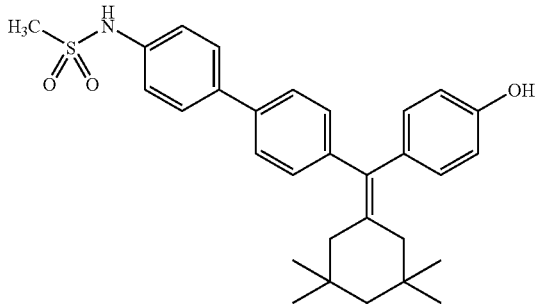

Step 1: N-{4'-[(4-Hydroxy-phenyl)-(3,3,5-5-tetramethyl-cyclohexylidene)-methyl]-biphenyl-4-yl}-methanesulfonamide (100)

The title compound was prepared using the conditions described in Example 97 using 4-[(4-bromophenyl)(3,3,5,5-tetramethylcyclohexylidene)methyl]phenol (14) (0.1 g, 0.250 mmol), [(4-methylsulfonyl)aminophenyl]boronic acid (0.178, 0.826 mmol), ethylene glycol dimethyl ether (8 ml), tetrakis(triphenylphosphine)palladium (0) (0.026 g, 0.023 mmol) and 2 M Na$_2$CO$_3$ (3 mL) to afford 0.070 g (57%) of compound 100 as a powder. $^1$H NMR (400 MHz, DMSO-d$_6$): δ 0.89 (s, 12 H), 1.25 (s, 2 H), 1.93 (s, 4 H), 2.99 (s, 3 H), 6.66 (d, J=8.4 Hz, 2 H), 6.94 (d, J=8.4 Hz, 2 H), 7.17 (d, J=8.3 Hz, 2 H) 7.25 (d, J=8.6 Hz, 2 H), 7.54 (d, J=8.2 Hz, 2 H), 7.61 (d, J=8.5 Hz, 2 H), 9.28 (s, 1 H), 9.82 (s, 1 H). HRMS (ESI) Calcd for C$_{30}$H$_{34}$NO$_3$S: 488.2259 (M–H)$^-$. Found 488.2265

Example 36 (102)

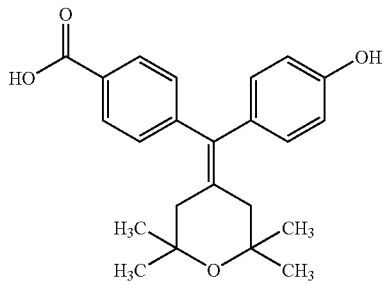

Step 1: methyl 4-[(4-hydroxyphenyl)(2,2,6,6-tetramethyltetrahydro-4H-pyran-4-ylidene)methyl]benzoate (101)

The general McMurry protocol, described for 14 was followed. Thus, methyl 4-[(4-hydroxyphenyl)carbonyl]benzoate (24) (0.196 g, 0.765 mmol) and 2,2,6,6-tetramethyltetrahydro-4H-pyran-4-one (52) (0.370 g, 2.37 mmol) were subjected for McMurry coupling reaction conditions. Standard work-up followed by purification by column chromatography gave 0.272 g (93%) of the title compound 101 as a white foam. $^1$H NMR (300 MHz, CDCl$_3$): δ 7.98 (d, J=8.1 Hz, 2H), 7.26 (d, J=8.7 Hz, 2H), 7.05 (d, J=8.7 Hz, 2H), 6.78 (d, J=8.4 Hz, 2H), 3.92 (s, 3H), 2.27 (s, 2H), 2.21 (s, 2H), 1.28 (s, 6H), 1.25 (s, 6H). LCMS (ESI): m/z 379 (M–H)$^-$.

Step 2: 4-[(4-hydroxyphenyl)(2,2,6,6-tetramethyltetrahydro-4H-pyran-4-ylidene)methyl]benzoic acid (102)

The hydrolysis procedure described for 191 was employed. Thus, methyl 4-[(4-hydroxyphenyl)(2,2,6,6-tetramethyltetrahydro-4H-pyran-4-ylidene)methyl]benzoate (101) (0.212 g, 0.557 mmol) in THF/EtOH (1:1, 6 mL) was treated with 1 N NaOH (3 mL, excess). Standard work-up followed by purification gave 0.170 g (83%) of compound 102 as a white solid. $^1$H NMR (300 MHz, DMSO-d$_6$): δ 12.77 (br s, 1H), 9.40 (br s, 1H), 7.88 (d, J=8.1 Hz, 2H), 7.27 (d, J=8.1 Hz, 2H), 6.97 (d, J=8.7 Hz, 2H), 6.71 (d, J=8.4 Hz, 2H), 2.18 (s, 2H), 2.11 (s, 2H), 1.14 (s, 6H), 1.12 (s, 6H). LCMS (ESI): m/z 365 (M–H)$^-$.

Example 37 (103)

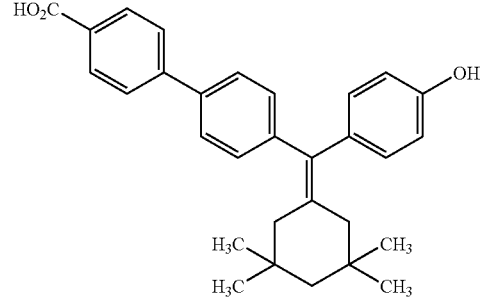

Step 1: 4'-[(4-Hydroxyphenyl)(3,3,5,5-tetramethylcyclohexylidene)methyl]-4-biphenylcarboxylic acid (103)

To a round-bottomed flask were added 4-[(4-bromophenyl)(3,3,5,5-tetramethyl cyclohexylidene)methyl]phenol (14) (0.105 g, 0.26 mmol), 4-dihydroxyborane-benzoic acid (0.093 g, 0.56 mmol, 2.2 eq), tetrakis(triphenylphosphine) palladium (0) (0.023 g, 0.02 mmol, 0.08 eq), aqueous Na$_2$CO$_3$ (2 M, 3 mL), and ethylene glycol dimethyl ether (5 mL). The reaction mixture was heated overnight at reflux with stirring under a nitrogen atmosphere. The reaction mixture was allowed to stand at RT under nitrogen for six days. To the reaction mixture were added 4-dihydroxyborane-benzoic acid (0.099 g, 0.60 mmol, 2.3 eq), tetrakis(triphenylphosphine)palladium (0) (0.031 g, 0.027 mmol, 0.10 eq), aqueous sodium carbonate (2 M, 2 mL), and ethylene glycol dimethyl ether (2 mL). The stirred reaction mixture was heated overnight at reflux under nitrogen. The reaction mixture was allowed to stand at RT under nitrogen for one week. The reaction mixture was partitioned between 1 N HCl (aqueous) and CH$_2$Cl$_2$. The organic phase was separated, washed with brine, dried over MgSO$_4$, filtered, and the filtrate was concentrated to give the crude product as an oil. The crude product was partially purified by flash chromatography on silica gel with a CH$_2$Cl$_2$:MeOH (100:0 to 96:4) gradient to give 0.052 g of the impure product as a an oil. The impure product was purified by reverse phase preparative HPLC using a C18 column and an CH$_3$CN:H$_2$O (75:25 to 100:0) gradient with 0.05% TFA as a modifier to give 9.3 mg (8%) of compound 103 as an off-white solid. $^1$H NMR (400 MHz, DMSO-d$_6$): δ 0.89 (br s, 12 H), 1.26 (br s, 2 H), 1.93 (br s, 4 H), 6.67 (d, J=8.5 Hz, 2 H), 6.96 (d, J=8.4 Hz, 2 H), 7.23 (d, J=8.1 Hz, 2 H), 7.65 (d, J=8.1 Hz, 2 H), 7.77 (d, J=8.2 Hz, 2 H), 7.98 (d, J=8.4 Hz, 2 H), 9.29 (s, 1 H), 12.94 (br s, 1 H).

Example 38 (108)

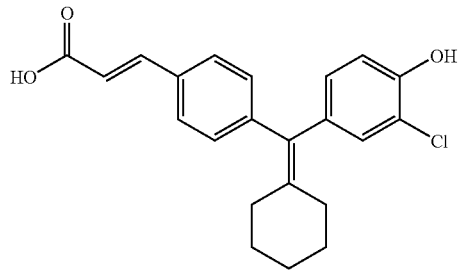

Step 1: (4-Bromophenyl)[3-chloro-4-(methyloxy)phenyl]methanone (104)

The title compound 104 (1.25 g, 84%) was obtained in a similar manner previously reported for 27. $^1$H NMR (400 MHz, CDCl$_3$): δ 3.98 (s, 3H), 6.99 (d, J=8.6 Hz, 1H), 7.62 (m, 4H), 7.71 (dd, J=2.1 Hz, 8.5 Hz, 1H), 7.85 (d, J=2.01 Hz, 1H).

Step 2: (4-Bromophenyl)(3-chloro-4-hydroxyphenyl)methanone (105)

The title compound 105 (1.06 g, 88%) was obtained in a similar manner previously reported for 28. $^1$H NMR (400 MHz, DMSO-d$_6$): δ 7.08 (d, J=8.4 Hz, 1H), 7.56 (dd, J=2.1 Hz, 8.5 Hz, 1H), 7.60 (d, J=8.4 Hz, 2H), 7.70 (d, J=2.0 Hz, 1H), 7.74 (d, J=8.4 Hz, 2H), 11.31 (s, 1H).

Step 3: 4-[(4-Bromophenyl)(cyclohexylidene)methyl]-2-chlorophenol (106)

The title compound was prepared according to the procedure described for 29, with modification. Upon cooling, the reaction mixture was quenched with 10% aqueous K$_2$CO$_3$ and filtered through a pad of Celite. The pad washed with EtOAc. The filtrate was transferred to a separatory funnel and the layers were separated. The organic phase was dried over MgSO$_4$, filtered, and the filtrate was concentrated to give the crude product. The crude product was purified by chromatography on silica gel with EtOAc:hexanes to afford 0.48 g (79%) of compound 106. $^1$H NMR (400 MHz, CDCl$_3$): δ 1.57 (m, 6H), 2.17-2.23 (m, 4H), 5.45 (s, 1H), 6.91 (d, J=2.2 Hz, 2H), 6.95 (d, J=8.2 Hz, 2H), 7.02 (m, 1H), 7.39 (d, J=8.4 Hz, 2H).

Step 4: Ethyl(2E)-3-{4-[(3-chloro-4-hydroxyphenyl)(cyclohexylidene)methyl]phenyl}-2-propenoate (107)

The title compound 107 (187 mg, 58%) was obtained in a similar manner previously reported for 30. $^1$H NMR (400 MHz, CDCl$_3$): δ 1.32 (t, J=7.1 Hz, 3H), 1.60 (br s, 6H), 2.22 (m, 4H), 4.25 (q, J=7.1 Hz, 2H), 6.39 (d, J=15.9 Hz, 1H), 6.92 (s, 2H), 7.04 (s, 1H), 7.10 (d, J=8.1 Hz, 2H), 7.43 (d, J=8.1 Hz, 2H), 7.65 (d, J=16.1 Hz, 1H).

Step 5: (2E)-3-{4-[(3-Chloro-4-hydroxyphenyl)(cyclohexylidene)methyl]phenyl}-2-propenoic acid (108)

The title compound 108 (0.14 g, 82%) was obtained in a similar manner previously reported for 31. $^1$H NMR (DMSO-d$_6$): δ 1.53 (br s, 6H), 2.12-2.14 (m, 4H), 6.45 (d, J=15.9 Hz, 1H), 6.82-6.89 (m, 2H), 6.94 (m, 1H), 7.07 (d, J=8.1 Hz, 2H), 7.53 (d, J=16.1 Hz, 1H), 7.59 (d, J=8.1 Hz, 2H), 10.11 (s, 1H), 12.32 (s, 1H). LRMS (ESI): m/z, 369 (M+H)$^+$.

Example 39 (113)

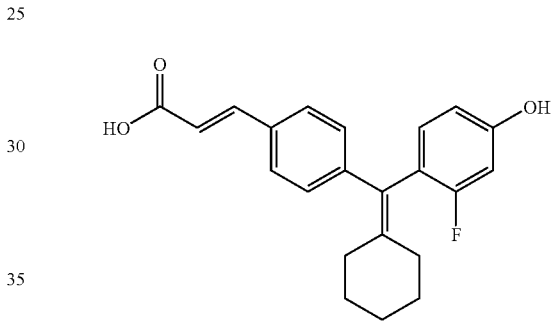

Step 1: (4-Bromophenyl)[2-fluoro-4-(methyloxy)phenyl]methanone (109)

The title compound (0.38 g, 26%) was obtained in a similar manner previously reported for 27. $^1$H NMR (400 MHz, CDCl$_3$): δ 3.87 (s, 3H), 6.65 (dd, J=2.4 Hz, 11.9 Hz, 1H), 6.79 (dd, J=2.3 Hz, 8.7 Hz, 1H), 7.57 (t, J=8.4 Hz, 1H), 7.59 (d, J=8.4 Hz, 2H), 7.65 (d, J=8.4 Hz, 2H).

Step 2: (4-Bromophenyl)(2-fluoro-4-hydroxyphenyl)methanone (110)

The title compound (0.31 g, 86%) was obtained in a similar manner previously reported for 28. $^1$H NMR (400 MHz, DMSO-d$_6$): δ 6.64 (dd, J=2.1 Hz, 12.5 Hz, 1H), 6.73 (dd, J=2.1 Hz, 8.5 Hz, 1H), 7.45 (t, J=8.6 Hz, 1H), 7.61 (d, J=8.2 Hz, 2H), 7.72 (d, J=8.4 Hz, 2H), 10.79 (s, 1H).

Step 3: 4-[(4-Bromophenyl)(cyclohexylidene)methyl]-3-fluorophenol (111)

The title compound was prepared according to the procedure described for 29, with modification. Upon cooling, the reaction mixture was quenched with 10% aqueous K$_2$CO$_3$ and filtered through a pad of Celite. The pad washed with EtOAc. The filtrate was transferred to a separatory funnel and the layers were separated. The organic phase was dried over MgSO$_4$, filtered, and the filtrate was concentrated to give the crude product. The crude product was purified by chromatography on silica gel with EtOAc:hexanes to give 0.32 g (86%) of compound 111. $^1$H NMR (400 MHz, CDCl$_3$): δ 1.57 (s, 6H), 2.07 (m, 2H), 2.23 (m, 2H), 4.90 (s, 1H), 6.51-6.55 (m, 2H), 6.91 (t, J=8.5 Hz, 1H), 7.00 (d, J=8.2 Hz, 2H), 7.38 (d, J=8.5 Hz, 2H).

Step 4: Ethyl(2E)-3-{4-[cyclohexylidene(2-fluoro-4-hydroxyphenyl)methyl]phenyl}-2-propenoate (112)

The title compound (0.22 g, 65%) was obtained in a similar manner previously reported for 30. $^1$H NMR (400 MHz, CDCl$_3$): δ 1.32 (t, J=7.1 Hz, 3H), 1.59 (s, 6H), 2.10 (m, 2H), 2.25 (m, 2H), 1.97 (q, J=7.1 Hz, 2H), 6.37 (d, J=15.9 Hz, 1H), 6.51-6.55 (m, 2H), 6.92 (t, J=8.5 Hz, 1H), 7.15 (d, J=8.2 Hz, 2H), 7.41 (d, J=8.2 Hz, 2H), 7.64 (d, J=15.9 Hz, 1H).

Step 5: (2E)-3-{4-[Cyclohexylidene(2-fluoro-4-hydroxyphenyl)methyl]phenyl}-2-propenoic acid (113)

The title compound (0.17 g, 86%) was obtained in a similar manner previously reported for 31. $^1$H NMR (400 MHz, DMSO-d$_6$): δ 1.52 (s, 6H), 2.02 (m, 2H), 2.17 (m, 2H), 6.44 (d, J=16.1 Hz, 1H), 6.48 (dd, J=2.2 Hz, 11.5 Hz, 1H), 6.54 (dd, J=2.2 Hz, 8.2 Hz, 1H), 6.89 (t, J=8.7 Hz, 1H), 7.07 (d, J=8.1 Hz, 2H), 7.52 (d, J=16.1 Hz, 1H), 7.57 (d, J=8.1 Hz, 2H), 9.8 (s, 1H), 12.32 (s, 1H). LCMS (ESI): m/z 385 (M+Na)$^+$.

Example 40 (118)

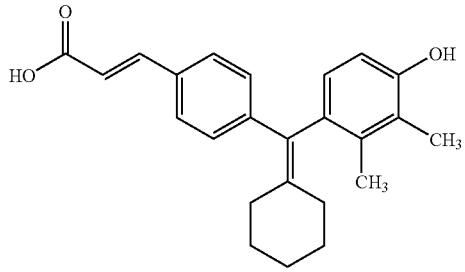

Step 1: (4-Bromophenyl)[2,3-dimethyl-4-(methyloxy)phenyl]methanone (114)

The title compound (1.46 g, 92%) was obtained in a similar manner previously reported for 27. $^1$H NMR (400 MHz, CDCl$_3$): δ 2.19 (s, 3H), 2.23 (s, 3H), 3.87 (s, 3H), 6.72 (d, J=8.4 Hz, 1H), 7.14 (d, J=8.6 Hz, 1H), 7.57 (d, J=8.4 Hz, 2H), 7.65 (d, J=8.4 Hz, 2H).

Step 2: (4-Bromophenyl)(4-hydroxy-2,3-dimethylphenyl)methanone (115)

The title compound (1.16 g, 83%) was obtained in a similar manner previously reported for 28. $^1$H NMR (400 MHz, DMSO-d$_6$): δ 2.08 (s, 3H), 2.11 (s, 3H), 6.71 (d, J=8.4 Hz, 1H), 6.96 (d, J=8.4 Hz, 1H), 7.57 (d, J=8.4 Hz, 2H), 7.70 (d, J=8.4 Hz, 2H), 9.94 (s, 1H).

Step 3: 4-[(4-Bromophenyl)(cyclohexylidene)methyl]-2,3-dimethylphenol (116)

The title compound was prepared according to the procedure described for 29, with modification. Upon cooling, the reaction mixture was quenched with 10% aqueous K$_2$CO$_3$ and filtered through a pad of Celite. The pad washed with EtOAc. The filtrate was transferred to a separatory funnel and the layers were separated. The organic phase was dried over MgSO$_4$, filtered, and the filtrate was concentrated to give the crude product. The crude product was purified by chromatography on silica gel with EtOAc:hexanes to give 0.53 g (87%) of compound 116. $^1$H NMR (400 MHz, CDCl$_3$): δ 1.59 (m, 6H), 1.97 (m, 2H), 2.06 (s, 3H), 2.13 (s, 3H), 2.29 (m, 2H), 4.60 (s, 1H), 6.59 (d, J=8.2 Hz, 1H), 6.79 (d, J=8.1 Hz, 1H), 6.99 (d, J=8.2 Hz, 2H), 7.34 (d, J=8.4 Hz, 2H).

Step 4: Ethyl(2E)-3-{4-[cyclohexylidene(4-hydroxy-2,3-dimethylphenyl)methyl]phenyl}-2-propenoate (117)

The title compound 117 (0.15 g, 49%) was obtained in a similar manner previously reported for 30. $^1$H NMR (400 MHz, CDCl$_3$): δ 1.32 (t, J=7.1 Hz, 3H), 1.59 (m, 6H), 1.98 (m, 2H), 2.08 (s, 3H), 2.14 (s, 3H), 2.32 (m, 2H), 4.24 (q, J=7.1 Hz, 2H), 4.70 (s, 1H), 6.36 (d, J=15.9 Hz, 1H), 6.60 (d, J=8.1 Hz, 1H), 6.81 (d, J=8.2 Hz, 1H), 7.13 (d, J=8.1 Hz, 2H), 7.39 (d, J=8.1 Hz, 2H), 7.63 (d, J=15.9 Hz, 1H).

Step 5: (2E)-3-{4-[Cyclohexylidene(4-hydroxy-2,3-dimethylphenyl)methyl]phenyl}-2-propenoic acid (118)

The title compound 118 (0.14 g, 100%) was obtained in a similar manner previously reported for 31. $^1$H NMR (400 MHz, DMSO-d$_6$): δ 1.49 (m, 6H), 1.90 (m, 2H), 1.96 (s, 3H), 1.99 (s, 3H), 2.23 (m, 2H), 6.42 (d, J=16.1 Hz, 1H), 6.59 (d, J=8.2 Hz, 1H), 6.68 (d, J=8.2 Hz, 1H), 7.08 (d, J=8.1 Hz, 2H), 7.50 (d, J=15.9 Hz, 1H), 7.54 (d, J=8.2 Hz, 2H), 9.05 (s, 1H), 12.31 (s, 1H). LCMS (ESI): m/z 363 (M+H)$^+$.

Example 41 (123)

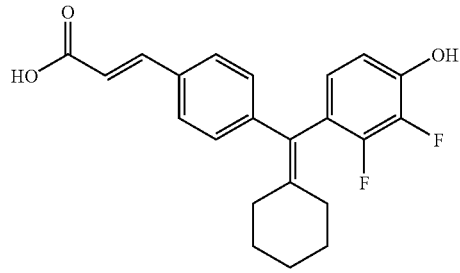

Step 1: (4-Bromophenyl)[2,3-difluoro-4-(methyloxy)phenyl]methanone (119)

The title compound 119 (0.94 g, 66%) was obtained in a similar manner previously reported for 27. $^1$H NMR (400 MHz, CDCl$_3$): δ 3.98 (s, 3H), 6.84 (m, 1H), 7.35 (m, 1H), 7.61 (d, J=8.6 Hz, 2H), 7.66 (d, J=8.5 Hz, 2H).

Step 2: (4-Bromophenyl)(2,3-difluoro-4-hydroxyphenyl)methanone (120)

The title compound 120 (0.76 g, 84%) was obtained in a similar manner previously reported for 28. $^1$H NMR (400 MHz, CDCl$_3$): 5.75 (s, 1H), 6.90 (m, 1H), 7.31 (m, 1H), 7.61-7.67 (m, 4H).

Step 3: 4-[(4-Bromophenyl)(cyclohexylidene)methyl]-2,3-difluorophenol (121)

The title compound was prepared according to the procedure described for 29, with modification. Upon cooling, the reaction mixture was quenched with 10% aqueous K$_2$CO$_3$ and filtered through a pad of Celite. The pad washed with EtOAc. The filtrate was transferred to a separatory funnel and the layers were separated. The organic phase was dried over MgSO$_4$, filtered, and the filtrate was concentrated to give the crude product. The crude product was purified by chromatography on silica gel with EtOAc:hexanes to give 0.77 g (85%) of compound 121. $^1$H NMR (400 MHz, CDCl$_3$): δ 1.58 (m, 6H), 2.06 (m, 2H), 2.22 (m, 2H), 5.80 (s, 1H), 6.69 (d, J=5.1 Hz, 2H), 7.00 (d, J=8.4 Hz, 2H), 7.38 (d, J=8.4 Hz, 2H).

Step 4: Ethyl(2E)-3-{4-[cyclohexylidene(2,3-difluoro-4-hydroxyphenyl)methyl]phenyl}-2-propenoate (122)

The title compound 122 (0.22 g, 70%) was obtained in a similar manner previously reported for 30. $^1$H NMR (400 MHz, CDCl$_3$): δ 1.32 (t, J=7.1 Hz, 3H), 1.59 (m, 6H), 2.10 (m, 2H), 2.25 (m, 2H), 4.25 (q, J=7.1 Hz, 2H), 6.38 (d, J=15.9 Hz, 1H), 6.70 (d, J=5.1 Hz, 2H), 7.14 (d, J=8.1 Hz, 2H), 7.42 (d, J=8.1 Hz, 2H), 7.64 (d, J=15.9 Hz, 1H).

Step 5: (2E)-3-{4-[Cyclohexylidene(2,3-difluoro-4-hydroxyphenyl)methyl]phenyl}-2-propenoic acid (123)

The title compound 123 (0.196 g, 98%) was obtained in a similar manner previously reported for 31. $^1$H NMR (400 MHz, DMSO-d$_6$): δ 1.53 (m, 6H), 2.03 (m, 2H), 2.19 (m, 2H), 6.45 (d, J=15.9 Hz, 1H), 6.71 (d, J=5.3 Hz, 2H), 7.09 (d, J=8.1 Hz, 2H), 7.52 (d, J=16.1 Hz, 1H), 7.59 (d, J=8.2 Hz, 2H), 10.31 (s, 1H), 12.35 (s, 1H). LCMS (ESI): m/z 393 (M+Na).

Example 42 (126)

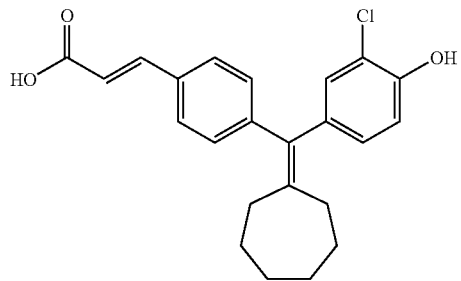

Step 1: 4-[(4-Bromophenyl)(cycloheptylidene)methyl]-2-chlorophenol (124)

To a stirred suspension of zinc powder (1.35 g, 20.5 mmol) in THF (40 mL) was slowly added TiCl$_4$ (1.13 mL, 10.3 mmol) via syringe at room temperature under a nitrogen atmosphere. The mixture was heated at reflux for 2 h. A solution of (4-bromophenyl)(3-chloro-4-hydroxyphenyl)methanone (105) (0.80 g, 2.57 mmol) and cycloheptanone (0.89 g, 7.70 mmol) in THF (15 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous K$_2$CO$_3$ (40 mL). The reaction mixture was filtered through a pad of Celite and the pad washed with EtOAc (100 mL). The filtrate was transferred to a separatory funnel and the layers were separated. The aqueous layer was further extracted with EtOAc (50 mL). The combined organic phase washed with brine, dried over Na$_2$SO$_4$, filtered, and the filtrate was concentrated to give the crude product as brown oil. The crude product was purified by flash chromatography on silica gel with hexanes:EtOAc (20:1) to give 0.64 g (64%) of compound 124 as a yellow viscous oil. $^1$H NMR (400 MHz, DMSO-d$_6$): δ 1.50 (br s, 8H), 2.10-2.25 (m, 4H), 6.85-6.92 (m, 2H), 7.02 (br s, 1H), 7.07 (d, J=8.4 Hz, 2H), 7.47 (d, J=8.4 Hz, 2H), 10.1 (s, 1H). LCMS (APCI): m/z 413 (M+Na)$^+$.

Step 2: Ethyl(2E)-3-{4-[(3-chloro-4-hydroxyphenyl)(cycloheptylidene)methyl]phenyl}-2-propenoate (125)

To a round-bottomed flask were added 4-[(4-bromophenyl)(cycloheptylidene)methyl]-2-chlorophenol (124) (0.32 g, 0.82 mmol), ethyl acrylate (0.90 mL, 8.17 mmol), dichlorobis(triphenylphosphine)palladium(II) (0.060 g, 0.08 mmol), triethylamine (0.60 mL, 4.08 mmol) and DMF (10 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried over Na$_2$SO$_4$, filtered, and the filtrate was concentrated to give reddish brown oil. The crude product was purified by chromatography on a silica gel column eluted with a gradient from hexanes to 15% EtOAc:hexanes to give 0.23 g (69%) of compound 125 as a colorless viscous oil. $^1$H NMR (400 MHz, CDCl$_3$): δ 1.33 (t, J=7.1 Hz, 3H), 1.58 (br s, 8H), 2.30 (br s, 4H), 4.25 (q, J=7.1 Hz, 2H), 5.42 (s, 1H), 6.39 (d, J=15.9 Hz, 1H), 6.90-7.00 (m, 2H), 7.10 (d, J=1.8 Hz, 1H), 7.14 (d, J=8.2 Hz, 2H), 7.44 (d, J=8.2 Hz, 2H), 7.65 (d, J=15.9 Hz, 1H). LCMS (ESI): m/z, 433 (M+Na)$^+$, 409 (M−H)$^−$.

Step 3: (2E)-3-{4-[(3-Chloro-4-hydroxyphenyl)(cycloheptylidene)methyl]phenyl}-2-propenoic acid (126)

To a solution of ethyl(2E)-3-{4-[(3-chloro-4-hydroxyphenyl)(cycloheptylidene)methyl]phenyl}-2-propenoate (125) (0.23 g, 0.56 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over Na$_2$SO$_4$. Upon concentration, light brown foam was obtained. Trituration with hexanes (containing 1% MeOH) afforded compound 126 as a white solid (0.175 g, 82%). mp 155-156° C. $^1$H NMR (400 MHz, DMSO-d$_6$): δ 1.51 (br s, 8H), 2.10-2.30 (m, 4H), 6.45 (d, J=15.9 Hz, 1H), 6.80-6.95 (m, 2H), 7.02 (s, 1H), 7.14 (d, J=7.8 Hz, 2H), 7.52 (d, J=16.1 Hz, 1H), 7.58 (d, J=7.8 Hz, 2H), 10.08 (s, 1H), 12.33 (s, 1H).

LCMS (ESI): m/z 383 (M+H)⁺, m/z 381 (M–H)⁻. Anal. Calcd for $C_{23}H_{23}ClO_3 \cdot 0.25H_2O$: C, 71.31; H, 6.11; Found: C, 71.26; H, 6.05.

Example 43 (129)

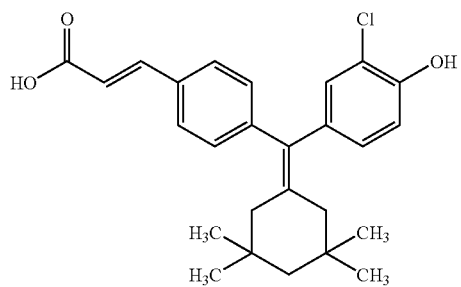

Step 1: 4-[(4-Bromophenyl)(3,3,5,5-tetramethylcyclohexylidene)methyl]-2-chlorophenol (127)

To a stirred suspension of zinc powder (0.59 g, 8.99 mmol) in THF (20 mL) was slowly added TiCl₄ (0.50 mL, 4.50 mmol) via syringe at room temperature under a nitrogen atmosphere. The mixture was heated at reflux for 2 h. A solution of (4-bromophenyl)(3-chloro-4-hydroxyphenyl) methanone (105) (0.35 g, 1.12 mmol) and 3,3,5,5-tetramethyl cyclohexanone (0.53 g, 3.37 mmol) in THF (6 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous $K_2CO_3$ (20 mL). The reaction mixture was filtered through a pad of Celite and the pad washed with EtOAc (50 mL). The filtrate was transferred to a separatory funnel and the layers were separated. The aqueous layer was further extracted with EtOAc (25 mL). The combined organic phase washed with brine, dried over Na₂SO₄, filtered, and the filtrate was concentrated to give the crude product as brown oil. The crude product was purified by flash chromatography on silica gel with hexanes:EtOAc (30:1) to give 0.38 g (78%) of 127 as a light yellow viscous oil. ¹H NMR (400 MHz, CDCl₃): δ 0.91 (s, 6H), 0.93 (s, 6H), 1.29 (s, 2H), 1.92 (s, 2H), 1.95 (s, 2H), 5.42 (s, 1H), 6.88-6.98 (m, 2H), 7.01 (d, J=8.3 Hz, 2H), 7.08 (s, 1H), 7.39 (d, J=8.2 Hz, 2H). LCMS (ESI): m/z 431 (M–H)⁻.

Step 2: Ethyl(2E)-3-{4-[(3-chloro-4-hydroxyphenyl)(3,3,5,5-tetramethyl cyclohexylidene)methyl]phenyl}-2-propenoate (128)

To a round-bottomed flask were added 4-[(4-bromophenyl)(3,3,5,5-tetramethyl cyclohexylidene)methyl]-2-chlorophenol (127) (0.38 g, 0.88 mmol), ethyl acrylate (0.96 mL, 8.80 mmol), dichlorobis(triphenylphosphine)palladium(II) (0.062 g, 0.09 mmol), Et₃N (0.61 mL, 4.38 mmol) and DMF (10 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried (Na₂SO₄), filtered, and the filtrate was concentrated to give reddish brown oil. The crude product was purified by chromatography on a silica gel column eluted with a gradient from hexanes to 15% EtOAc:hexanes to give 0.26 g (66%) of compound 128 as a yellow viscous oil. ¹H NMR (400 MHz, CDCl₃): δ 0.92 (s, 6H), 0.94 (s, 6H), 1.30 (s, 2H), 1.33 (t, J=7.1 Hz, 3H), 1.96 (s, 2H), 1.97 (s, 2H), 4.25 (q, J=7.1 Hz, 2H), 5.43 (s, 1H), 6.39 (d, J=15.9 Hz, 1H), 6.90-7.00 (m, 2H), 7.11 (d, J=1.8 Hz, 1H), 7.16 (d, J=8.1 Hz, 2H), 7.44 (d, J=8.1 Hz, 2H), 7.65 (d, J=15.9 Hz, 1H). LCMS (ESI): m/z, 453 (M+H)⁺, 451 (M–H)⁻.

Step 3: (2E)-3-{4-[(3-Chloro-4-hydroxyphenyl)(3,3,5,5-tetramethylcyclohexylidene)methyl]phenyl}-2-propenoic acid (129)

To a solution of ethyl(2E)-3-{4-[(3-chloro-4-hydroxyphenyl)(3,3,5,5-tetramethyl cyclohexylidene)methyl]phenyl}-2-propenoate (128) (0.26 g, 0.57 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over Na₂SO₄. Upon concentration and adding hexanes, the title compound 129 was obtained as light yellow foam (0.24 g, 99%). mp 111-114° C. ¹H NMR (400 MHz, DMSO-d₆): δ 0.86 (s, 6H), 0.88 (s, 6H), 1.25 (s, 2H), 1.87 (s, 2H), 1.90 (s, 2H), 6.45 (d, J=15.9 Hz, 1H), 6.80-6.95 (m, 2H), 7.06 (s, 1H), 7.16 (d, J=7.7 Hz, 2H), 7.53 (d, J=15.9 Hz, 1H), 7.59 (d, J=7.5 Hz, 2H), 10.08 (s, 1H), 12.33 (s, 1H). LCMS (ESI): m/z 423 (M–H)⁻. Anal. Calcd for $C_{26}H_{29}ClO_3$: C, 73.48; H, 6.88; Found: C, 73.18; H, 7.06.

Example 44 (132)

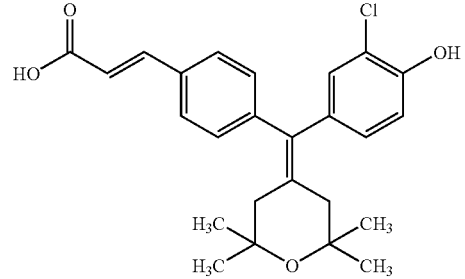

Step 1: 4-[(4-Bromophenyl)(2,2,6,6-tetramethyltetrahydro-4H-pyran-4-ylidene)methyl]-2-chlorophenol (130)

To a stirred suspension of zinc powder (0.59 g, 8.99 mmol) in THF (20 mL) was slowly added TiCl₄ (0.50 mL, 4.50 mmol) via syringe at room temperature under a nitrogen atmosphere. The mixture was heated at reflux for 2 h. A solution of (4-bromophenyl)(3-chloro-4-hydroxyphenyl) methanone (105) (0.35 g, 1.12 mmol) and 2,2,6,6-tetramethyl tetrahydro-4H-pyran-4-one (0.54 g, 3.37 mmol) in THF (6 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous $K_2CO_3$ (20 mL). The reaction mixture was filtered through a pad of Celite and the pad was washed with EtOAc (100 mL). The filtrate was transferred to a separatory funnel and the layers were separated. The aqueous layer was further extracted with EtOAc (25 mL). The combined organic phase washed with brine, dried over Na$_2$SO$_4$, filtered, and the filtrate was concentrated to give the crude product as yellow viscous oil. The crude product was purified by chromatography on a silica gel column eluted with a gradient from hexanes to 15% EtOAc:hexanes to give 0.47 g (96%) of compound 130 as a yellow viscous oil. $^1$H NMR (400 MHz, CDCl$_3$): δ 1.20 (s, 6H), 1.22 (s, 6H), 2.18 (s, 2H), 2.22 (s, 2H), 5.47 (s, 1H), 6.90-7.00 (m, 2H), 7.02 (d, J=8.4 Hz, 2H), 7.09 (d, J=1.6 Hz, 1H), 7.43 (d, J=8.3 Hz, 2H). LCMS (ESI), m/z 433 (M–H)$^-$.

Step 2: Ethyl(2E)-3-{4-[(3-chloro-4-hydroxyphenyl) (2,2,6,6-tetramethyltetrahydro-4H-pyran-4-ylidene) methyl]phenyl}-2-propenoate (131)

To a round-bottomed flask were added 4-[(4-bromophenyl)(2,2,6,6-tetramethyltetrahydro-4H-pyran-4-ylidene)methyl]-2-chlorophenol (130) (0.47 g, 1.08 mmol), ethyl acrylate (1.20 mL, 10.8 mmol), dichlorobis(triphenylphosphine)palladium(II) (0.076 g, 0.11 mmol), Et$_3$N (0.75 mL, 5.39 mmol) and DMF (12 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried over Na$_2$SO$_4$, filtered, and the filtrate was concentrated to give brown oil. The crude product was purified by chromatography on a silica gel column eluted with a gradient from hexanes to 20% EtOAc: hexanes to give 0.32 g (65%) of the title compound as a yellow viscous oil. $^1$H NMR (400 MHz, CDCl$_3$): δ 1.21 (s, 6H), 1.23 (s, 6H), 1.33 (t, J=7.1 Hz, 3H), 2.22 (s, 2H), 2.23 (s, 2H), 4.26 (q, J=7.1 Hz, 2H), 5.47 (s, 1H), 6.41 (d, J=15.9 Hz, 1H), 6.90-7.00 (m, 2H), 7.11 (d, J=1.6 Hz, 1H), 7.17 (d, J=8.3 Hz, 2H), 7.46 (d, J=8.0 Hz, 2H), 7.66 (d, J=15.9 Hz, 1H). LCMS (ESI), m/z, 455 (M+H)$^+$, 453 (M–H)$^-$.

Step 3: (2E)-3-{4-[(3-Chloro-4-hydroxyphenyl)(2,2, 6,6-tetramethyltetrahydro-4H-pyran-4-ylidene)methyl]phenyl}-2-propenoic acid (132)

To a solution of Ethyl(2E)-3-{4-[(3-chloro-4-hydroxyphenyl)(2,2,6,6-tetramethyl tetrahydro-4H-pyran-4-ylidene)methyl]phenyl}-2-propenoate (131) (0.32 g, 0.70 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over Na$_2$SO$_4$. Upon concentration and adding hexanes, the title compound 132 was obtained as a white powder (0.255 g, 85%). mp 118-121° C. $^1$H NMR (400 MHz, DMSO-d$_6$): δ 1.10 (s, 6H), 1.12 (s, 6H), 2.11 (s, 2H), 2.13 (s, 2H), 6.47 (d, J=15.9 Hz, 1H), 6.85-7.00 (m, 2H), 7.08 (d, J=1.8 Hz, 1H), 7.19 (d, J=8.2 Hz, 2H), 7.54 (d, J=15.9 Hz, 1H), 7.62 (d, J=8.2 Hz, 2H), 10.15 (s, 1H), 12.36 (s, 1H). LCMS (ESI): m/z 425 (M–H)$^-$. Anal. Calcd for C$_{25}$H$_{27}$ClO$_4$.0.2H$_2$O: C, 69.74; H, 6.41; Found: C, 69.82; H, 6.56.

Example 45 (135)

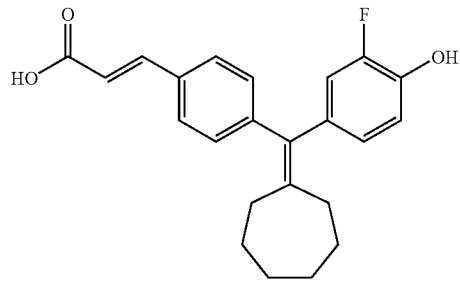

Step 1: 4-[(4-Bromophenyl)(cycloheptylidene)methyl]-2-fluorophenol (133)

To a stirred suspension of zinc powder (0.54 g, 8.13 mmol) in THF (20 mL) was slowly added TiCl$_4$ (0.45 mL, 4.07 mmol) via syringe at room temperature under a nitrogen atmosphere. The mixture was heated at reflux for 2 h. A solution of (4-bromophenyl)(3-fluoro-4-hydroxyphenyl)methanone (82) (0.30 g, 1.02 mmol) and cycloheptanone (0.35 g, 3.05 mmol) in THF (6 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous K$_2$CO$_3$ (20 mL). The reaction mixture was filtered through a pad of Celite and the pad washed with EtOAc (100 mL). The filtrate was transferred to a separatory funnel and the layers were separated. The aqueous layer was further extracted with EtOAc (25 mL). The combined organic phase washed with brine, dried over Na$_2$SO$_4$, filtered, and the filtrate was concentrated to give the crude product as brown oil. The crude product was purified by flash chromatography on silica gel with hexanes:EtOAc (100:0 to 20:1) to give 0.30 g (79%) of compound 133 as a yellow solid. mp 102-104° C. $^1$H NMR (400 MHz, CDCl$_3$): δ 1.56 (br s, 8 H), 2.20-2.35 (m, 4 H), 4.96 (br s, 1H), 6.75-6.86 (m, 2H), 6.90 (t, J=8.6 Hz, 1H), 7.00 (d, J=8.3 Hz, 2 H), 7.39 (d, J=8.3 Hz, 2H). LCMS (ES): m/z 373 (M–H)$^-$.

Step 2: Ethyl(2E)-3-{4-[(3-fluoro-4-hydroxyphenyl) (cycloheptylidene)methyl]phenyl}-2-propenoate (134)

To a round-bottomed flask were added 4-[(4-bromophenyl)(cycloheptylidene)methyl]-2-fluorophenol (133) (0.30 g, 0.80 mmol), ethyl acrylate (0.88 mL, 8.00 mmol), dichlorobis (triphenylphosphine)palladium(II) (0.056 g, 0.08 mmol), triethylamine (0.56 mL, 4.00 mmol) and DMF (10 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried over Na$_2$SO$_4$, filtered, and the filtrate was concentrated to give reddish brown oil. The crude product was purified by chromatography on a silica gel column eluted with a gradient from hexanes to 15% EtOAc:hexanes to give 0.22 g (70%) of compound 134 as a colorless viscous oil. $^1$H NMR (400 MHz, CDCl$_3$): δ 1.33 (t, J=7.1 Hz, 3H), 1.57 (br s, 8H), 2.25-2.35 (m, 4H), 4.25 (q, J=7.1 Hz, 2H), 4.99 (d, J=4.0 Hz, 1H), 6.39 (d, J=15.9 Hz, 1H), 6.75-6.88 (m, 2H), 6.91 (t, J=8.7 Hz, 1H), 7.14 (d, J=8.2 Hz, 2H), 7.44 (d, J=8.1 Hz, 2H), 7.65 (d, J=16.0 Hz, 1H). LCMS (ES): m/z, 395 (M+H)⁺, 393 (M−H)⁻.

Step 3: (2E)-3-{4-[(3-fluoro-4-hydroxyphenyl)(cycloheptylidene)methyl]phenyl}-2-propenoic acid (135)

To a solution of ethyl(2E)-3-{4-[(3-fluoro-4-hydroxyphenyl)(cycloheptylidene)methyl]phenyl}-2-propenoate (134) (0.22 g, 0.56 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over Na₂SO₄. Upon concentration, light brown foam was obtained. It was triturated with hexanes (contains 1% MeOH) to give compound 135 as a pale yellow solid (0.171 g, 84%). mp 164-165° C. ¹H NMR (400 MHz, DMSO-d₆): δ 1.51 (br s, 8H), 2.10-2.30 (m, 4H), 6.45 (d, J=15.9 Hz, 1H), 6.70-6.78 (m, 1H), 6.80-6.90 (m, 1H), 7.14 (d, J=8.2 Hz, 2H), 7.53 (d, J=16.2 Hz, 1H), 7.59 (d, J=8.0 Hz, 2H), 9.74 (s, 1H), 12.35 (s, 1H). LCMS (ES): m/z 367 (M+H)⁺, m/z 365 (M−H)⁻. Anal. Calcd for C₂₃H₂₃FO₃. 0.1H₂O: C, 75.02; H, 6.35; Found: C, 74.93; H, 6.44.

Example 46 (138)

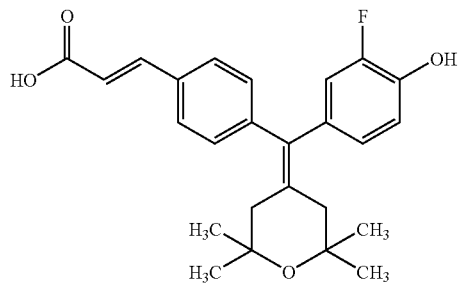

Step 1: 4-[(4-Bromophenyl)(2,2,6,6-tetramethyltetrahydro-4H-pyran-4-ylidene)methyl]-2-fluorophenol (136)

To a stirred suspension of zinc powder (0.54 g, 8.13 mmol) in THF (20 mL) was slowly added TiCl₄ (0.45 mL, 4.07 mmol) via syringe at room temperature under a nitrogen atmosphere. The mixture was heated at reflux for 2 h. A solution of (4-bromophenyl)(3-fluoro-4-hydroxyphenyl)methanone (82) (0.30 g, 1.02 mmol) and 2,2,6,6-tetramethyl tetrahydro-4H-pyran-4-one (0.49 g, 3.05 mmol) in THF (6 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous K₂CO₃ (20 mL). The reaction mixture was filtered through a pad of Celite and the pad was washed with EtOAc (100 mL). The filtrate was transferred to a separatory funnel and the layers were separated. The aqueous layer was further extracted with EtOAc (25 mL). The combined organic phase washed with brine, dried over Na₂SO₄, filtered, and the filtrate was concentrated to give the crude product as yellow oil. The crude product was purified by chromatography on a silica gel column eluted with a gradient from hexanes to 15% EtOAc:hexanes to give 0.40 g (94%) of compound 136 as a yellow foam. ¹H NMR (400 MHz, CDCl₃): δ 1.20 (s, 6H), 1.22 (s, 6H), 2.18 (s, 2H), 2.23 (s, 2H), 5.04 (d, J=4.0 Hz, 1H), 6.80-6.88 (m, 2H), 6.93 (t, J=8.6 Hz, 1H), 7.02 (d, J=8.4 Hz, 2H), 7.42 (d, J=8.3 Hz, 2H). LCMS (ES): m/z 417 (M−H)⁻.

Step 2: Ethyl(2E)-3-{4-[(3-fluoro-4-hydroxyphenyl)(2,2,6,6-tetramethyltetrahydro-4H-pyran-4-ylidene)methyl]phenyl}-2-propenoate (137)

To a round-bottomed flask were added 4-[(4-bromophenyl)(2,2,6,6-tetramethyltetrahydro-4H-pyran-4-ylidene)methyl]-2-fluorophenol (136) (0.40 g, 0.95 mmol), ethyl acrylate (1.05 mL, 9.54 mmol), dichlorobis(triphenylphosphine)palladium(II) (0.067 g, 0.10 mmol), Et₃N (0.70 mL, 4.77 mmol) and DMF (12 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried over Na₂SO₄, filtered, and the filtrate was concentrated to give brown oil. The crude product was purified by chromatography on a silica gel column eluted with a gradient from hexanes to 20% EtOAc:hexanes to give 0.31 g (74%) of the title compound 137 as a light yellow foam. ¹H NMR (400 MHz, CDCl3): δ 1.21 (s, 6H), 1.23 (s, 6H), 1.33 (t, J=7.1 Hz, 3H), 2.22 (s, 2H), 2.24 (s, 2H), 4.26 (q, J=7.1 Hz, 2H), 5.44 (br s, 1H), 6.40 (d, J=15.9 Hz, 1H), 6.80-6.90 (m, 2H), 6.93 (t, J=8.5 Hz, 1H), 7.17 (d, J=8.1 Hz, 2H), 7.46 (d, J=8.3 Hz, 2H), 7.65 (d, J=15.9 Hz, 1H). LCMS (ES): m/z, 439 (M+H)⁺, 437 (M−H)⁻.

Step 3: (2E)-3-{4-[(3-fluoro-4-hydroxyphenyl)(2,2,6,6-tetramethyltetrahydro-4H-pyran-4-ylidene)methyl]phenyl}-2-propenoic acid (138)

To a solution of ethyl(2E)-3-{4-[(3-fluoro-4-hydroxyphenyl)(2,2,6,6-tetramethyl tetrahydro-4H-pyran-4-ylidene)methyl]phenyl}-2-propenoate (137) (0.30 g, 0.68 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over Na₂SO₄. Upon concentration and adding hexanes, the title compound 138 was obtained as an off-white solid (0.227 g, 81%). mp 125-128° C. ¹H NMR (400 MHz, DMSO-d₆): δ1.10 (s, 6H), 1.12 (s, 6H), 2.10 (s, 2H), 2.14 (s, 2H), 6.47 (d, J=15.9 Hz, 1H), 6.75-6.80 (m, 1H), 6.82-6.95 (m, 2H), 7.19 (d, J=8.2 Hz, 2H), 7.54 (d, J=15.9 Hz, 1H), 7.61 (d, J=8.2 Hz, 2H), 9.80 (s, 1H), 12.36 (s, 1H). LCMS (ES): m/z 409 (M−H)⁻. Anal. Calcd for C₂₅H₂₇FO₄.0.4H₂O: C, 71.89; H, 6.71; Found: C, 71.88; H, 6.92.

Example 47 (141)

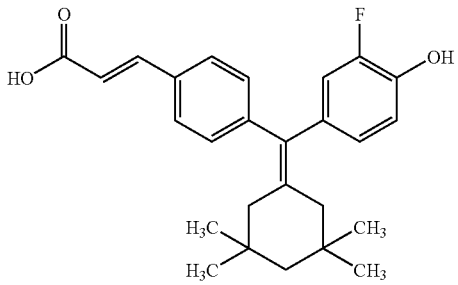

Step 1: 4-[(4-Bromophenyl)(3,3,5,5-tetramethylcyclohexylidene)methyl]-2-fluorophenol (139)

To a stirred suspension of zinc powder (0.54 g, 8.13 mmol) in THF (20 mL) was slowly added TiCl₄ (0.45 mL, 4.07 mmol) via syringe at room temperature under a nitrogen atmosphere. The mixture was heated at reflux for 2 h. A solution of (4-bromophenyl)(3-fluoro-4-hydroxyphenyl) methanone (82) (0.30 g, 1.02 mmol) and 3,3,5,5-tetramethyl cyclohexanone (0.48 g, 3.05 mmol) in THF (6 mL) was added to the mixture. The reaction mixture was heated at reflux with stirring under a nitrogen atmosphere for 1 h. The reaction mixture was allowed to cool to room temperature. To the reaction mixture was slowly added 10% aqueous $K_2CO_3$ (20 mL). The reaction mixture was filtered through a pad of Celite and the pad washed with EtOAc (100 mL). The filtrate was transferred to a separatory funnel and the layers were separated. The aqueous layer was further extracted with EtOAc (25 mL). The combined organic phase washed with brine, dried over $Na_2SO_4$, filtered, and the filtrate was concentrated to give the crude product as yellow oil. The crude product was purified by flash chromatography on silica gel with hexanes: EtOAc (100:0 to 30:1) to give 0.33 g (78%) of compound 139 as a light yellow viscous oil. ¹H NMR (400 MHz, CDCl₃): δ 0.91 (s, 6H), 0.93 (s, 6H), 1.29 (s, 2H), 1.92 (s, 2H), 1.97 (s, 2H), 4.99 (d, J=3.8 Hz, 1H), 6.78-6.87 (m, 2H), 6.90 (t, J=8.6 Hz, 1H), 7.01 (d, J=8.3 Hz, 2H), 7.40 (d, J=8.4 Hz, 2H). LCMS (ES): m/z 415 (M−H)⁻.

Step 2: Ethyl(2E)-3-{4-[(3-fluoro-4-hydroxyphenyl)(3,3,5,5-tetramethyl cyclohexylidene)methyl]phenyl}-2-propenoate (140)

To a round-bottomed flask were added 4-[(4-bromophenyl)(3,3,5,5-tetramethyl cyclohexylidene)methyl]-2-fluorophenol (139) (0.33 g, 0.79 mmol), ethyl acrylate (0.87 mL, 7.90 mmol), dichlorobis(triphenylphosphine)palladium(II) (0.056 g, 0.08 mmol), Et₃N (0.55 mL, 3.95 mmol) and DMF (10 mL). The stirred reaction mixture was heated overnight at 100° C. under a nitrogen atmosphere. The reaction mixture was allowed to cool to room temperature and transferred to a separatory funnel with the aid of water and EtOAc (100 mL). The layers were separated and the organic phase washed with water, brine, dried over $Na_2SO_4$, filtered, and the filtrate was concentrated to give brown oil. The crude product was purified by chromatography on a silica gel column eluted with a gradient from hexanes to 15% EtOAc:hexanes to give 0.235 g (68%) of compound 140 as a light yellow viscous oil. ¹H NMR (400 MHz, CDCl3): δ 0.92 (s, 6H), 0.94 (s, 6H), 1.29 (s, 2H), 1.32 (t, J=7.1 Hz, 3H), 1.95 (s, 2H), 1.97 (s, 2H), 4.25 (q, J=7.1 Hz, 2H), 4.98 (d, J=4.2 Hz, 1H), 6.39 (d, J=16.0 Hz, 1H), 6.80-6.95 (m, 3H), 7.16 (d, J=8.1 Hz, 2H), 7.43 (d, J=8.1 Hz, 2H), 7.65 (d, J=16.1 Hz, 1H). LCMS (ES): m/z, 437 (M+H)⁺, 435 (M−H)⁻.

Step 3: (2E)-3-{4-[(3-fluoro-4-hydroxyphenyl)(3,3,5,5-tetramethylcyclohexylidene)methyl]phenyl}-2-propenoic acid (141)

To a solution of Ethyl(2E)-3-{4-[(3-fluoro-4-hydroxyphenyl)(3,3,5,5-tetramethyl cyclohexylidene)methyl]phenyl}-2-propenoate (140) (0.235 g, 0.54 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 2 N HCl. The mixture was extracted with EtOAc (2×50 mL). The combined organic extract washed with brine and dried over $Na_2SO_4$. Upon concentration and adding hexanes, compound 141 was obtained as pale yellow solid (0.182 g, 83%). mp 193-195° C. ¹H NMR (400 MHz, DMSO-d₆): δ 0.87 (s, 6H), 0.89 (s, 6H), 1.25 (s, 2H), 1.88 (s, 2H), 1.91 (s, 2H), 6.45 (d, J=15.9 Hz, 1H), 6.76 (dd, J₁=8.2 Hz, J₂=1.6 Hz, 1H), 6.80-6.92 (m, 2H), 7.17 (d, J=8.0 Hz, 2H), 7.53 (d, J=16.1 Hz, 1H), 7.59 (d, J=8.2 Hz, 2H), 9.72 (s, 1H), 12.32 (s, 1H). LCMS (ES): m/z 407 (M−H)⁻. Anal. Calcd for $C_{26}H_{29}FO_3 \cdot \frac{1}{6}H_2O$: C, 75.89; H, 7.19; Found: C, 75.91; H, 7.17.

Example 48 (145)

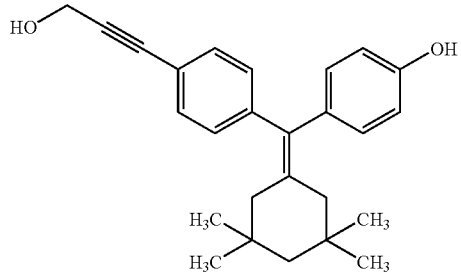

Step 1: (4-Iodophenyl)[4-(methyloxy)phenyl]methanone (142)

4-Iodobenzoic acid (3.0 g, 11.58 mmol) was suspended in $CH_2Cl_2$ (50 mL). Oxalyl chloride (2.20 mL, 23.71 mmol) was added dropwise, followed by addition of three drops of DMF. The reaction mixture was stirred at room temperature for 3 h. $CH_2Cl_2$ and the excess of oxalyl chloride were removed under vacuum. The residue was dissolved in $CH_2Cl_2$ (35 mL) with anisole (1.70 mL, 15.41 mmol). Cooled in an ice bath, AlCl₃ (2.40 g, 17.78 mmol) was added in portions. The mixture was stirred at 0° C. for 3 h, poured into 1 N HCl (50 mL) with ice, the mixture was extracted with $CH_2Cl_2$ (2×100 mL). The combined $CH_2Cl_2$ extract washed with saturated aqueous NaHCO₃, brine, dried over $Na_2SO_4$, filtered, and the filtrate was concentrated to give brown solid. The crude product was triturated with hot hexanes to give 3.91 g (98%) of compound 142 as light beige solid. ¹H NMR (400 MHz, CDCl₃): δ 3.89 (s, 3H), 6.96 (d, J=8.8 Hz, 2H), 7.47 (d, J=8.4 Hz, 2H), 7.79 (d, J=8.8 Hz, 2H), 7.83 (d, J=8.5 Hz, 2H). LCMS (APCI): m/z, 339 (M+H)⁺.

Step 2: (4-Hydroxyphenyl)(4-iodophenyl)methanone (143)

A mixture of (4-Iodophenyl)[4-(methyloxy)phenyl]methanone (142) (1.50 g, 4.44 mmol) and AlCl$_3$ (2.40 g, 17.74 mmol) were refluxed in benzene (50 mL) for 1.5 h and then cooled to 0° C. in an ice bath. Water (50 mL) was added slowly, and the mixture was extracted with ether (2×100 mL). The combined ethereal extracts were washed with water, brine, and dried over Na$_2$SO$_4$. Concentration and trituration with hot hexanes afforded 1.36 g (95%) of the title compound as light brown solid. $^1$H NMR (400 MHz, CDCl$_3$): δ 5.37 (br s, 1H), 6.90 (d, J=8.6 Hz, 2H), 7.47 (d, J=8.4 Hz, 2H), 7.75 (d, J=8.6 Hz, 2H), 7.83 (d, J=8.5 Hz, 2H). LCMS (ESI): m/z, 325 (M+H)$^+$, 323 (M−H)$^−$.

Step 3: 4-[(4-Iodophenyl)(3,3,5,5-tetramethylcyclohexylidene)methyl]phenol (144)

To a stirred suspension of zinc powder (2.20 g, 33.6 mmol) in THF (75 mL) was slowly added TiCl$_4$ (1.85 mL, 16.8 mmol) via syringe at room temperature under a nitrogen atmosphere. The mixture was heated at reflux for 2 h. A solution of (4-hydroxyphenyl) (4-iodophenyl)methanone (143) (1.36 g, 4.20 mmol) and 3,3,5,5-tetramethylcyclohexanone (1.98 g, 12.6 mmol) in THF (20 mL) was added to the mixture. The reaction mixture was heated at reflux with stirring under a nitrogen atmosphere for 25 minutes. The reaction mixture was allowed to cool to room temperature. To the reaction mixture was slowly added 10% aqueous K$_2$CO$_3$ (75 mL). The reaction mixture was filtered through a pad of Celite and the pad was washed with EtOAc (200 mL). The filtrate was transferred to a separatory funnel and the layers were separated. The aqueous layer was further extracted with EtOAc (50 mL). The combined organic phase washed with water, brine, dried over Na$_2$SO$_4$, filtered, and the filtrate was concentrated to give the crude product as yellow oil. The crude product was purified by chromatography on a silica gel column eluted with a gradient from hexanes to 15% EtOAc:hexanes to give a solid residue, which was triturated with hot hexanes to afford 1.03 g (55%) compound 144 as white solid. mp 148-149° C. $^1$H NMR (400 MHz, DMSO-d$_6$): δ 0.86 (s, 6H), 0.87 (s, 6H), 1.23 (s, 2H), 1.85 (s, 2H), 1.89 (s, 2H), 6.65 (d, J=8.4 Hz, 2H), 6.85-6.95 (m, 4H), 7.61 (d, J=8.3 Hz, 2H), 9.29 (s, 1H). LCMS (ESI): m/z 445 (M−H)$^−$.

Step 4: 4-[[4-(3-hydroxy-1-propyn-1-yl)phenyl](3,3,5,5-tetramethylcyclohexylidene)methyl]phenol (145)

To a degassed solution of 4-[(4-iodophenyl)(3,3,5,5-tetramethylcyclohexylidene)methyl]phenol (144) (0.17 g, 0.38 mmol) in DMF (3 mL) were added Pd(PPh$_3$)$_2$Cl$_2$ (27 mg, 0.04 mmol), CuI (8 mg, 0.04 mmol), N,N-diisopropylethylamine (0.30 mL, 1.71 mmol) and propargyl alcohol (45 µL, 0.76 mmol). The reaction mixture was stirred at room temperature overnight, poured into saturated aqueous NH$_4$Cl (15 mL) and water (5 mL), extracted with EtOAc (3×50 mL). The combined organic phase washed with water, brine, dried over Na$_2$SO$_4$, filtered, and the filtrate was concentrated to give the crude product as brown oil. The crude product was purified by chromatography on a silica gel column eluted with a gradient from hexanes to 30% EtOAc:hexanes to give 0.106 g (74%) of compound 145 as pale yellow solid. mp 141-142° C. $^1$H NMR (400 MHz, DMSO-d$_6$): δ 0.85 (s, 6H), 0.87 (s, 6H), 1.23 (s, 2H), 1.85 (s, 2H), 1.89 (s, 2H), 4.25 (d, J=5.9 Hz, 2H), 5.28 (t, J=5.9 Hz, 1H), 6.65 (d, J=8.4 Hz, 2H), 6.91 (d, J=8.2 Hz, 2H), 7.10 (d, J=8.0 Hz, 2H), 7.31 (d, J=8.0 Hz, 2H), 9.29 (s, 1H). LCMS (ESI): m/z 375 (M+H)$^+$, 373 (M−H)$^−$. Anal. Calcd for C$_{26}$H$_{30}$O$_2$.0.1H$_2$O: C, 82.98; H, 8.09; Found: C, 82.88; H, 8.19.

Example 49 (147)

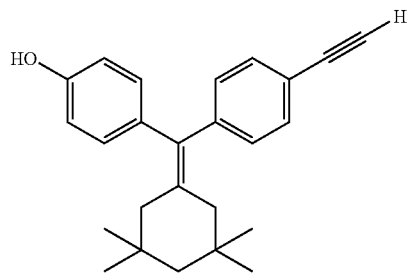

Step 1: 4-((3,3,5,5-Tetramethylcyclohexylidene){4-[(trimethylsilyl)ethynyl]phenyl}methyl)phenol (146)

To a degassed solution of 4-[(4-Iodophenyl)(3,3,5,5-tetramethylcyclohexylidene)methyl]phenol (144) (0.305 g, 0.68 mmol) in DMF (8 mL) were added Pd(PPh$_3$)$_2$Cl$_2$ (48 mg, 0.07 mmol), CuI (13 mg, 0.07 mmol), N,N-diisopropylethylamine (0.55 mL, 3.10 mmol) and trimethylsilyl acetylene (0.12 mL, 0.82 mmol). The reaction mixture was stirred at room temperature overnight, poured into saturated aqueous NH$_4$Cl (20 mL) and water (10 mL), extracted with EtOAc (2×50 mL). The combined organic phase washed with water, brine, dried over Na$_2$SO$_4$, filtered, and the filtrate was concentrated to give the crude product as dark brown oil. The crude product was purified by chromatography on a silica gel column eluted with a gradient from hexanes to 15% EtOAc:hexanes to give light brown solid, which washed with cold hexanes to yield 0.18 g (64%) of the title compound 146 as an off-white solid. $^1$H NMR (400 MHz, CDCl$_3$): δ 0.22 (s, 9H), 0.89 (s, 6H), 0.92 (s, 6H), 1.27 (s, 2H), 1.91 (s, 2H), 1.97 (s, 2H), 4.55 (br s, 1H), 6.72 (d, J=8.5 Hz, 2H), 7.00 (d, J=8.4 Hz, 2H), 7.08 (d, J=8.2 Hz, 2H), 7.36 (d, J=8.3 Hz, 2H). LCMS (ESI): m/z 415 (M−H)$^−$.

Step 2: 4-[(4-Ethynylphenyl)(3,3,5,5-tetramethylcyclohexylidene)methyl]phenol (147)

4-((3,3,5,5-Tetramethylcyclohexylidene){4-[(trimethylsilyl)ethynyl]phenyl}methyl)phenol (146) (0.175 g, 0.42 mmol) was dissolved in MeOH (10 mL). To this solution was added K$_2$CO$_3$ (0.18 g, 1.26 mmol). The reaction mixture was stirred at room temperature overnight, poured into water (10 mL) and extracted with EtOAc (2×50 mL). The combined organic phase washed with brine, dried over Na$_2$SO$_4$, filtered, and the filtrate was concentrated to give the crude product as brown solid. The crude product was purified by chromatography on a silica gel column eluted with a gradient from hexanes to 15% EtOAc:hexanes to give 0.14 g (97%) of the title compound 147 as white solid. mp 138-139° C. $^1$H NMR (400 MHz, CDCl$_3$): δ 0.91 (s, 6H), 0.92 (s, 6H), 1.28 (s, 2H), 1.93 (s, 2H), 1.97 (s, 2H), 3.03 (s, 1H), 4.55 (br s, 1H), 6.73 (d, J=8.5 Hz, 2H), 7.01 (d, J=8.4 Hz, 2H), 7.11 (d, J=8.2 Hz, 2H), 7.39 (d, J=8.2 Hz, 2H). LCMS (ESI): m/z 343 (M−H)⁻.

9.31 (s, 1H), 13.73 (s, 1H). HRMS (EI) Calcd for $C_{32}H_{44}O_3Si_2$: 532.2829 (M⁺); Found: 532.1591.

Example 50 (149)

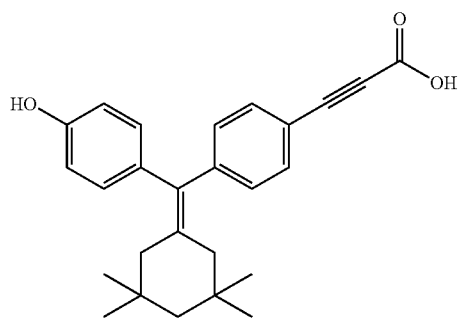

Example 51 (154)

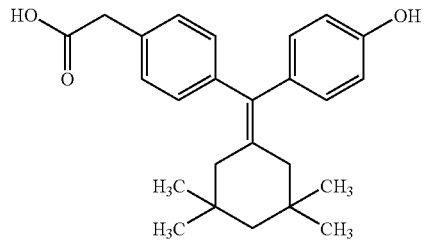

Step 1: Ethyl 3-{4-[(4-{[(ethyloxy)carbonyl]oxy}phenyl)(3,3,5,5-tetramethyl cyclohexylidene)methyl]phenyl}-2-propynoate (148)

Tris(dibenzylidene acetone) dipalladium (10 mg, 0.01 mmol) and P(o-tolyl)₃ (14 mg, 0.04 mmol) were stirred in CH₂Cl₂ (2 mL) at room temperature for 1 h. To this mixture was added 1,2,2,6,6-pentamethylpiperidine (0.15 mL, 0.81 mmol) followed by a solution of 4-[(4-ethynylphenyl)(3,3,5,5-tetramethylcyclohexylidene)methyl]phenol (147) (0.127 g, 0.37 mmol) and catalytic amount of DMAP in CH₂Cl₂ (2 mL). The resulting mixture was heated under slow reflux. Ethyl chloroformate (0.12 mL, 1.18 mmol) was added dropwise. The reaction mixture was stirred at 40° C. overnight, poured into water, extracted with EtOAc (2×30 mL). The combined organic phase washed with brine, dried over Na₂SO₄, filtered, and the filtrate was concentrated to give the crude product as brown oil. The crude product was purified by chromatography on a silica gel column eluted with a gradient from hexanes to 15% EtOAc:hexanes to yield 88 mg (49%) of compound 148 as yellow oil. ¹H NMR (400 MHz, CDCl₃): δ 0.91 (s, 6H), 0.92 (s, 6H), 1.29 (s, 2H), 1.30-1.40 (m, 6H), 1.93 (s, 2H), 1.96 (s, 2H), 4.20-4.35 (m, 4H), 7.05-7.20 (m, 6H), 7.49 (d, J=7.9 Hz, 2H). LCMS (ESI): m/z 489 (M+H)⁺.

Step 2: 3-{4-[(4-Hydroxyphenyl)(3,3,5,5-tetramethylcyclohexylidene)methyl]phenyl}-2-propynoic acid (149)

To a solution of ethyl 3-{4-[(4-{[(ethyloxy)carbonyl]oxy}phenyl)(3,3,5,5-tetramethyl cyclohexylidene)methyl]phenyl}-2-propynoate (148) (88 mg, 0.18 mmol) in a mixture of EtOH (4 mL) and THF (4 mL) was added an aqueous solution of 1 N NaOH (5 mL). The mixture was stirred at 60° C. for 2 h. Upon cooling, the mixture was acidified to pH=2 with an aqueous solution of 1 N HCl. The mixture was extracted with EtOAc (2×50 mL). The combined organic extract washed with water, brine and dried over Na₂SO₄. Upon concentration and trituration with hot 1:1 hexanes/ether (contained 1% of methanol), (35 mg (50%) of compound 149 was obtained as white solid. mp 172-174° C. (dec.). ¹H NMR (400 MHz, DMSO-d₆): δ 0.86 (s, 6H), 0.87 (s, 6H), 1.24 (s, 2H), 1.85 (s, 2H), 1.91 (s, 2H), 6.66 (d, J=8.4 Hz, 2H), 6.92 (d, J=8.4 Hz, 2H), 7.19 (d, J=8.1 Hz, 2H), 7.52 (d, J=8.1 Hz, 2H), Step 1: 4-[2-(Methyloxy)-2-oxoethyl]benzoic acid (150)

To a suspension of 4-(carboxymethyl)benzoic acid (2.43 g, 13.5 mmol) in methanol (30 mL) was added thionyl chloride (50 μL, 0.67 mmol). The reaction mixture was stirred at room temperature for 5.5 h, and a clear solution was obtained. The solvent was removed under reduced pressure. The residue was taken up in ether (100 mL), washed with saturated aqueous NaHCO₃ (2×50 mL) and water (30 mL). The combined NaHCO₃ and water extract was acidified with concentrated HCl in an ice bath. The white precipitation was collected and washed with water, dried to yield 2.30 g (88%) compound 150 as white solid. The material was used without further purification. mp 134-136° C. ¹H NMR (400 MHz, CDCl₃): δ 3.71 (s, 5H), 7.40 (d, J=8.2 Hz, 2H), 8.07 (d, J=8.2 Hz, 2H). LCMS (ESI), m/z, 193 (M−H)⁻.

Step 2: Methyl(4-{[4-(methyloxy)phenyl]carbonyl}phenyl)acetate (151)

4-[2-(Methyloxy)-2-oxoethyl]benzoic acid (150) (1.0 g, 5.15 mmol) was dissolved in CH₂Cl₂(25 mL). Oxalyl chloride (0.92 mL, 10.3 mmol) was added dropwise, followed by addition of two drops of DMF. The reaction mixture was stirred at room temperature for 2 h. CH₂Cl₂ and the excess of oxalyl chloride were removed under vacuum. The residue was dissolved in CH₂Cl₂ (15 mL) with anisole (0.74 mL, 6.70 mmol). Cooled in an ice bath, AlCl₃ (1.04 g, 7.73 mmol) was added in portions. The mixture was stirred at 0° C. for 4 h, then stirred at room temperature for 20 minutes. Poured into 1 N HCl (25 mL) with ice, the mixture was extracted with CH₂Cl₂ (2×60 mL). The combined CH₂Cl₂ extract washed with saturated aqueous NaHCO₃, brine, dried over Na₂SO₄, filtered, and the filtrate was concentrated to give yellow oil. The crude product was purified by chromatography on a silica gel column eluted with hexanes:EtOAc (5:1) to give 1.00 g (68%) of compound 151 as colorless oil. ¹H NMR (400 MHz, CDCl₃): δ 3.71 (s, 2H), 3.72 (s, 3H), 3.88 (s, 3H), 6.96 (d, J=8.8 Hz, 2H), 7.38 (d, J=8.0 Hz, 2H), 7.72 (d, J=8.1 Hz, 2H), 7.82 (d, J=8.8 Hz, 2H). LCMS (ESI): m/z, 285 (M+H)⁺, 283 (M−H)⁻.

Step 3: Methyl{4-[(4-hydroxyphenyl)carbonyl]phenyl}acetate (152)

A mixture of methyl(4-{[4-(methyloxy)phenyl]carbonyl}phenyl)acetate (151) (1.00 g, 3.52 mmol) and AlCl₃ (1.90 g, 14.07 mmol) were refluxed in benzene (40 mL) for 1 h and then cooled to 0° C. in an ice bath. Water (35 mL) was added slowly, and the mixture was extracted with ether (2×50 mL, each contained 15 mL of EtOAc). The combined ethereal extract washed with water, brine, and dried over $Na_2SO_4$. Concentration gave light brown oil, which was purified by chromatography on a silica gel column eluted with a gradient from hexanes to 45% EtOAc:hexanes to afford 0.86 g (90%) of compound 152 as colorless oil. $^1$H NMR (400 MHz, $CDCl_3$): δ 3.71 (s, 2H), 3.72 (s, 3H), 5.63 (br s, 1H), 6.89 (d, J=8.6 Hz, 2H), 7.38 (d, J=8.0 Hz, 2H), 7.72 (d, J=8.1 Hz, 2H), 7.77 (d, J=8.6 Hz, 2H), 8.24 (d, J=7.9 Hz, 1H). LCMS (ESI): m/z 271 $(M+H)^+$, 269 $(M-H)^-$.

Step 4: Methyl{4-[(4-hydroxyphenyl)(3,3,5,5-tetramethylcyclohexylidene)methyl]phenyl}acetate (153)

To a stirred suspension of zinc powder (1.67 g, 25.45 mmol) in THF (60 mL) was slowly added $TiCl_4$ (1.40 mL, 12.72 mmol) via syringe at room temperature under a nitrogen atmosphere. The mixture was heated at reflux for 2 h. A solution of methyl {4-[(4-hydroxyphenyl)carbonyl]phenyl}acetate (152) (0.86 g, 3.18 mmol) and 3,3,5,5-tetramethyl cyclohexanone (1.50 g, 9.55 mmol) in THF (20 mL) was added to the mixture. The reaction mixture was heated at reflux with stirring under a nitrogen atmosphere for 1.5 h. The reaction mixture was allowed to cool to room temperature. To the reaction mixture was slowly added 10% aqueous $K_2CO_3$ (60 mL). The reaction mixture was filtered through a pad of Celite and the pad washed with EtOAc (150 mL). The filtrate was transferred to a separatory funnel and the layers were separated. The aqueous layer was further extracted with EtOAc (50 mL). The combined organic phase washed with water, brine, dried over $Na_2SO_4$, filtered, and the filtrate was concentrated to give the crude product as brown oil. The crude product was purified by chromatography on a silica gel column eluted with a gradient from hexanes to 20% EtOAc:hexanes to give light brown oil, which upon adding hexanes solidified. The solid was triturated with hot hexanes to afford 0.90 g (72%) of 153 as a white solid. mp 154-155° C. $^1$H NMR (400 MHz, $CDCl_3$): δ 0.91 (s, 6H), 0.92 (s, 6H), 1.27 (s, 2H), 1.95 (s, 2H), 1.96 (s, 2H), 3.58 (s, 2H), 3.68 (s, 3H), 4.56 (br s, 1H), 6.72 (d, J=8.6 Hz, 2H), 7.01 (d, J=8.5 Hz, 2H), 7.10 (d, J=8.0 Hz, 2H), 7.17 (d, J=8.1 Hz, 2H). LCMS (ESI): m/z 393 $(M+H)^+$, 391 $(M-H)^-$.

Step 5: {4-[(4-Hydroxyphenyl)(3,3,5,5-tetramethylcyclohexylidene)methyl]phenyl}acetic acid (154)

To a solution of methyl{4-[(4-hydroxyphenyl)(3,3,5,5-tetramethylcyclohexylidene)methyl]phenyl}acetate (153) (0.20 g, 0.51 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 1 N HCl. The mixture was extracted with EtOAc (2×50 mL). The combined organic extract washed with brine and dried over $Na_2SO_4$. Upon concentration and trituration with hot hexanes (containing 1% methanol), the title compound 154 was obtained as a white solid (0.185 g, 96%). mp 220-221° C. $^1$H NMR (400 MHz, DMSO-$d_6$): δ 0.86 (s, 6H), 0.87 (s, 6H), 1.23 (s, 2H), 1.87 (s, 2H), 1.89 (s, 2H), 3.49 (s, 2H), 6.64 (d, J=8.4 Hz, 2H), 6.90 (d, J=8.5 Hz, 2H), 7.03 (d, J=8.1 Hz, 2H), 7.14 (d, J=8.1 Hz, 2H), 9.24 (s, 1H), 12.26 (s, 1H). LCMS (ESI): m/z 401 $(M+Na)^+$, 377 $(M-H)^-$. Anal. Calcd for $C_{25}H_{30}O_3$. ⅛$H_2O$: C, 78.71; H, 8.01; Found: C, 78.73; H, 7.98.

Example 52 (155)

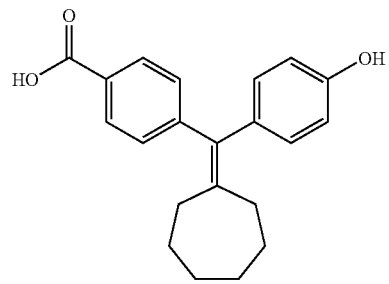

Step 1: 4-[Cycloheptylidene(4-hydroxyphenyl)methyl]benzoic acid (155)

To a 3-necked round-bottomed flask equipped with a reflux condenser, magnetic stir bar, and two nitrogen inlets, were added zinc powder (0.39 g, 5.97 mmoL), and anhydrous THF (15 mL). To the stirred suspension was added $TiCl_4$ (0.31 mL, 0.54 g, 2.83 mmoL) slowly via syringe at RT under a nitrogen atmosphere. (Note: significant fuming occurred during $TiCl_4$ addition. Two nitrogen inlets were used to accommodate the possible transient pressure increase during $TiCl_4$ addition). The reaction mixture was heated at reflux with stirring under a nitrogen atmosphere for 2.5 h. A solution of cycloheptanone (0.26 mL, 0.25 g, 2.23 mmoL) and methyl 4-[(4-hydroxyphenyl)carbonyl]benzoate (24) (0.19 g, 0.74 mmoL) in THF (15 mL) was added to the reaction mixture. The stirred reaction mixture was heated at reflux under a nitrogen atmosphere for 2 h. The oil bath was removed and the reaction mixture was allowed to cool at RT. To the stirred reaction mixture was added $H_2O$ (5 mL) followed by 10% aqueous $K_2CO_3$ (5 mL). The quenched reaction mixture was filtered through a pad of Celite with the aid of $H_2O$ and EtOAc. The filtrate was transferred to a separatory funnel and the layers were separated. The organic phase was dried ($MgSO_4$), filtered, and the filtrate was concentrated to give the crude product as a yellow liquid. The crude product was partially purified by flash chromatography on silica gel using a $CH_2Cl_2$:MeOH gradient (100:0 to 95:5) to give 0.228 g of the impure methyl ester as a colorless oil. To a solution of methyl 4-[cycloheptylidene (4-hydroxyphenyl)methyl]benzoate (0.23 g) in THF (3 mL) and EtOH (3 mL) was added 1 N NaOH (6 mL) at RT under a nitrogen atmosphere. The stirred reaction mixture was heated at 85° C. under a nitrogen atmosphere for 4 h. The oil bath was removed and the reaction mixture was allowed to stand at RT overnight. The reaction mixture was partially concentrated in vacuo to remove the THF and EtOH. To the basic aqueous solution was added 1 N HCl to pH ~1 (as judged by litmus paper). The turbid acidic aqueous mixture was transferred to a separatory funnel with the aid of $H_2O$ and $CH_2Cl_2$ and the layers were separated. The organic phase was dried ($MgSO_4$), filtered, and the filtrate was concentrated to give the crude product as a white solid. The crude product was purified by reverse phase preparative HPLC using a C-18 column and a $CH_3CN$:$H_2O$ gradient (50:50 to 100:0) with 0.05% TFA as a modifier to give 0.070 g (29% over two steps)

of the title compound 155 as a white solid. $^1$H NMR (400 MHz, DMSO-$d_6$): δ 1.51 (m, 8 H), 2.17 (m, 2 H), 2.24 (m, 2 H), 6.66 (d, J=8.6 Hz, 2 H), 6.91 (d, J=8.4 Hz, 2 H), 7.21 (d, J=8.1 Hz, 2 H), 7.84 (d, J=8.0 Hz, 2 H), 9.31 (s, 1 H), 12.81 (s, 1 H). HRMS (ESI) Calcd for $C_{21}H_{21}O_3$: 321.1491 (M−H)$^-$. Found: 321.1513.

Example 53 (157)

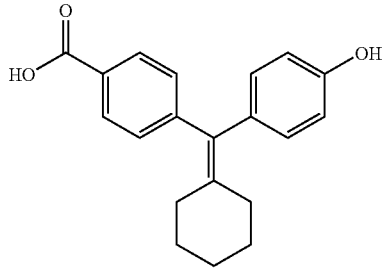

Step 1: Methyl 4-[cyclohexylidene(4-hydroxyphenyl)methyl]benzoate (156)

To a 3-necked round-bottomed flask were added zinc powder (0.40 g, 6.12 mmoL) and anhydrous THF (15 mL). To the stirred suspension was slowly added by syringe TiCl$_4$ (0.32 mL, 0.55 g, 2.9 mmoL) at RT under a nitrogen atmosphere. The reaction mixture was heated at reflux for 2 h. A solution of cyclohexanone (0.24 mL, 0.227 g, 2.3 mmoL) and methyl 4-[(4-hydroxyphenyl)carbonyl]benzoate (24) (0.20 g, 0.78 mmoL) in anhydrous THF (5 mL) was added to the reaction mixture. The reaction mixture was heated a reflux for 2 h. The oil bath was removed and the reaction mixture was allowed to cool at RT. To the reaction mixture was added H$_2$O (5 mL) followed by 10% K$_2$CO$_3$ (5 mL). The quenched reaction mixture was filtered through a pad of Celite with the aid of H$_2$O and EtOAc. The filtrate was transferred to a separatory funnel and the layers were separated. The organic phase was dried (MgSO$_4$), filtered, and the filtrate was concentrated to give the crude product as a yellow oil. The crude product was purified by flash chromatography on silica gel with a CH$_2$Cl$_2$:MeOH gradient (100:0 to 95:5) to give 0.176 g (70%) of compound 156 as a white solid. $^1$H NMR (400 MHz, DMSO-$d_6$): δ 1.53 (m, 6 H), 2.10 (m, 2 H), 2.17 (m, 2 H), 3.80 (s, 3 H), 6.66 (d, J=8.3 Hz, 2 H), 6.84 (d, J=8.2 Hz, 2 H), 7.17 (d, J=8.1 Hz, 2 H), 7.86 (d, J=7.8 Hz, 2 H), 9.34 (s, 1 H).

Step 2: 4-[Cyclohexylidene(4-hydroxyphenyl)methyl]benzoic acid (157)

To a solution of methyl 4-[cyclohexylidene(4-hydroxyphenyl)methyl]benzoate (156) (0.175 g, 0.54 mmoL) in THF (3 mL) and EtOH (3 mL) was added 1 N NaOH (6 mL) at RT. The reaction mixture was heated between 85-90° C. under a nitrogen atmosphere for 2 h. The oil bath was removed and the reaction mixture was allowed to cool to RT. The reaction mixture was partially concentrated in vacuo to remove the THF and EtOH. The basic aqueous mixture was diluted with H$_2$O and the pH was adjusted to ~1 (as judged by litmus paper) with 1 N HCl. The acidic aqueous mixture was extracted with CH$_2$Cl$_2$ (2×). The organic extracts were combined, dried (MgSO$_4$), filtered, and the filtrate was concentrated to give the 0.087 g (52%) of compound 157 as a white solid. $^1$H NMR (400 MHz, DMSO-$d_6$): δ 1.53 (m, 6 H), 2.11 (m, 2 H), 2.17 (m, 2 H), 6.67 (d, J=8.5 Hz, 2 H), 6.85 (d, J=8.5 Hz, 2 H), 7.15 (d, J=8.1 Hz, 2 H), 7.84 (d, J=8.3 Hz, 2 H), 9.35 (s, 1 H), 12.81 (br s, 1). LRMS (ESI): m/z 307 (M−H)$^-$.

Example 54 (159)

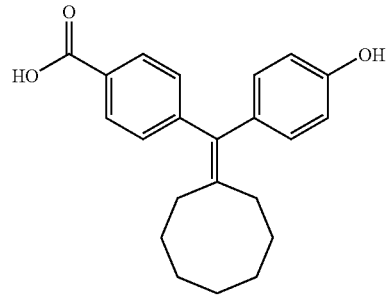

Step 1: Methyl 4-[cyclooctylidene(4-hydroxyphenyl)methyl]benzoate (158)

To a 3-neck round-bottomed flask was added zinc powder (0.40 g, 6.12 mmoL) followed by anhydrous THF (15 mL). To the stirred suspension was slowly added TiCl$_4$ (0.32 mL, 0.55 g, 2.9 mmoL) at RT under a nitrogen atmosphere. The reaction mixture was heated at reflux for 2 h. To the reaction mixture was added a solution of methyl 4-[(4-hydroxyphenyl)carbonyl]benzoate (24) (0.193 g, 0.75 mmoL) and cyclooctanone (0.31 g, 2.46 mmoL) in anhydrous THF (5 mL). The reaction mixture was heated at reflux under a nitrogen atmosphere to 2 h. The oil bath was removed and the reaction mixture was allowed to cool at RT. To the reaction mixture was added H$_2$O (5 mL) followed by 10% K$_2$CO$_3$ (5 mL). The reaction mixture was filtered through a pad of Celite with the aid of H$_2$O and EtOAc. The filtrate was transferred to a separatory funnel and the layers were separated. The organic phase was dried (MgSO$_4$), filtered, and the filtrate was concentrated to give a yellow oil. The crude product was purified by flash chromatography on silica gel with a CH$_2$Cl$_2$:MeOH gradient (100:0 to 95:5) to give 0.159 g (60%) of compound 158 as an oil. $^1$H NMR (400 MHz, DMSO-$d_6$): δ 1.36-1.54 (m, 8 H), 1.59 (m, 2 H), 2.14 (m, 2 H), 2.20 (m, 2 H), 3.80 (s, 3 H), 6.67 (d, J=8.3 Hz, 2 H), 6.93 (d, J=8.3 Hz, 2 H), 7.26 (d, J=8.1 Hz, 2 H), 7.87 (d, J=8.1 Hz, 2 H), 9.30 (s, 1 H).

Step 2: 4-[Cyclooctylidene(4-hydroxyphenyl)methyl]benzoic acid (159)

To methyl 4-[cyclooctylidene(4-hydroxyphenyl)methyl]benzoate (158) (0.159 g, 0.45 mmoL) was added THF (3 mL) and EtOH (3 mL) followed by 1 N NaOH (6 mL). The stirred reaction mixture was heated between 85-90° C. under a nitrogen atmosphere for 2 h. The oil bath was removed and the reaction mixture was allowed to cool at RT. The reaction mixture was partially concentrated in vacuo to remove the THF and EtOH. To the basic aqueous mixture was added water. The pH of the basic solution was adjusted to ~1 (according to litmus paper) with 1 N HCl. The acidic aqueous mixture was extracted with CH₂Cl₂ (2×). The organic extracts were combined, dried (MgSO₄), filtered, and the filtrate was concentrated in vacuo to give the crude product. The crude product was purified by reverse phase preparative HPLC using a C-18 column with a CH₃CN:H₂O gradient (50:50 to 100:0) with 0.05% TFA as a modifier to give 0.075 g (49%) of compound as a white solid. $^1$H NMR (400 MHz, DMSO-d$_6$): δ 1.38-1.56 (m, 8 H), 1.60 (m, 2 H), 2.15 (m, 2 H), 2.21 (m, 2 H), 6.68 (d, J=8.4 Hz, 2 H), 6.94 (d, J=8.5 Hz, 2 H), 7.23 (d, J=8.1 Hz, 2 H), 7.85 (d, J=8.1 Hz, 2 H), 9.30 (s, 1 H), 12.81 (s, 1 H). Anal. Calcd for C$_{22}$H$_{24}$O$_3$: C, 78.54; H, 7.19. Found: C, 78.29; H, 7.17

Example 55 (160)

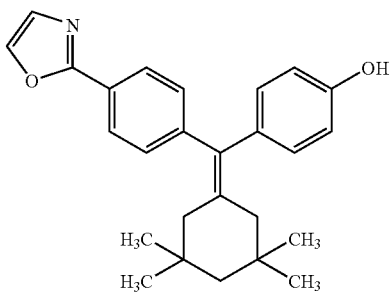

Step 1: 4-[[4-(1,3-Oxazol-2-yl)phenyl](3,3,5,5-tetramethylcyclohexylidene)methyl]phenol (160)

To a stirred suspension of 4-[(4-hydroxyphenyl)(3,3,5,5-tetramethylcyclohexylidene)methyl]benzoic acid (26) (0.373 g, 1.02 mmoL) in CH₂Cl₂ (10 mL) was added dropwise via syringe oxalyl chloride (0.15 mL, 0.218 g, 1.72 mmoL) followed by DMF (4 drops) at RT under a nitrogen atmosphere. Bubbling occurred upon addition of DMF. After several minutes, CH₂Cl₂ (10 mL) was added and the reaction mixture was stirred at RT under a nitrogen atmosphere for 0.5 h. The reaction mixture was concentrated in vacuo and toluene was added to the residue. The toluene was removed in vacuo to give the crude acid chloride. To the crude acid chloride was added tetramethylene sulfone (3 mL), K₂CO₃ (0.38 g, 2.75 mmoL) and 1H-1,2,3-triazole (0.065 mL, 0.077 g, 1.12 mmoL). The stirred reaction mixture was heated overnight at 140° C. under a nitrogen atmosphere. The oil bath was removed and the reaction mixture was allowed to cool at RT. The crude reaction mixture was applied to an SiO₂ precolumn and the title compound was partially purified by flash chromatography on silica gel with a hexanes:EtOAc gradient (100:0 to 50:50) to give 0.072 g of the impure product as a viscous yellow oil. The impure product was purified by reverse phase preparative HPLC using a C-18 column and a CH₃CN:H₂O gradient (75:25 to 100:0) with 0.05% TFA as a modifier to give 0.023 g (6%) of compound 160 as an off-white solid. $^1$H NMR (400 MHz, DMSO-d$_6$): δ 0.87 (s, 6 H), 0.89 (s, 6 H), 1.26 (s, 2 H), 1.89 (s, 2 H), 1.93 (s, 2 H), 6.67 (d, J=8.5 Hz, 2 H), 6.95 (d, J=8.5 Hz, 2 H), 7.27 (d, J=8.3 Hz, 2 H), 7.34 (s, 1 H), 7.89 (d, J=8.3 Hz, 2 H), 8.18 (s, 1 H), 9.31 (s, 1 H). HRMS (ESI) Calcd for C$_{26}$H$_{30}$NO$_2$: 388.2277 (M+H)$^+$. Found: 388.2288.

Example 56 (161)

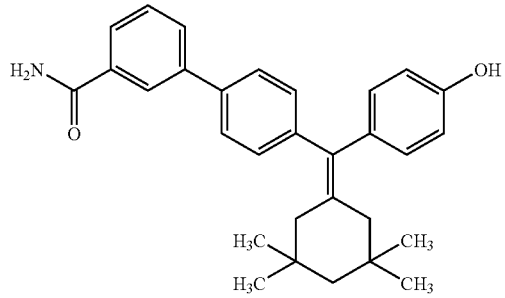

Step 1: 4'-[(4-Hydroxyphenyl)(3,3,5,5-tetramethylcyclohexylidene)methyl]-3-biphenylcarboxamide (161)

To a round-bottomed flask were added 4-[(4-bromophenyl)(3,3,5,5-tetramethylcyclohexylidene)methyl]phenol (14) (85% pure—contains 15% 3,3,5,5-tetramethylcyclohexanone) (0.10 g, 0.21 mmoL), benzamide 3-boronic acid (0.095 g, 0.58 mmoL), tetrakis(triphenylphosphine)palladium (0) (0.025 g, 0.022 mmoL), 2 M Na₂CO₃ (3 mL), and ethylene glycol dimethyl ether (5 mL). The stirred reaction mixture was heated at reflux under a nitrogen atmosphere for 3 h. The oil bath was removed and the reaction mixture was allowed to cool at RT. The reaction mixture was partitioned between H₂O and CH₂Cl₂. The organic phase was separated, washed with H₂O followed by brine, dried over MgSO₄, filtered, and the filtrate was concentrated to give the crude product as a dark brown oil. The crude product was partially purified by flash chromatography on silica gel with a CH₂Cl₂:MeOH gradient (100:0 to 98:2) to give 0.074 g of impure product. The impure product was purified by reverse phase preparative HPLC using a CH₃CN:H₂O gradient (50:50 to 100:0) with 0.05% TFA as a modifier to give 0.024 g (26%) of compound 161 as a white solid. $^1$H NMR (400 MHz, DMSO-d$_6$): δ 0.89 (s, 12 H), 1.26 (s, 2 H), 1.93 (s, 4 H), 6.67 (d, J=8.4 Hz, 2 H), 6.95 (d, J=8.4 Hz, 2 H), 7.22 (d, J=8.2 Hz, 2 H), 7.39 (br s, 1 H), 7.50 (t, J=7.7 Hz, 1 H), 7.63 (d, J=8.1 Hz, 2 H), 7.80 (m, 2 H), 8.06 (br s, 1 H), 8.12 (s, 1 H), 9.27 (s, 1 H). HRMS (ESI) Calcd for C$_{30}$H$_{34}$NO$_2$: 440.2590 (M+H)$^+$. Found: 440.2604.

Example 57 (162)

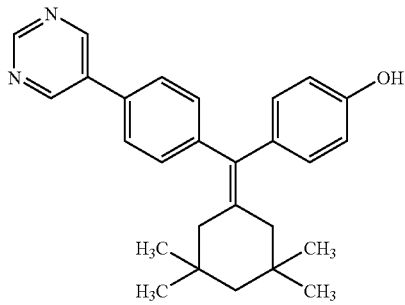

Step 1: 4-[[4-(5-Pyrimidinyl)phenyl](3,3,5,5-tetramethylcyclohexylidene)methyl]phenol (162)

To a round-bottomed flask were added 4-[(4-bromophenyl)(3,3,5,5-tetramethylcyclohexylidene)methyl]phenol

(14) (85% pure—contains 15% 3,3,5,5-tetramethylcyclohexanone) (0.116 g, 0.25 mmoL), pyrimidine-5-boronic acid (0.103 g, 0.83 mmoL), tetrakis(triphenylphosphine)palladium (0) (0.025 g, 0.022 mmoL), 2 M Na$_2$CO$_3$ (3 mL), and ethylene glycol dimethyl ether (8 mL). The stirred reaction mixture was heated at reflux under a nitrogen atmosphere for 3.5 h. The oil bath was removed and the reaction mixture was allowed to cool at RT. The reaction mixture was transferred to a separatory funnel and partitioned between H$_2$O and EtOAc. The organic phase was separated and the aqueous phase was extracted with EtOAc. The organic extracts were combined, dried over MgSO$_4$, filtered, and the filtrate was concentrated in vacuo to give a brown oil. The crude product was partially purified by flash chromatography on silica gel with a hexanes:EtOAc gradient (100:0 to 90:10) to give the impure product. The impure product was purified by reverse phase preparative HPLC with a C-18 column and a CH$_3$CN:H$_2$O gradient (75:25 to 100:0) with 0.05% TFA as a modifier to give 0.045 g (45%) of compound 162 as a white solid. $^1$H NMR (400 MHz, DMSO-d$_6$): δ 0.89 (s, 12 H), 1.26 (s, 2 H), 1.93 (s, 4 H), 6.67 (d, J=8.4 Hz, 2 H), 6.95 (d, J=8.4 Hz, 2 H), 7.26 (d, J=8.2 Hz, 2 H), 7.72 (d, J=8.3 Hz, 2 H), 9.11 (s, 2 H), 9.14 (s, 1 H), 9.29 (s, 1 H). HRMS (ESI) Calcd for C$_{27}$H$_{31}$N$_2$O: 399.2436 (M+H)$^+$. Found: 399.2437.

Example 58 (163)

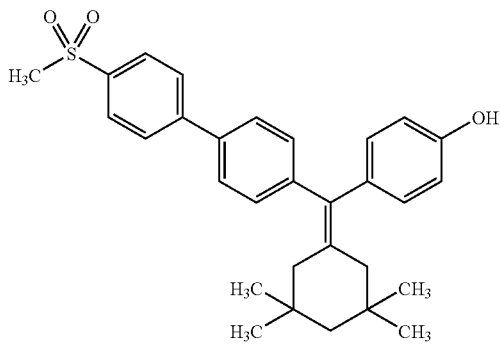

Step 1: 4-[[4'-(Methylsulfonyl)-4-biphenylyl](3,3,5,5-tetramethylcyclohexylidene)methyl]phenol (163)

To a round-bottomed flask were added 4-[(4-bromophenyl)(3,3,5,5-tetramethylcyclohexylidene)methyl]phenol (14) (85% pure—contains 15% 3,3,5,5-tetramethylcyclohexanone) (0.117 g, 0.25 mmoL), 4-(methanesulphonyl)benzeneboronic acid (0.165 g, 0.82 mmoL), tetrakis(triphenylphosphine)palladium (0) (0.026 g, 0.023 mmoL), 2 M Na$_2$CO$_3$ (3 mL), and ethylene glycol dimethyl ether (8 mL). The stirred reaction mixture was heated at reflux under a nitrogen atmosphere for 3.5 h. The oil bath was removed and the reaction mixture was allowed to cool at RT. The reaction mixture was transferred to a separatory funnel and partitioned between H$_2$O and EtOAc. The organic phase was separated and the aqueous phase was extracted with EtOAc. The organic extracts were combined, dried over MgSO$_4$, filtered, and the filtrate was concentrated in vacuo to give a brown oil. The crude product was purified by flash chromatography on silica gel using a hexanes:EtOAc gradient (100:0 to 75:25) to give 0.063 g (53%) of compound 163 as a white solid. $^1$H NMR (400 MHz, DMSO-d$_6$): δ 0.89 (s, 12 H), 1.26 (s, 2 H), 1.93 (s, 4 H), 3.23 (s, 3 H), 6.67 (d, J=8.5 Hz, 2 H), 6.95 (d, J=8.4 Hz, 2 H), 7.25 (d, J=8.2 Hz, 2 H), 7.67 (d, J=8.3 Hz, 2 H), 7.91 (d, J=8.6 Hz, 2 H), 7.95 (d, J=8.6 Hz, 2 H), 9.29 (s, 1 H). HRMS (ESI) Calcd for C$_{30}$H$_{33}$O$_3$S: 473.2150 (M–H)$^-$. Found: 473.2168.

Example 59 (164)

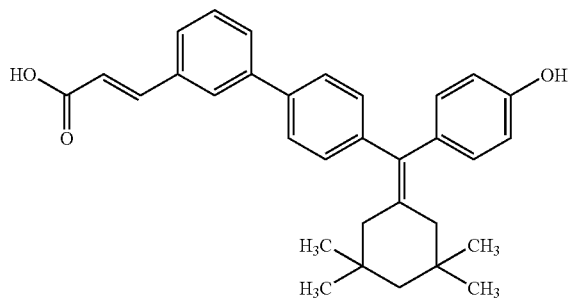

Step 1: (2E)-3-{4'-[(4-Hydroxyphenyl)(3,3,5,5-tetramethylcyclohexylidene)methyl]-3-biphenylyl}-2-propenoic acid (164)

To a round-bottomed flask were added 4-[(4-bromophenyl)(3,3,5,5-tetramethylcyclohexylidene)methyl]phenol (14) (85% pure—contains 15% 3,3,5,5-tetramethylcyclohexanone) (0.117 g, 0.25 mmoL), 3-(2-carboxyvinyl)benzeneboronic acid (0.117 g, 0.61 mmoL), tetrakis(triphenylphosphine)palladium (0) (0.026 g, 0.022 mmoL), 2 M Na$_2$CO$_3$ (3 mL), and ethylene glycol dimethyl ether (8 mL). The stirred reaction mixture was heated at reflux under a nitrogen atmosphere for 3 h. The oil bath was removed and the reaction mixture was allowed to cool at RT.

The reaction mixture was transferred to a separatory funnel and partitioned between H$_2$O and EtOAc. The organic phase was separated, dried (MgSO$_4$), filtered, and the filtrate was concentrated in vacuo to give an oil. The crude product was purified by reverse phase preparative HPLC on a C-18 column with a CH$_3$CN:H$_2$O gradient (75:25 to 100:0) and 0.05% TFA as a modifier to give 0.046 g (39%) of compound 164 as an off-white solid. $^1$H NMR (400 MHz, DMSO-d$_6$): δ 0.89 (s, 12 H), 1.26 (s, 2 H), 1.93 (s, 4 H), 6.63 (d, J=16.2 Hz, 1 H), 6.67 (d, J=8.4 Hz, 2 H), 6.95 (d, J=8.5 Hz, 2 H), 7.20 (d, J=8.2 Hz, 2 H), 7.46 (t, J=7.7 Hz, 1 H), 7.65 (m, 5 H), 7.95 (s, 1 H), 9.27 (s, 1 H), 12.39 (br s, 1 H). Anal. Calcd for C$_{32}$H$_{34}$O$_3$·0.25H$_2$O: C, 81.58; H, 7.38. Found: C, 81.62; H, 7.33.

Example 60 (165)

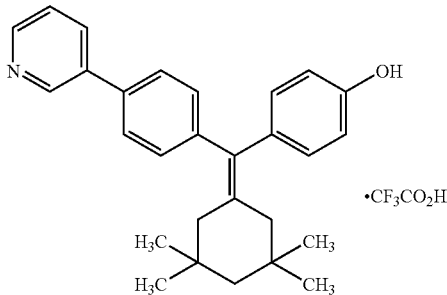

Step 1: 4-[[4-(3-Pyridinyl)phenyl](3,3,5,5-tetramethylcyclohexylidene)methyl]phenol trifluoroacetate (165)

To a round-bottomed flask were added 4-[(4-bromophenyl)(3,3,5,5-tetramethylcyclohexylidene)methyl]phenol (14) (85% pure—contains 15% 3,3,5,5-tetramethylcyclohexanone) (0.10 g, 0.21 mmoL), pyridine-3-boronic acid (0.077 g, 0.63 mmoL), tetrakis(triphenylphosphine)palladium (0) (0.028 g, 0.024 mmoL), 2 M $Na_2CO_3$ (3 mL), and ethylene glycol dimethyl ether (8 mL). The stirred reaction mixture was heated at reflux under a nitrogen atmosphere for 3 h. The oil bath was removed and the reaction mixture was allowed to cool at RT. The reaction mixture was transferred to a separatory funnel and partitioned between $H_2O$ and EtOAc. The organic phase was separated, washed with brine, dried over $MgSO_4$, filtered, and the filtrate was concentrated in vacuo to give a brown-orange oil. The crude product was purified by reverse phase preparative HPLC with a C-18 column and a $CH_3CN:H_2O$ gradient (50:50 to 100:0) using 0.05% TFA as a modifier to give 0.018 g (17%) of compound 165 as an off-white solid. $^1$H NMR (400 MHz, DMSO-$d_6$): δ 0.89 (s, 12 H), 1.26 (s, 2 H), 1.93 (s, 4 H), 6.67 (d, J=8.4 Hz, 2 H), 6.95 (d, J=8.4 Hz, 2 H), 7.25 (d, J=8.3 Hz, 2 H), 7.60 (m, 1 H), 7.68 (d, J=8.0 Hz, 2 H), 8.24 (br d, J=8.0 Hz, 1 H), 8.60 (d, J=4.6 Hz, 1 H), 8.95 (m, 1 H), 9.29 (br s, 1 H). HRMS (ESI) Calcd for $C_{28}H_{32}NO$: 398.2484 $(M+H)^+$. Found: 398.2484.

Example 61 (170)

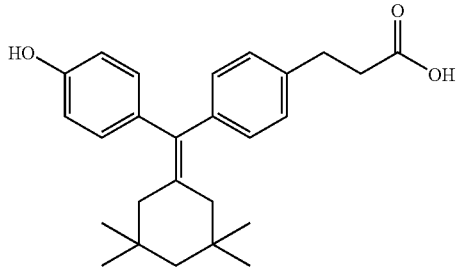

Step 1: 4-[3-(Methyloxy)-3-oxopropyl]benzoic acid (166)

To a suspension of 3-(4-carboxyphenyl)propionic acid (2.0 g, 10.1 mmol) in methanol (20 mL) was added thionyl chloride (38 μL, 0.50 mmol). The reaction mixture was stirred at room temperature for 16 h, and a clear solution was obtained. The solvent was removed under reduced pressure. The residue was taken up in ether (100 mL), washed with saturated aqueous $NaHCO_3$ (2×50 mL) and water (50 mL). The combined $NaHCO_3$ and water extract was acidified with concentrated HCl in an ice bath. The precipitated white solid was collected, washed with water and dried to yield 1.76 g (84%) of compound 166 as off-white solid. The material was used without further purification. mp 146-148° C. $^1$H NMR (400 MHz, $CDCl_3$): δ 2.66 (t, J=7.7 Hz, 2H), 3.02 (t, J=7.7 Hz, 2H), 3.67 (s, 3H), 7.30 (d, J=8.3 Hz, 2H), 8.03 (d, J=8.1 Hz, 2H). LCMS (ES), m/z, 209 $(M+H)^+$, 207 $(M-H)^-$.

Step 2: Methyl 3-(4-{[4-(methyloxy)phenyl]carbonyl}phenyl)propanoate (167)

4-[3-(Methyloxy)-3-oxopropyl]benzoic acid (166) (1.0 g, 4.80 mmol) was dissolved in $CH_2Cl_2$ (25 mL). Oxalyl chloride (0.86 mL, 9.61 mmol) was added dropwise, followed by addition of two drops of DMF. The reaction mixture was stirred at room temperature for 2 h. Methylene chloride and the excess of oxalyl chloride were removed under vacuum. The residue was dissolved in $CH_2Cl_2$ (15 mL) with anisole (1.05 mL, 9.60 mmol). Cooled in an ice bath, $AlCl_3$ (0.97 g, 7.20 mmol) was added in portions. The mixture was stirred at 0° C. for 3.5 h, then stirred at room temperature for 1.5 h. Poured into 1 N HCl (25 mL) with ice, the mixture was extracted with $CH_2Cl_2$ (3×50 mL). The combined $CH_2Cl_2$ extract washed with saturated aqueous $NaHCO_3$, brine, dried over $Na_2SO_4$, filtered, and the filtrate was concentrated to give brown oil. The crude product was purified by chromatography on a silica gel column eluted with hexanes:EtOAc (8:1 to 5:1) to give 0.90 g (63%) of the title compound 167 as cotton-like white solid. $^1$H NMR (400 MHz, $CDCl_3$): δ 2.68 (t, J=7.7 Hz, 2H), 3.03 (t, J=7.7 Hz, 2H), 3.68 (s, 3H), 3.89 (s, 3H), 6.96 (d, J=8.8 Hz, 2H), 7.30 (d, J=8.1 Hz, 2H), 7.70 (d, J=8.1 Hz, 2H), 7.81 (d, J=8.8 Hz, 2H). LCMS (ESI): m/z 299 $(M+H)^+$.

Step 3: Methyl 3-{4-[(4-hydroxyphenyl)carbonyl]phenyl}propanoate (168)

A mixture of methyl 3-(4-{[4-(methyloxy)phenyl]carbonyl}phenyl)propanoate (167) (0.45 g, 1.51 mmol) and $AlCl_3$ (0.82 g, 6.03 mmol) were refluxed in benzene (20 mL) for 1 h and then cooled to 0° C. in an ice bath. Water (15 mL) was added slowly, and the mixture was extracted with ether (2×50 mL). The combined ethereal extract was washed with water, brine, and dried over $Na_2SO_4$. Concentration gave light brown oil, which was purified by chromatography on a silica gel column eluted with a gradient from hexanes to 45% EtOAc:hexanes to afford 0.41 g (96%) of the title compound 168 as colorless oil. $^1$H NMR (400 MHz, $CDCl_3$): δ 2.68 (t, J=7.7 Hz, 2H), 3.03 (t, J=7.7 Hz, 2H), 3.68 (s, 3H), 5.44 (s, 1H), 6.89 (d, J=8.7 Hz, 2H), 7.30 (d, J=8.1 Hz, 2H), 7.69 (d, J=8.1 Hz, 2H), 7.77 (d, J=8.8 Hz, 2H). LCMS (ESI): m/z 285 $(M+H)^+$, m/z 283 $(M-H)^-$.

Step 4: Methyl 3-{4-[(4-hydroxyphenyl)(3,3,5,5-tetramethylcyclohexylidene)methyl]phenyl}propanoate (169)

To a stirred suspension of zinc powder (0.76 g, 11.54 mmol) in THF (30 mL) was slowly added $TiCl_4$ (0.64 mL, 5.77 mmol) via syringe at room temperature under a nitrogen atmosphere. The mixture was heated at reflux for 2 h. A solution of methyl 3-{4-[(4-hydroxyphenyl)carbonyl]phenyl}propanoate (168) (0.41 g, 1.44 mmol) and 3,3,5,5-tetramethyl cyclohexanone (0.68 g, 4.33 mmol) in THF (10 mL) was added to the mixture. The reaction mixture was heated at reflux with stirring under a nitrogen atmosphere for 2 h. The reaction mixture was allowed to cool to room temperature. To the reaction mixture was slowly added 10% aqueous $K_2CO_3$ (30 mL). The reaction mixture was filtered through a pad of Celite and the pad washed with EtOAc (100 mL). The filtrate was transferred to a separatory funnel and the layers were separated. The aqueous layer was further extracted with EtOAc (25 mL). The combined organic phase washed with water, brine, dried over $Na_2SO_4$, filtered, and the filtrate was concentrated to give the crude product as yellow oil. The crude product was purified by chromatography on a silica gel column eluted with a gradient from hexanes to 20% EtOAc:hexanes to give light brown oil, which upon adding hexanes solidified. The solid was triturated with hot hexanes to afford 0.40 g (68%) of compound 169 as white solid. mp 129-130° C. $^1$H NMR (400 MHz, $CDCl_3$): δ 0.92 (s, 12H), 1.27 (s, 2H), 1.94 (s, 2H), 1.95 (s, 2H), 2.61 (t, J=7.5 Hz, 2H), 2.91 (t, J=7.5 Hz, 2H), 3.66 (s, 3H), 4.57 (s, 1H), 6.73 (d, J=8.5 Hz, 2H), 7.02 (d, J=8.4 Hz, 2H), 7.04-7.10 (m, 4H). LCMS (ESI): m/z 429 (M+Na)$^+$, m/z 405 (M−H)$^−$.

Step 5: 3-{4-[(4-Hydroxyphenyl)(3,3,5,5-tetramethylcyclohexylidene)methyl]phenyl}propanoic acid (170)

To a solution of methyl 3-{4-[(4-hydroxyphenyl)(3,3,5,5-tetramethylcyclohexylidene)methyl]phenyl}propanoate (9) (0.20 g, 0.49 mmol) in a mixture of EtOH (6 mL) and THF (6 mL) was added an aqueous solution of 1 N NaOH (7 mL). The mixture was stirred at 60° C. for 2 h. Upon cooling, the mixture was acidified to pH=2 with an aqueous solution of 1 N HCl. The mixture was extracted with EtOAc (2×50 mL). The combined organic extract washed with brine and dried over $Na_2SO_4$. Upon concentration and trituration with hot hexanes (contained 1% methanol), the title compound 170 was obtained as white solid (0.177 g, 92%). mp 243-244° C. $^1$H NMR (400 MHz, $CD_3OD$): δ 0.91 (s, 6H), 0.92 (s, 6H), 1.29 (s, 2H), 1.95 (s, 2H), 1.98 (s, 2H), 2.58 (t, J=7.7 Hz, 2H), 2.87 (t, J=7.7 Hz, 2H), 6.67 (d, J=8.5 Hz, 2H), 6.94 (d, J=8.5 Hz, 2H), 7.05 (d, J=8.1 Hz, 2H), 7.12 (d, J=8.1 Hz, 2H). LCMS (ESI): m/z 393 (M+H)$^+$, m/z 391 (M−H)$^−$.

Example 62 (172)

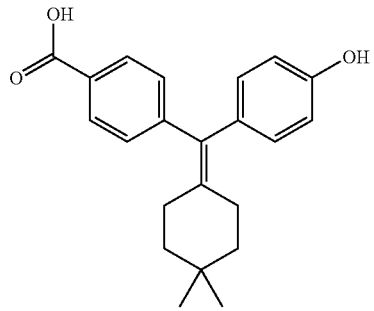

Step 1: 4-[(4,4-Dimethyl-cyclohexylidene)-(4-hydroxy-phenyl)-methyl]-benzoic acid methyl ester (171)

To a slurry of zinc powder (0.26 g, 4.01 mmol) in dry tetrahydrofuran (9 mL) was slowly added titanium tetrachloride (0.21 mL, 1.95 mmol). The reaction mixture was heated at reflux for 2.5 h, then a solution of 4,4-dimethyl-cyclohexanone (0.2 g, 1.58 mmol) and 4-(4-hydroxy-benzoyl)-benzoic acid methyl ester (24) (0.135 g, 0.53 mmol) in dry tetrahydrofuran (9 mL) was added. The reaction mixture was heated at reflux for 2 h. The reaction mixture was cooled to room temperature, water (5 mL) was added followed by 10% $K_2CO_3$ (5 mL). The reaction mixture was filtered through a pad of Celite and the pad washed with EtOAc. The filtrate was transferred to a separatory funnel and the layers were separated. The aqueous layer was extracted with EtOAc and the combined organic layers were washed with brine, dried over $Na_2SO_4$, filtered and concentrated. The crude material was loaded onto silica and purified by flash chromatography with a hexanes:EtOAc gradient (100:0 to 80:20) to give 0.162 g (88%) of the title compound 171 as an oil. $^1$H NMR (400 MHz, DMSO-$d_6$): δ 0.93 (s, 6 H), 1.31-1.33 (m, 4 H), 2.12-2.19 (m, 4 H), 3.81 (s, 3 H), 6.66 (d, J=8.4 Hz, 2 H), 6.84 (d, J=8.6 Hz, 2 H), 7.18 (d, J=8.3 Hz, 2 H), 7.86 (d, J=8.3 Hz, 2 H), 9.36 (s, 1 H).

Step 2: 4-[(4,4-Dimethyl-cyclohexylidene)-(4-hydroxy-phenyl)-methyl]-benzoic acid (172)

To a solution of THF (2 mL) and ethanol (2 mL) containing 4-[(4,4-dimethyl-cyclohexylidene)-(4-hydroxy-phenyl)-methyl]-benzoic acid methyl ester (171) (0.16 g, 0.457 mmol) was added 1 N NaOH (4 mL). The reaction mixture was heated at 65° C. for 4 h. The reaction mixture was partially concentrated to remove the EtOH and THF. To the basic aqueous mixture was added 1 N HCl to pH~1 (according to litmus paper). The acidic aqueous solution was extracted with dichloromethane and the organic extract washed with brine, dried over $Na_2SO_4$, filtered and concentrated. The crude material was triturated with dichloromethane, filtered, and dried to give 0.132 g (85%) of the title compound 172 as a white powder. $^1$H NMR (400 MHz, DMSO-$d_6$): δ 0.93 (s, 6 H), 1.32 (s, 4 H), 2.12-2.19 (m, 4 H), 6.66 (d, J=8.3 Hz, 2 H), 6.84 (d, J=8.4 Hz, 2 H), 7.14 (d, J=8.1 Hz, 2 H), 7.83 (d, J=8 Hz, 2 H), 9.33 (s, 1 H), 12.74 (s, 1 H). HRMS (ESI) Calcd for $C_{22}H_{23}O_3$: 335.1647 (M−H)$^−$. Found: 335.1640.

Example 63 (174)

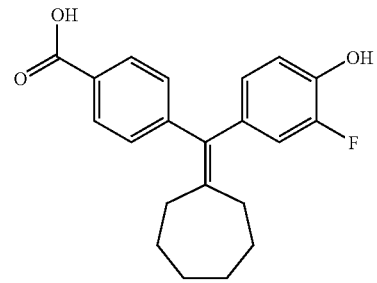

Step 1: 4-(3-Fluoro-4-methoxy-benzoyl)-benzoic acid methyl ester (173)

To an ice-cooled slurry of $AlCl_3$ (2.01 g, 15.1 mmol) in dichloromethane (10 mL) was slowly added 4-chlorocarbonyl-benzoic acid methyl ester (2 g, 10.1 mmol) in dichloromethane (5 mL). The reaction mixture was stirred for 20 min in the ice bath then 2-fluoroanisole (1.4 mL, 12.1 mmol)

in dichloromethane (5 mL) was added. The reaction mixture was stirred at room temperature for 20 h. The reaction mixture was poured into ice cold 1 N HCl (10 mL) and the mixture was stirred for 15 min. The reaction mixture was transferred to a separatory funnel and the layers were separated. The aqueous layer was extracted with dichloromethane and the organic extracts were combined, washed with brine, dried over Na$_2$SO$_4$, filtered and concentrated. The crude solid was triturated with hot hexanes, filtered and washed with hexanes to give 0.5 g (17%) of compound 173 as a white powder. $^1$H NMR (400 MHz, DMSO-d$_6$): δ 3.89 (s, 3 H), 3.94 (s, 3 H), 7.32 (t, J=8.5 Hz, 1 H), 7.57 (d, J=8.8 Hz, 1 H), 7.59-7.63 (m, 1 H), 7.81 (d, J=8.2 Hz, 2 H), 8.04 (s, 1 H), 8.10 (d, J=8.3 Hz, 2 H).

Step 2: 4-[Cycloheptylidene-(3-fluoro-4-hydroxy-phenyl)-methyl]-benzoic acid (174)

AlCl$_3$ (0.97 g, 7.28 mmol) was added portionwise via an addition funnel to a solution of 4-(3-fluoro-4-methoxy-benzoyl)-benzoic acid methyl ester (173) (0.50 g, 1.73 mmol) in toluene (8 mL). The reaction mixture was heated at reflux for 20 h and allowed to cool to RT. Water (10 mL) was slowly added to the reaction mixture. The reaction mixture was transferred to a separatory funnel and extracted with EtOAc, the organic extract washed with brine, dried over Na$_2$SO$_4$, filtered, and concentrated to give a solid. The resulting solid was triturated with dicholormethane. The suspension was filtered, and the filtered solid was dried to give 0.37 g of the crude product as a mixture of 4-(3-fluoro-4-hydroxy-benzoyl)-benzoic acid and 4-(3-fluoro-4-hydroxy-benzoyl)-benzoic acid methyl ester according to $^1$H NMR and LCMS (ESI). The crude product was used without further purification. To a slurry of zinc powder (0.67 g, 10.3 mmol) in dry THF (11 mL) was slowly added TiCl$_4$ (0.55 mL, 4.99 mmol) at RT under a nitrogen atmosphere. The reaction mixture was heated at reflux for 2.5 h. To the reaction mixture was added a solution of cycloheptanone (0.48 mL, 4.05 mmol) and the aforementioned mixture of 4-(3-fluoro-4-hydroxy-benzoyl)-benzoic acid and 4-(3-fluoro-4-hydroxy-benzoyl)-benzoic acid methyl ester (0.37 g) in dry tetrahydrofuran (11 mL). The reaction mixture was heated at reflux under a nitrogen atmosphere for 2 h. The reaction mixture was cooled to room temperature, water (15 mL) was added followed by 10% K$_2$CO$_3$(15 mL). The reaction was filtered through a pad of Celite, and the pad washed with EtOAc. The filtrate was transferred to a separatory funnel and the layers were separated. The aqueous layer was extracted with EtOAc and the combined organic extracts were washed with brine, dried over Na$_2$SO$_4$, filtered and concentrated. The crude material was loaded onto silica gel and partially purified by flash chromatography with a CH$_2$Cl$_2$:MeOH gradient (100:0 to 98:2) to yield the impure title compound (0.15 g) as well as impure 4-[cycloheptylidene-(3-fluoro-4-hydroxy-phenyl)-methyl]-benzoic acid methyl ester (0.22 g) according to $^1$H NMR. The impure benzoic acid was purified by reverse phase preparative HPLC using a C-18 column and a CH$_3$CN:H$_2$O gradient (50:50 to 100:0) with 0.05% TFA as a modifier to give 0.072 g (12% based on 4-(3-fluoro-4-methoxy-benzoyl)-benzoic acid methyl ester) of compound 174 as a yellow amorphous solid. $^1$H NMR (400 MHz, DMSO-d$_6$): δ 1.51 (m, 8 H), 2.16 (m, 2 H), 2.18 (m, 2 H), 6.71 (d, J=1.8 Hz, 1 H), 6.75-6.88 (m, 2 H), 7.21 (d, J=8 Hz, 2 H), 7.85 (d, J=8.2 Hz, 2 H), 9.76 (s, 1 H), 12.84 (s, 1 H). HRMS (ESI) Calcd for C$_{21}$H$_{20}$FO$_3$: 339.1396 (M−H)$^-$. Found: 339.1411.

Example 64 (177)

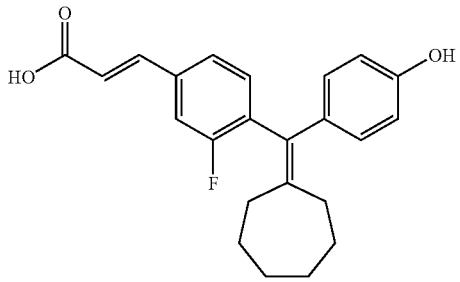

Step 1: 4-[(4-Bromo-2-fluoro-phenyl)-cycloheptyl-idene-methyl]-phenol (175)

To a slurry of Zn powder (3.4 g, 51.5 mmol) in dry tetrahydrofuran (50 mL) was slowly added TiCl$_4$ (2.7 mL, 25.1 mmol) at RT under a nitrogen atmosphere. The reaction mixture was heated at reflux for 2.5 h. To the reaction mixture was added a solution of cycloheptanone (2.4 mL, 20.3 mmol) and (4-bromo-2-fluoro-phenyl)-(4-hydroxy-phenyl)-methanone (76) (2 g, 6.78 mmol) in dry tetrahydrofuran (50 mL). The reaction mixture was heated at reflux for 2 h. The reaction mixture was cooled to room temperature, then water (40 mL) was added followed by 10% K$_2$CO$_3$ (40 mL). The reaction mixture was filtered through a pad of Celite and the pad washed with EtOAc. The filtrate was transferred to a separatory funnel and the layers were separated. The aqueous layer was extracted with EtOAc and the combined organic layers were washed with brine, dried over Na$_2$SO$_4$, filtered and concentrated. The crude material was loaded onto silica gel and purified by flash chromatography with a hexanes:EtOAc gradient (100:0 to 90:10) to give 2.24 g (88%) of compound 175. $^1$H NMR indicates that the product contains ~3% cycloheptanone. $^1$H NMR (400 MHz, DMSO-d$_6$): δ 1.43-1.50 (m, 8 H), 2.05-2.08 (m, 2 H), 2.23-2.24 (m, 2 H), 6.65 (d, J=8.4 Hz, 2 H), 6.91 (d, J=8.4 Hz, 2 H), 7.14, (t, J=8.1 Hz, 1 H), 7.32-7.35 (m, 1 H), 7.44-7.47 (m, 1 H), 9.33 (s, 1 H).

Step 2: 3-{4-[Cycloheptylidene-(4-hydroxy-phenyl)-methyl]-3-fluoro-phenyl}-acrylic acid ethyl ester (176)

To a solution of 4-[(4-bromo-2-fluoro-phenyl)-cycloheptylidene-methyl]-phenol (175) (1.0 g, 2.66 mmol) in DMF (27 mL) was added ethyl acrylate (2.9 mL, 26.6 mmol), dichlorobis(triphenylphosphine)palladium(II) (0.187 g, 0.266 mmol) and Et$_3$N (2.2 mL, 15.99 mmol). The reaction mixture was heated at 100° C. for 20 h. The reaction mixture was cooled to room temperature and diluted with water (10 mL) and EtOAc (20 mL). The aqueous mixture was transferred to a separatory funnel and the layers were separated. The aqueous layer was extracted with EtOAc and the combined organic layers were washed with brine, dried over Na$_2$SO$_4$, filtered and concentrated. The crude material was loaded onto silica gel and purified by flash chromatography with a hexanes:EtOAc gradient (100:0 to 90:10) to give 0.85 g (81%) of the title compound 176 as an oil. $^1$H NMR (400 MHz, DMSO-d$_6$): δ 1.22 (t, J=7.1 Hz, 3 H), 1.48-1.51 (m, 8

H), 2.07-2.10 (m, 2 H), 2.25 (s, 2 H), 4.13-4.18 (m, 2 H), 6.61-6.66 (m, 3 H), 6.92 (d, J=8.6 Hz, 2 H), 7.20 (t, J=7.8 Hz, 1 H), 7.47 (d, J=6.6 Hz, 1 H), 7.56-7.60 (m, 2 H), 9.32 (s, 1 H).

Step 3: 3-{4-[Cycloheptylidene-(4-hydroxy-phenyl)-methyl]-3-fluoro-phenyl}-acrylic acid (177)

To a solution of 3-{4-[cycloheptylidene-(4-hydroxy-phenyl)-methyl]-3-fluoro-phenyl)-acrylic acid ethyl ester (176) (0.8 g, 2.15 mmol) in THF (10 mL) and ethanol (10 mL) was added 1 N sodium hydroxide (21 mL). The reaction mixture was heated at 65° C. for 2.5 h. The reaction mixture was partially concentrated to remove the EtOH and THF. To the basic aqueous mixture was added 1 N HCl to pH~1 (according to litmus paper). The acidic aqueous solution was extracted with dichloromethane and the organic extract washed with brine, dried over $Na_2SO_4$, filtered and concentrated. The crude material was triturated with dichloromethane, filtered and dried to give 0.065 g (10%) of compound 177 as a white powder. $^1$H NMR (400 MHz, DMSO-$d_6$): δ 1.51 (b, 8 H), 2.09 (m, 2 H), 2.25 (m, 2 H), 6.52 (d, J=16.1 Hz, 1 H), 6.65 (d, J=8.4 Hz, 2 H), 6.92 (d, J=8.4 Hz, 2 H), 7.19 (t, J=7.8 Hz, 1 H), 7.43-7.49 (m, 1 H), 7.51-7.53 (m, 2 H), 9.32 (s, 1 H), 12.43 (s, 1 H). HRMS (ESI) Calcd for $C_{23}H_{22}FO_3$: 365.1553 (M−H)$^-$. Found: 365.1543.

Example 65 (181)

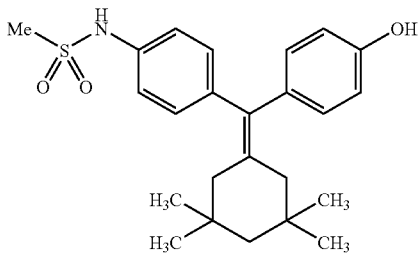

Step 1: (4-Amino-phenyl)-(4-methoxy-phenyl)-methanone (178)

Sodium dithionite (8.1 g, 46.6 mmol) was added to a slurry of 4-methoxy-4-nitrobenzophenone (3 g, 11.66 mmol) in 95% ethanol (73 mL) and heated at reflux for 20 h. The reaction mixture was cooled to room temperature and concentrated to remove the ethanol. The concentrated material was partitioned between EtOAc and water and the layers were separated. The aqueous layer was extracted with EtOAc, and the organic extracts were combined, washed with brine, dried over $Na_2SO_4$, filtered, and concentrated to give an oil, which solidified upon standing. The solid was purified by flash chromatography with a $CH_2Cl_2$:MeOH gradient of (100:0 to 99:1) to give 1.72 g (65%) of the title compound 178 as an off white powder. $^1$H NMR (400 MHz, DMSO-$d_6$): δ 3.81 (s, 3 H), 6.04 (s, 2 H), 6.57 (d, J=8.6 Hz, 2 H), 7.02 (d J=8.8 Hz, 2 H), 7.47 (d, J=8.6 Hz, 2 H), 7.60 (d, J=8.8 Hz, 2 H).

Step 2: N-[4-(4-Methoxy-benzoyl)-phenyl]-methanesulfonamide (179)

Methanesulfonyl chloride (0.15 mL, 1.94 mmol) was slowly added to an ice-cooled solution of (4-amino-phenyl)-(4-methoxy-phenyl)-methanone (178) (0.4 g, 1.76 mmol) and pyridine (0.16 mL, 1.94 mmol) in dry dichloromethane (5 mL). The reaction mixture was stirred at room temperature for 20 h then diluted with EtOAc and water. The layers were separated and the aqueous layer was extracted with EtOAc. The organic extracts were combined, washed with brine, dried over $Na_2SO_4$, filtered and concentrated to give 0.5 g (93%) of compound 179 as a solid. $^1$H NMR (400 MHz, DMSO-$d_6$): δ 3.11 (s, 3 H), 3.84 (s, 3 H), 7.06 (d, J=8.8 Hz, 2 H), 7.30 (d, J=8.6 Hz, 2 H), 7.68-7.72 (m, 4 H), 10.31 (s, 1 H).

Step 3: N-{4-[(4-Methoxy-phenyl)-(3,3,5,5-tetramethyl-cyclohexylidene)-methyl]-phenyl}-methanesulfonamide (180)

Titanium tetrachloride (0.66 mL, 6.06 mmol) was slowly added to a slurry of Zn powder (0.81 g, 12.4 mmol) in dry THF (14 mL). The reaction mixture was heated at reflux for 2.5 h. A solution of 3,3,5,5-tetramethyl-cyclohexanone (0.86 mL, 4.91 mmol) and N-[4-(4-methoxy-benzoyl)-phenyl]-methanesulfonamide (9) (0.5 g, 1.64 mmol) in dry THF (14 mL) was added to the reaction mixture and heated at reflux for another 2 h. The reaction mixture was cooled to room temperature and diluted with water (10 mL) followed by 10% $K_2CO_3$ (10 mL).The reaction mixture was filtered through a pad of Celite and the pad washed with EtOAc. The filtrate was transferred to a separatory funnel and the layers were separated. The aqueous layer was extracted with EtOAc and the combined organic layers were washed with brine, dried over $Na_2SO_4$, filtered, and concentrated. The crude material was loaded onto silica gel and purified by flash chromatography with a hexanes:EtOAc gradient (100:0 to 60:40) to give 0.5 g (71%) of the title compound 180 as a white solid. $^1$H NMR (400 MHz, DMSO-$d_6$): δ 0.87 (s, 6 H), 0.87 (s, 6 H), 1.24 (s, 2 H), 1.88-1.89 (m 4 H), 2.95 (s, 3 H), 3.70 (s, 3 H), 6.83 (d, J=8.8 Hz, 2 H), 7.03 (d, J=8.6 Hz, 2 H), 7.08 (m, 4 H), 9.66 (s, 1 H).

Step 4: N-{4-[(4-Hydroxy-phenyl)-(3,3,5,5-tetramethyl-cyclohexylidene)-methyl]-phenyl}-methanesulfonamide (181)

To a solution of N-{4-[(4-methoxy-phenyl)-(3,3,5,5-tetramethyl-cyclohexylidene)-methyl]-phenyl}-methanesulfonamide (180) (0.25 g, 0.585 mmol) in dry dichloromethane (20 mL) was slowly added $BBr_3$ (1 N in dichloromethane) (1.75 mL, 1.75 mmol) at −5 to 0° C. The reaction mixture was stirred at −5 to 0° C. under nitrogen for 3 h. The reaction mixture was poured onto ice and stirred for several minutes. The quenched reaction mixture was transferred to a separatory funnel and the layers were separated. The aqueous layer was extracted with EtOAc and the organic extracts were combined, washed with brine, dried over $MgSO_4$, filtered, and concentrated to give an off white solid. The solid was triturated with hexanes followed by dichloromethane. The product was filtered, washed with methanol, and dried to give 0.174 g (72%) of compound 181 as a white powder. $^1$H NMR (400 MHz, DMSO-$d_6$): δ 0.86 (s, 12 H), 1.23 (s, 2 H), 1.86 (s, 2 H), 1.89 (s, 2 H), 2.94 (s, 3 H), 6.64 (d, J=8.6 Hz, 2 H), 6.90 (d, J=8.5 Hz, 2 H), 7.06 (s, 2 H), 7.07 (s, 2 H), 9.25 (s, 1 H), 9.64 (s, 1 H). HRMS (ESI) calcd for $C_{24}H_{30}NO_3S$: 412.1946 (M−H)$^-$. Found: 412.1942.

Example 66 (184)

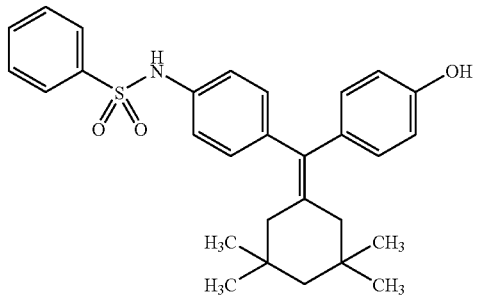

Step 1: N-[4-(4-Methoxy-benzoyl)-phenyl]-benzenesulfonamide (182)

Benzenesulfonyl chloride (0.26 mL, 2.03 mmol) was slowly added to an ice-cooled solution of (4-amino-phenyl)-(4-methoxy-phenyl)-methanone (178) (0.42 g, 1.85 mmol) and pyridine (0.16 mL, 2.03 mmol) in dry dichloromethane (5 mL). The reaction mixture was stirred at room temperature for 20 h then partitioned between EtOAc and water. The layers were separated and the aqueous layer was extracted with EtOAc. The organic extracts were combined, washed with brine, dried over $Na_2SO_4$, filtered, and concentrated to give a solid. The solid was recrystallized from hot dichloromethane and methanol to give 0.451 g (66%) of the title compound 182. $^1$H NMR (400 MHz, DMSO-$d_6$): δ 3.82 (s, 3 H), 7.03 (d, J=8.8 Hz, 2 H), 7.22 (d, J=8.6 Hz, 2 H), 7.57-7.65 (m, 7 H), 7.84 (d, J=7.3 Hz, 2 H), 10.87 (s, 1 H).

Step 2: N-{4-[(4-Methoxy-phenyl)-(3,3,5,5-tetramethyl-cyclohexylidene)-methyl]-phenyl}-benzenesulfonamide (183)

Titanium tetrachloride (0.50 mL, 4.53 mmol) was slowly added to a slurry of zinc powder (0.61 g, 9.31 mmol) in dry tetrahydrofuran (10 mL). The reaction mixture was heated at reflux for 2.5 h. A solution of 3,3,5,5-tetramethyl-cyclohexanone (0.64 mL, 3.67 mmol) and N-[4-(4-methoxy-benzoyl)-phenyl]-benzenesulfonamide (182) (0.45 g, 1.22 mmol) in dry tetrahydrofuran (10 mL) was added to the reaction mixture and heated at reflux for another 2 h. The reaction mixture was cooled to room temperature and diluted with water (10 mL) followed by 10% $K_2CO_3$ (10 mL). The reaction mixture was filtered through a pad of Celite and the pad washed with EtOAc. The filtrate was transferred to a separatory funnel and the layers were separated. The aqueous layer was extracted with EtOAc and the combined organic layers were washed with brine, dried over $Na_2SO_4$, filtered, and concentrated. The crude material was purified by flash chromatography on silica gel with a hexanes:EtOAc gradient (100:0 to 55:45) to give 0.48 g (80%) of compound 183 as a white powder. $^1$H NMR (400 MHz, DMSO-$d_6$): δ 0.81 (s, 6 H), 0.84 (s, 6 H), 1.21 (s, 2 H), 1.75, (s, 2 H), 1.85 (s, 2 H), 3.68 (s, 3 H), 6.79 (d, J=8.6 Hz, 2 H), 6.95-6.98 (m, 6 H), 7.47-7.50 (m, 2 H), 7.55-7.58 (m, 1 H), 7.69 (d, J=7.3 Hz, 2 H), 10.17 (s, 1 H).

Step 3: N-{4-[(4-Hydroxy-phenyl)-(3,3,5,5-tetramethyl-cyclohexylidene)-methyl]-phenyl}-benzenesulfonamide (184)

To a solution of N-{4-[(4-methoxy-phenyl)-(3,3,5,5-tetramethyl-cyclohexylidene)-methyl]-phenyl}-benzenesulfonamide (183) (0.24 g, 0.490 mmol) in dry dichloromethane (17 mL) was slowly added $BBr_3$ (1 N in dichloromethane) (1.47 mL, 1.47 mmol) at −5 to 0° C. The reaction mixture was stirred under nitrogen at −5 to 0° C. over 3 h. The reaction mixture was poured onto ice and stirred for several minutes. The quenched reaction mixture was transferred to a separatory funnel and the layers were separated. The aqueous layer was extracted with EtOAc and the organic layers were combined, washed with brine, dried over $MgSO_4$, filtered, and concentrated to give an oil. The crude oil was purified by reverse phase preparative HPLC using a C-18 column and a $CH_3CN$:$H_2O$ gradient (75:25 to 100:0) with 0.05% TFA as a modifier to give 0.087 g (37%) of the title compound 184 as an off white powder. $^1$H NMR (400 MHz, DMSO-$d_6$): δ 0.80 (s, 6 H), 0.84 (s, 6 H), 1.20 (s, 2 H), 1.73 (s, 2 H), 1.85 (s, 2 H), 6.61 (d, J=8.6 Hz, 2 H), 6.84 (d, J=8.4 Hz, 2 H), 6.94 (s, 4 H), 7.48-7.50 (m, 2 H), 7.54-7.58 (m, 1 H), 7.68-7.70 (m, 2 H), 9.23 (s, 1 H), 10.16 (s, 1 H). HRMS (ESI) Calcd for $C_{29}H_{32N}O_3S$: 474.2103 (M−H)$^-$. Found: 474.2098.

Example 67 (188)

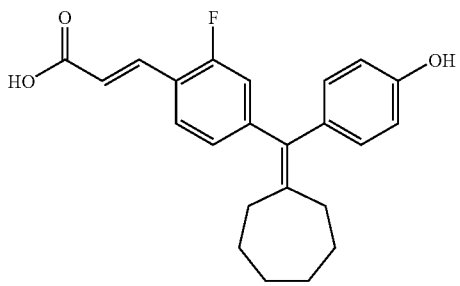

Step 1: (4-Bromo-3-fluorophenyl)[4-(methyloxy)phenyl]methanone (185)

To a stirred solution of 4-bromo-3-fluorobenzoyl chloride (3.00 g, 12.6 mmol) and anisole (1.65 mL, 1.65 g, 15.2 mmol, 1.20 eq) in DCM (30 mL) at −5° C. was added, portion-wise, over 5 minutes, $AlCl_3$ (2.54 g, 19.0 mmol, 1.50 eq) as a powder. The reaction was stirred at −5° C. for 2 h. The reaction was poured onto a mixture of 1 N HCl (100 mL) and ice (200 g) and stirred for 1 h. The DCM layer washed with saturated aq. $NaHCO_3$ (100 mL) and brine (100 mL) then dried ($MgSO_4$) and concentrated. The resulting white solid was triturated with ~100 mL hexanes, filtered and air-dried overnight to afford 3.26 g (83%) of compound 185. $^1$H NMR (400 MHz, DMSO-$d_6$): δ 3.87 (s, 3 H), 7.11 (d, J=8.9 Hz, 2 H), 7.45 (d, J=8.9 Hz, 1H), 7.64 (d, J=8.9 Hz, 1 H), 7.78 (d, J=8.9 Hz, 2H), 7.91 (t, J=7.1 Hz, 1H).

Step 2: (4-Bromo-3-fluorophenyl)(4-hydroxyphenyl)methanone (186)

To a stirred solution of (4-bromo-3-fluorophenyl)[4-(methyloxy)phenyl]methanone (185) (3.20 g, 10.4 mmol) in benzene (80 mL) was slowly added $AlCl_3$ (5.91 g, 44.2 moL., 4.3 eq) via a powder addition funnel under a nitrogen atmosphere at room temperature. The stirred reaction mixture was heated at reflux for 3 h under a nitrogen atmosphere. The reaction mixture was allowed to cool to room temperature and then poured onto a mixture of 1 N HCl (150 mL) and ice (300 g).

The quenched reaction mixture was transferred to a separatory funnel and EtOAc (200 mL) added. The organic phase was separated and the aqueous phase was extracted with EtOAc. The organic phase washed with brine (200 mL), dried over MgSO$_4$, filtered, and the filtrate was concentrated in vacuo to give 3.44 g of a brown solid. Crystallization from toluene yielded 2.68 g (88%) of the title compound 186 as a brown crystalline solid. $^1$H NMR (400 MHz, DMSO-d$_6$): δ 6.91 (d, J=8.7 Hz, 2 H), 7.43 (d, J=8.2 Hz, 1 H), 7.61 (d, J=8.2 Hz, 1 H), 7.69 (d, J=8.7 Hz, 2 H), 7.89 (t, J=7.1 Hz, 1H), 10.54 (s, 1 H).

Step 3: 4-[(4-Bromo-3-fluorophenyl)(cycloheptylidene)methyl]phenol (187)

To a stirred suspension of zinc powder (0.90 g, 13.8 mmoL) in anhydrous THF (20 mL) was slowly added TiCl$_4$ (0.75 mL, 1.3 g, 6.8 mmoL) via syringe at RT under a nitrogen atmosphere. (Note: significant fuming occurred upon addition of TiCl$_4$.) The reaction mixture was heated at reflux with stirring under nitrogen for 2.25 h. A solution of (4-bromo-3-fluorophenyl)(4-hydroxyphenyl)methanone (186) (0.50 g, 1.7 mmoL) and cycloheptanone (0.6 mL, 0.57 g, 5.09 mmoL) in THF (10 mL) was added to the reaction mixture via syringe. The reaction mixture was heated at reflux for 2 h. The oil bath was removed and the reaction mixture was allowed to cool at RT. To the reaction mixture was added H$_2$O (10 mL) followed by 10% K$_2$CO$_3$ (10 mL). The quenched reaction mixture was filtered through a pad of Celite with the aid of EtOAc and H$_2$O. The pad washed with EtOAc and the filtrate was transferred to a separatory funnel. The layers were separated and the organic phase was allowed to stand at RT over the weekend. The organic phase was dried over MgSO$_4$, filtered, and the filtrate was concentrated in vacuo to give the crude product. The crude product was purified by flash chromatography on silica gel with a hexanes:EtOAc gradient (100:0 to 50:50) to give 0.48 g (75%) of compound 187 as an off-white solid. $^1$H NMR (400 MHz, DMSO-d$_6$): δ 1.50 (m, 8 H), 2.20 (m, 4 H), 6.67 (d, J=8.4 Hz, 2 H), 6.88 (dd, J=1.9 Hz, 8.3 Hz, 1 H), 6.92 (d, J=8.4 Hz, 2 H), 7.08 (dd, J=1.8 Hz, 10.0 Hz, 1 H), 7.59 (t, J=7.9 Hz, 1 H), 9.33 (s, 1 H). LRMS (ESI): m/z 373 (M−H)$^−$.

Step 4: (2E)-3-{4-[Cycloheptylidene(4-hydroxyphenyl)methyl]-2-fluorophenyl}-2-propenoic acid (188)

To a round-bottomed flask were added 4-[(4-bromo-3-fluorophenyl)(cycloheptylidene)methyl]phenol (187) (0.21 g, 0.56 mmoL), tert-butylacrylate (0.25 mL, 0.22 g, 1.7 mmoL), palladium(II)acetate (0.023 g, 0.10 mmoL), triethylamine (0.22 mL, 0.16 g, 1.6 mmoL), P(o-tolyl)$_3$ (0.071 g, 0.23 mmol) and anhydrous CH$_3$CN (10 mL). The stirred reaction mixture was heated at 75° C. under a nitrogen atmosphere for 15 h. The oil bath was removed and the reaction mixture was allowed to cool at RT. Thin layer chromatography (hexanes:EtOAc (9:1)) indicated that only starting material was present. The reaction mixture was concentrated in vacuo to give an orange oil. To the oil were added tert-butylacrylate (0.82 mL, 0.72 g, 5.6 mmoL), triethylamine (0.40 mL, 0.29 g, 2.87 mmoL), dichlorobis(triphenylphosphine)palladium(II) (0.091 g, 0.13 mmoL), and anhydrous DMF (5 mL). The stirred reaction mixture was heated overnight at 110° C. under a nitrogen atmosphere. The oil bath was removed and the dark brown reaction mixture was allowed to cool at RT. The reaction mixture was partitioned between EtOAc and H$_2$O. The layers were separated and the organic phase was dried over MgSO$_4$, filtered and the filtrate was concentrated in vacuo to give the crude acrylate ester. The acrylate ester intermediate was partially purified by flash chromatography on silica gel with a hexanes:EtOAc gradient (100:0 to 50:50) to give 0.171 g of impure 1,1-dimethylethyl (2E)-3-{4-[cycloheptylidene(4-hydroxyphenyl)methyl]-2-fluorophenyl}-2-propenoate. To a stirred solution of the impure tert-butylacrylate ester (0.17 g) in CH$_2$Cl$_2$ (4 mL) was added trifluoroacetic acid (2 mL) at RT. The reaction mixture was stirred at RT under a nitrogen atmosphere for 2.75 h. The reaction mixture was concentrated in vacuo to give the crude acrylic acid. The crude product was purified by reverse phase preparative HPLC using a C-18 column and a CH$_3$CN:H$_2$O gradient (75:25 to 100:0) with 0.05% TFA as a modifier to give 0.080 g (39% over two steps) of compound 188 as a pale yellow solid. $^1$H NMR (400 MHz, DMSO-d$_6$): δ 1.50 (m, 8 H), 2.21 (m, 4 H), 6.51 (d, J=16.1 Hz, 1 H), 6.67 (d, J=8.4 Hz, 2 H), 6.92 (d, J=8.2 Hz, 2H), 6.97 (m, 2 H), 7.58 (d, J=16.1 Hz, 1 H), 7.72 (t, J=8.2 Hz, 1 H), 9.32 (s, 1 H), 12.50 (br s, 1 H). HRMS (ESI) Calcd for C$_{23}$H$_{22}$O$_3$F: 365.1553 (M−H)$^−$. Found: 365.1570.

Example 68 (191)

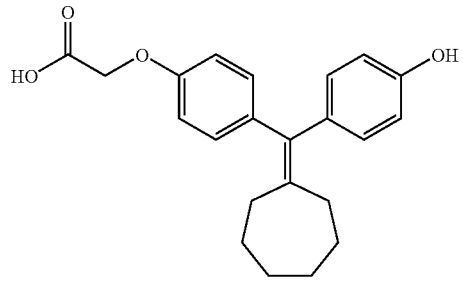

Step 1: 4,4'-(Cycloheptylidenemethanediyl)diphenol (189)

To a stirred suspension of zinc powder (15.0 g, 0.23 mol) in THF (300 mL) was slowly added TiCl$_4$ (12.5 mL, 0.115 mol) via a syringe at room temperature under a nitrogen atmosphere. The reaction mixture was heated at reflux for 1 h. A solution of bis(4-hydroxyphenyl)methanone (4.9 g, 0.023 mol) and cycloheptanone (7.74 g, 0.07 mol) in THF (100 mL) was added to the reaction mixture. The reaction mixture was heated at reflux with stirring under a nitrogen atmosphere for an additional 2 h. The reaction mixture was allowed to cool to room temperature. The reaction mixture was poured into a 10% aqueous K$_2$CO$_3$ (1 L). The reaction mixture was filtered through a pad of Celite and the pad washed with EtOAc. The filtrate was transferred to a separatory funnel and the layers were separated. The aqueous phase was further extracted with EtOAc (4×250 mL). The combined organic phase washed with brine (2×100 mL), dried (Na$_2$SO$_4$), filtered, and then concentrated under reduced pressure to give the crude product as a gold-yellow oil. The crude product was purified by flash chromatography on silica gel with hexanes:EtOAc (100:0 to 50:50) as an eluent to afford 6.75 g (99%) of the title compound 189 as a white solid. $^1$H NMR (DMSO-d$_6$): δ 9.21 (s, 2H), 6.84 (d, J=6.3 Hz, 4H), 6.63 (d, J=6.3 Hz, 4H), 2.19 (br s, 4H), 1.48 (br s, 8H). LCMS (ESI): m/z 294 (M+H)$^+$.

Step 2: Ethyl({4-[cycloheptylidene(4-hydroxyphenyl)methyl]phenyl}oxy)acetate (190)

To a stirred suspension of 4,4'-(cycloheptylidenemethanediyl)diphenol (189) (1.176 g, 4 mmol), K$_2$CO$_3$ (0.692 g, 5 mmol), and acetone (100 mL) was added bromo-EtOAc (0.664 mL, 6 mmol) under a nitrogen atmosphere at room temperature. The reaction mixture was refluxed for 3 h then cooled to RT and filtered. The filtrate was concentrated under reduced pressure and the crude product purified by flash chromatography on silica gel with hexanes and EtOAc (19:1 to 4:1) to afford 0.440 g (29%) of the title compound 190 as a white solid and 0.408 g (22%) of dialkylated product as a white solid. Around 0.40 g of starting material 189 was also recovered. Data for ethyl({4-[cycloheptylidene(4-hydroxyphenyl)methyl]phenyl}oxy)acetate: $^1$H NMR (300 MHz, CDCl$_3$): δ 7.28 (s, 1H), 7.07 (d, J=8.7 Hz, 2H), 7.02 (d, J=8.7 Hz, 2H), 6.82 (d, J=8.7 Hz, 2H), 6.75 (d, J=8.4 Hz, 2H), 4.70 (s, 1H), 4.60 (s, 2H), 4.28 (q, J=6.9 Hz, 2H), 2.31 (br s, 4H), 1.58 (br s, 8H), 1.31 (t, J=7.2 Hz, 3H). LCMS (ESI): m/z 403 (M+Na)$^+$.

Step 3: ({4-[Cycloheptylidene(4-hydroxyphenyl)methyl]phenyl}oxy)acetic acid (191)

Ethyl({4-[cycloheptylidene(4-hydroxyphenyl)methyl]phenyl}oxy)acetate (190) (0.20 g, 0.53 mmol) was dissolved in THF and EtOH (1:1, 6 mL). To the above solution was added 1 N NaOH (2.5 mL) at room temperature. The reaction was heated at 70° C. with stirring for 0.5 h and then cooled at RT. Reaction mixture was acidified with 20% aqueous HCl, and then extracted with EtOAc. The organic layer washed with brine, dried (Na$_2$SO$_4$), and concentrated under reduced pressure to afford the crude product. The product was purified by flash column chromatography with chloroform and methanol (9:1 to 4:1) as an eluent to give 0.182 g of compound 191 as an off-white solid. mp 170-171° C. $^1$H NMR (300 MHz, DMSO-d$_6$): δ 12.92 (s, 1H), 9.25 (s, 1H), 7.1d, J=8.4 Hz, 2H), 6.89 (d, J=8.4 Hz, 2H), 6.81 (d, J=8.7 Hz, 2H), 6.66 (d, J=8.4 Hz, 2H), 4.62 (s, 2H), 2.22 (br s, 4H), 1.5 (br s, 8H). LCMS (ESI): m/z 375.08 (M+Na)$^+$. Anal. Calcd for C$_{22}$H$_{24}$O$_4$: C, 74.98; H, 6.86; Found: C, 73.05; H, 6.74.

Example 69 (195)

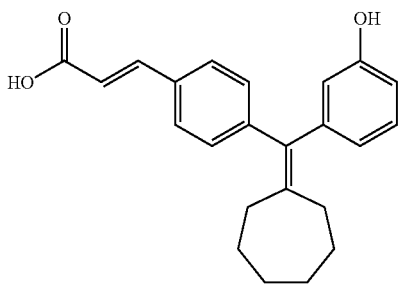

Step 1: {(4-Bromophenyl)[3-(methyloxy)phenyl]methylidene}cycloheptane (192)

The general McMurry coupling procedure, described for 14 was followed. Coupling between (4-bromophenyl)[3-(methyloxy)phenyl]methanone and cycloheptanone afforded 2.1 g (82%) of compound 192 as a white solid. $^1$H NMR (300 MHz, CDCl$_3$): δ 7.41 (d, J=8.4 Hz, 2H), 7.22 (dd, J$_1$=15.6 Hz, J$_2$=7.8 Hz, 1H), 7.06 (d, J=8.4 Hz, 2H), 6.77-6.71 (m, 4H).

Step 2: 3-[(4-Bromophenyl)(cycloheptylidene)methyl]phenol (193)

To a cold (5° C.) solution of {(4-bromophenyl)[3-(methyloxy)phenyl]methylidene}cycloheptane (192) (0.557 g, 1.5 mmol) in CH$_2$Cl$_2$ (50 mL) was added BBr$_3$ (0.425 mL, 4.5 mmol) slowly. The reaction mixture was stirred between 5° C. and 20° C. for 4 h and then carefully poured into water (100 mL). The layers were separated and the aqueous layer was further extracted with CH$_2$Cl$_2$ (2×50 mL) and the combined organic layer dried (Na$_2$SO$_4$). Concentration and purification by flash column chromatography gave 0.44 g (82%) of compound 193 as an off-white solid. $^1$H NMR (300 MHz, CDCl$_3$): δ 7.41 (d, J=8.4 Hz, 2H), 7.17 (dd, J$_1$=7.8 Hz, J$_2$=7.8 Hz, 1H), 7.05 (d, J=8.4 Hz, 2H), 6.74 (br d, J=7.5 Hz, 1H), 6.69 and 6.67 (dd, J$_1$=2.4 Hz, J$_2$=8.1 Hz, 1H), 6.62 (app t, J=1.8 Hz), 4.71 (s, 1H), 2.32 (br, m, 4H), 1.59 (br s, 8H).

Step 3: 1,1-dimethylethyl(2E)-3-{4-[cycloheptylidene(3-hydroxyphenyl)methyl]phenyl}-2-propenoate (194)

Heck reaction with {(4-bromophenyl)[3-(methyloxy)phenyl]methylidene}cycloheptane (193) (0.420 g, 1.47 mmol) and ethyl acrylate (as described in Example 6, Step 2) followed by standard work-up purification gave 0.26 g (47%) of compound as 194 an off-white foam. $^1$H NMR (300 MHz, CDCl$_3$): δ 7.56 (d, J=15.9 Hz, 1H), 7.42 (d, J=7.8 Hz, 1H), 7.19-7.15 (m, 3H), 6.76 (br d, J=7.5 Hz, 1H), 6.7 and 6.68 (br dd, J$_1$=2.4 Hz, J$_2$=8.1 Hz, 1H), 6.4 (s, 1H), 6.33 (d, J=15.9 Hz, 1H), 4.86 (s, 1H), 2.33 (br s, 4H), 1.60 (s, 8H), 1.55 (s, 9H). LCMS (ESI): m/z 405 (M−H)$^-$.

Step 4: (2E)-3-{4-[cycloheptylidene(3-hydroxyphenyl)methyl]phenyl}-2-propenoic acid (195)

To a cold (5° C.) solution of 1,1-dimethylethyl(2E)-3-{4-[cycloheptylidene(3-hydroxyphenyl)methyl]phenyl}-2-propenoate (194) (0.200 g, 0.49 mmol) in CH$_2$Cl$_2$ (8 mL) was added TFA (2 mL). The resultant mixture was stirred for 3 h at RT. The reaction mixture was concentrated under reduced pressure and the crude product. purified by silica gel chromatography using n-hexanes:EtOAc (4:1 to 3:2) as an eluent to afford 0.155 g (90%) of compound 195 as an off-white foam. $^1$H NMR (300 MHz, CD$_3$OD): δ 7.65 (d, J=15.9 Hz, 1H), 7.51 (d, J=8.1 Hz, 2H), 7.21 (d, J=7.8 Hz, 2H), 7.10 (app t, J=7.5 Hz, 1H), 6.32 (br d, J=8.7 Hz, 3H), 6.45 (d, J=15.9 Hz, 1H). 2.33 (br s, 4H), 1.61 (br s, 8H). LCMS (ESI): m/z 347 (M−H)$^-$.

Example 70 (199)

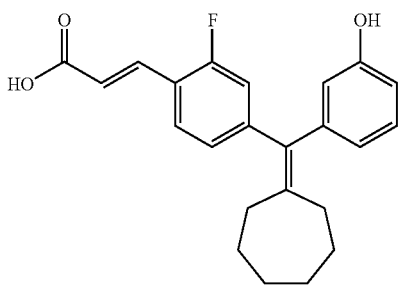

Step 1: (4-Bromo-3-fluorophenyl)(3-hydroxyphenyl)methanone (196)

The demethylation procedure described for 2 was employed. To a stirred solution of (4-bromo-3-fluorophenyl)[3-(methyloxy)phenyl]methanone (1.0 g, 2.5 mol) in toluene (50 mL) was slowly added $AlCl_3$ (1.3 g, 9.7 mol) via a powder addition funnel under a nitrogen atmosphere at room temperature. The stirred reaction mixture was heated at reflux for 3 h. The reaction mixture was allowed to cool to room temperature and then poured into 10% aqueous HCl (200 mL). Standard work-up yielded 0.935 g (100%) of the title compound 196 as a tan solid. $^1$H NMR (300 MHz, $CDCl_3$): δ 7.71 and 7.68 (dd, $J_1$=6.6 Hz, $J_2$=6.6 Hz, 1 H), 7.60 and 7.57 (dd, $J_1$=8.7 Hz, $J_2$=1.5 Hz, 1H), 7.50 and 7.47 (dd, $J_1$=8.1 Hz, $J_2$=1.2 Hz, 1H), 7.41-7.31 (m 3H), 7.15 and 7.13 (dd, $J_1$=7.8 Hz, $J_2$=1.8 Hz, 1H), 5.93 (s, 1H).

Step 2: 3-[(4-Bromo-3-fluorophenyl)(cycloheptylidene)methyl]phenol (197)

The general McMurry protocol, described for 14 was followed. Reaction of (4-bromo-3-fluorophenyl)(3-hydroxyphenyl)methanone (196 (0.860 g, 2.3 mmol) and cycloheptanone (0.814 mL, 6.87 mmol) afforded 0.80 g, (93%) of the title compound 197 as a white solid. $^1$H NMR (300 MHz, $CDCl_3$): δ 7.89 (app t, J=7.5 Hz, 1H), 7.17 (app t, J=7.8 Hz, 1H), 6.96 and 6.92 (dd, $J_1$=9.6 Hz, $J_2$=1.8 Hz, 1H), 6.86 and 6.84 (dd, $J_1$=8.1 Hz, $J_2$=1.8 Hz, 1H), 6.73 (app br d, J=8.1 Hz, 1H), 6.70 and 6.68 (dd, $J_1$=8.4 Hz, $J_2$=2.4 Hz, 1H), 6.61 (app t, J=1.8 Hz, 1H), 4.86 (s, 1H), 2.31 (br s, 4H), 1.59 (br s, 8H).

Step 3: 1,1-dimethylethyl(2E)-3-{4-[cycloheptylidene(3-hydroxyphenyl)methyl]-2-fluorophenyl}-2-propenoate (198)

The general Heck protocol, described for 15 was followed. Heck coupling between 3-[(4-bromo-3-fluorophenyl)(cycloheptylidene)methyl]phenol (197) (0.800 g, 2.13 mmol) and ethyl acrylate afforded 0.460 g, (51%) of the title compound 198 as an off-white foam. $^1$H NMR (300 MHz, $CDCl_3$): δ 7.68 (d, J=16.2 Hz, 1H), 7.41 (app t, J=8.1 Hz, 1H), 7.18 (app t, J=7.8 Hz, 1H), 6.97 and 6.94 (app br, dd, $J_1$=8.1 Hz, 1H), 6.93 and 6.88 (br dd, $J_1$=11.4 Hz, 1H), 6.73 (br d, J=7.50 Hz, J=7.5 Hz, 1H), 6.72 and 6.69 (app $J_1$=8.1 Hz, $J_2$=2.4 Hz, 1H), 6.70 and 6.68 (dd, $J_1$=8.4 Hz, $J_2$=2.4 Hz, 1H), 6.63 (app t, J=1.8 Hz, 1H), 6.42 (d, J=15.9 Hz, 1H), 4.97 (s, 1H), 2.33 (br s, 4H), 1.61 and 1.59 (br s, 8H), 1.55 (br s, 9H). LCMS (ESI): m/z 421 (M–H)$^-$.

Step 4: (2E)-3-{4-[Cycloheptylidene (3-hydroxyphenyl)methyl]-2-fluorophenyl}-2-propenoic acid (199)

The general hydrolysis procedure, described for 195 was followed. Thus, 1,1-dimethylethyl(2E)-3-{4-[cycloheptylidene(3-hydroxyphenyl)methyl]-2-fluorophenyl}-2-propenoate (198) (0.380 g, 0.9 mmol) in $CH_2Cl_2$ was treated with TFA to afford 0.305 g (92%) of the title compound as an off-white foam. $^1$H NMR (300 MHz, $CD_3OD$): δ 7.76 (d, J=15.9 Hz, 1H), 7.59 (appt, J=7.8 Hz, 1H), 7.18 (app t, J=7.8 Hz, 1H), 7.04 (br d, J=8.1 Hz, 1H), 6.94 (br d, J=11.7 Hz, 1H), 6.67-6.60(m, 3H), 6.56 (d, J=16.2 Hz, 1H), 2.34 (br s, 4H), 1.62 (br s, 8H). LCMS (ESI): m/z 365 (M–H)$^-$. Anal. Calcd for $C_{23}H_{23}FO_3 \cdot 1.5H_2O$, C, 70.38; H, 6.63; F, 4.84; Found: C, 69.96; H, 5.95; F, 4.73.

Example 71 (201)

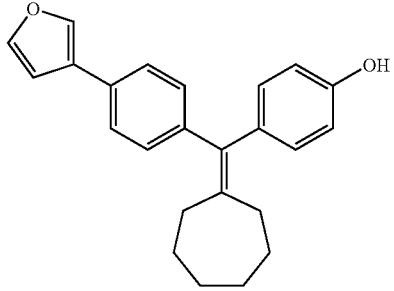

Step 1: 4-[(4-Bromophenyl)(cycloheptylidene)methyl]phenol (200)

The general McMurry coupling protocol, described for 14 was followed. Reaction of (4-bromophenyl)(4-hydroxyphenyl)methanone (2.77 g, 10 mmol), and cycloheptanone (3.6 mL, 30 mmol) afforded 2.795 g (78%) of the title compound 200 as an off-white solid. $^1$H NMR (300 MHz, $CDCl_3$): δ 7.41 (d, J=8.1 Hz, 2H), 7.04 (d, J=6.3 Hz, 2H), 7.01 (d, J=6.3 Hz, 2H), 6.76 (d, J=8.4 Hz, 2H), 4.74 (s, 1H), 2.32 (m, 4H), 1.59 (s, 8H).

Step 2: 4-{cycloheptylidene[4-(3-furanyl)phenyl]methyl}phenol (201)

A round-bottom flash was charged with 4-[(4-bromophenyl)(cycloheptylidene)methyl]phenol (200) (1.0 g, 2.8 mmol), $Pd(PPh_3)_4$, (0.323 g, 0.28 mmol), 3-furanylboronic acid (0.627 g, 5.6 mmol), aqueous 2 M $Na_2CO_3$, (1.2 g, 4.7 mL, 11.2 mmol), and DME (15 mL) under a nitrogen atmosphere. The reaction mixture was refluxed for 5 h. Reaction mixture was cooled at room temperature, diluted with $Et_2O$ (30 ml) and filtered. The filtrate was diluted with EtOAc (100 mL), washed with brine, dried ($Na_2SO_4$) and concentrated under reduced pressure to afford the crude product. The product was purified by silica gel chromatography using n-hexanes:EtOAc (19:1 to 4:1) as an eluent to give 0.887 g (92%) of the title compound 201 as a white solid. $^1$H NMR (300 MHz, $CDCl_3$): δ 7.73 (s, 1H), 7.48 (t, J=1.5 Hz, 1H), 7.42 (d, J=8.1 Hz, 2H), 7.18 (d, J=8.1 Hz, 2H), 7.07 (d, J=8.4 Hz, 2H), 6.77 (d, J=8.4 Hz, 1H), 6.70 (d, J=1.2 Hz, 1H), 2.37 (br s, 4H), 1.62

(br s, 8H). LCMS (ESI): m/z 343 (M–H)⁻. Anal. Calcd for C₂₄H₂₄O₂, C, 83.69; H, 7.02; Found: C, 82.69; H, 7.06.

Example 72 (202)

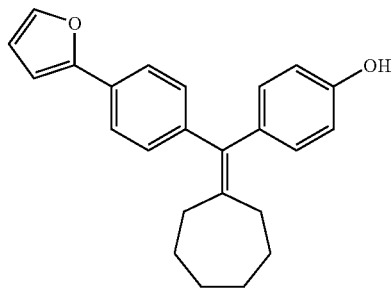

Step 1: 4-{Cycloheptylidene[4-(2-furanyl)phenyl]methyl}phenol (202)

The round-bottom flask was charged with 4-[(4-bromophenyl)(cycloheptylidene)methyl]phenol (9) (0.100 g, 0.28 mmol), PdCl₂(PPh₃)₂, (0.020 g, 0.028 mmol), 2-furanylboronic acid (0.063 g, 0.56 mmol), aqueous 2 M Na₂CO₃, (0.06 g, 0.56 mmol), and THF/H₂O mixture (4:1, 5 mL) under a nitrogen atmosphere. The reaction mixture was refluxed for 10 h. Reaction mixture was cooled to room temperature, diluted with Et₂O (10 mL) and filtered. The filtrate was diluted with EtOAc (30 mL), washed with brine, dried (Na₂SO₄), and concentrated under reduced pressure to afford the crude product. The product was purified by silica gel chromatography using hexanes:EtOAc (19:1 to 4:1) as an eluent to give 0.0.42 g (44%) of compound 202 as a white solid. ¹H NMR (300 MHz, DMSO-d₆): δ 69.28 (s, 1H), 7.70 (br s, 1H), 7.59 (d, J=6.0 Hz, 2H), 7.12 (d, J=6.0 Hz, 2H), 6.91 (d, J=6.3 Hz, 2H), 6.86 (d, J=2.4 Hz, 1H), 6.66 (d, J=6.3 Hz, 1H), 6.55 (br s, 1H), 2.37 (br s, 4H), 1.62 (br s, 8H). LCMS (ESI): m/z 343 (M–H)⁻.

Example 73 (203)

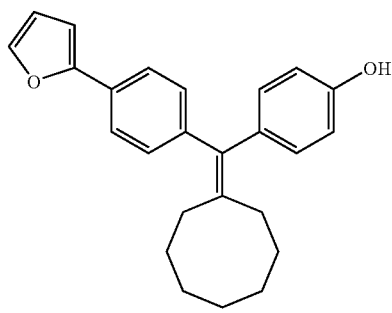

Step 1: 4-{cyclooctylidene[4-(2-furanyl)phenyl]methyl}phenol (203)

The procedure described for 202 was employed. A round-bottomed flask was charged with 4-[(4-bromophenyl)(cyclooctylidene)methyl]phenol (49) (0.150 g, 0.404 mmol), PdCl₂(PPh₃)₂, (0.028 g, 0.40 mmol), 2-furanylboronic acid (0.090 g, 0.80 mmol), Na₂CO₃ (0.086 g, 0.808 mmol), and THF/H₂O (4:1, 5 mL). The reaction mixture was refluxed for 10 h. Standard workup and purification by flash silica gel chromatography provided 110 mg (76%) of the title compound 203 as a white solid. ¹H NMR (300 MHz, DMSO-d₆): δ 9.27 (s, 1H), 7.70 (d, J=0.9 Hz, 1H), 7.59 (d, J'6.0 Hz, 2H), 7.15 (d, J=6.3 Hz, 2H), 6.94 (d, J=6.6 Hz, 2H), 6.86 (d, J=2.4 Hz, 1H), 6.67 (d, J=6.3 Hz, 1H), 6.55 and 6.54 (dd, J₁=2.4 Hz, J₂=1.2 Hz, 1H), 2.48-2.47 (m, 4H), 1.60 (br s, 2H), 1.50-1.45 (m, 8H). 2.37 (br s, 4H), 1.62 (br s, 8H). LCMS (ESI): m/z 357 (M–H)⁻.

Example 74 (204)

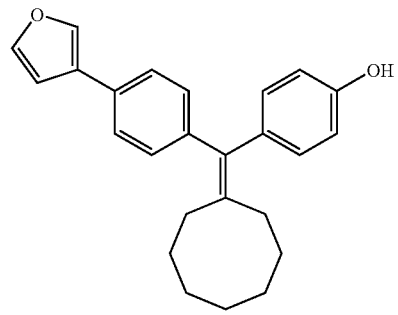

Step 1: 4-{Cyclooctylidene[4-(3-furanyl)phenyl]methyl}phenol (204)

The procedure described for 202 was used. A round-bottomed flask was charged with 4-[(4-bromophenyl)(cyclooctylidene)methyl]phenol (49) (0.150 g, 0.404 mmol), PdCl₂(PPh₃)₂, (0.028 g, 0.40 mmol), 3-furanylboronic acid (0.090 g, 0.80 mmol), Na₂CO₃ (0.086 g, 0.808 mmol), and THF/H₂O (4:1, 5 mL). The reaction mixture was refluxed for 10 h. Upon usual work-up and purification by flash silica gel chromatography provided 0.110 g (76%) of compound 204 as a white solid. ¹H NMR (300 MHz, DMSO-d₆): δ 9.29 (s, 1H), 8.10 (s, 1H), 7.70 (s, 1H), 7.50 (d, J=6.00 Hz, 2H), 7.11 (d, J=6.00 Hz, 2H), 6.94 (d, J=6.3 Hz, 2H), 6.89 (s, 1H), 6.67 (d, J=6.3 Hz, 2H), 2.19 (br s, 4H), 1.60 (br s, 2H), 1.50-1.45 (m, 8H). LCMS (ESI): m/z 359 (M+H)⁺.

Example 75 (205)

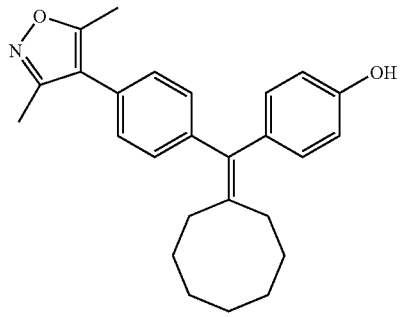

Step 1: 4-{cyclooctylidene[4-(3,5-dimethyl-4-isoxazolyl)phenyl]methyl}phenol (205)

The procedure described for 202 was used. A round-bottomed flask was charged with 4-[(4-bromophenyl)(cyclooctylidene)methyl]phenol (49) (0.150 g, 0.404 mmol), PdCl₂

(PPh₃)₂, (0.028 g, 0.40 mmol), (3,5-dimethyl-4-isoxazolyl) boronic acid (0.113 g, 0.80 mmol), Na₂CO₃ (0.086 g, 0.808 mmol), and THF/H₂O (4:1, 5 mL). The reaction mixture was refluxed for 10 h. Standard workup and purification by flash silica gel chromatography provided 0.120 g (77%) of the title compound 205 as an off-white solid. ¹H NMR (300 MHz, CDCl₃): δ 9.27 (s, 1H), 7.30 (d, J=6.00 Hz, 2H), 7.21 (d, J=6.30 Hz, 2H), 6.96 (d, J=6.0 Hz, 2H), 6.69 (d, J=6.0 Hz, 2H), 2.37 (br s, 3H), 2.19 (s, 7H), 2.60 (br s, 2H), 1.50 (br s, 8H). LCMS (ESI): m/z 386 (M−H)⁻.

Example 76 (206)

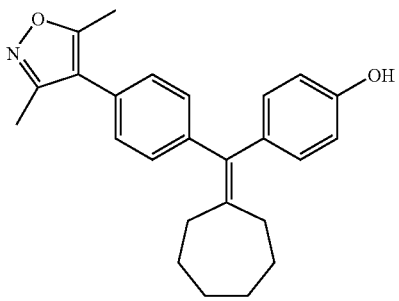

Step 1: 4-{cycloheptylidene[4-(3,5-dimethyl-4-isoxazolyl)phenyl]methyl}phenol (206)

The procedure described for 202 was followed. A round-bottomed flask was charged with 4-[(4-bromophenyl)(cycloheptylidene)methyl]phenol (9) (0.100 g, 0.28 mmol), PdCl₂(PPh₃)₂, (0.020 g, 0.028 mmol), (3,5-dimethyl-4-isoxazolyl) boronic acid (0.079 g, 0.56 mmol), Na₂CO₃ (0.060 g, 0.56 mmol), and THF/H₂O (5 mL, 4:1). The reaction mixture was refluxed for 10 h. Standard workup and purification by flash silica gel chromatography provided 0.120 g (78%) of the title compound 206 as an off-white solid. ¹H NMR (300 MHz, CDCl₃): δ 9.28 (s, 1H), 7.28 (d, J=6.00 Hz, 2H), 7.18 (d, J=6.0 Hz, 2H), 6.94 (d, J=6.6 Hz, 2H), 6.67 (d, J=6.3 Hz, 2H), 2.37 (s, 3H), 2.23-2.22 (br, m, s, 4H), 1.52 (br s, 8H). LCMS (ESI): m/z 372 (M−H)⁻.

Example 77 (208)

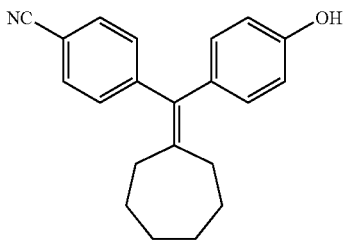

Step 1: 4-{Cycloheptylidene[4-(methyloxy)phenyl] methyl}benzonitrile (207)

The general McMurry protocol, described for 14 was employed. The coupling was conducted between cycloheptanone (1.5 mL, 12.64 mmol), and 4-{[4-(methyloxy)phenyl] carbonyl}benzonitrile (1.0 g, 4.2 mmol) to afford 0.750 g (56%) of the title compound 207 as a white solid. IR (film): 2920, 2225, 1603, 1508, 1242, 825, cm¹. ¹H NMR (300 MHz, CDCl₃): δ 7.58 (d, J=8.1 Hz, 2H), 7.25 (d, J=8.4 Hz, 2H), 7.08 (d, J=8.7 Hz, 2H), 6.84 (d, J=8.7 Hz, 2H), 3.80 (s, 3H), 2.36 (br s, 2H), 2.29 (br s, 2H), 1.60 (s, 8H).

Step 2: 4-[cycloheptylidene(4-hydroxyphenyl)methyl]benzonitrile (208)

To a cold (5° C.) solution of 4-{cycloheptylidene[4-(methyloxy)phenyl]methyl}benzonitrile (207) (0.300 g, 0.94 mmol) in CH₂Cl₂ (20 mL) was added BBr₃ (0.358 mL, 3.79 mL). The resultant reaction mixture was stirred between 5° C. and 20° C. for 3 h. Reaction mixture was poured into water (125 mL) and then extracted with CH₂Cl₂ (3×50 mL). The combined organic layer was dried and concentrated under reduced pressure to afford the crude product. The product was purified by flash column chromatography to give 0.245 g (86%) of compound 208 as a white solid. mp 110-111° C. IR (film): 3391, 2921, 2852, 2229, 1609, 1509, 1213, 829, 731 cm⁻¹. ¹H NMR (300 MHz, CDCl₃): δ 7.57 (d, J=8.4 Hz, 2H), 7.27 (d, J=8.4 Hz, 2H), 7.00 (d, J=8.7 Hz, 2H), 6.79 (d, J=8.4 Hz, 2H), 4.97 (br s, 1H), 2.35 (br s, 2H), 2.29 (br s, 2H), 1.60 (br s, 8H). LCMS (ESI): m/z 302 (M−H)⁻. Anal. Calcd for C₂₁H₂₁NO, C, 83.13; H, 6.98; N, 4.62; Found: C, 83.13; H, 6.96; N, 4.62.

Example 78 (210)

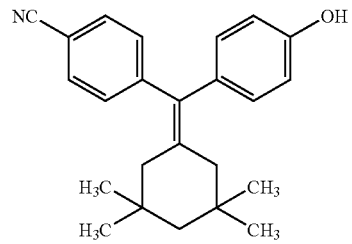

Step 1: 4-[[4-(Methyloxy)phenyl](3,3,5,5-tetramethylcyclohexylidene)methyl]benzonitrile (209)

The general McMurry protocol, described for 14 was used. The reaction was conducted between 4-{[4-(methyloxy)phenyl]carbonyl}benzonitrile (1.00 g, 4.21 mmol) and 3,3,5,5-tetramethylcyclohexanone (1.95 g, 12.64 mmol) to afford 0.760 g (50%) of the title compound 209 as a white solid. ¹H NMR (300 MHz, CDCl₃): δ 7.58 (d, J=8.4 Hz, 2H), 7.29 (d, J=8.1 Hz, 2H), 7.07 (d, J=8.7 Hz, 2H), 6.85 (d, J=8.7 Hz, 2H), 3.81 (s, 3H), 2.01 (s, 2H), 1.95 (s, 2H), 1.32 (s, 2H), 0.96 (s, 6H), 0.95 (s, 6H).

Step 2: 4-[(4-Hydroxyphenyl)(3,3,5,5-tetramethylcyclohexylidene)methyl]benzonitrile (210)

The demethylation protocol described for 208 was used. 4-[[4-(methyloxy)phenyl](3,3,5,5-tetramethylcyclohexylidene)methyl]benzonitrile (209) (0.700 g, 1.95 mmol) was treated with BBr₃ to afford 0.350 g (52%) of compound 210 as a white solid. ¹H NMR (300 MHz, CDCl₃): δ 7.58 (d, J=8.1 Hz, 2H), 7.29 (d, J=8.1 Hz, 2H), 7.02.(d, J=8.4 Hz, 2H), 6.79

(d, J=8.7 Hz, 2H), 2.01 (s, 2H), 1.94 (s, 2H), 1.33 (s, 2H), 0.96 (s, 6H), 0.95 (s, 6H). LCMS (ESI): m/z 344 (M−H)⁻.

Example 79 (213)

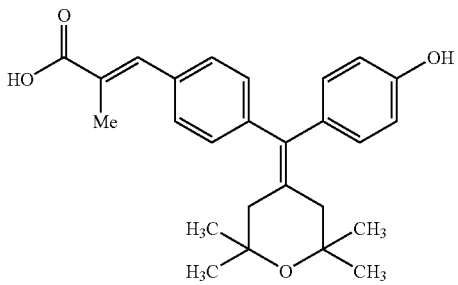

Step 1: 4-[(4-Bromophenyl)(2,2,6,6-tetramethyltetrahydro-4H-pyran-4-ylidene)methyl]phenol (211)

The general McMurry procedure, described for 14 was employed using (4-bromophenyl)(4-hydroxyphenyl)methanone (2) (2.10 g, 7.58 mmol), and 2,2,6,6-tetramethyltetrahydro-4H-pyran-4-one (1.40 g, 8.96 g). Standard work-up followed by purification gave 2.64 g (87%) of the title compound 211 as an off-white solid. ¹H NMR (300 MHz, DMSO-d₆): δ 9.37 (s, 1H), 7.49 (d, J=8.7 Hz, 2H), 7.10 (d, J=8.4 Hz, 2H), 6.95 (d, J=8.7 Hz, 2H), 6.70 (d, J=8.4 Hz, 2H), 2.16 (s, 2H), 2.10 (s, 2H), 1.13 (s, 6H), 1.12 (s, 6H). LCMS (ESI): m/z 399 and 401 (M−H)⁻.

Step 2: 1,1-Dimethylethyl(2E)-3-{4-[(4-hydroxyphenyl)(2,2,6,6-tetramethyltetrahydro-4H-pyran-4-ylidene)methyl]phenyl}-2-methyl-2-propenoate (212)

The general Heck reaction procedure, described for 15 was followed. 4-[(4-bromophenyl)(2,2,6,6-tetramethyltetrahydro-4H-pyran-4-ylidene)methyl]phenol (211) (0.440 g, 1.096 mmol) was reacted with 1,1-dimethylethyl 2-methyl-2-propenoate in the presence of PdCl₂(PPh₃)₂ to afford the title compound as a mixture of Z and E isomers. The pure E-isomer (212) was isolated by HPLC as a white solid. ¹H NMR (300 MHz, CDCl₃): δ 7.58 (s, 1H), 7.34 (d, J=8.1 Hz, 2H), 7.19 (d, J=8.1 Hz, 2H), 7.05 (d, J=8.4 Hz, 2H), 7.81 (d, J=8.4 Hz, 2H), 5.80 (br s, 1H), 2.30 (d, J=3.0 Hz, 4H), 2.10 (s, 3H), 1.56 (s, 9H), 1.27 (s, 12H). LCMS (ESI): m/z 461 (M−H)⁻.

Step 3: (2E)-3-{4-[(4-Hydroxyphenyl)(2,2,6,6-tetramethyltetrahydro-4H-pyran-4-ylidene)methyl]phenyl}-2-methyl-2-propenoic acid (213)

The general hydrolysis protocol, described for 195 was followed. Thus, 1,1-dimethylethyl(2E)-3-{4-[(4-hydroxyphenyl)(2,2,6,6-tetramethyltetrahydro-4H-pyran-4-ylidene)methyl]phenyl}-2-methyl-2-propenoate (212) (0.190 g, 0.41 mmol) was treated with TFA in CH₂Cl₂ to afford 0.158 g (95%) of the title compound 213 as an off-white solid. ¹H NMR (300 MHz, CD₃OD): δ 7.68 (s, 1H), 7.40 (d, J=7.8 Hz, 2H), 7.23 (d, J=7.8 Hz, 2H), 7.01 (d, J=8.4 Hz, 2H), 6.75 (d, J=8.1 Hz, 2H), 2.83 (d, J=5.7 Hz, 4H), 2.11 (s, 3H), 1.22 (s, 12H). LCMS (ESI): m/z 405 (M−H)⁻. Anal. Calcd for C₂₆H₃₀O₄, C, 76.82; H, 7.44; Found: C, 74.81; H, 7.42.

Example 80 (215)

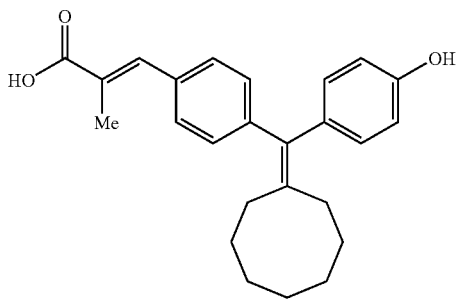

Step 1: (1,1-Dimethylethyl-3-{4-[cyclooctylidene(4-hydroxyphenyl)methyl]phenyl}-2-methyl-2-propenoate (214)

The general Heck Protocol, described for 15 was followed. 4-[(4-bromophenyl) (cyclooctylidene)methyl]phenol (49) (0.371 g, 1 mmol) was treated with 1,1-dimethylethyl 2-methyl-2-propenoate in the presence of PdCl₂(PPh₃)₂ to afford 0.205 g (47%) of 214 as a mixture of E and Z (~65:35) isomers.

Step 2: (2E)-3-{4-[cyclooctylidene(4-hydroxyphenyl)methyl]phenyl}-2-methyl-2-propenoic acid (215)

The general hydrolysis procedure described for 195 was followed. (1,1-dimethylethyl (2E/2Z)-3-{4-[cyclooctylidene (4-hydroxyphenyl)methyl]phenyl}-2-methyl-2-propenoate (214) (0.200 g, 0.46 mmol) was treated with TFA to afford 0.160 g (92%) of the title compound 215 as a mixture of E and Z (~65:35) isomers. The pure E isomer was isolated by HPLC to afford the title compound 214 as a white solid. ¹H NMR (300 MHz, CD₃OD): δ 7.67 (s, 1H), 7.38 (br d, J=6.0 Hz, 2H), 7.22 (br, d, J=6.6 Hz, 2H), 7.00 (br d, J=6.6 Hz, 2H), 6.72 (br d, J=6.3 Hz, 2H), 2.31 (br s, 4H), 2.10 (s, 3H), 1.70 (br s, 2H), 1.58 (br s, 8H). LCMS (ESI): m/z 375 (M−H)⁻.

Example 81 (216)

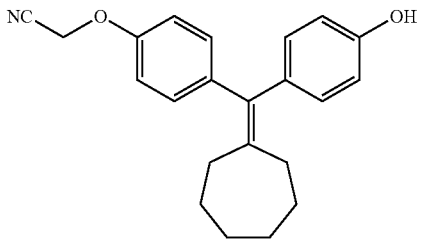

Step 1: ({4-[Cycloheptylidene(4-hydroxyphenyl)methyl]phenyl}oxy)acetonitrile (216)

The O-alkylation procedure described for 190 was followed. To stirred mixture of 4,4'-(cycloheptylidenemethanediyl)diphenol (189) (1.18 g, 4 mmol), K$_2$CO$_3$ (0.691 g, 5 mmol) and acetone (50 mL) was added bromoacetonitrile (0.418 mL, 6.0 mmol). The reaction mixture was refluxed for 3.5 h. Standard work-up and purification by silica gel chromatography afforded 0.175 g (13%) of compound 216 as a white solid and 0.700 g (47%) of the bis-alkylated material 2,2'-[(cycloheptylidenemethanediyl) bis(benzene-4,1-diyloxy)]diacetonitrile as a white solid. IR (film): 3413, 2921, 1605, 1504, 1210, 1170, 828, 729 cm−1. $^1$H NMR (300 MHz, CDCl$_3$): δ 7.14 (d, J=8.4 Hz, 2H), 7.02 (d, J=8.4 Hz, 2H), 6.91 (d, J=8.4 Hz, 2H), 6.76 (d, J=8.1 Hz, 2H), 5.0 (br, 1H), 4.74 (s, 2H), 2.33 (br s, 4H), 1.60 (s, 8H). LCMS (ESI): m/z 332 (M−H)$^-$. Anal. Calcd for C$_{22}$H$_{23}$NO$_2$, C, 79.25; H, 6.95; N, 4.20; Found: C, 79.14; H, 6.90; N, 4.21.

Example 82 (218)

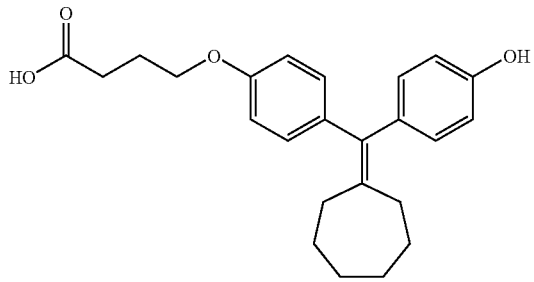

Step 1: Ethyl 4-({4-[cycloheptylidene(4-hydroxyphenyl)methyl]phenyl}oxy)butanoate (217)

The O-alkylation procedure described for 190 was used. A round-bottom flask was charged with 4,4'-(cycloheptylidenemethanediyl)diphenol (189) (0.882 g, 3 Mmol), K$_2$CO$_3$ (0.518 g, 3.75 mmol) and acetone (100 mL). To the above mixture ethyl 4-bromobutanoate (0.644 mL, 4.5 mmol) was added at room RT and the mixture was refluxed for 24 h. Regular work-up and purification by column chromatography afforded 0.400 g (33%) of the title compound 217 as a white solid and 0.560 g (36%) of dialkylated product. 0.125 g unreacted of SM was also recovered. $^1$H NMR (300 MHz, CDCl$_3$): δ 7.06 (d, J=8.4 Hz, 2H), 7.02 (d, J=8.4 Hz, 2H), 6.81 (d, J=8.7 Hz, 2H), 6.75 (d, J=8.4 Hz, 2H), 5.40 (s, 1H), 4.17 (q, J=14.1 Hz, 6.9 Hz, 2H), 4.00 (t, J=6.0 Hz, 2H), 2.54 (t, J=7.2 Hz, 2H), 2.34 (br s, 4H), 2.12 (quintet, J=13.2 Hz, J$_2$=6.9 Hz, 2H), 1.59 (s, 8H), 1.28 (t, J=7.2 Hz, 3H). LCMS (ESI): m/z 407 (M−H)$^-$.

Step 2: 4-({4-[cycloheptylidene(4-hydroxyphenyl)methyl]phenyl}oxy)butanoic acid (218)

The hydrolysis conditions described for 191 were employed. Thus, ethyl 4-({4-[cycloheptylidene(4-hydroxyphenyl)methyl]phenyl}oxy)butanoate (217) (0.155 g, 0.39 mmol) was dissolved in THF and EtOH (1:1, 10 mL) and then treated with 1 N NaOH (2 ml) at 70° C. for 1 h. Upon acidification, work-up, and purification afforded 0.110 g (74%) of the title compound 218. $^1$H NMR (300 MHz, CD$_3$OD): δ 7.02 (d, J=8.4 Hz, 2H), 6.94 (d, J=8.4 Hz, 2H), 6.83 (d, J=8.4 Hz, 2H), 6.69 (d, J=8.1 Hz, 2H), 4.00 (t, J=6.3 Hz, 2H), 2.49 (t, J=7.5 Hz, 2H), 2.31 (br s, 4H), 2.05 (quintet, J$_1$=13.5 Hz, J$_2$=6.9 Hz, 2H), 1.60 (s, 8H). LCMS (ESI): m/z 379 (M−H)$^-$. Anal. Calcd for C$_{24}$H$_{28}$O$_4$, C, 75.76; H, 7.42; Found: C, 75.81; H, 7.64.

Example 83 (221)

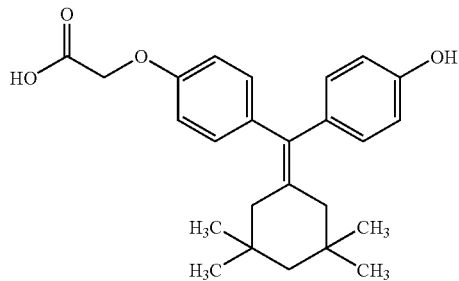

Step 1: 4,4'-[(3,3,5,5-Tetramethylcyclohexylidene)methanediyl]diphenol (219)

The general McMurry coupling protocol, described for 14 was followed. Coupling of bis(4-hydroxyphenyl)methanone (4.28 g, 0.02 mol) and 3,3,5,5-tetramethylcyclohexanone (9.26 g, 0.06 mol) under the under the standard reaction conditions afforded 5.65 g (84%) of the title compound 221 as an off-white solid. $^1$H NMR (300 MHz, CDCl$_3$): δ 6.96 (d, J=8.4 Hz, 4H), 6.70 (d, J=8.4 Hz, 4H), 1.99 (s, 4H), 0.94 (s, 12H).

Step 2: Ethyl({4-[(4-hydroxyphenyl)(3,3,5,5-tetramethylcyclohexylidene)methyl]phenyl}oxy)acetate (220)

The O-alkylation procedure described for 190 was followed. To a suspension of 4,4'-[(3,3,5,5-tetramethylcyclohexylidene)methanediyl]diphenol (219) (1.01 g, 3 mmol), K$_2$CO$_3$ (0.518 g, 3.8 mmol), and acetone (100 mL) was added bromoEtOAc (0.50 mL, 4.5 mmol) at RT. The reaction mixture was refluxed for 3 h, and filtered. The filtrate was concentrated and purified by flask column chromatography to afford 0.35 g (28%) of the title compound. In addition, 0.84 g (55%) of dialkylated product and 0.12 g of starting material (219) was recovered $^1$H NMR (300 MHz, CDCl$_3$): δ 7.28 (s, 1H), 7.09 (d, J=8.7 Hz, 2H), 7.03 (d, J=8.7 Hz, 2H), 6.83 (d, J=8.7 Hz, 2H), 6.75(d, J=8.4 Hz, 2H), 4.70 (br s, 1H), 4.61 (s, 3H), 4.29 (q, J$_1$=14.1 Hz, J$_2$=6.9 Hz, 2H), 1.98 (d, J=3.6 Hz, 4H), 1.31 (s, 2H), 1.29 (t, J=4.2 Hz, 3H), 0.94 (s, 12H). LCMS (ESI): m/z 421 (M−H)$^-$.

Step 3: ({4-[(4-Hydroxyphenyl)(3,3,5,5-tetramethylcyclohexylidene)methyl]phenyl}oxy)acetic acid (221)

The hydrolysis procedure described for 191 was followed. A solution of ethyl({4-[(4-hydroxyphenyl)(3,3,5,5-tetramethylcyclohexylidene)methyl]phenyl}oxy)acetate (220) (0.280 g, 0.66 mmol) in THF/EtOH (1:1, 10 mL) was treated with 1 N NaOH (5 ml, excess) at 70° C. for 1 h. Acid work-up and purification afforded 0.20 g (77%) of the title compound 221. mp 163-164° C. $^1$H NMR (300 MHz, CD$_3$OD): δ 7.05 (d, J=8.1 Hz, 2H), 6.95 (d, J=8.4 Hz, 2H), 6.85 (d, J=8.4 Hz, 2H), 6.69 (d, J=8.4 Hz, 2H), 4.46 (s, 2H), 2.99 (d, J=4.8 Hz, 4H), 1.30 (s, 2H), 0.94 (s, 12H). LCMS (ESI): m/z 393 (M–H)$^-$.

Example 84 (223)

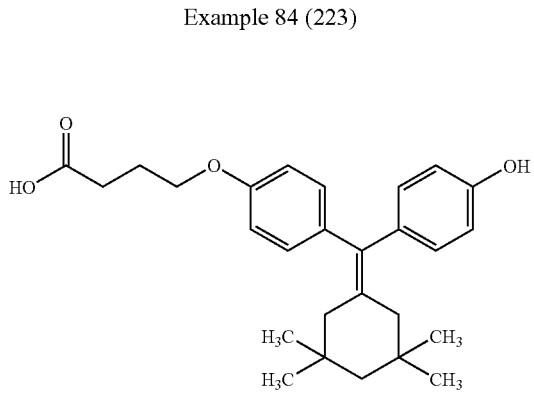

Step 1: Ethyl 4-({4-[(4-hydroxyphenyl)(3,3,5,5-tetramethylcyclohexylidene)methyl]phenyl}oxy)butanoate (222)

The O-alkylation procedure described for 190 was followed. To a solution of 4,4'-[(3,3,5,5-tetramethylcyclohexylidene)methanediyl]diphenol (219) (1.01 g, 3 mmol), K$_2$CO$_3$ (0.518 g, 3.8 mmol), and acetone (100 mL) was added bromoEtOAc (0.644 mL, 4.5 mmol) at RT. The reaction mixture was refluxed for 18 h and filtered. The filtrate was concentrated and purified by flash silica gel column chromatography to afford 1.08 g (40%) of the title compound 222 as an off-white foam. In addition, 0.16 g of unreacted SM (219) was recovered. LCMS (ESI): m/z 449 (M–H)$^-$.

Step 2: 4-({4-[(4-hydroxyphenyl)(3,3,5,5-tetramethylcyclohexylidene)methyl]phenyl}oxy)butanoic acid (223)

The hydrolysis conditions described for 191 was followed. A solution of ethyl 4-({4-[(4-hydroxyphenyl)(3,3,5,5-tetramethylcyclohexylidene)methyl]phenyl}oxy)butanoate (222) (0.760 g, 1.7 mmol) in THF/EtOH (1:1, 40 mL) was treated with 1 N NaOH (20 ml, excess) at 70° C. for 1 h. The reaction mixture was poured into 20% aqueous HCl (200 mL). The precipitated product was filtered and dried under reduced pressure to afford 0.68 g (95%) of compound 223 as an off-white solid. mp 203-204° C. $^1$H NMR (300 MHz, CD$_3$OD): δ 7.05 (d, J=8.7 Hz, 2H), 6.96 (d, J=8.4 Hz, 2H), 6.83 (d, J=8.7 Hz, 2H), 6.70 (d, J=8.4 Hz, 2H), 4.00 (t, J=6.3 Hz, 2H), 2.50 (t, J=7.2 Hz, 2H), 2.06 (quintet, J$_1$=13.5, J$_2$=6.9 Hz, 2H), 2.00 (d, J=4.2 Hz, 4H), 1.31 (s, 2H), 0.94 (s, 12H). LCMS (ESI): m/z 421 (M–H)$^-$. Anal. Calcd for C$_{27}$H$_{34}$O$_4$, C, 76.75; H, 8.11; Found: C, 75.63; H, 8.03.

Example 85 (224)

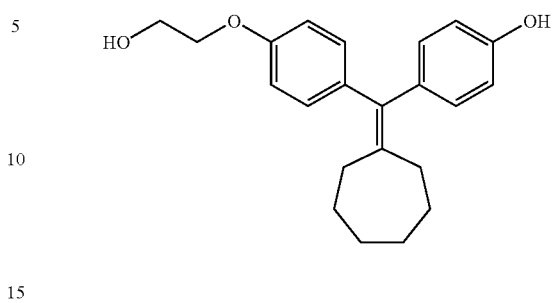

Step 1: 4-(Cycloheptylidene{4-[(2-hydroxyethyl)oxy]phenyl}methyl)phenol (224)

To a cold (5° C.) solution of ethyl({4-[cycloheptylidene(4-hydroxyphenyl)methyl]phenyl}oxy)acetate (190) (0.200 g, 0.53 mmol) in THF (10 mL) was added 1 M solution of LiAlH$_4$ (1.3 mL, 2.5 mmol). The reaction mixture was stirred at that temperature for 0.5 h. Reaction mixture was quenched with EtOAc (5 mL) and stirred for an additional 10 min before pouring into 20% aqueous HCl (50 ml). The reaction mixture was extracted with EtOAc (3×50 mL) and the combined organics washed with brine (1×25 ml), dried (Na$_2$SO$_4$) and concentrated under reduced pressure. The crude product was purified by flash chromatography on silica gel using hexanes and EtOAc (4:1 to 3:2) as an eluent to afford 155 mg (86%) of compound 224 as a white solid. $^1$H NMR (300 MHz, CD$_3$OD): δ 7.04 (d, J=8.7 Hz, 2H), 6.94 (d, J=8.4 Hz, 2H), 6.86 (d, J=8.4 Hz, 2H), 6.70 (d, J=8.4 Hz, 2H), 4.03 (t, J=5.1 Hz, 2H), 3.86 (t, J=5.1 Hz, 2H), 2.32 (d, J=4.5 Hz, 4H), 1.60 (br s, 8H). LCMS (ESI): m/z 337 (M–H)$^-$.

Example 86 (226)

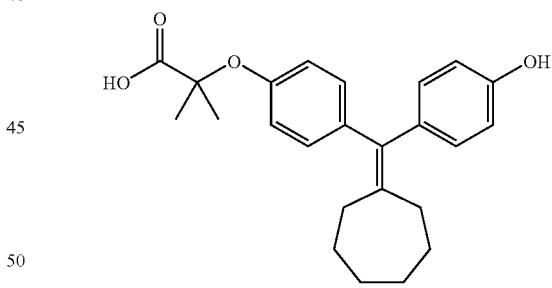

Step 1: Ethyl 2-({4-[cycloheptylidene(4-hydroxyphenyl)methyl]phenyl}oxy)-2-methylpropanoate (225)

The O-alkylation procedure described for 190 was used. To a suspension of 4,4'-(cycloheptylidenemethanediyl)diphenol (189) (0.510 g, 1.74 mmol), K$_2$CO$_3$ (0.300 g, 2.17 mmol), and acetone (75 mL) was added ethyl 2-bromo-2-methylpropanoate (0.0.382 mL, 2.6 mmol) at RT. The reaction mixture was refluxed for 48 h and filtered. The filtrate was concentrated and purified to afford 0.320 g (45%) of the title compound 225 as a white foam. In addition, 0.210 g of unreacted starting material was recovered. $^1$H NMR (300 MHz, CD$_3$OD): δ 7.02 (d, J=1.8 Hz, 2H), 6.99 (d, J=2.1 Hz, 2H), 6.76 (d, J=1.5 Hz, 2H), 6.73 (d, J=1.5 Hz, 2H), 4.71 (br s, 1H), 4.24 (q, J=7.2 Hz, 2H), 2.30 (br d, J=3.3 Hz, 4H), 1.59 (s, 6H), 1.58 (br s, 8H), 1.24 (t, J=6.9 Hz, 3H). LCMS (ESI): m/z 407 (M−H)⁻.

Step 2: 2-({4-[Cycloheptylidene(4-hydroxyphenyl)methyl]phenyl}oxy)-2-methylpropanoic acid (226)

The hydrolysis procedure described for 191 was employed. Ethyl 2-((4-[cycloheptylidene(4-hydroxyphenyl)methyl]phenyl}oxy)-2-methylpropanoate (225) (0.150 g, 0.37 mmol) was dissolved in THF and EtOH (1:1, 6 mL) and then treated with 1 N NaOH (3 mL, excess) at 70° C. for 1 h. The reaction mixture was cooled and poured into 20% aqueous HCl (40 mL). Standard work-up and purification afforded 0.105 g (75%) of the title compound 226 as an off-white solid. $^1$H NMR (300 MHz, DMSO-$d_6$): δ 13.06 (br s, 1H), 9.26 (s, 1H), 6.98 (d, J=8.4 Hz, 2H), 6.90 (d, J=7.8 Hz, 2H), 6.72 (d, J=8.4 Hz, 2H), 6.67 (d, J=8.1 Hz, 2H), 2.21 (br s, 4H), 1.52 (br s, 8H), 1.48 (s, 6H). LCMS (ESI): m/z 379 (M−H)⁻. Anal. Calcd for $C_{24}H_{28}O_4$, C, 75.76; H, 7.42; Found: C, 75.07; H, 7.52.

Example 87 (228)

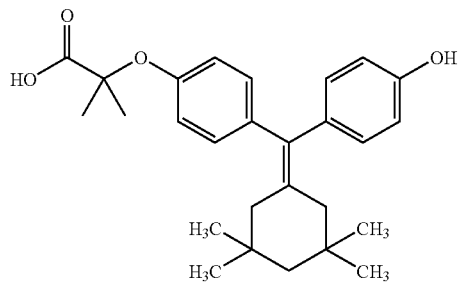

Step 1: Ethyl 2-({4-[(4-hydroxyphenyl)(3,3,5,5-tetramethylcyclohexylidene)methyl]phenyl}oxy)-2-methylpropanoate (227)

The O-alkylation procedure described for 190 was employed. To a suspension of 4,4'-[(3,3,5,5-tetramethylcyclohexylidene)methanediyl]diphenol (219) (0.500 g, 1.74 mmol), $K_2CO_3$ (0.257 g, 1.86 mmol), and acetone (75 mL) was added ethyl 2-bromo-2-methylpropanoate (0.33 mL, 2.3 mmol) at RT. The reaction mixture was refluxed for 48 h, and filtered. The filtrate was concentrated and purified to afford 0.272 g (40%) of compound 227 as a white foam. In addition, 0.200 g of unreacted SM was recovered. $^1$H NMR (300 MHz, CDCl₃): δ 7.04 (d, J=1.8 Hz, 2H), 7.01 (d, J=1.8 Hz, 2H), 6.76 (d, J=1.5 Hz, 2H), 6.77 (d, J=2.7 Hz, 2H), 6.74 (d, J=2.4 Hz, 2H), 4.75 (br s, 1H), 4.24 (q, J=7.2 Hz, 2H), 1.96 (d, J=6.9 Hz, 4H), 1.60 (s, 6H), 1.29 (s, 2H), 1.23 (t, J=7.2 Hz, 3H), 0.934 (s, 6H), 0.92 (s, 6H). LCMS (ESI): m/z 449 (M−H)⁻.

Step 2: 2-({4-[(4-Hydroxyphenyl)(3,3,5,5-tetramethylcyclohexylidene)methyl phenyl}oxy)-2-methylpropanoic acid (228)

The hydrolysis conditions described for 191 were used. A solution of ethyl 2-({4-[(4-hydroxyphenyl)(3,3,5,5-tetramethylcyclohexylidene)methyl]phenyl}oxy)-2 methylpropanoate (227) (0.15 g, 0.33 mmol) in THF/EtOH (1:1, 6 mL) was treated with 1 N NaOH (3 mL, excess) at 70° C. for 1 h. Reaction mixture was cooled and poured into 20% aqueous HCl (40 mL). Standard work-up followed by purification afforded 0.115 g (82%) of the title compound 228 as an off-white solid.

$^1$H NMR (300 MHz, DMSO-$d_6$): δ 13.0 (br s, 1H), 9.26 (s, 1H), 7.00 (d, J=8.7 Hz, 2H), 6.92 (d, J=8.4 Hz, 2H), 6.72 (d, J=8.7 Hz, 2H), 6.67 (d, J=8.4 Hz, 2H), 1.89 (d, J=4.5 Hz, 4H), 1.48 (s, 6H), 1.25 9 br s, 2H), 0.88 (s, 12H). LCMS (ESI): m/z 421 (M−H)⁻. Anal. Calcd for $C_{27}H_{34}O_4 \cdot H_2O$, C, 73.77; H, 8.19; Found: C, 74.78; H, 8.14.

Example 88 (229)

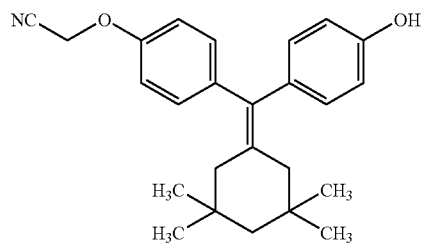

Step 1: ({4-[(4-Hydroxyphenyl)(3,3,5,5-tetramethylcyclohexylidene)methyl]phenyl}oxy)acetonitrile (229)

The O-alkylation procedure described for 190 was used. To a stirred suspension of 4,4'-[(3,3,5,5-tetramethylcyclohexylidene) methanediyl]diphenol (219) (0.600 g, 1.78 mmol), $K_2CO_3$ (0.368 g, 2.67 mmol), and acetone (60 mL) was added bromoacetonitrile (0.200 mL, 2.85 mmol) under a nitrogen atmosphere at RT. The reaction mixture was refluxed for 3 h, cooled to RT and filtered. Standard work-up followed by purification afforded 0.196 g (29%) of the title compound 229 as a white solid along with 0.38 g (52%) of the bis-alkylated compound 2,2'-[[(3,3,5,5-tetramethylcyclohexylidene) methanediyl]bis(benzene-4,1-diyloxy)]diacetonitrile. In addition, 0.10 g of unreacted starting material (219) was recovered. $^1$H NMR (300 MHz, CDCl₃): δ 7.15 (d, J=8.7 Hz, 2H), 7.04 (d, J=8.4 Hz, 2H), 6.90 (d, J=8.7 Hz, 2H), 6.76 (d, J=8.4 Hz, 2H), 4.75 (s, 2H), 2.00 (s, 2H), 1.98 (s, 2H), 1.31 (s, 2H), 0.95 (s, 12H). LCMS (ESI): m/z 374 (M−H)⁻. Anal. Calcd for $C_{25}H_{29}NO_2$, C, 79.96; H, 7.78; N, 3.73; Found: C, 79.95; H, 7.84; N, 3.73.

Example 89 (230)

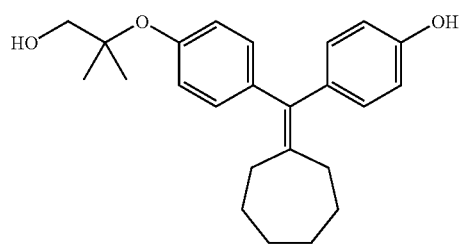

Step 1: 4-(Cycloheptylidene(4-[(2-hydroxy-1,1-dimethylethyl)oxy]phenyl}methyl)phenol (230)

The reduction procedure described for 224 was used. Ethyl 2-({4-[cycloheptylidene(4-hydroxyphenyl)methyl]

phenyl}oxy)-2-methylpropanoate (225) (0.125 g, 0.31 mmol) was treated with LiAlH₄ (0.8 mL) in THF (5 mL). Standard work-up followed by purification afforded 0.086 g (76%) of the title compound 230 as white foam. ¹H NMR (300 MHz, DMSO-d₆): δ 9.27 (s, 1H), 7.00 (d, J=7.8 Hz, 2H), 6.91 (d, J=4.5 Hz, 4H), 6.68 (d, J=8.4 Hz, 2H), 4.84 (t, J=5.7 Hz, 1H), 3.34 (d, J=3.6 Hz, 2H), 2.21 (br s, 4H), 1.52 (br s, 8H), 1.17 (s, 6H). LCMS (ESI): m/z 367 (M−H)⁻.

Example 90 (231)

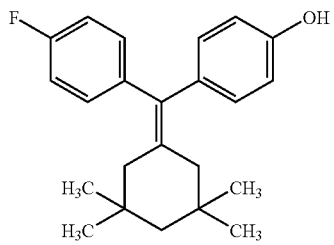

Step 1: 4-[(4-Fluorophenyl)(3,3,5,5-tetramethylcyclohexylidene)methyl]phenol (231)

The general McMurry coupling procedure described for 14 was followed. To a stirred suspension of zinc powder (13.0 g, 0.2 mol) in THF (400 mL) was slowly added TiCl₄ (11 mL, 0.10 mol) via a syringe at room temperature under a nitrogen atmosphere. The reaction mixture was heated at reflux for 1 h. A solution of (4-fluorophenyl)(4-hydroxyphenyl)methanone (4.32 g, 0.02 mol) and 3,3,5,5-tetramethylcyclohexanone (9.26 g, 0.06 mol) in THF (100 mL) was added to the reaction mixture. The reaction mixture was heated at reflux for an additional 2 h. Standar work-up followed by purification gave 5.450 g (80%) of compound 231 as a white solid. ¹H NMR (300 MHz, CDCl₃): δ 7.14 (d, J=5.7 Hz, 1H), 7.12 (d, J=5.7 Hz, 1H), 7.04 (d, J=8.7 Hz, 2H), 6.97 (dd, J=8.7 Hz, 2H), 6.76 (d, J=8.7 Hz, 2H), 4.68 (s, 1H), 1.99 (s, 2H), 1.96 (s, 2H), 1.31 (s, 2H), 0.95 (s, 6H), 0.94 (s, 6H).

Example 91 (232)

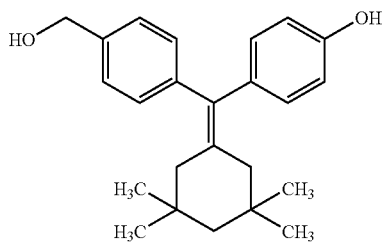

Step 1: 4-[[4-(Hydroxymethyl)phenyl](3,3,5,5-tetramethylcyclohexylidene)methyl]phenol (232)

To a solution of 4-[(4-hydroxyphenyl)(3,3,5,5-tetramethylcyclohexylidene)methyl]benzoic acid (26) (0.15 g, 0.41 mmol) in THF (10 mL) at 0° C. was added LAH (1 M in THF, 1.44 mL, 1.44 mmol) dropwise. The reaction mixture was stirred at 0° C. for 1 h, then heated at 50° C. for 1 h. Upon cooling in an ice bath, EtOAc (5 mL) was added, and stirring continued for 10 minutes. The mixture was then acidified to pH=2 with an aqueous solution of 1 N HCl, extracted with EtOAc (2×50 mL). The combined organic extract washed with water, brine and dried (Na₂SO₄) filtered, and the filtrate was concentrated to give the crude product as colorless oil. The crude product was purified by flash chromatography on silica gel eluted with a gradient from hexanes to 40% EtOAc: hexanes to give a white residue, which upon trituration with hot hexanes containing 1% of MeOH yielded 0.12 g (83%) of compound 231 as a white solid. mp 134-135° C. ¹H NMR (400 MHz, DMSO-d₆): δ 0.85 (s, 6H), 0.87 (s, 6H), 1.23 (s, 2H), 1.86 (s, 2H), 1.90 (s, 2H), 4.42 (d, J=5.7 Hz, 2H), 5.08 (t, J=5.7 Hz, 1H), 6.63 (d, J=8.4 Hz, 2H), 6.90 (d, J=8.4 Hz, 2H), 7.04 (d, J=8.1 Hz, 2H), 7.19 (d, J=8.1 Hz, 2H), 9.24 (s, 1H). LCMS (ES): m/z 349 (M−H)⁻.

Example 92 (232)

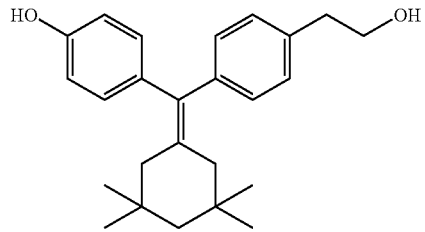

Step 1: 4-[[4-(2-Hydroxyethyl)phenyl](3,3,5,5-tetramethyl cyclohexylidene)methyl]phenol (232)

To a solution of methyl {4-[(4-hydroxyphenyl)(3,3,5,5-tetramethylcyclohexylidene)methyl]phenyl}acetate (153) (0.22 g, 0.56 mmol) in THF (10 mL) at 0° C. was added LAH (1 M in THF, 1.40 mL, 1.40 mmol) dropwise. The reaction mixture was stirred at 0° C. for 1 h, EtOAc (5 mL) was added, and stirring continued for 10 min. The mixture was then acidified to pH=2 with an aqueous solution of 1 N HCl, extracted with EtOAc (2×50 mL). The combined organic extract washed with water, brine and dried (Na₂SO₄) filtered, and the filtrate was concentrated to give the crude product as colorless oil. The crude product was purified by flash chromatography on silica gel eluted with a gradient from hexanes to 40% EtOAc:hexanes to give a white residue, which upon trituration with hot hexanes containing 1% of MeOH yielded 0.185 g (91%) of the title compound 232 as a white solid. mp 159-160° C. ¹H NMR (400 MHz, DMSO-d₆): δ 0.87 (s, 12H), 1.23 (s, 2H), 1.87 (s, 2H), 1.89 (s, 2H), 2.65 (t, J=7.1 Hz, 2H), 3.50-3.60 (m, 2H), 4.58 (t, J=5.2 Hz, 1H), 6.64 (d, J=8.2 Hz, 2H), 6.90 (d, J=8.4 Hz, 2H), 7.00 (d, J=7.9 Hz, 2H), 7.10 (d, J=8.1 Hz, 2H), 9.22 (s, 1H). LCMS (ES): m/z 365 (M+H)⁺, 363 (M−H)⁻.

Example 93 (233)

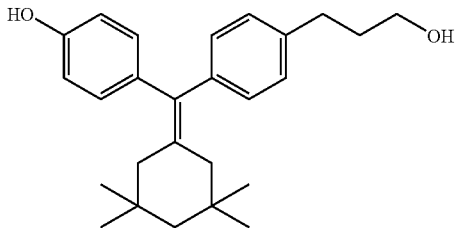

Step 1: 4-[[4-(3-Hydroxypropyl)phenyl](3,3,5,5-tetramethylcyclohexylidene)methyl]phenol (233)

To a solution of methyl 3-{4-[(4-hydroxyphenyl)(3,3,5,5-tetramethylcyclohexylidene)methyl]phenyl}propanoate (169) (0.176 g, 0.43 mmol) in THF (10 mL) at 0° C. was added LAH (1 M in THF, 1.10 mL, 1.10 mmol) dropwise. The reaction mixture was stirred at 0° C. for 1 h, EtOAc (5 mL) was added, and stirring continued for 10 min. The mixture was then acidified to pH=2 with an aqueous solution of 1 N HCl, extracted with EtOAc (2×50 mL). The combined organic extract washed with water, brine and dried ($Na_2SO_4$), filtered, and the filtrate was concentrated to give the crude product as white solid. The crude product was purified by flash chromatography on silica gel eluted with a gradient from hexanes to 40% EtOAc:hexanes to give a white residue, which upon trituration with hot hexanes containing 1% of MeOH yielded 0.15 g (92%) of compound 233 as a white solid. mp 160-161° C. $^1$H NMR (400 MHz, DMSO-$d_6$): δ 0.85 (s, 6H), 0.86 (s, 6H), 1.23 (s, 2H), 1.60-1.70 (m, 2H), 1.86 (s, 2H), 1.88 (s, 2H), 2.53 (t, J=7.8 Hz, 2H), 3.35-3.40 (m, 2H), 4.42 (t, J=5.1 Hz, 1H), 6.64 (d, J=8.5 Hz, 2H), 6.89 (d, J=8.5 Hz, 2H), 6.99 (d, J=8.1 Hz, 2H), 7.07 (d, J=8.1 Hz, 2H), 9.23 (s, 1H). LCMS (ES): m/z 401 (M+Na)$^+$, 377 (M−H)$^-$.

Example 94 (234)

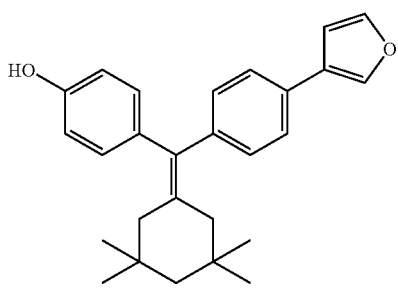

Step 1: 4-[[4-(3-furanyl)phenyl](3,3,5,5-tetramethyl-cyclohexylidene)methyl]phenol (234)

The Suzuki protocol described for (163) was employed. A round-bottomed flask was charged with 4-[(4-bromophenyl)(3,3,5,5-tetramethylcyclohexylidene)methyl]phenol (14) (0.270 g, 0.676 mmol), $PdCl_2(PPh_3)_2$ (0.048 g, 0.068 mmol), 3-furanylboronic acid (0.152 g, 1.35 mmol), aqueous 2 M $Na_2CO_3$ (1.4 mL, 0.144 g, 1.35 mmol) solution, and 4:1 THF:$H_2O$ mixture (10 mL) under a nitrogen atmosphere. The reaction mixture was refluxed for 6 h. Reaction mixture was cooled to room temperature, diluted with $Et_2O$ (10 mL) and filtered. The filtrate was diluted with EtOAc (60 mL), washed with brine, dried ($Na_2SO_4$), and concentrated under reduced pressure to afford the crude product. The product was purified by $SiO_2$ chromatography using hexanes:EtOAc (19:1 to 4:1) as an eluent to give 0.180 g (69%) of the title compound (234) as white solid. mp 128° C.-129° C. $^1$H NMR (400 MHz, $CDCl_3$): δ 7.71 (s, 1H), 7.45 (s, 1H), 7.39 (d, J=8.0 Hz, 2H), 7.16 (d, J=8.0 Hz, 2H), 7.05 (d, J=8.4 Hz, 2H), 6.74 (d, J=8.4 Hz, 2H), 6.68 (br s, 1H), 4.66 (s, 1H), 2.00 (s, 2H), 1.99 (s, 2H), 1.29 (s, 2H), 0.94 (s, 12H). LCMS (ESI): m/z 385.31 (M−H)$^-$.

Example 95 (235)

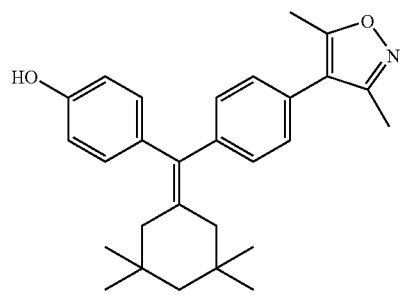

Step 1: 4-[[4-(3,5-dimethyl-4-isoxazolyl)phenyl](3,3,5,5-tetramethylcyclohexylidene)methyl]phenol (235)

The Suzuki protocol described for (163) was employed. A round bottom flash was charged with 4-[(4-bromophenyl)(3,3,5,5-tetramethylcyclohexylidene)methyl]phenol (14) (0.200 g, 0.5 mmol), $PdCl_2(PPh_3)_2$ (0.035 g, 0.05 mmol), (3,5-dimethyl-4-isoxazolyl)boronic acid (0.141 g, 1.0 mmol), aqueous 2 M $Na_2CO_3$ (1.0 mL, 0.106 g, 1.0 mmol) solution, and 4:1 THF:$H_2O$ mixture (5 mL) under a nitrogen atmosphere. The reaction mixture was refluxed for 3 h. Regular work-up and purification gave 0.172 g (83%) of the title compound (235) as an off-white solid. $^1$H NMR (400 MHz, DMSO-$d_6$): δ 9.30 (s, 1H), 7.29 (d, J=8.0 Hz, 2H), 7.21 (d, J=8.4 Hz, 2H), 6.94 (d, J=8.4 Hz, 2H), 6.67 (d, J=8.4 Hz, 2H), 2.38 (s, 3H), 2.20 (s, 2H), 1.91 (br s, 4H), 1.25 (s, 2H), 0.892 (s, 6H), 0.88 (s, 6H). LCMS (APCI): m/z 416.10 (M+H)$^+$.

Example 96 (236)

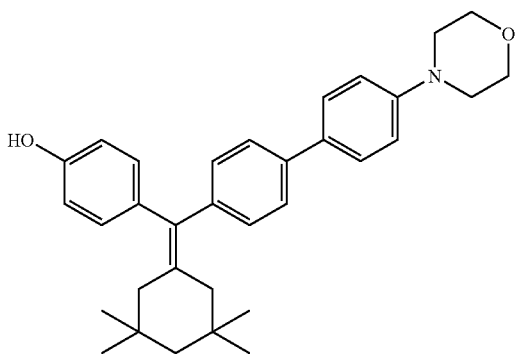

Step 1: 4-[[4'-(4-morpholinyl)-4-biphenylyl](3,3,5,5-tetramethylcyclohexylidene)methyl]phenol (236)

The Suzuki protocol described for (163) was employed. A round bottom flash was charged with 4-[(4-bromophenyl)(3,3,5,5-tetramethylcyclohexylidene)methyl]phenol (14) (0.200 g, 0.5 mmol), PdCl$_2$(PPh$_3$)$_2$ (0.035 g, 0.05 mmol), [4-(4-morpholinyl)phenyl]boronic acid (0.270 g, 1.0 mmol), aqueous 2 M Na$_2$CO$_3$ (1.0 mL, 0.106 g, 1.0 mmol) solution, and 4:1 THF:H$_2$O mixture (5 mL) under a nitrogen atmosphere. The reaction mixture was refluxed for 3 h. Regular work-up and purification gave 0.142 g (59%) of the title compound (236) as an off-white solid. $^1$H NMR (400 MHz, DMSO-d$_6$): δ 9.27 (s, 1H), 7.52 (d, J=5.2 Hz, 2H), 7.50 (d, J=4.4 Hz, 2H), 7.13 (d, J=8.4 Hz, 2H), 6.98 (d, J=8.8 Hz, 2H), 6.94 (d, J=8.4 Hz, 2H), 6.66 (d, J=8.4 Hz, 2H), 3.72 (t, J=4.4 Hz, 4H), 3.12 (t, J=4.8 Hz, 4H), 1.93 (s, 2H), 1.92 (s, 2H), 1.25 (s, 2H), 0.89 (s, 12H). LCMS (APCI): m/z 482.08 (M+H)$^+$.

Example 97 (237)

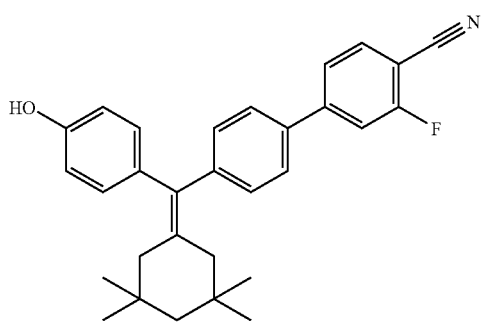

Step 1: 3-fluoro-4'-[(4-hydroxyphenyl)(3,3,5,5-tetramethylcyclohexylidene)methyl]-4-biphenylcarbonitrile (237)

The Suzuki protocol described for (163) was employed. A round-bottomed flask was charged with 4-[(4-bromophenyl)(3,3,5,5-tetramethylcyclohexylidene)methyl]phenol (14) (0.200 g, 0.5 mmol), PdCl$_2$(PPh$_3$)$_2$ (0.035 g, 0.05 mmol), (4-cyano-3-fluorophenyl)boronic acid (0.165 g, 1.0 mmol), aqueous 2 M Na$_2$CO$_3$ (1.0 mL, 0.106 g, 1.0 mmol) solution, and 4:1 THF:H$_2$O (5 mL) under a nitrogen atmosphere. The reaction mixture was refluxed for 12 h. Regular work-up and purification gave 0.158 g (72%) of the title compound (237) as an off-white solid. $^1$H NMR (400 MHz, DMSO-d$_6$): δ 9.30 (s, 1H), 7.96 (dd, J$_1$=7.2 Hz, J$_2$=7.2 Hz, 1H), 7.88 and 7.85 (dd, J$_1$=11.2 Hz, J$_2$=1.2 Hz, 1H), 7.73 (d, J=8.4 Hz, 3H), 7.25 (d, J=8.4 Hz, 2H), 7.45 (d, J=8.8 Hz, 2H), 7.17 (d, J=8.4 Hz, 2H), 1.93 (s, 2H), 1.92 (s, 2H), 1.26 (s, 2H), 0.89 (s, 6H), 0.88 (s, 6H). LCMS (APCI): m/z 437.97 (M–H)$^-$.

Example 98 (238)

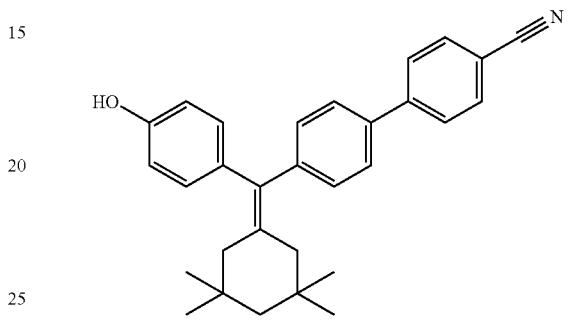

Step 1: 4'-[(4-hydroxyphenyl)(3,3,5,5-tetramethylcyclohexylidene)methyl]-4-biphenyl carbonitrile (238)

The Suzuki protocol described for (163) was employed. A round-bottomed flask was charged with 4-[(4-bromophenyl)(3,3,5,5-tetramethylcyclohexylidene)methyl]phenol (14) (0.200 g, 0.5 mmol), PdCl$_2$(PPh$_3$)$_2$ (0.035 g, 0.05 mmol), (4-cyanophenyl)boronic acid (0.165 g, 1.0 mmol), aqueous 2 M Na$_2$CO$_3$ (1.0 mL, 0.106 g, 1.0 mmol) solution, and 4:1 THF:H$_2$O (5 mL) under a nitrogen atmosphere. The reaction mixture was refluxed for 12 h. Regular work-up and purification gave 0.155 g (74%) of the title compound (238) as an off-white solid. $^1$H NMR (400 MHz, DMSO-d$_6$): δ 9.30 (s, 1H), 7.88 (d, J=8.4 Hz, 1H), 7.87 (d, J=4.8 Hz, 2H), 7.85 (d, J=8.4 Hz, 1H), 7.67 (d, J=8.0 Hz, 3H), 7.25 (d, J=8.4 Hz, 2H), 6.95 (d, J=8.8 Hz, 2H), 6.67 (d, J=8.4 Hz, 2H), 1.92 (br s, 4H), 1.25 (s, 2H), 0.88 (s, 12H). LCMS (APCI): m/z 419.97 (M–H)$^-$.

Example 99 (239)

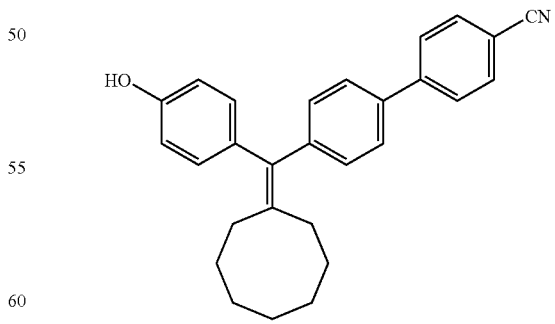

Step 1: 4'-[cyclooctylidene(4-hydroxyphenyl)methyl]-4-biphenylcarbonitrile (239)

The Suzuki protocol described for (163) was employed. A round-bottomed flask was charged with 4-[(4-bromophenyl)

(cyclooctylidene)methyl]phenol (49) (0.140 g, 0.37 mmol), PdCl$_2$(PPh$_3$)$_2$ (0.027 g, 0.05 mmol), (4-cyanophenyl)boronic acid (0.109 g, 1.0 mmol), aqueous 2 M Na$_2$CO$_3$ (0.7 mL, 0.74 mL, 0.079 g, 1.0 mmol) solution, and 4:1 THF:H$_2$O mixture (5 mL) under a nitrogen atmosphere. The reaction mixture was refluxed for 6 h. Upon regular work-up and purification gave 0.110 g (76%) of the title compound (239) as an off-white solid. $^1$H NMR (400 MHz, DMSO-d$_6$): δ 9.32 (s, 1H), 7.86 (d, J=4.4 Hz, 1H), 7.85 (d, J=8.4 Hz, 2H), 7.84 (d, J=8.4 Hz, 1H), 7.67 (d, J=8.00 Hz, 2H), 7.24 (d, J=8.00 Hz, 2H), 6.95 (d, J=8.4 Hz, 2H), 6.68 (d, J=8.00 Hz, 2H), 2.21 (br s, 4H), 1.61 (br s, 2H), 1.49 (br m, 8H). LCMS (ESI): m/z 392.21 (M–H)$^-$.

Example 100 (240)

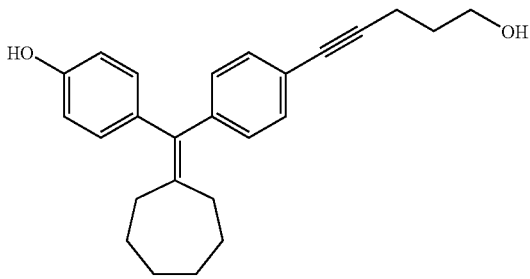

Step 1: 4-{Cycloheptylidene[4-(5-hydroxy-1-pentyn-1-yl)phenyl]methyl}phenol (240)

To a degassed solution of 4-[(4-bromophenyl)(cycloheptylidene)methyl]phenol (9) (0.20 g, 0.56 mmol) in DMF (5 mL) were added Pd(PPh$_3$)$_2$Cl$_2$ (40 mg, 0.06 mmol), CuI (11 mg, 0.06 mmol), N,N-diisopropylethylamine (0.45 mL, 2.52 mmol) and 4-pentyn-1-ol (0.11 mL, 1.12 mmol). The reaction mixture was stirred at 80° C. overnight, poured into saturated aqueous NH$_4$Cl (15 mL) and water (5 mL), extracted with ethyl acetate (3×50 mL). The combined organic phase washed with water, brine, dried over Na$_2$SO$_4$, filtered, and the filtrate was concentrated to give the crude product as brown oil. The crude product was purified by chromatography on a silica gel column eluted with a gradient from hexanes to 45% EtOAc in hexanes to give a light brown solid. The solid was triturated with hot hexanes containing 1% MeOH to afford 91 mg (45%) of the title compound (240) as beige solid. mp 125-126° C. $^1$H NMR (400 MHz, DMSO-d$_6$): δ 1.49 (bs, 8H), 1.60-1.70 (m, 2H), 2.10-2.25 (m, 4H), 2.41 (t, J=7.0 Hz, 2H), 3.40-3.50 (m, 2H), 4.49 (t, J=5.2 Hz, 1H), 6.65 (d, J=8.4 Hz, 2H), 6.88 (d, J=8.4 Hz, 2H), 7.04 (d, J=8.0 Hz, 2H), 7.26 (d, J=8.2 Hz, 2H), 9.27 (s, 1H). LCMS (ESI): m/z 361 (M+H)$^+$, 359 (M–H)$^-$.

Example 101 (241)

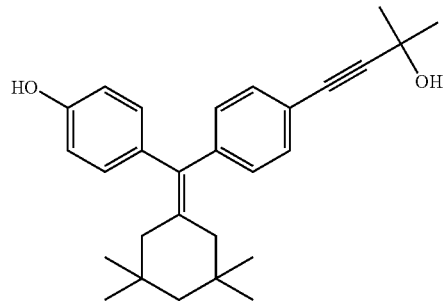

Step 1: 4-[[4-(3-hydroxy-3-methyl-1-butyn-1-yl)phenyl](3,3,5,5-tetramethyl cyclohexylidene)methyl]phenol (241)

To a degassed solution of 4-[(4-Iodophenyl)(3,3,5,5-tetramethylcyclohexylidene)methyl]phenol (144) (0.25 g, 0.56 mmol) in DMF (5 mL) were added Pd(PPh$_3$)$_2$Cl$_2$ (40 mg, 0.06 mmol), CuI (11 mg, 0.06 mmol), N,N-diisopropylethylamine (0.45 mL, 2.52 mmol) and 2-methyl-3-butyn-2-ol (0.11 mL, 1.12 mmol). The reaction mixture was stirred at room temperature overnight, poured into saturated aqueous NH$_4$Cl (15 mL) and water (5 mL), extracted with ethyl acetate (2×50 mL). The combined organic phase washed with water, brine, dried over Na$_2$SO$_4$, filtered, and the filtrate was concentrated to give the crude product as brown oil. The crude product was purified by chromatography on a silica gel column eluted with a gradient from hexanes to 30% EtOAc in hexanes to give a light brown solid. The solid was triturated with hot hexanes containing 1% MeOH and 5% EtOAc in hexanes to afford 150 mg (67%) of the title compound (241) as off-white solid. mp 186-187° C. $^1$H NMR (400 MHz, DMSO-d$_6$): δ 0.85 (s, 6H), 0.87 (s, 6H), 1.23 (s, 2H), 1.42 (s, 6H), 1.84 (s, 2H), 1.90 (s, 2H), 5.41 (s, 1H), 6.65 (d, J=8.4 Hz, 2H), 6.91 (d, J=8.3 Hz, 2H), 7.08 (d, J=8.1 Hz, 2H), 7.27 (d, J=8.0 Hz, 2H), 9.29 (s, 1H). LCMS (ESI): m/z 401 (M–H)$^-$.

Example 102 (242)

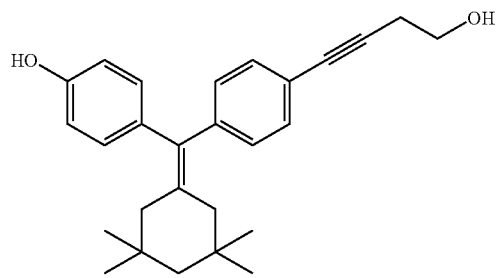

Step 1: 4-[[4-(4-hydroxy-1-butyn-1-yl)phenyl](3,3,5,5-tetramethylcyclohexylidene)methyl]phenol (242)

To a degassed solution of 4-[(4-Iodophenyl)(3,3,5,5-tetramethylcyclohexylidene)methyl]phenol (144) (0.20 g, 0.45 mmol) in DMF (5 mL) were added Pd(PPh$_3$)$_2$Cl$_2$ (32 mg, 0.05 mmol), CuI (9 mg, 0.05 mmol), N,N-diisopropylethylamine (0.36 mL, 2.02 mmol) and 3-butyn-1-ol (70 μL, 0.90 mmol). The reaction mixture was stirred at room temperature overnight, poured into saturated aqueous NH$_4$Cl (15 mL) and water (5 mL), extracted with ethyl acetate (2×50 mL). The combined organic phase washed with water, brine, dried over Na$_2$SO$_4$, filtered, and the filtrate was concentrated to give the crude product as brown oil. The crude product was purified by chromatography on a silica gel column eluted with a gradient from hexanes to 40% EtOAc in hexanes to give a light brown solid. The solid was triturated with hot hexanes containing 2% MeOH and 2% CH$_2$Cl$_2$ to afford 133 mg (76%) of the title compound (242) as light beige solid. mp 183-184° C. $^1$H NMR (400 MHz, CH$_3$OH-d$_4$): δ 0.91 (s, 6H), 0.92 (s, 6H), 1.29 (s, 2H), 1.94 (s, 2H), 1.98 (s, 2H), 2.58 (t, J=6.8 Hz, 2H), 3.70 (t, J=6.8 Hz, 2H), 6.68 (d, J=8.6 Hz, 2H), 6.94 (d, J=8.4 Hz, 2H), 7.07 (d, J=8.3 Hz, 2H), 7.28 (d, J=8.0 Hz, 2H). LCMS (APCI): m/z 389 (M+H)$^+$, 387 (M−H)$^-$.

Example 103 (244)

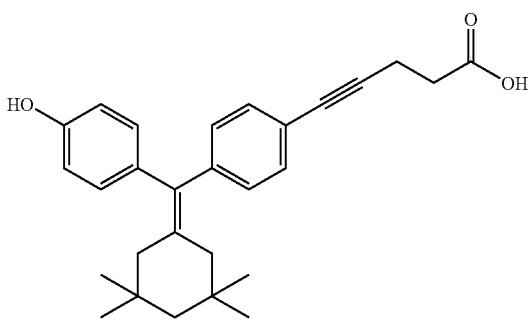

Step 1: Methyl 5-{4-[(4-hydroxyphenyl)(3,3,5,5-tetramethylcyclohexylidene)methyl]phenyl}-4-pentynoate (243)

4-Pentynoic acid (0.50 g, 5.0 mmol) was dissolved in DMF (15 mL). To this solution was added K$_2$CO$_3$ (2.76 g, 20 mmol) followed by CH$_3$I (0.95 mL, 15 mmol). The reaction mixture was stirred at room temperature overnight. Water was added to dissolve all solid, and the mixture was extracted with ether (2×75 mL). The organic extracts were combined and washed with saturated NaHCO$_3$, water, brine and dried over Na$_2$SO$_4$, filtered, and the filtrate was concentrated to give the crude methyl 4-pentynoate as colorless oil (0.29 g, 52%). To a degassed solution of 4-[(4-Iodophenyl)(3,3,5,5-tetramethylcyclohexylidene)methyl]phenol (144) (0.25 g, 0.56 mmol) in DMF (5 mL) were added Pd(PPh$_3$)$_2$Cl$_2$ (40 mg, 0.06 mmol), CuI (11 mg, 0.06 mmol), N,N-diisopropylethylamine (0.45 mL, 2.52 mmol) and methyl 4-pentynoate (0.15 g). The reaction mixture was stirred at room temperature overnight, poured into saturated aqueous NH$_4$Cl (15 mL) and water (5 mL), extracted with ethyl acetate (2×50 mL). The combined organic phase washed with water, brine, dried over Na$_2$SO$_4$, filtered, and the filtrate was concentrated to give the crude product as brown oil. The crude product was purified by chromatography on a silica gel column eluted with a gradient from hexanes to 20% EtOAc in hexanes to give a light brown solid. The solid was triturated with hot hexanes containing 1% to afford 184 mg (76%) of the title compound (243) as off-white solid. mp 159-160° C. $^1$H NMR (400 MHz, CDCl$_3$): δ 0.90 (s, 6H), 0.91 (s, 6H), 1.27 (s, 2H), 1.92 (s, 2H), 1.96 (s, 2H), 2.55-2.65 (m, 2H), 2.65-2.75 (m, 2H), 3.71 (s, 3H), 4.58 (s, 1H), 6.72 (d, J=8.4 Hz, 2H), 7.00 (d, J=8.4 Hz, 2H), 7.06 (d, J=8.2 Hz, 2H), 7.28 (d, J=8.3 Hz, 2H). LCMS (ESI): m/z 431 (M+H)$^+$, 429 (M−H)$^-$.

Step 2: 5-{4-[(4-Hydroxyphenyl)(3,3,5,5-tetramethylcyclohexylidene)methyl]phenyl}-4-pentynoic acid (244)

To a solution of methyl 5-{4-[(4-hydroxyphenyl)(3,3,5,5-tetramethylcyclohexylidene)methyl]phenyl}-4-pentynoate (243) (0.16 g, 0.38 mmol) in a mixture of EtOH (5 mL) and THF (5 mL) was added an aqueous solution of 1N NaOH (6 mL). The mixture was stirred at 60° C. for 2 h. Upon cooling, the mixture was acidified to pH=2 with an aqueous solution of 1 N HCl. The mixture was extracted with EtOAc (2×50 mL). The combined organic extract washed with brine and dried over Na$_2$SO$_4$. Concentration gave a white residue, which was triturated with hot hexanes containing 1% MeOH to yield the title compound (244) as white solid (0.15 g, 95%), mp 233-234° C. $^1$H NMR (400 MHz, CH$_3$OH-d$_4$): δ 0.91 (s, 6H), 0.92 (s, 6H), 1.29 (s, 2H), 1.94 (s, 2H), 1.98 (s, 2H), 2.50-2.60 (m, 2H), 2.60-2.70 (m, 2H), 6.68 (d, J=8.6 Hz, 2H), 6.94 (d, J=8.6 Hz, 2H), 7.07 (d, J=8.3 Hz, 2H), 7.25 (d, J=8.1 Hz, 2H). LCMS (ESI): m/z 417 (M+H)$^+$, 415 (M−H)$^-$.

Example 104 (245)

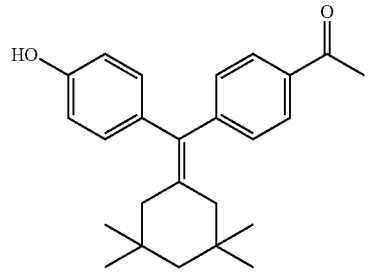

Step 1: 1-{4-[(4-Hydroxyphenyl)(3,3,5,5-tetramethylcyclohexylidene)methyl]phenyl}ethanone (245)

A stirred solution of 4-[(4-hydroxyphenyl)(3,3,5,5-tetramethylcyclohexylidene)methyl]benzoic acid (26) (0.138 g, 0.38 mmol) in THF (4 mL) was cooled to 0° C. in an ice bath and treated rapidly with methyllithium (1.6 M in ether, 1.9 mL, 3.0 mmol). After 2 h at 0° C., Me$_3$SiCl (1.40 mL, 10.4 mmol) was rapidly added while stirring continued. The ice bath was then removed and the reaction mixture was allowed to come to room temperature at which point 1 N HCl (3 mL) was added, and the resulting two-phase mixture was stirred at room temperature for 0.5 h, extracted with ether. The etheral layers were combined and washed with water, brine, dried over Na$_2$SO$_4$, filtered, and the filtrate was concentrated to give the crude product as colorless oil. The crude product was purified by chromatography on a silica gel column eluted with a gradient from hexanes to 35% EtOAc in hexanes to give 70 mg (51%) of the title compound (245) as white solid. mp 195-196° C. $^1$H NMR (400 MHz, DMSO-d$_6$): δ 0.86 (s, 6H), 0.88 (s, 6H), 1.25 (s, 2H), 1.86 (s, 2H), 1.92 (s, 2H), 2.52

(s, 3H), 6.66 (d, J=8.4 Hz, 2H), 6.93 (d, J=8.4 Hz, 2H), 7.24 (d, J=8.1 Hz, 2H), 7.86 (d, J=8.2 Hz, 2H), 9.30 (s, 1H). LCMS (ESI): m/z 361 (M−H)$^-$.

Example 105 (246)

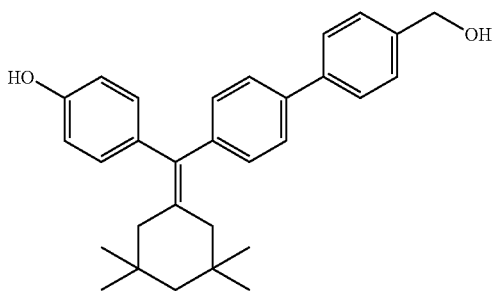

Step 1: 4-[[4'-(Hydroxymethyl)-4-biphenylyl](3,3,5,5-tetramethylcyclohexylidene)methyl]phenol (246)

A sealed tube containing 4-[(4-bromophenyl)(3,3,5,5-tetramethylcyclohexylidene)methyl]phenol (14) (0.20 g, 0.50 mmol), 4-(hydroxymethyl)phenyl boronic acid (0.16 g, 1.0 mmol), Pd(PPh$_3$)$_4$ (58 mg, 0.05 mmol), 2 M Na$_2$CO$_3$ (4 mL) and DME (4 mL) was heated at 160° C. for 25 min. Cooled to room temperature, the mixture was extracted with EtOAc. The EtOAc extracts were combined and washed with water, brine, dried over Na$_2$SO$_4$, filtered, and the filtrate was concentrated to give the crude product as dark brown oil. The crude product was purified by chromatography on a silica gel column eluted with a gradient from hexanes to 35% EtOAc in hexanes to give 0.16 g (75%) of the title compound (246) as pale yellow solid. mp 222-223° C. $^1$H NMR (400 MHz, DMSO-d$_6$): δ 0.89 (s, 12H), 1.25 (s, 2H), 1.92 (s, 2H), 1.93 (s, 2H), 4.50 (d, J=5.7 Hz, 2H), 5.17 (t, J=5.7 Hz, 1H), 6.66 (d, J=8.4 Hz, 2H), 6.94 (d, J=8.5 Hz, 2H), 7.18 (d, J=8.1 Hz, 2H), 7.35 (d, J=8.1 Hz, 2H), 7.56 (d, J=8.2 Hz, 2H), 7.58 (d, J=8.0 Hz, 2H), 9.26 (s, 1H). LCMS (ESI): m/z 425 (M−H)$^-$.

Example 106 (247)

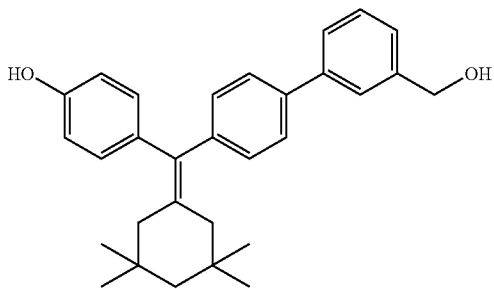

Step 1: 4-[[3'-(Hydroxymethyl)-4-biphenylyl](3,3,5,5-tetramethylcyclohexylidene)methyl]phenol (247)

A sealed tube containing 4-[(4-bromophenyl)(3,3,5,5-tetramethylcyclohexylidene)methyl]phenol (14) (0.20 g, 0.50 mmol), 3-(hydroxymethyl)phenyl boronic acid (0.16 g, 1.0 mmol), Pd(PPh$_3$)$_4$ (58 mg, 0.05 mmol), 2 M Na$_2$CO$_3$ (4 mL) and DME (4 mL) was heated at 160° C. for 25 minutes. Cooled to room temperature, the mixture was extracted with EtOAc. The EtOAc extracts were combined and washed with water, brine, dried over Na$_2$SO$_4$, filtered, and the filtrate was concentrated to give the crude product as dark brown oil. The crude product was purified by chromatography on a silica gel column eluted with a gradient from hexanes to 30% EtOAc in hexanes to give 0.14 g (66%) of the title compound (247) as pale yellow solid. mp 197-198° C. $^1$H NMR (400 MHz, DMSO-d$_6$): δ 0.89 (s, 12H), 1.25 (s, 2H), 1.93 (s, 4H), 4.52 (d, J=5.9 Hz, 2H), 5.20 (t, J=5.9 Hz, 1H), 6.66 (d, J=8.4 Hz, 2H), 6.95 (d, J=8.4 Hz, 2H), 7.19 (d, J=8.0 Hz, 2H), 7.26 (d, J=7.5 Hz, 1H), 7.37 (t, J=7.6 Hz, 1H), 7.48 (d, J=7.7 Hz, 1H), 7.52-7.58 (m, 3H), 9.27 (s, 1H). LCMS (ESI): m/z 427 (M+H)$^+$, 425 (M−H)$^-$.

Example 107 (249)

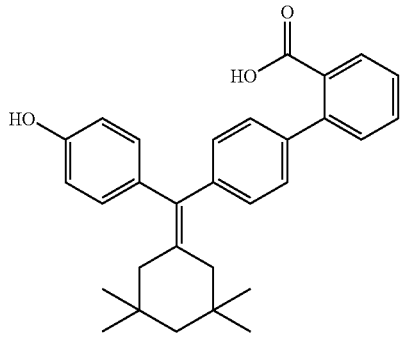

Step 1: Methyl 4'-[(4-hydroxyphenyl)(3,3,5,5-tetramethylcyclohexylidene)methyl]-2-biphenylcarboxylate (248)

A sealed tube containing 4-[(4-bromophenyl)(3,3,5,5-tetramethylcyclohexylidene)methyl]phenol (14) (0.30 g, 0.75 mmol), (2-methoxycarbonylphenyl)boronic acid (0.29 g, 1.50 mmol), Pd(PPh$_3$)$_4$ (87 mg, 0.08 mmol), 2 M Na$_2$CO$_3$ (4 mL) and DME (4 mL) was heated at 160° C. for 25 minutes. Cooled to room temperature, the mixture was extracted with EtOAc. The EtOAc extracts were combined and washed with water, brine, dried over Na$_2$SO$_4$, filtered, and the filtrate was concentrated to give the crude product as dark brown oil. The crude product was purified by chromatography on a silica gel column eluted with a gradient from hexanes to 20% EtOAc in hexanes to give 0.23 g (68%) of the title compound (248) as off-white solid. mp 177-178° C. $^1$H NMR (400 MHz, CDCl$_3$): δ 0.96 (s, 6H), 0.97 (s, 6H), 1.32 (s, 2H), 2.03 (s, 4H), 3.57 (s, 3H), 4.60 (s, 1H), 6.78 (d, J=8.5 Hz, 2H), 7.10 (d, J=8.5 Hz, 2H), 7.15-7.25 (m, 4H), 7.36-7.44 (m, 2H), 7.48-7.56 (m, 1H), 7.76-7.82 (m, 1H). LCMS (ESI): m/z 455 (M+H)$^+$, 453 (M−H)$^-$.

Step 2: 4'-[(4-Hydroxyphenyl)(3,3,5,5-tetramethylcyclohexylidene)methyl]-2-biphenylcarboxylic acid (249)

To a solution of methyl 4'-[(4-hydroxyphenyl)(3,3,5,5-tetramethylcyclohexylidene)methyl]-2-biphenylcarboxylate (248) (0.108 g, 0.24 mmol) in a mixture of EtOH (6 mL) and THF (4 mL) was added an aqueous solution of 1N NaOH (10 mL). The mixture was stirred at 60° C. overnight. Upon cooling, the mixture was acidified to pH=2 with an aqueous solution of 1 N HCl. The mixture was extracted with EtOAc (2×50 mL). The combined organic extract washed with brine and dried over $Na_2SO_4$. Concentration gave a white residue, which was triturated with hot hexanes containing 1% MeOH to yield the title compound (249) as white solid (92.8 mg, 89%). mp 230-231° C. $^1$H NMR (400 MHz, DMSO-$d_6$): δ 0.88 (s, 6H), 0.89 (s, 6H), 1.25 (s, 2H), 1.91 (s, 4H), 6.67 (d, J=8.4 Hz, 2H), 6.95 (d, J=8.2 Hz, 2H), 7.14 (d, J=8.0 Hz, 2H), 7.23 (d, J=8.0 Hz, 2H), 7.34-7.44 (m, 2H), 7.50-7.55 (m, 1H), 7.65 (d, J=7.7 Hz, 1H), 9.27 (s, 1H), 12.72 (s, 1H). LCMS (ESI): m/z 441 (M+H)$^+$, 439 (M−H)$^-$.

Example 108 (250)

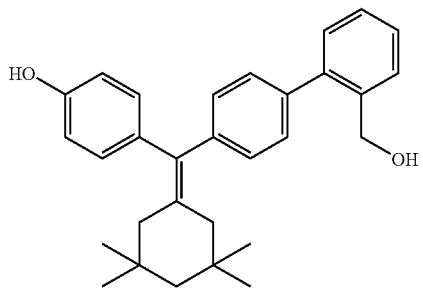

Step 1: 4-[[2'-(Hydroxymethyl)-4-biphenylyl](3,3,5, 5-tetramethylcyclohexylidene)methyl]phenol (250)

To a solution of methyl 4'-[(4-hydroxyphenyl)(3,3,5,5-tetramethylcyclohexylidene)methyl]-2-biphenylcarboxylate (248) (0.102 g, 0.23 mmol) in THF (8 mL) at 0° C. was added lithium aluminum hydride (1 M in THF, 0.56 mL, 0.56 mmol) dropwise. The reaction mixture was stirred at 0° C. for 1 h. EtOAc (5 mL) was added, and stirring continued for 10 minutes. The mixture was then acidified to pH=2 with an aqueous solution of 1 N HCl, extracted with EtOAc (2×50 mL). The combined organic extract washed with water, brine and dried over $Na_2SO_4$, filtered, and the filtrate was concentrated to give the crude product as light yellow oil. The crude product was purified by flash chromatography over $SiO_2$ eluted with a gradient from hexanes to 40% EtOAc in hexanes to give 83 mg (87%) of the title compound (250) as a white solid. mp 171-172° C. $^1$H NMR (400 MHz, DMSO-$d_6$): δ 0.88 (s, 6H), 0.90 (s, 6H), 1.25(s, 2H), 1.91 (s, 2H), 1.92 (s, 2H), 4.36 (d, J=5.1 Hz, 2H), 5.10 (t, J=5.3 Hz, 1H), 6.67 (d, J=8.2 Hz, 2H), 6.96 (d, J=8.2 Hz, 2H), 7.12-7.23 (m, 3H), 7.24-7.36 (m, 4H), 7.53 (d, J=7.5 Hz, 1H), 9.27 (s, 1H). LCMS (ESI): m/z 425 (M−H)$^-$.

Biological Data

Competition Binding Assay:

Recombinant full length human ERα and ERβ protein was purchased from PanVera (PanVera-Invitrogen Discovery Screening, Discovery Center, 501 Charmany Drive, Madison, Wis. 53719, USA). Polylysine coated Yttrium Silicate SPA beads (Amersham #RPNQ 0010) are resuspended in assay buffer [10 mM potassium phosphate buffer pH 7.0 containing 2 mM EDTA, 50 mM NaCl, 1 mM DTT, 2 mM CHAPs, 10% glycerol] to a concentration of 1 g/60 ml. 30 ul (0.5 mg) of the SPA beads are then added to each well of a Packard OptiPlate (Packard 6005190, Packard Instruments, Meriden, Conn.). The ERα or ERβ protein is diluted to the appropriate concentration (empirically determined for each protein prep by generating a protein curve using 0.5 to 10 ug total protein and 1 nM [3H] Estradiol and selecting a protein concentration that does not deplete the radioligand) and added as 30 μl aliquots to each well. [2, 4, 6, 7, 16, 17-3H(N)]-Estradiol is added as a 30 μl aliquot to give a final assay concentration of 1 nM. To give a final volume of 100 ul, either 10 μl of a test compound solution (typically in 10% DMSO as solvent), solvent containing no test compound (to determine total binding, T), or solvent containing 17-b-estradiol at 100 μM (to determine non-specific binding, NS) are finally added to the plate. The plates are shaken vigorously for two hours then counted on a Packard TopCount using the protocol for counting tritium yttrium silicate SPA beads. Data analysis was done by standard methods.

% Bound was Calcd for each concentration of each test compound using the equation % Bound=100*((Test−NS)/(T−NS)).

% Bound was plotted vs concentration and curve fitting was accomplished using non-linear regression.

At least two binding curves were generated for each compound.

The compounds of the present invention generally exhibited $pIC_{50}$ values ranging from 10 μM to 1 nM.

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I):

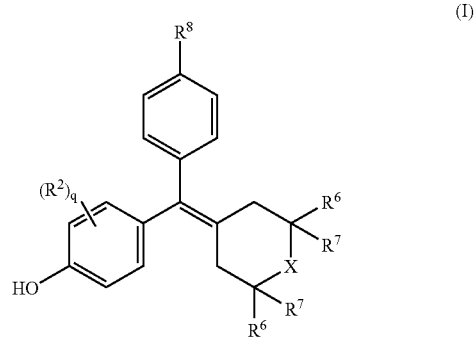

or a pharmaceutically acceptable salt thereof wherein
each $R^2$ is independently selected from OH, alkyl, or halogen;
q is independently selected from 0, 1, or 2;
X is —$(CH_2)_n$— where n is 0, 1, 2, or 3, —$C(R^g)_2$—, or —O—;
each of $R^6$ and $R^7$ are selected from H or alkyl;
$R^8$ is —$CO_2H$, —$(R^h)_tCO_2H$, or —$CONR^aR^b$;
t is 1 to 8;

$R^a$ is H, alkyl, cycloalkyl, aryl, heteroaryl, or heterocyclyl;
$R^b$ is H, alkyl, cycloalkyl, aryl, heteroaryl, or heterocyclyl; or
$R^a$ and $R^b$ may combine with the atoms to which they are bound to form a heteroaryl or heterocyclyl ring;
$R^g$ is alkyl; and
each $R^h$ independently is —$CR^jR^k$—, where each of $R^j$ and $R^k$ independently are selected from H and alkyl.

2. The compound of claim 1 wherein alkyl is $C_{1-8}$alkyl.

3. The compound of claim 1 wherein q is 0.

4. The compound of claim 1 wherein each of $R^6$ and $R^7$ are H or $C_{1-8}$ alkyl.

5. The compound of claim 1 wherein X is —$(CH_2)_n$—.

6. The compound of claim 5 wherein n is 1.

7. The compound of claim 6 wherein $R^6$ and $R^7$ are alkyl.

8. The compound of claim 5 wherein n is 2 or 3.

9. The compound of claim 8 wherein $R^6$ and $R^7$ are hydrogen.

10. The compound of claim 1 wherein X is —O—.

11. The compound of claim 10 wherein $R^6$ and $R^7$ are alkyl.

12. The compound of claim 1 wherein $R^8$ is —$CO_2H$.

13. The compound of claim 1 wherein $R^8$ is —$CONR^aR^b$, and $R^a$ and $R^b$ combine to form a 5 or 6 membered heterocyclyl ring optionally substituted with —$CO_2H$.

14. The compound selected from:
 4-[Cycloheptylidene(4-hydroxyphenyl)methyl]benzoic acid;
 4-[Cyclohexylidene(4-hydroxyphenyl)methyl]benzoic acid;
 4-[Cyclooctylidene(4-hydroxyphenyl)methyl]benzoic acid;
 3-{4-[(4-Hydroxyphenyl)(3,3,5,5-tetramethylcyclohexylidene)methyl]phenyl} propanoic acid;
 4-[(4,4-Dimethyl-cyclohexylidene)-(4-hydroxy-phenyl)-methyl]-benzoic acid;
 4-[Cycloheptylidene-(3-fluoro-4-hydroxy-phenyl)-methyl]-benzoic acid;
 4-[(4-hydroxyphenyl)(3,3,5,5-tetramethylcyclohexylidene)methyl]benzamide; and
pharmaceutically acceptable salts thereof.

15. A pharmaceutical composition comprising a compound according to claim 1, and a pharmaceutically acceptable carrier, diluent, or excipient.

* * * * *